United States Patent
Han et al.

(10) Patent No.: US 10,538,497 B2
(45) Date of Patent: Jan. 21, 2020

(54) COMPOUNDS AS INDOLEAMINE 2,3-DIOXYGENASE INHIBITORS

(71) Applicant: Merck Sharp & Dohme Corp., Rahway, NJ (US)

(72) Inventors: Yongxin Han, Needham, MA (US); Abdelghani Achab, Melrose, MA (US); Purakkattle Biju, Westwood, MA (US); Yongqi Deng, Newton, MA (US); Xavier Fradera, Brookline, MA (US); Liangqin Guo, Monroe, NJ (US); Shuwen He, Fanwood, NJ (US); Joseph Kozlowski, Princeton, NJ (US); Ravi Kurukulasuriya, Niantic, CT (US); Kun Liu, Needham, MA (US); Meredeth Ann McGowan, Boston, MA (US); Qinglin Pu, Needham, MA (US); Nunzio Sciammetta, Sudbury, MA (US); Hongjun Zhang, Boston, MA (US); Hua Zhou, Acton, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/061,597

(22) PCT Filed: Dec. 12, 2016

(86) PCT No.: PCT/US2016/066061
§ 371 (c)(1),
(2) Date: Jun. 12, 2018

(87) PCT Pub. No.: WO2017/106062
PCT Pub. Date: Jun. 22, 2017

(65) Prior Publication Data
US 2018/0362482 A1 Dec. 20, 2018

Related U.S. Application Data

(60) Provisional application No. 62/267,335, filed on Dec. 15, 2015.

(51) Int. Cl.
| | | |
|---|---|---|
| A61K 31/4245 | (2006.01) | |
| A61K 31/433 | (2006.01) | |
| C07D 271/08 | (2006.01) | |
| C07D 285/10 | (2006.01) | |
| C07D 413/12 | (2006.01) | |
| C07D 417/12 | (2006.01) | |
| A61P 35/00 | (2006.01) | |
| A61P 31/12 | (2006.01) | |
| A61P 25/24 | (2006.01) | |
| A61P 25/28 | (2006.01) | |
| A61P 37/06 | (2006.01) | |
| A61P 27/12 | (2006.01) | |

(Continued)

(52) U.S. Cl.
CPC ............ *C07D 271/08* (2013.01); *A61P 25/24* (2018.01); *A61P 25/28* (2018.01); *A61P 27/12* (2018.01); *A61P 31/14* (2018.01); *A61P 35/02* (2018.01); *A61P 37/06* (2018.01); *C07D 285/10* (2013.01); *C07D 413/12* (2013.01)

(58) Field of Classification Search
CPC .............. A61K 31/4245; A61K 31/433; C07D 271/08; C07D 285/10; C07D 413/12; C07D 417/12; A61P 35/00; A61P 31/12; A61P 25/24; A61P 25/28; A61P 37/06; A61P 27/12
USPC ................... 514/364, 362; 548/132, 144, 135
See application file for complete search history.

(56) References Cited

U.S. PATENT DOCUMENTS

| 8,951,536 B2 | 2/2015 | Combs et al. |
|---|---|---|
| 2006/0258719 A1 | 11/2006 | Combs et al. |

(Continued)

FOREIGN PATENT DOCUMENTS

| CN | 201610631523.5 A | 8/2016 |
|---|---|---|
| EP | 3495354 A1 | 6/2019 |

(Continued)

OTHER PUBLICATIONS

Golub et al., "Molecular classification of Cancer: Class discovery and class prediction by gene expression monitoring", Science (1999), 286: pp. 531-538. (Year: 1999).*

(Continued)

*Primary Examiner* — Matthew P Coughlin
*Assistant Examiner* — Sagar Patel
(74) *Attorney, Agent, or Firm* — Yong Zhao; Anna L. Cocuzzo

(57) ABSTRACT

Disclosed herein are compounds of formula (I) which are inhibitors of an IDO enzyme: (I). Also disclosed herein are uses of the compounds in the potential treatment or prevention of an IDO-associated disease or disorder. Also disclosed herein are compositions comprising these compounds. Further disclosed herein are uses of the compositions in the potential treatment or prevention of an IDO-associated disease or disorder.

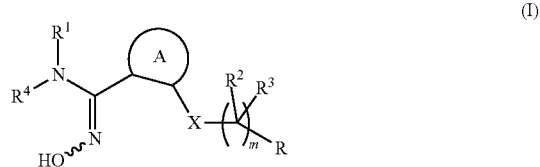

(I)

19 Claims, No Drawings

(51) Int. Cl.
*A61P 31/14* (2006.01)
*A61P 35/02* (2006.01)

(56) References Cited

U.S. PATENT DOCUMENTS

| | | |
|---|---|---|
| 2007/0099844 A1 | 5/2007 | Prendergast et al. |
| 2015/0133674 A1 | 5/2015 | Tao et al. |
| 2019/0169140 A1 † | 6/2019 | Zhang |

FOREIGN PATENT DOCUMENTS

| | | | |
|---|---|---|---|
| GB | 2461167 A | 12/2009 | |
| WO | WO-2006122150 A1 * | 11/2006 | ........... C07D 271/08 |
| WO | WO2007075598 A2 | 7/2007 | |
| WO | WO2008058178 A1 | 5/2008 | |
| WO | 2010005958 A2 | 1/2010 | |

OTHER PUBLICATIONS

Lala, P. and A. Orucevic, "Role of nitric oxide in tumor progression: Lessons from experimental tumors", Cancer and Meta. Rev. (1998), 17: pp. 91-106. (Year: 1998).*

Pubchem CID 56679032, Mar. 6, 2012, p. 4.

Abdelghani Achab, D3—U.S. Appl. No. 62/267,335, 77 pages.†

Yang Zhang, D2—CN201610631523.5, 78 pages, Feb. 8, 2018.†

Chinese Priority Application 201610631523.5 (Published Feb. 8, 2018).†

U.S. Appl. No. 62/267,335 (published Jun. 22, 2017).†

\* cited by examiner
† cited by third party

COMPOUNDS AS INDOLEAMINE 2,3-DIOXYGENASE INHIBITORS

CROSS-REFERENCE TO RELATED APPLICATIONS

The present application is a 371 national phase application of international application no. PCT/US2016/066061, filed Dec. 12, 2016, which claims the benefit of U.S. Provisional Application No. 62/267,335, filed Dec. 15, 2015; hereby incorporated by reference in its entirety.

BACKGROUND OF THE INVENTION

Tryptophan (Trp) is an essential amino acid required for the biosynthesis of proteins, niacin and the neurotransmitter 5-hydroxytryptamine (serotonin). The enzyme indoleamine 2,3-dioxygenase (IDO) catalyzes the first and rate limiting step in the degradation of L-tryptophan to N-formyl-kynurenine. In human cells, a depletion of Trp resulting from IDO activity is a prominent gamma interferon (IFN-γ)-inducible antimicrobial effector mechanism. IFN-γ stimulation induces activation of IDO, which leads to a depletion of Trp, thereby arresting the growth of Trp-dependent intracellular pathogens such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process (Daubener, et al, 1999, Adv. Exp. Med. Biol, 467: 517-24; Taylor, et al, 1991, FASEB J., 5: 2516-22).

It has been observed that HeLa cells co-cultured with peripheral blood lymphocytes (PBLs) acquire an immuno-inhibitory phenotype through up-regulation of IDO activity. A reduction in PBL proliferation upon treatment with interleukin-2 (IL2) was believed to result from IDO released by the tumor cells in response to IFN-γ secretion by the PBLs. This effect was reversed by treatment with 1-methyl-tryptophan (1-MT), a specific IDO inhibitor. It was proposed that IDO activity in tumor cells may serve to impair anti-tumor responses (Logan, et al, 2002, Immunology, 105: 478-87).

Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. For example, increased levels of IFNs and elevated levels of urinary Trp metabolites have been observed in autoimmune diseases; it has been postulated that systemic or local depletion of Trp occurring in autoimmune diseases may relate to the degeneration and wasting symptoms of these diseases. In support of this hypothesis, high levels of IDO were observed in cells isolated from the synovia of arthritic joints. IFNs are also elevated in human immunodeficiency virus (HIV) patients and increasing IFN levels are associated with a worsening prognosis. Thus, it was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol, 294: 425-35). To this end, it has recently been shown that IDO inhibition can enhance the levels of virus-specific T cells and, concomitantly, reduce the number of virally-infected macrophages in a mouse model of HIV (Portula et al., 2005, Blood, 106: 2382-90).

IDO is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to 1-MT, and a rapid, T cell-induced rejection of all allogeneic conception was observed. Thus, by catabolizing tryptophan, the mammalian conceptus appears to suppress T-cell activity and defends itself against rejection, and blocking tryptophan catabolism during murine pregnancy allows maternal T cells to provoke fetal allograft rejection (Moan, et al., 1998, Science, 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, Nature Med., 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al, 2005, Nature Med., 11: 312-9).

One mechanism contributing to immunologic unresponsiveness toward tumors may be presentation of tumor antigens by tolerogenic host APCs. A subset of human IDO-expressing antigen-presenting cells (APCs) that coexpressed CD 123 (IL3RA) and CCR6 and inhibited T-cell proliferation have also been described. Both mature and immature CD123-positive dendritic cells suppressed T-cell activity, and this IDO suppressive activity was blocked by 1-MT (Munn, et al, 2002, Science, 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs. Within the population of pDCs, the majority of the functional IDO-mediated suppressor activity segregated with a novel subset of pDCs coexpressing the B-lineage marker CD19. Thus, it was hypothesized that IDO-mediated suppression by pDCs in TDLNs creates a local microenvironment that is potently suppressive of host antitumor T cell responses (Munn, et al., 2004, J. Clin. Invest, 114(2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al, 2003, Trends Immunol, 24: 242-8). In states of persistent immune activation, availability of free serum Trp is diminished and, as a consequence of reduced serotonin production, serotonergic functions may also be affected (Wirleitner, et al., 2003, Curr. Med. Chem., 10: 1581-91).

Small molecule inhibitors of IDO are being developed to treat or prevent IDO-related diseases such as those described above. For example, oxadiazole and other heterocyclic IDO inhibitors are reported in US 2006/0258719 and US 2007/0185165. PCT Publication WO 99/29310 reports methods for altering T cell-mediated immunity comprising altering local extracellular concentrations of tryptophan and tryptophan metabolites, using an inhibitor of IDO such as 1-methyl-DL-tryptophan, p-(3-benzofuranyl)-DL-alanine, p-[3-benzo(b)thienyl]-DL-alanine, and 6-nitro-L-tryptophan) (Munn, 1999). Reported in WO 03/087347, also published as European Patent 1501918, are methods of making antigen-presenting cells for enhancing or reducing T cell tolerance (Munn, 2003). Compounds having IDO inhibitory activity are further reported in WO 2004/094409; and U.S. Patent Application Publication No. 2004/0234623 is directed to methods of treating a subject with a cancer or an infection by the administration of an inhibitor of IDO in combination with other therapeutic modalities.

In light of the experimental data indicating a role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. Compounds disclosed herein are useful in the potential treatment or prevention of IDO-related diseases.

SUMMARY OF THE INVENTION

Disclosed herein are novel compounds of formula (I) which are inhibitors of the IDO enzyme. Also disclosed herein are uses of these compounds in the potential treatment or prevention of an IDO-associated disease or disorder. Also disclosed herein are compositions comprising one or more of the compounds. Further disclosed herein are uses of these compositions in the potential prevention or treatment of an IDO-associated disease or disorder.

DETAILED DESCRIPTION OF THE INVENTION

Disclosed herein are compounds of Formula I, or pharmaceutically acceptable salts thereof:

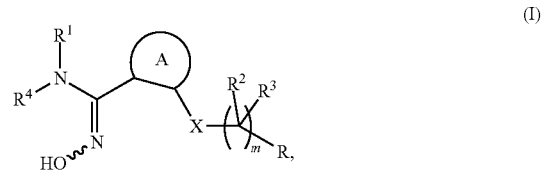

(I)

wherein:
m is 0, 1, 2, 3, 4, 5 or 6;
X is O or S;
ring A is selected from (a) a 5- or 6-membered carbocyclyl and (b) a 5- or 6-membered heterocyclyl; each of which is optionally substituted with:
  (i) halogen,
  (ii) $C_{1-6}$ alkyl, optionally substituted with one to four halogens,
  (iii) $C_{3-6}$ cycloalkyl,
  (iv) $C_{2-6}$ alkenyl,
  (v) $C_{2-6}$ alkynyl,
  (vi) aryl,
  (vii) heteroaryl,
  (viii) CN,
  (ix) $NO_2$,
  (x) $OR^4$,
  (xi) $SR^4$,
  (xii) $C(O)R^4$,
  (xiii) $NR^4R^4$,
  (xiv) $S(O)R^4$, and
  (xv) $S(O)_2R^4$;
R is selected from:
  (a) hydrogen,
  (b) $OR^a$,
  (c) $C_{3-6}$cycloalkyl, optionally substituted with one to four substituents independently selected from:
    (i) $C_{1-6}$alkyl,
    (ii) CN, and
    (iii) —(C=O)—O—$C_{1-6}$alkyl,
  (d) aryl, optionally substituted with one to four substituents independently selected from:
    (i) halogen,
    (ii) $C_{1-6}$alkyl, optionally substituted with one to three halogens,
    (iii) oxo, and
    (iv) —$S(O)_2$—NH—$R^4$,
  (e) a 4-, 5- or 6-membered heterocyclyl, optionally substituted with one to four substituents independently selected from:
    (i) halogen,
    (ii) $C_{1-6}$alkyl, optionally substituted with one to three halogens,
    (iii) oxo,
    (iv) —$S(O)_2$—NH—$R^4$,
    (v) —(C=O)—$C_{1-6}$alkyl, and
    (vi) —(C=O)NH—$R^4$,
  (f) CN,
  (g) —(C=O)—$R^a$, (h) —(C=O)NH—R$^a$,
(i) —P(O)(OR$^a$)$_2$,
(j) —P(O)(NHR$^a$)(OR$^a$),
(k) —P(O)(NR$^4$R$^a$)$_2$,
(l) C$_{2-4}$alkynyl,
(m) —NR$^x$R$^y$, wherein each of R$^x$ and R$^y$ is independently selected from:
  (i) hydrogen,
  (ii) C$_{1-6}$alkyl, optionally substituted with a 4-, 5- or 6-membered heterocyclyl,
  (iii) C$_{3-6}$cycloalkenyl, optionally substituted with one to four substituents independently selected from NH—R$^a$, oxo, and 4-, 5- or 6-membered heterocyclyl,
  (iv) C$_{2-4}$alkenyl, optionally substituted with one to four substituents independently selected from NR$^4$ and NO$_2$,
  (v) —(C=O)—R$^a$,
  (vi) —(C=O)—C$_{3-6}$cycloalkyl,
  (vii) —(C=O)—NR$^4$R$^a$,
  (viii) aryl,
  (ix) heteroaryl,
  (x) —(C=NH)(NH$_2$)—CN,
  (xi) —S(O)$_2$—R$^a$, and
  (xii) —S(O)$_2$—NH—R$^a$;
R$^1$ is aryl, optionally substituted with one to four substituents independently selected from:
  (a) halogen,
  (b) C$_{1-6}$ alkyl, optionally substituted with one to four halogens,
  (c) CN,
  (d) C$_{2-6}$ alkenyl,
  (e) C$_{2-6}$ alkynyl,
  (f) C$_{3-6}$cycloalkyl,
  (g) OR$^4$,
  (h) SR$^4$,
  (i) C(O)R$^4$,
  (j) C(O)NR$^4$R$^4$,
  (k) S(O)R$^4$,
  (l) S(O)$_2$R$^4$, and
  (m) S(O)$_2$NR$^4$R$^4$;
each occurrence of R$^2$ and R$^3$ is independently selected from:
  (a) R$^4$,
  (b) OR$^4$,
  (c) NH—R$^4$,
  (d) NH—(C=O)—R$^4$,
  (e) halogen,
  (f) C$_{3-6}$cycloalkyl, and
  (g) C$_{1-6}$alkoxy;
or alternatively, R$^2$ and R$^3$ together form an oxo group;
or alternatively, R$^2$ and R$^3$ together with the carbon to which they are attached form a C$_{3-6}$cycloalkyl group;
each occurrence of R$^4$ is independently selected from hydrogen and C$_{1-6}$ alkyl; and
each occurrence of R$^a$ is independently selected from the group consisting of:
  (a) hydrogen,
  (b) C$_{1-6}$alkyl, optionally substituted with one or three substituents independently selected from halogen, OR$^4$, —O—(C=O)—O—C$_{1-6}$alkyl, —(C=O)—O—C$_{1-6}$alkyl, aryl, and 4-, 5- or 6-membered heterocyclyl,
  (c) C$_{3-6}$cycloalkyl, optionally substituted with one or three substituents independently selected from halogen, C$_{1-6}$alkyl and OR$^4$,
  (d) —O—C$_{1-6}$alkyl,
  (e) —(C=O)—O—C$_{1-6}$alkyl,
  (f) aryl, optionally substituted with C$_{1-6}$alkyl, and
  (g) 4, 5- or 6-membered heterocyclyl, optionally substituted with —C$_{1-6}$alkyl or —C$_{1-6}$alkyl-OR$^4$.

In one embodiment of formula (I) as defined above, a compound disclosed herein is of Formula (Ia), or a pharmaceutically acceptable salt thereof:

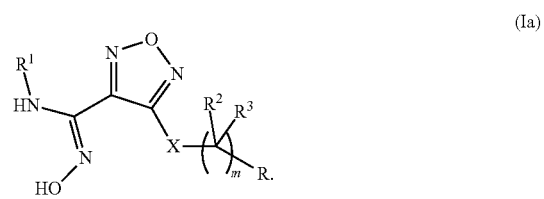

(Ia)

In one embodiment of formula (I) or (Ia) as defined above:
R$^1$ is aryl, optionally substituted with one to four substituents independently selected from:
  (a) halogen,
  (b) C$_{1-6}$ alkyl, optionally substituted with one to four halogens, and
  (c) CN; and
each occurrence of R$^2$ and R$^3$ is independently selected from:
  (a) R$^4$,
  (b) OR$^4$,
  (c) NH—R$^4$,
  (d) halogen, and
  (e) C$_{3-6}$cycloalkyl;
or R$^2$ and R$^3$ together form an oxo group;
or R$^2$ and R$^3$ together with the carbon to which they are attached form a C$_{3-6}$cycloalkyl group.

In one embodiment of formula (I) or (Ia) as defined above:
X is S,
R$^1$ is phenyl, optionally substituted with one to four substituents independently selected from:
  (a) halogen,
  (b) C$_{1-6}$ alkyl, optionally substituted with one to four halogens, and
  (c) CN; and
each occurrence of R$^2$ and R$^3$ is independently selected from:
  (a) R$^4$,
  (b) OH,
  (c) NH—R$^4$, and
  (d) halogen;
or R$^2$ and R$^3$ together form an oxo group.

In one embodiment of formula (I) or (Ia) as defined above:
X is O,
R$^1$ is phenyl, optionally substituted with one to four substituents independently selected from:
  (a) halogen,
  (b) C$_{1-6}$ alkyl, optionally substituted with one to four halogens, and
  (c) CN; and
each occurrence of R$^2$ and R$^3$ is independently selected from:
  (a) R$^4$,
  (b) OH,
  (c) NH—R$^4$, and
  (d) halogen;
or R$^2$ and R$^3$ together form an oxo group.

In one embodiment of formula (I) or (Ia) as defined above:
each occurrence of aryl is phenyl; and each occurrence of the 4-, 5- or 6-membered heterocyclyl is independently selected from: azetidinyl, 1,2,5-thiadiazolidinyl, imidazolidinyl, oxazolidinyl, oxetanyl, pyrrolidinyl, piperidinyl, piperazinyl, morpholinyl, tetrahydropyranyl, tetrahydro-2H-thiopyranyl, 4,5-dihydro-1H-1,2,4-triazolyl, dihydropyridazinyl, dihydropyridinyl, furanyl, imidazolyl, dihydro-oxadiazolyl, oxadiazolyl, pyridinyl, thiazolyl, and triazolyl.

In one embodiment of formula (I) or (Ia) as defined above:
R is selected from:
(a) hydrogen,
(b) $OR^a$,
(c) $C_{3-6}$cycloalkyl, optionally substituted with one to four substituents independently selected from:
  (i) $C_{1-6}$alkyl, and
  (ii) CN,
(d) phenyl, optionally substituted with one to four substituents independently selected from:
  (i) halogen,
  (ii) $C_{1-6}$alkyl, and
  (iii) —S(O)$_2$—NH—$R^4$,
(e) a 4-, 5- or 6-membered heterocyclyl selected from azetidinyl, 1,2,5-thiadiazolidinyl, imidazolidinyl, oxazolidinyl, oxetanyl, pyrrolidinyl, piperidinyl, piperazinyl, morpholinyl, tetrahydropyranyl, tetrahydro-2H-thiopyranyl, 4,5-dihydro-1H-1,2,4-triazolyl, dihydropyridazinyl, dihydropyridinyl, furanyl, imidazolyl, dihydro-oxadiazolyl, pyridinyl, thiazolyl, and triazolyl; each of which is optionally substituted with one to four substituents independently selected from:
  (i) halogen,
  (ii) $C_{1-6}$alkyl, optionally substituted with one to three halogens,
  (iii) oxo,
  (iv) —S(O)$_2$—NH—$R^4$, and
  (v) —(C=O)—$C_{1-6}$alkyl,
(f) CN,
(g) —(C=O)—$R^a$,
(h) —(C=O)NH—$R^a$,
(i) —P(O)(O$R^a$)$_2$,
(j) —P(O)(NH$R^a$)(O$R^a$),
(k) $C_{2-4}$alkynyl,
(m) —N$R^xR^y$, wherein each of $R^x$ and $R^y$ is independently selected from:
  (i) hydrogen,
  (ii) $C_{1-6}$alkyl, optionally substituted with a 4-, 5- or 6-membered heterocyclyl,
  (iii) $C_{3-6}$cycloalkenyl, optionally substituted with one to four substituents independently selected from NH—$R^a$, oxo, and 4-, 5- or 6-membered heterocyclyl,
  (iv) $C_{2-4}$alkenyl, optionally substituted with one to four substituents independently selected from N$R^4$ and NO$_2$,
  (v) —(C=O)—$R^a$,
  (vi) —(C=O)—$C_{3-6}$cycloalkyl,
  (vii) —(C=O)—N$R^4R^a$,
  (viii) aryl,
  (ix) heteroaryl,
  (x) —(C=NH)(NH$_2$)—CN,
  (xi) —S(O)$_2$—$R^a$, and
  (xii) —S(O)$_2$—NH—$R^a$;

In one embodiment of formula (I) or (Ia) as defined above:
R is selected from:
(a) $R^4$,
(b) $OR^4$,
(c) $C_{4-6}$cycloalkyl, optionally substituted with one to three substituents independently selected from (i) $C_{1-4}$alkyl and (ii) —(C=O)—O—$C_{1-4}$alkyl,
(d) phenyl, optionally substituted with one to three halogens,
(e) a 4-, 5- or 6-membered heterocyclyl independently selected from: azetidinyl, 1,2,5-thiadiazolidinyl, imidazolidinyl, oxazolidinyl, oxetanyl, pyrrolidinyl, piperidinyl, piperazinyl, morpholinyl, tetrahydropyranyl, tetrahydro-2H-thiopyranyl, 4,5-dihydro-1H-1,2,4-triazolyl, dihydropyridazinyl, dihydropyridinyl, furanyl, imidazolyl, dihydro-oxadiazolyl, oxadiazolyl, pyridinyl, thiazolyl, and triazolyl each of which is optionally substituted with one to three substituents independently selected from (i) $C_{1-6}$alkyl and (ii) halogen,
(f) —(C=O)—$R^a$,
(g) —(C=O)—NH—$R^a$,
(h) —P(O)(O$R^a$)$_2$, wherein each $R^a$ is independently selected from (i) hydrogen, (ii) C1-4alkyl, and (iii) C—O—C(O)—O-iPr, and
(i) —N$R^xR^y$, wherein each of $R^x$ and $R^y$ is independently selected from (i) $R^4$, (ii) —(C=O)—O—$R^4$, (iii) —(C=O)—$R^4$, (iv) aryl, (v) heteroaryl, and (vii) —S(O)$_2$—NH$_2$.

In one embodiment of formula (I) or (Ia) as defined above:
R is selected from:
(a) hydrogen,
(b) hydroxyl,
(c) $C_{4-6}$cycloalkyl, optionally substituted with —(C=O)—O—$C_{1-4}$alkyl,
(d) —(C=O)—$R^a$,
(e) —(C=O)—NH—$R^a$,
(f) —P(O)(O—$C_{1-4}$alkyl)$_2$,
(g) —P(O)(O—C—O—C(O)—O-iPr)$_2$,
(h) —P(O)H(O—C—O—C(O)—O-iPr),
(i) —P(O)(OH)$_2$,
(j) —NH—C(O)—O—$C_{1-4}$alkyl,
(k) —NH—C(O)—$C_{1-4}$alkyl and
(l) a 4- or 5-membered heterocyclyl containing one ring nitrogen atom, optionally substituted with a halogen or —$C_{1-4}$alkyl.

In one embodiment of formula (I) or (Ia) as defined above:
each of $R^2$ and $R^3$ is independently selected from (i) $R^4$, (ii) OH and (iii) halogen;
or $R^2$ and $R^3$ together form an oxo group.

In one embodiment of formula (I) or (Ia) as defined above:
each occurrence of $R^a$ is independently selected from the group consisting of:
(a) hydrogen,
(b) $C_{1-6}$alkyl, optionally substituted with one or three substituents independently selected from halogen, $OR^4$, —O—(C=O)—O—$C_{1-6}$alkyl, —(C=O)—O—$C_{1-6}$alkyl, aryl, and 4-, 5- or 6-membered heterocyclyl,
(c) $C_{3-6}$cycloalkyl, optionally substituted with one or three substituents independently selected from halogen, $C_{1-6}$alkyl and $OR^4$,
(d) —O—$C_{1-6}$alkyl,
(e) —(C=O)—O—$C_{1-6}$alkyl,
(f) phenyl, optionally substituted with one or three substituents independently selected from $C_{1-6}$alkyl and halogen, and
(g) a 4, 5- or 6-membered heterocyclyl independently selected from: azetidinyl, 1,2,5-thiadiazolidinyl, imidazolidinyl, oxazolidinyl, oxetanyl, pyrrolidinyl, piperidinyl, piperazinyl, morpholinyl, tetrahydropyranyl, tetrahydro-2H-thiopyranyl, 4,5-dihydro-1H-1,2,4-triazolyl, dihydropyridazinyl, dihydropyridinyl, furanyl, imidazolyl, dihydro-oxadiazolyl, oxadiazolyl, pyridinyl, thiazolyl, and triazolyl; each of which is optionally substituted with —$C_{1-6}$alkyl or —$C_{1-6}$alkyl-OR$^4$.

In one embodiment of formula (I) or (Ia) as defined above:
m is 0, 1, 2 or 3;
X is S,
R$^1$ is phenyl, optionally substituted with one to four halogens;
each occurrence of R$^2$ and R$^3$ is independently selected from:
  (a) R$^4$,
  (b) OH,
  (c) NH—R$^4$, and
  (d) halogen;
R is selected from:
  (a) hydrogen,
  (b) hydroxyl,
  (c) $C_{4-6}$cycloalkyl, optionally substituted with —(C=O)—O—$C_{1-4}$alkyl,
  (d) —(C=O)—R$^a$,
  (e) —(C=O)—NH—R$^a$,
  (f) —P(O)(O—$C_{1-4}$alkyl)$_2$,
  (g) —P(O)(O—C—O—C(O)—O-iPr)$_2$,
  (h) —P(O)H(O—C—O—C(O)—O-iPr),
  (i) —P(O)(OH)$_2$,
  (j) —NH—C(O)—O—$C_{1-4}$alkyl,
  (k) —NH—C(O)—$C_{1-4}$alkyl and
  (l) a 4- or 5-membered heterocyclyl containing one ring nitrogen atom, optionally substituted with a halogen or —$C_{1-4}$alkyl; and
each occurrence of R$^a$ is independently selected from the group consisting of:
  (a) hydrogen,
  (b) $C_{1-6}$alkyl, optionally substituted with one or three substituents independently selected from halogen, OR$^4$, —O—(C=O)—O—$C_{1-6}$alkyl, —(C=O)—O—$C_{1-6}$alkyl, aryl, and 4-, 5- or 6-membered heterocyclyl,
  (c) $C_{3-6}$cycloalkyl, optionally substituted with one or three substituents independently selected from halogen, $C_{1-6}$alkyl and OR$^4$,
  (d) —O—$C_{1-6}$alkyl,
  (e) —(C=O)—O—$C_{1-6}$alkyl,
  (f) phenyl, optionally substituted with one or three substituents independently selected from $C_{1-6}$alkyl and halogen, and
  (g) a 4, 5- or 6-membered heterocyclyl independently selected from: azetidinyl, 1,2,5-thiadiazolidinyl, imidazolidinyl, oxazolidinyl, oxetanyl, pyrrolidinyl, piperidinyl, piperazinyl, morpholinyl, tetrahydropyranyl, tetrahydro-2H-thiopyranyl, 4,5-dihydro-1H-1,2,4-triazolyl, dihydropyridazinyl, dihydropyridinyl, furanyl, imidazolyl, dihydro-oxadiazolyl, oxadiazolyl, pyridinyl, thiazolyl, and triazolyl; each of which is optionally substituted with —$C_{1-6}$alkyl or —$C_{1-6}$alkyl-OR$^4$.

In one embodiment of formula (I) or (Ia) as defined above:
each occurrence of R$^a$ is independently selected from the group consisting of:
  (a) hydrogen,
  (b) $C_{1-6}$alkyl, optionally substituted with one or three substituents independently selected from halogen, OR$^4$, —O—(C=O)—O—$C_{1-6}$alkyl, —(C=O)—O—$C_{1-6}$alkyl, aryl, and 4-, 5- or 6-membered heterocyclyl,
  (c) $C_{3-6}$cycloalkyl, optionally substituted with one or three substituents independently selected from halogen, $C_{1-6}$alkyl and OR$^4$,
  (d) —O—$C_{1-6}$alkyl,
  (e) —(C=O)—O—$C_{1-6}$alkyl,
  (f) phenyl, optionally substituted with one or three substituents independently selected from $C_{1-6}$alkyl and halogen, and
  (g) a 4, 5- or 6-membered heterocyclyl independently selected from: azetidinyl, 1,2,5-thiadiazolidinyl, imidazolidinyl, oxazolidinyl, oxetanyl, pyrrolidinyl, piperidinyl, piperazinyl, morpholinyl, tetrahydropyranyl, tetrahydro-2H-thiopyranyl, 4,5-dihydro-1H-1,2,4-triazolyl, dihydropyridazinyl, dihydropyridinyl, furanyl, imidazolyl, dihydro-oxadiazolyl, oxadiazolyl, pyridinyl, thiazolyl, and triazolyl; each of which is optionally substituted with —$C_{1-6}$alkyl or —$C_{1-6}$alkyl-OR$^4$.

In one embodiment of formula (I) or (Ia) as defined above:
m is 0, 1, 2 or 3;
X is O,
R$^1$ is phenyl, optionally substituted with one to four halogens;
each occurrence of R$^2$ and R$^3$ is independently selected from:
  (a) R$^4$, and
  (b) halogen;
R is selected from:
  (a) hydrogen,
  (b) hydroxyl,
  (c) $C_{4-6}$cycloalkyl, optionally substituted with —(C=O)—O—$C_{1-4}$alkyl,
  (d) —(C=O)—R$^a$,
  (e) —(C=O)—NH—R$^a$,
  (f) —P(O)(O—$C_{1-4}$alkyl)$_2$,
  (g) —P(O)(O—C—O—C(O)—O-iPr)$_2$,
  (h) —P(O)H(O—C—O—C(O)—O-iPr),
  (i) —P(O)(OH)$_2$,
  (j) —NH—C(O)—O—$C_{1-4}$alkyl,
  (k) —NH—C(O)—$C_{1-4}$alkyl and
  (l) a 4- or 5-membered heterocyclyl containing one ring nitrogen atom, optionally substituted with a halogen or —$C_{1-4}$alkyl; and
each occurrence of R$^a$ is independently selected from the group consisting of:
  (a) hydrogen,
  (b) $C_{1-6}$alkyl, optionally substituted with one or three substituents independently selected from halogen, OR$^4$, —O—(C=O)—O—$C_{1-6}$alkyl, —(C=O)—O—$C_{1-6}$alkyl, aryl, and 4-, 5- or 6-membered heterocyclyl,
  (c) $C_{3-6}$cycloalkyl, optionally substituted with one or three substituents independently selected from halogen, $C_{1-6}$alkyl and OR$^4$,
  (d) —O—$C_{1-6}$alkyl,
  (e) —(C=O)—O—$C_{1-6}$alkyl,
  (f) phenyl, optionally substituted with one or three substituents independently selected from $C_{1-6}$alkyl and halogen, and
  (g) a 4, 5- or 6-membered heterocyclyl independently selected from: azetidinyl, 1,2,5-thiadiazolidinyl, imidazolidinyl, oxazolidinyl, oxetanyl, pyrrolidinyl, piperidinyl, piperazinyl, morpholinyl, tetrahydropyranyl, tetrahydro-2H-thiopyranyl, 4,5-dihydro-1H-1,2,4-triazolyl, dihydropyridazinyl, dihydropyridinyl, furanyl, imidazolyl, dihydro-oxadiazolyl, oxadiazolyl, pyridinyl, thiazolyl, and triazolyl; each of which is optionally substituted with —$C_{1-6}$alkyl or —$C_{1-6}$alkyl-OR$^4$.

In one embodiment, a compound disclosed herein is of formula (Ib), or a pharmaceutically acceptable salt thereof:

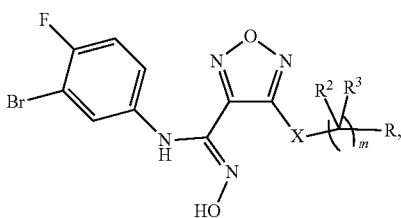

(Ib)

wherein:
m is 0, 1, 2, 3, 4, 5 or 6;
X is S or O;
each occurrence of $R^2$ and $R^3$ is independently selected from:
 (a) hydrogen,
 (b) hydroxyl,
 (c) halogen and
 (d) $C_{1-4}$alkyl;
or $R^2$ and $R^3$ together form an oxo group; and
R is selected from:
 (a) $R^4$,
 (b) $OR^4$,
 (c) $C_{4-6}$cycloalkyl, optionally substituted with one to three substituents independently selected from (a) $C_{1-4}$alkyl and (b) —(C=O)—O—$C_{1-4}$alkyl,
 (d) a 4-, 5- or 6-membered heterocyclyl,
 (e) —(C=O)—$R^a$,
 (f) —(C=O)—NH—$R^a$,
 (g) —P(O)($OR^a$)$_2$, and
 (h) —$NR^xR^y$, wherein each of $R^x$ and $R^y$ is independently selected from (i) hydrogen, (ii) $C_{1-4}$alkyl, (iii) —(C=O)—O—$C_{1-4}$alkyl, (iv) —(C=O)—$C_{1-4}$alkyl, (v) aryl, (vi) heteroaryl, and (vii) —S(O)$_2$—NH$_2$.

In one embodiment of formula (Ib) as defined above:
each occurrence of $R^2$ and $R^3$ is independently selected from:
 (a) $R^4$,
 (b) $OR^4$, and
 (c) halogen.

In one embodiment of formula (Ib) as defined above:
R is selected from:
 (a) hydrogen,
 (b) hydroxyl,
 (c) cyclobutyl substituted with —(C=O)—O—CH$_3$,
 (d) —(C=O)—$R^a$,
 (e) —(C=O)—NH—$R^a$,
 (f) —P(O)(O—CH$_2$CH$_3$)$_2$,
 (g) —P(O)(O—C—O—C(O)—O-iPr)$_2$,
 (h) —P(O)H(O—C—O—C(O)—O-iPr),
 (i) —P(O)(OH)$_2$,
 (j) —NH—C(O)—O—CH$_3$,
 (k) —NH—C(O)—CH$_3$ and
 (l) azetidinyl.

In one embodiment of formula (Ib) as defined above:
R is selected from:
 (a) hydrogen,
 (b) hydroxyl,
 (c) cyclobutyl substituted with —(C=O)—O—CH$_3$,
 (d) —P(O)(O—CH$_2$CH$_3$)$_2$,
 (e) —P(O)(O—C—O—C(O)—O-iPr)$_2$,
 (f) —P(O)H(O—C—O—C(O)—O-iPr),
 (g) —P(O)(OH)$_2$,
 (h) —NH—C(O)—O—CH$_3$,
 (i) —NH—C(O)—CH$_3$ and
 (j) azetidinyl.

In one embodiment, a compound disclosed herein is selected from the group consisting of the compounds exemplified herein, for example, in Examples 1-214, or a pharmaceutically acceptable salt thereof.

Also disclosed herein is a pharmaceutical composition comprising a compound of Formula I or (Ia), and at least one pharmaceutically acceptable carrier.

Also disclosed herein is a method of inhibiting activity of indoleamine 2,3-dioxygenase (IDO) comprising contacting IDO with a compound of Formula I or (Ia), or a pharmaceutically acceptable salt thereof.

Also disclosed herein is a method of inhibiting immunosuppression in a patient comprising administering to said patient an effective amount of a compound of Formula I or (Ia), or a pharmaceutically acceptable salt thereof.

Also disclosed herein is a method of treating cancer, viral infection, depression, a neurodegenerative disorder, trauma, age-related cataracts, organ transplant rejection, or an autoimmune disease in a patient comprising administering to said patient an effective amount of a compound of Formula I or (Ia), or a pharmaceutically acceptable salt thereof.

Also disclosed herein is a method of treating melanoma in a patient comprising administering to said patient an effective amount of a compound of Formula I, or a pharmaceutically acceptable salt thereof.

Further disclosed herein is a compound of Formula I or (Ia), or a pharmaceutically acceptable salt thereof, for use in therapy. In one embodiment, disclosed herein is the use of a compound of Formula I or (Ia), or a pharmaceutically acceptable salt thereof, for the preparation of a medicament for use in therapy.

As used herein, "alkenyl" refers to both branched- and straight-chain unsaturated aliphatic hydrocarbon groups of 2 to 12 carbon atoms and having at least one carbon-carbon double bond. Alkenyl groups may be optionally substituted with one or more substituents as defined herein. Examples of such groups include, but are not limited to, ethenyl, propenyl, n-butenyl, 3-methylbut-2-enyl, n-pentenyl, octenyl and decenyl. "$C_{2-6}$alkenyl" refers to an alkenyl group as defined herein having 2 to 6 carbon atoms.

"Alkyl" refers to both branched- and straight-chain saturated aliphatic hydrocarbon groups of 1 to 18 carbon atoms, or more specifically, 1 to 12 carbon atoms. Examples of such groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tert-butyl (t-Bu), isopentyl, and isohexyl. Alkyl groups may be optionally substituted with one or more substituents as defined herein. "$C_{1-6}$alkyl" refers to an alkyl group as defined herein having 1 to 6 carbon atoms.

"Aryl" refers to an aromatic monocyclic or multicyclic ring moiety comprising 6 to 14 ring carbon atoms, or more specifically, 6 to 10 ring carbon atoms. Monocyclic aryl rings include, but are not limited to, phenyl. Multicyclic rings include, but are not limited to, naphthyl and bicyclic rings wherein phenyl is fused to a $C_{5-7}$cycloalkyl or $C_{5-7}$cycloalkenyl ring. Aryl groups may be optionally substituted with one or more substituents as defined herein. Bonding can be through any of the carbon atoms of any ring.

"Carbocyclyl" refers to a saturated, partially unsaturated or aromatic ring moiety having only ring carbon atoms. In one embodiment, a carbocyclyl is an aryl. Carbocyclyl moieties include both monocyclic and multicyclic (e.g., bicyclic) ring moieties. Bicyclic carbocyclyl moieties include fused, spirocyclic and bridged bicyclic rings. Examples of carbocyclyl moieties include, but are not limited to, cyclopentyl, cyclohexyl, cycloheptyl, cyclooctyl, cyclopentenyl, cyclohexenyl, cyclohexadienyl, phenyl, and naphthyl. Carbocyclic rings may be optionally substituted with one or more substituents as defined herein. "$C_{3-10}$carbocycle" refers to a carbocycle group as defined herein having 3 to 10 ring carbon atoms. In one embodiment, a carbocyclyl moiety is aryl.

In one embodiment, a carbocyclyl is a bridged bicyclic or multicyclic moiety. Non-limiting examples of these type of moieties include

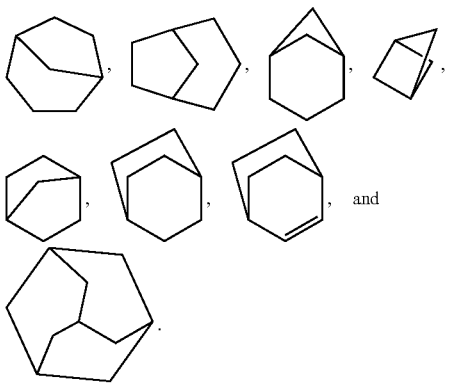

In one embodiment, a carbocycle is a $C_{3-7}$cycloalkyl. "Cycloalkyl" refers to a monocyclic saturated carbocyclic ring having the specified number of carbon atoms. For example, $C_{3-7}$ cycloalkyl refers to a cycloalkyl group as defined herein having 3 to 7 carbon atoms. Examples of cycloalkyl include, but are not limited to, cyclopropyl, cyclobutyl, cyclopentyl, cyclohexyl and cycloheptanyl. Cycloalkyl groups may be optionally substituted with one or more substituents as defined herein.

In one embodiment, a carbocyclyl moiety is a $C_{4-7}$cycloalkenyl. "Cycloalkenyl" refers to a monocyclic partially unsaturated carbocyclic ring having the specified number of carbon atoms and at least one carbon-carbon double bond. Examples of cycloalkenyl include, but are not limited to, cyclobutenyl, cyclopentenyl, cyclohexenyl, cyclohexa-1,4-dienyl, and cycloheptenyl.

"Halo" or "halogen" refers to fluoro, chloro, bromo or iodo, unless otherwise noted.

"Heterocycle" or "heterocyclyl" refers to a saturated, partially unsaturated or aromatic ring moiety having at least one ring heteroatom and at least one ring carbon atom. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocyclic and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

In one embodiment, partially unsaturated and aromatic 4-7 membered monocyclic heterocyclyl moieties include, but are not limited to, 2,3-dihydro-1,4-dioxinyl, dihydro-oxadiazolyl, dihydropyranyl, dihydropyrazinyl, dihydropyridazinyl, dihydropyridinyl, dihydropyrimidinyl, furanyl, imidazolyl, isothiazolyl, isoxazolyl, oxadiazolyl, oxazolyl, pyranyl, pyrazinyl, pyrazolyl, pyridazinyl, pyridinyl, pyrimidinyl, pyrrolyl, tetrahydropyrazinyl, tetrahydropyridazinyl, tetrahydropyridinyl, tetrahydropyrimidinyl, tetrazolyl, thiadiazolyl, thiazolyl, thienyl, thiophenyl, and triazolyl. In one embodiment, a partially unsaturated 5- or 6-membered heterocyclyl is selected from 4,5-dihydro-1H-1,2,4-triazolyl, dihydropyridazinyl, dihydropyridinyl, furanyl, imidazolyl, oxadiazolyl, pyridinyl, dihydro-oxadiazolyl, thiazolyl, and triazolyl.

In one embodiment, saturated 4-7 membered monocyclic heterocyclyl moieties include, but are not limited to, azetidinyl, 1,4-dioxanyl, hexahydroazepinyl, imidazolidinyl, morpholinyl, 1,4-oxazepanyl, oxazolidinyl, oxetanyl, piperazinyl, piperidinyl, pyridin-2-onyl, pyrrolidinyl, tetrahydrofuranyl, tetrahydropyranyl, 1,2,5-thiadiazolidinyl, thiomorpholinyl, tetrahydro-2H-thiopyranyl, tetrahydrothienyl, and tetrahydrothiophenyl. In one embodiment, a saturated 5-membered monocyclic heterocyclyl is selected from azetidinyl, 1,2,5-thiadiazolidinyl, imidazolidinyl, oxazolidinyl, oxetanyl, pyrrolidinyl, piperidinyl, piperazinyl, morpholinyl, tetrahydropyranyl, and tetrahydro-2H-thiopyranyl.

In one embodiment, a heterocyclyl is a fused bicyclic ring moiety wherein a 4-6 membered heterocyclic ring comprising 1-4 heteroatoms selected from oxygen, sulfur and nitrogen and a 5-6 membered heterocyclic ring comprising 1-4 heteroatoms selected from oxygen, sulfur and nitrogen are connected through two atoms. Exemplary heterocycles of this type include, but are not limited to, azaindolyl, dihydronaphthyridinyl, imidazopyridinyl, indolizinyl, naphthyridinyl, pteridinyl, purinyl, quinolizinyl, tetrahydroindolizinyl, tetrahydronaphthyridinyl, tetrahydroquinolizinyl,

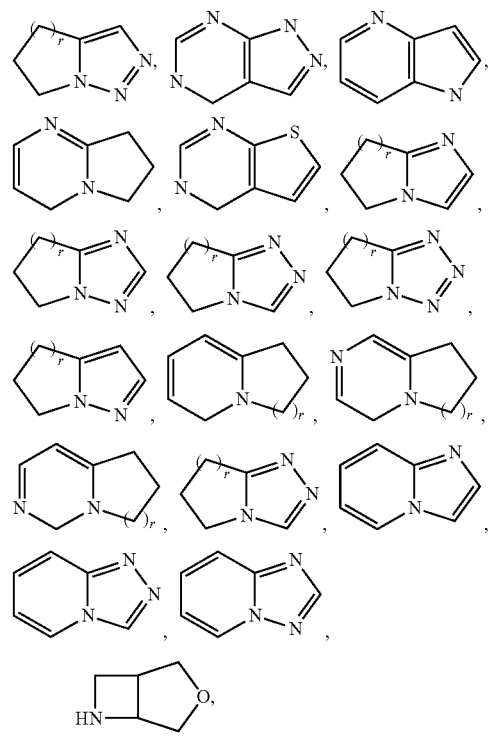

(3-oxa-6-azabicyclo[3.2.0]heptane)

-continued

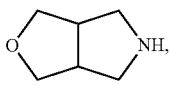
(hexahydro-1H-furo[3,4-c]pyrrole)

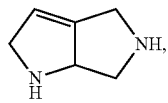
(1,2,4,5,6,6a-hexahydropyrrolo[3,4-b]pyrrole)

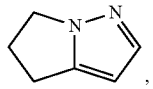
(5,6-dihydro-4H-pyrrolo[1,2-b]pyrazole)

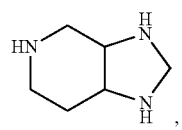
(octahydro-1H-imidazo[4,5-c]pyridine)

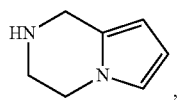
(1,2,3,4-tetrahydropyrrolo[1,2-a]pyrazine)

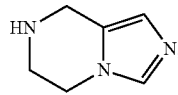
(5,6,7,8-tetrahydroimidazo[1,2-a]pyrazine)

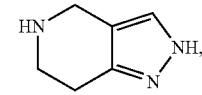
(4,5,6,7-tetrahydro-2H-pyrazolo[4,3-c]pyridine)

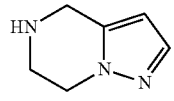
(4,5,6,7-tetrahydropyrazolo[1,5-a]pyrazine)

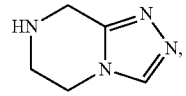
(5,6,7,8-tetrahydro-[1,2,4]triazolo[4,3-a]pyrazine)

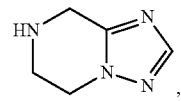
(5,6,7,8-tetrahydro-[1,2,4]triazolo[1,5-a]pyrazine)

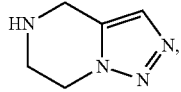
(4,5,6,7-tetrahydro-[1,2,3]triazolo[1,5-a]pyrazine)

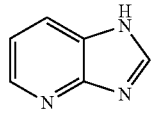 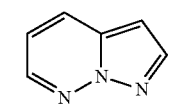 and
(1H-imidazo[4,5-b]pyridine) (pyrazolo[1,5-b]pyridazine)

-continued

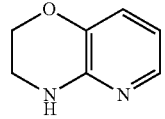
(3,4-dihydro-2H-pyrido[3,2-b][1,4]oxazine)

wherein r is 1 or 2. In one embodiment, an azaindole is

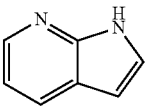 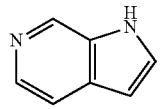
(1H-pyrrolo[2,3-b]pyridine) (1H-pyrrolo[2,3-c]pyridine)

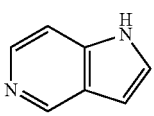 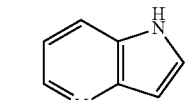
(1H-pyrrolo[3,2-c]pyridine) (1H-pyrrolo[3,2-b]pyridine)

Such fused ring may be attached to the rest of the molecule via a carbon atom or a nitrogen atom on either ring. A heterocycle of this type includes a bicyclic ring comprising only one nitrogen as the sole heteroatom when the nitrogen is located at the bridgehead.

In one embodiment, a heterocyclyl is a fused bicyclic ring moiety wherein a 4-6 membered heterocyclic ring comprising 1-4 heteroatoms selected from oxygen, sulfur and nitrogen and a $C_{5-10}$ carbocyclic ring are connected through two carbon atoms. Exemplary heterocycles of this type include, but are not limited to, benzimidazolonyl, benzimidazolyl, benzisothiazolyl, benzisoxazolyl, benzofuranyl, benzofurazanyl, benzothienyl, benzotriazolyl, benzoxazolyl, benzthiazolyl, chromanyl, chromenyl, cinnolinyl, dihydroindazolyl, indazolyl, indolyl, isoindolyl, isoquinolinyl, quinazolinyl, quinolinyl, quinoxalinyl, tetrahydroindazolyl, tetrahydroquinolinyl,

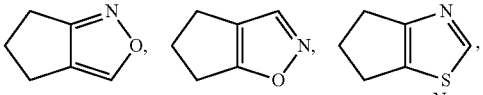
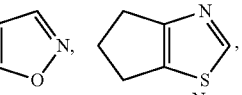

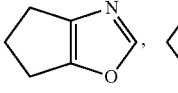 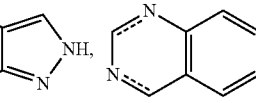

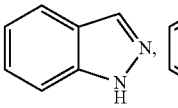 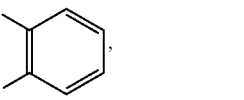

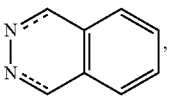 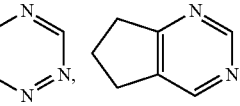

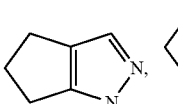 

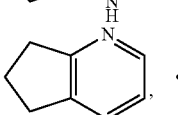

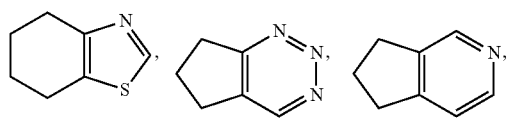
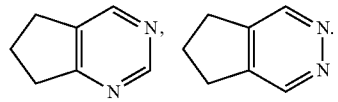

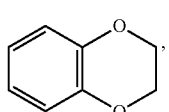
(2,3-dihydrobenzo[b][1,4]dioxine)

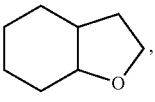
(octahydrobenzofuran)

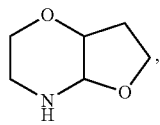
(octahydrocyclopenta[1,4]oxazine)

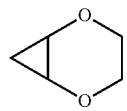 and 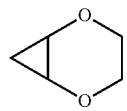
(2,5-dioxabicyclo[4.1.0]heptanyl)   (octahydro-2H-chromene)

Such fused ring may be attached to the rest of the molecule via a carbon atom or a nitrogen atom on either ring.

In one embodiment, a heterocyclyl is a spirocyclyl ("spiro") bicyclic moiety wherein two rings are connected through one atom, and either or both of the rings comprise at least one heteroatom. In one embodiment, a spiro bicyclic heterocycle comprises a 4-7 membered heterocyclic ring comprising 1-4 heteroatoms selected from oxygen, sulfur and nitrogen connected through a single atom to either a 3-6 membered ring comprising 1-2 heteroatoms selected from oxygen, sulfur and nitrogen or a 3-6 membered carbocyclic ring. Exemplary spiro heterocycles of this type include, but are not limited to:

(2-azaspiro[3.3]heptane)   (2-oxa-6-azaspiro[3.3]heptane)

   
(1,6-diazaspiro[3.3]heptane)   (2,6-diazaspiro[3.3]heptane)

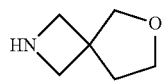   
(6-oxa-2-azaspiro[3.4]octane)   (7-oxa-2,5-diazaspiro[3.4]octane)

   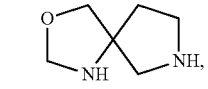
(6-oxa-2-azaspiro[3.5]nonanyl)   (3-oxa-1,7-diazaspiro[4.4]nonane)

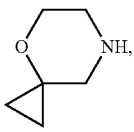 and 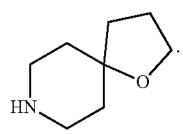
(4-oxa-7-azaspiro[2.5]octane)   (1-oxa-8-azaspiro[4.5]decane)

Such spiro bicyclic moieties may be attached to the rest of the molecule via a carbon atom or a nitrogen atom on either ring.

In one embodiment, a heterocycle is a bridged bicyclic moiety selected from the group consisting of:

(6-oxa-3-azabicyclo[3.1.1]heptane)

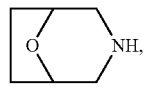   
(8-oxa-3-azabicyclo[3.2.1]octane)   (2-oxa-5-azabicyclo[2.2.2]octane)

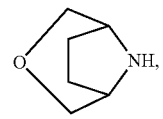
(3-oxa-8-azabicyclo[3.2.1]octane)

   
(2-oxa-5-azabicyclo[2.2.1]heptane)   (8-azabicyclo[3.2.1]octanyl)

   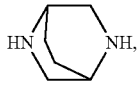
(3,8-diazabicyclo[3.2.1]octane)   (2,5-diazabicyclo[2.2.2]octane)

(8-azabicyclo[3.2.1]octane)

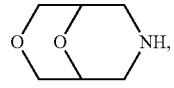 and
(3,9-dioxa-7-azabicyclo[3.3.1]nonanyl)

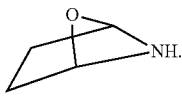
(5-oxa-6-azabicyclo[2.1.1]hexane)

Such bridged bicyclic moieties may be attached to the rest of the molecule via a carbon atom or a nitrogen atom on either ring.

Heterocycles include ring moieties wherein a ring sulfur atom is oxidized to form SO and $SO_2$. In one embodiment, a heterocycle of this type is

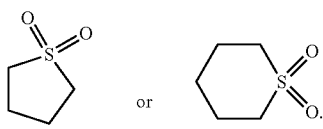 [SMILES: O=S1(=O)CCCC1 ; O=S1(=O)CCCCC1]

Heterocyclic groups may be optionally substituted with one or more substituents as defined herein.

"Optionally substituted" refers to "unsubstituted or substituted," and therefore, the generic structural formulas described herein encompass compounds containing the specified optional substituent(s) as well as compounds that do not contain the optional substituent(s). Each substituent is independently defined each time it occurs within the generic structural formula definitions.

Polymorphism

A compound of formula (I) or (Ia), including a salt or solvate thereof, may exist in crystalline form, non-crystalline form, or a mixture thereof. A compound or a salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound of formula (I) or (Ia).

Optical Isomers—Diastereomers—Geometric Isomers—Tautomers

Included herein are various isomers of the compounds of formula (I). The term "isomers" refers to compounds that have the same composition and molecular weight but differ in physical and/or chemical properties. The structural difference may be in constitution (geometric isomers) or in the ability to rotate the plane of polarized light (stereosiomers). With regard to stereoisomers, a compound of formula (I) may have one or more asymmetric carbon atom and may occur as a racemic mixture or as individual enantiomers or diastereomers. All such isomeric forms are included herein, including mixtures thereof. If a compound of formula (I) or (Ia) contains a double bond, the substituent may be in the E or Z configuration. If a compound of formula (I) or (Ia) contains a disubstituted cycloalkyl, the cycloalkyl substituent may have a cis- or trans-configuration. All tautomeric forms are also intended to be included.

Any asymmetric atom (e.g., carbon) of a compound of formula (I) or (Ia) can be present in racemic mixture or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

A compound of formula (I) or (Ia) can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of the final compounds of the examples or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds can also be resolved by chiral chromatography, e.g., high pressure liquid chromatography (HPLC) using a chiral adsorbent.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are included within the scope of the present invention.

Isotopic Variations

Compounds of formula (I) or (Ia) include unlabeled forms, as well as isotopically labeled forms. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, sulfur, fluorine, iodine and chlorine, such as $^2H$ (i.e., Deuterium or "D"), $^3H$, $^{11}C$, $^{13}C$, $^{14}C$, $^{13}N$, $^{15}N$, $^{15}O$, $^{17}O$, $^{18}O$, $^{32}P$, $^{35}S$, $^{18}F$, $^{123}I$, $^{125}I$ and $^{36}Cl$. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, substitution with positron emitting isotopes, such as $^{11}C$, $^{18}F$, $^{15}O$ and $^{13}N$, may be particularly desirable for PET or SPECT studies.

Isotopically-labeled compounds of formula (I) or (Ia) can generally be prepared by conventional techniques known to those skilled in the art. Furthermore, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index.

Pharmaceutically Acceptable Salts

The term "pharmaceutically acceptable salt" refers to a salt prepared from a pharmaceutically acceptable non-toxic base or acid, including inorganic or organic base and inorganic or organic acid. Salts derived from inorganic bases include aluminum, ammonium, calcium, copper, ferric, ferrous, lithium, magnesium, manganic salts, manganous, potassium, sodium, zinc, and the like. Particular embodiments include ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound of formula (I) or (Ia) is basic, a salt may be prepared from a pharmaceutically acceptable non-toxic acid, including an inorganic and organic acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid (TFA) and the like. Particular embodiments include the citric, hydrobromic, hydrochloric, maleic, phosphoric, sulfuric, fumaric, tartaric and trifluoroacetic acids. It will be understood that, as used herein, references to the compounds disclosed herein are meant to also include pharmaceutically acceptable salts thereof.

Methods of Use

Compounds of the invention can inhibit activity of the enzyme indoleamine-2,3-dioxygenase (IDO). For example, the compounds disclosed herein can potentially be used to inhibit activity of IDO in cell or in an individual in need of modulation of the enzyme by administering an effective amount of a compound. Further disclosed herein are methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound or composition provided herein. Methods of measuring tryptophan levels and tryptophan degradation are routine in the art.

Also disclosed herein are methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, viral replication, etc.

Also disclosed herein are methods of treating diseases associated with activity or expression, including abnormal activity and/or overexpression, of IDO in an individual (e.g., patient) by administering to the individual in need of such treatment an effective amount or dose of a compound disclosed herein or a pharmaceutical composition thereof. Example diseases can include any disease, disorder or condition that may be directly or indirectly linked to expression or activity of the IDO enzyme, such as over expression or abnormal activity. An IDO-associated disease can also include any disease, disorder or condition that may be prevented, ameliorated, or cured by modulating enzyme activity. Examples of IDO-associated diseases include cancer, viral infection such as HIV and HCV, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis, and systemic lupus erythematosus. Example cancers potentially treatable by the methods herein include cancer of the colon, pancreas, breast, prostate, lung, brain, ovary, cervix, testes, renal, head and neck, lymphoma, leukemia, melanoma, and the like. The compounds of the invention may also be useful in the treatment of obesity and ischemia. As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound disclosed herein includes the administration of a compound of the present invention to an individual or patient, such as a human, as well as, for example, introducing a compound of the invention into a sample containing a cellular or purified preparation containing the IDO enzyme.

A subject administered with a compound disclosed herein, or a pharmaceutically acceptable salt thereof, is generally a mammal, such as a human being, male or female. A subject also refers to cows, sheep, goats, horses, dogs, cats, rabbits, rats, mice, fish, and birds. In one embodiment, the subject is a human.

As used herein, the terms "treatment" and "treating" refer to all processes wherein there may be a slowing, interrupting, arresting, controlling, or stopping of the progression of a disease or disorder that may be associated with IDO enzyme activity. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering a" compound should be understood to include providing a compound described herein, or a pharmaceutically acceptable salt thereof, and compositions of the foregoing to a subject.

The amount of a compound administered to a subject is an amount sufficient to inhibit IDO enzyme activity in the subject. In an embodiment, the amount of a compound can be an "effective amount", wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound. It is recognized that one skilled in the art may affect physiological disorders associated with an IDO enzyme activity by treating a subject presently afflicted with the disorders, or by prophylactically treating a subject likely to be afflicted with the disorders, with an effective amount of a compound disclosed herein, or a pharmaceutically acceptable salt thereof.

An effective amount of a compound will vary with the particular compound chosen (e.g. considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 0.1 mg to about 2 grams, or more specifically, 0.1 mg to 500 mg, or even more specifically, 0.2 mg to 100 mg, of a compound of formula (I) or (Ia).

One embodiment of the present invention provides for a method of treating a disease or disorder associated with IDO enzyme activity comprising administration of an effective amount of a compound of formula (I) or (Ia) to a subject in need of treatment thereof. In one embodiment, the disease or disorder associated with an IDO enzyme is a cell proliferation disorder.

In one embodiment, disclosed herein is the use of a compound of formula (I) or (Ia) in a therapy. The compound may be useful in a method of inhibiting IDO enzyme activity in a subject, such as a mammal in need of such inhibition, comprising administering an effective amount of the compound to the subject.

In one embodiment, disclosed herein is a pharmaceutical composition comprising a compound of formula (I) or (Ia), or a pharmaceutically acceptable salt thereof, for use in potential treatment of a disorder or disease related to IDO enzyme activity.

Compositions

The term "composition" as used herein is intended to encompass a dosage form comprising a specified compound in a specified amount, as well as any dosage form which results, directly or indirectly, from combination of a specified compound in a specified amount. Such term is intended to encompass a dosage form comprising a compound of formula (I) or (Ia), or a pharmaceutically acceptable salt thereof, and one or more pharmaceutically acceptable carriers or excipients. Accordingly, the compositions of the present invention encompass any composition made by admixing a compound of the present invention and one or more pharmaceutically acceptable carrier or excipients. By "pharmaceutically acceptable" it is meant the carriers or excipients are compatible with the compound disclosed herein and with other ingredients of the composition.

In one embodiment, disclosed herein is a composition comprising a compound of formula (I) or (Ia), or a pharmaceutically acceptable salt thereof, and one or more pharmaceutically acceptable carriers or excipients. The composition may be prepared and packaged in bulk form wherein an effective amount of a compound of the invention can be extracted and then given to a subject, such as with powders or syrups. Alternatively, the composition may be prepared and packaged in unit dosage form wherein each physically discrete unit contains an effective amount of a compound of formula (I) or (Ia). When prepared in unit dosage form, the composition of the invention typically contains from about 0.1 mg to 2 grams, or more specifically, 0.1 mg to 500 mg, or even more specifically, 0.2 mg to 100 mg, of a compound of formula (I) or (Ia), or a pharmaceutically acceptable salt thereof.

A compound disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the invention are prepared using techniques and methods known to those skilled in the art. Some methods commonly used in the art are described in Remington's Pharmaceutical Sciences (Mack Publishing Company).

In one embodiment, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, polepsilon caprolactone, polyhydroxy butyric acid, polyorthoesters, polyacetals, polydihydropyrans, polycyanacrylates and cross-linked or amphipathic block copolymers of hydrogels.

In one embodiment, the invention is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the invention in a suitably flavored aqueous solution; while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the invention is directed to compositions for parenteral administration. Compositions adapted for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

A compound disclosed herein may be used in combination with one or more other active agents, including but not limited to, other anti-cancer agents, that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

When a compound disclosed herein is used contemporaneously with one or more other active agents, a composition containing such other active agents in addition to the compound disclosed herein is contemplated. Accordingly, the compositions of the present invention include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a compound of formula (I) or (Ia) and one or more other active agent(s) together in the same pharmaceutical composition, or a compound of formula (I) or (Ia) and one or more other therapeutic agent(s) in separate form, e.g. in the form of a kit.

The weight ratio of a compound disclosed herein to a second active agent may be varied and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein and other active agents will generally also be within the aforementioned range, but in each case, an effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, the invention provides a composition comprising a compound of formula (I) or (Ia) and at least one other therapeutic agent as a combined preparation for simultaneous, separate or sequential use in therapy. In one embodiment, the therapy is the treatment of a disease or disorder associated with IDO enzyme activity.

In one embodiment, the invention provides a kit comprising two or more separate pharmaceutical compositions, at least one of which contains a compound of formula (I) or (Ia). In one embodiment, the kit comprises means for separately retaining said compositions, such as a container, divided bottle, or divided foil packet. An example of such a kit is a blister pack, as typically used for the packaging of tablets, capsules and the like.

A kit disclosed herein may be used for administering different dosage forms, for example, oral and parenteral, for administering the separate compositions at different dosage intervals, or for titrating the separate compositions against one another. To assist with compliance, a kit of the invention typically comprises directions for administration.

Disclosed herein is a use of a compound of formula (I) or (Ia) for treating a disease or disorder associated with IDO enzyme activity, wherein the medicament is prepared for administration with another active agent. The invention also provides the use of another active agent for treating a disease or disorder associated with an IDO enzyme, wherein the medicament is administered with a compound of formula (I) or (Ia).

The invention also provides the use of a compound of formula (I) or (Ia) for treating a disease or disorder associated with IDO enzyme activity, wherein the patient has previously (e.g. within 24 hours) been treated with another active agent. The invention also provides the use of another therapeutic agent for treating a disease or disorder associated with IDO enzyme activity, wherein the patient has previously (e.g. within 24 hours) been treated with a compound of formula (I) or (Ia). The second agent may be applied a week, several weeks, a month, or several months after the administration of a compound disclosed herein.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)-2-aminopropanoate, also known as BMS-582664), motesanib (N-(2,3-dihydro-3,3-dimethyl-1H-indol-6-yl)-2-[(4-pyridinyimethyj)amino]-3-pyfidinecarboxamide. and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX and MYLERAN), carboplatin (sold under the tradename PARAPLATIN), lomustine (also known as CCNU, sold under the tradename CeeNU), cisplatin (also known as CDDP, sold under the tradenames PLATINOL and PLATINOL-AQ), chlorambucil (sold under the tradename LEUKERAN), cyclophosphamide (sold under the tradenames CYTOXAN and NEOSAR), dacarbazine (also known as DTIC, DIC and imidazole carboxamide, sold under the tradename DTIC-DOME), altretamine (also known as hexamethylmelamine (HMM) sold under the tradename HEXALEN), ifosfamide (sold under the tradename IFEX), procarbazine (sold under the tradename MATULANE), mechlorethamine (also known as nitrogen mustard, mustine and mechloroethamine hydrochloride, sold under the tradename MUSTARGEN), streptozocin (sold under the tradename ZANOSAR), thiotepa (also known as thiophosphoamide, TESPA and TSPA, and sold under the tradename THIOPLEX).

Examples of anti-tumor antibiotics include, but are not limited to, doxorubicin (sold under the tradenames ADRIAMYCIN and RUBEX), bleomycin (sold under the tradename LENOXANE), daunorubicin (also known as dauorubicin hydrochloride, daunomycin, and rubidomycin hydrochloride, sold under the tradename CERUBIDINE), daunorubicin liposomal (daunorubicin citrate liposome, sold under the tradename DAUNOXOME), mitoxantrone (also known as DHAD, sold under the tradename NOVANTRONE), epirubicin (sold under the tradename ELLENCE), idarubicin (sold under the tradenames IDAMYCIN, IDAMYCIN PFS), and mitomycin C (sold under the tradename MUTAMYCIN).

Examples of anti-metabolites include, but are not limited to, claribine (2-chlorodeoxyadenosine, sold under the tradename LEUSTATIN), 5-fluorouracil (sold under the tradename ADRUCIL), 6-thioguanine (sold under the tradename PURINETHOL), pemetrexed (sold under the tradename ALIMTA), cytarabine (also known as arabinosylcytosine (Ara-C), sold under the tradename CYTOSAR-U), cytarabine liposomal (also known as Liposomal Ara-C, sold under the tradename DEPOCYT), decitabine (sold under the tradename DACOGEN), hydroxyurea (sold under the tradenames HYDREA, DROXIA and MYLOCEL), fludarabine (sold under the tradename FLUDARA), floxuridine (sold under the tradename FUDR), cladribine (also known as 2-chlorodeoxyadenosine (2-CdA) sold under the tradename LEUSTATIN), methotrexate (also known as amethopterin, methotrexate sodium (MTX), sold under the tradenames RHEUMATREX and TREXALL), and pentostatin (sold under the tradename NIPENT).

Examples of retinoids include, but are not limited to, alitretinoin (sold under the tradename PANRETIN), tretinoin (all-trans retinoic acid, also known as ATRA, sold under the tradename VESANOID), Isotretinoin (13-c/s-retinoic acid, sold under the tradenames ACCUTANE, AMNESTEEM, CLARAVIS, CLARUS, DECUTAN, ISOTANE, IZOTECH, ORATANE, ISOTRET, and SOTRET), and bexarotene (sold under the tradename TARGRETIN).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments. Examples of PD-1 antagonists include, but are not limited to, pembrolizumab (sold under the tradename KEYTRUDA) and nivolumab (sold under the tradename OPDIVO).

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename TRISENOX), asparaginase (also known as L-asparaginase, and *Erwinia* L-asparaginase, sold under the tradenames ELSPAR and KIDROLASE).

EXPERIMENTAL

The following examples are intended to be illustrative only and not limiting in any way. Abbreviations used are those conventional in the art or the following.

ACN acetonitrile
° C. degree Celsius
DCM dichloromethane
DMA dimethylamine
DMF N,N-dimethylformamide
DMSO dimethylsulfoxide
EtOAc ethyl acetate
EtOH ethanol
g gram(s)
h hour(s)
HPLC high pressure liquid chromatography
kg kilogram(s)
L liter(s)
LC liquid chromatography
LCMS liquid chromatography and mass spectrometry
MeOH methanol
MS mass spectrometry
MTBE methyl tert-butyl ether
min minute(s)
mL milliliter(s)
m/z mass to charge ratio
nm nanometer
nM nanomolar
N normal
MR nuclear magnetic resonance
RT room temperature
sat. saturated
TEA triethyl amine
TFA trifluoroacetic acid
THF tetrahydrofuran General Synthetic Schemes The compounds of formula (I) or (Ia) may be prepared by methods known in the art of organic synthesis as set forth in part by the following synthetic schemes and synthetic procedures and conditions for the illustrative intermediates and examples.

In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art.

The compounds described herein may be made from commercially available starting materials or synthesized using known organic, inorganic, and/or enzymatic processes.

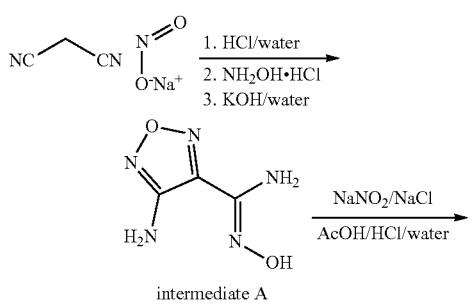

intermediate A

-continued

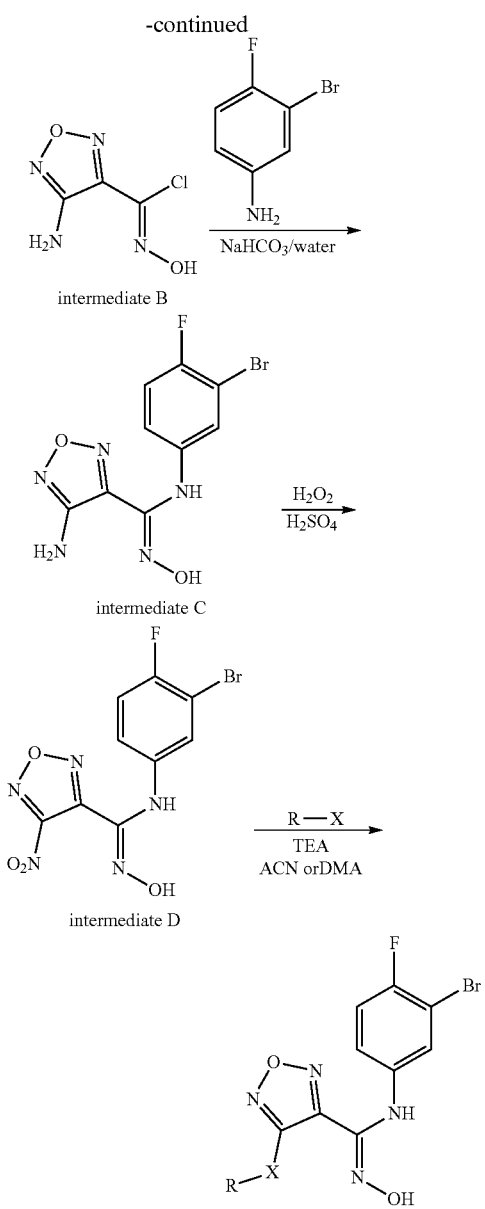

wherein X is O or S.

In Scheme 1, processes for preparing Intermediates A, B, C and D and active compounds are described in more detail below.

Intermediate A: (Z)-4-Amino-N'-hydroxy-1,2,5-oxadiazole-3-carboximidamide

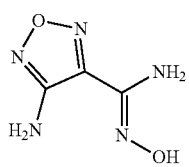

Intermediate A is prepared according to Scheme A1 via nitrosation of malononitrile in aqueous acid followed by the addition of hydroxylamine hydrochloride and subsequent pH adjustment to 9-11.

Malononitrile (15 g, 227 mmol) in 2N HCl (200 ml) was stirred till dissolved. With the reaction temperature kept between 15° C.-20° C., a solution of sodium nitrite (31.3 g, 454 mmol) in 45 ml of water was added dropwise and stirred at ambient for a further 16 h. An aqueous solution of hydroxylamine hydrochloride (35.0 g, 504 mmol) in 25 ml of water was added and the pH of the solution was brought to about 10 by addition of 10 N NaOH while maintaining the temperature below 20° C. The temperature of the reaction was brought to 30° C. for 1 h then refluxed for 3 h. Heating was discontinued and the reaction gradually warmed to room temperature overnight. The reaction was cooled in an ice bath, pH adjusted to 8 with 6N HCl and stirred for 30 min. The solids were filtered and washed with cold water to afford the title compound. MS: 144 (M+1). $^{13}$C NMR (500 MHz, CD3OD): δ 154.5, 144.3, 139.8.

Intermediate B: (Z)-4-Amino-N-hydroxy-1,2,5-oxadiazole-3-carbimidoyl chloride

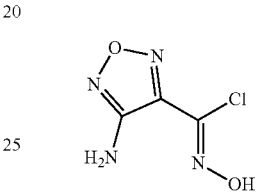

To a solution of (Z)-4-amino-N'-hydroxy-1,2,5-oxadiazole-3-carboximidamide (5.09 g, 35.6 mmol) in 70 ml of water was added AcOH (35 ml) and 6N hydrogen chloride (17.78 ml, 107 mmol). The reaction mixture was warmed to 40° C. till all solids were dissolved. The reaction was cooled to ambient and solid sodium chloride (6.24 g, 107 mmol) was added, stirred, then the reaction mixture was cooled to 0° C. A solution of sodium nitrite (2.5 g, 35.6 mmol) in 8.4 ml of water was added dropwise over 3 h and the reaction was stirred at 0° C. for a further 1.5 h, then warmed to 15° C. for 15 min. The solid precipitates were filtered and washed with cold water to afford the title product. MS: 163 (M+1). $^{13}$C NMR (500 MHz, DMSO-$d_6$): δ 154.4, 142.3, 126.8. $^1$HNMR (500 MHz, DMSO-$d_6$): δ 13.41 (s, 1H), 6.29 (s, 2H).

Intermediate C: (Z)-4-Amino-N-(3-bromo-4-fluorophenyl)-N'-hydroxy-1,2,5-oxadiazole-3-carboximidamide

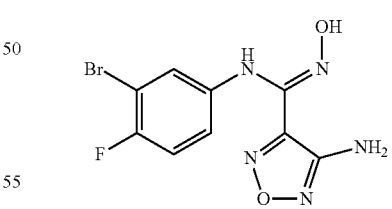

A solution of (Z)-4-amino-N-hydroxy-1,2,5-oxadiazole-3-carbimidoyl chloride (1.63 g, 10.01 mmol) in water (20 mL) was warmed to 55° C. and solid 3-bromo-4-fluoroaniline (2.092 g, 11.01 mmol) was added in one portion. The reaction was stirred for 20 min at that temperature followed by the addition of an aqueous solution of sodium bicarbonate (1.26 g, 15.02 mmol) in water (3 mL), dropwise, over 5 min. The reaction was stirred for a further 20 min at 55° C., cooled to ambient then in an ice bath for 1 h. The product was filtered and washed with cold water and dried in vacuo to afford the title compound. MS: 316.1 (M+1). ¹HNMR (500 MHz, DMSO-$d_6$): δ 11.43 (s, 1H), 8.87 (s, 1H), 7.17 (t, J=9 Hz, 1H), 7.10 (m, 1H), 6.7 (m, 1H), 6.25 (broad s, 2H).

Intermediate D: (Z)—N-(3-Bromo-4-fluorophenyl)-N'-hydroxy-4-nitro-1,2,5-oxadiazole-3-carboximidamide

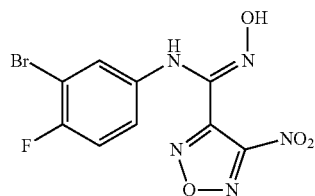 [SMILES: O=[N+]([O-])c1nonc1/C(=N/O)Nc1ccc(F)c(Br)c1]

An ice cold solution of 30% hydrogen peroxide (5.04 mL, 57.6 mmol) in 2 mL of conc. sulfuric acid ($H_2SO_4$) was added to a solution of (Z)-4-amino-N-(3-bromo-4-fluorophenyl)-N'-hydroxy-1,2,5-oxadiazole-3-carboximidamide (2.6 g, 8.23 mmol) in conc. $H_2SO_4$ (11 mL) cooled in an ice bath. Subsequently, the reaction was gradually warmed to ambient temperature. The reaction mixture was poured to ice and extracted with EtOAc. The organics were washed with water, brine, dried and concentrated. The material was then purified by silica gel chromatography (Biotage 50 g SNAP cartridge, 0-45% ethyl acetate in hexanes) to afford the title compound. MS: 345.9 (M+1). ¹HNMR (500 MHz, DMSO-$d_6$): d 11.80 (s, 1H), 9.20 (s, 1H), 7.33 (t, J=10 Hz, 1H), 7.16 (m, 1H), 6.70 (m, 1H).

Scheme 2

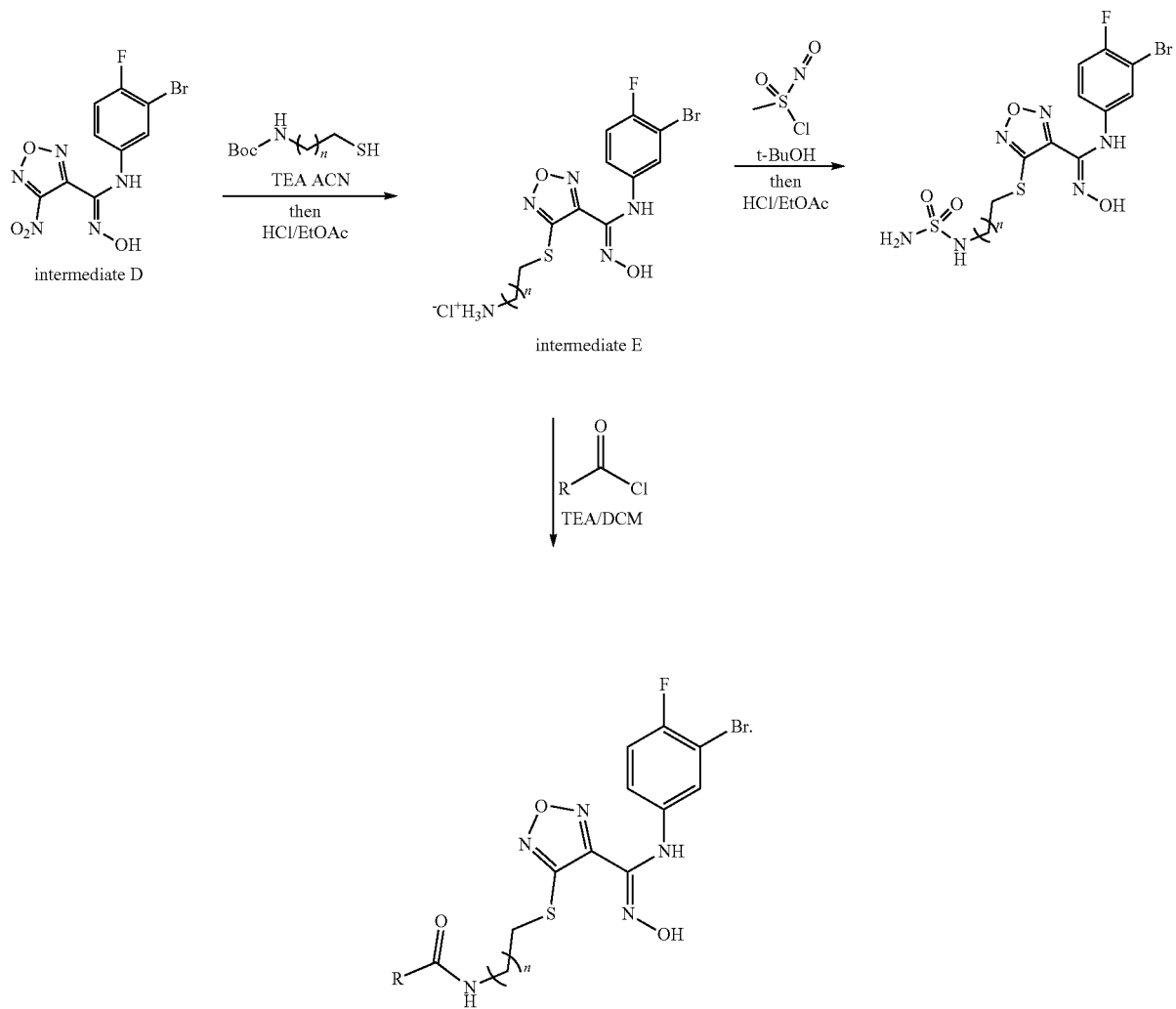

wherein n is 0, 1, 2 or 3

In Scheme 2, processes for preparing compounds, for example those in Examples 1 and 9, are described in more detail below.

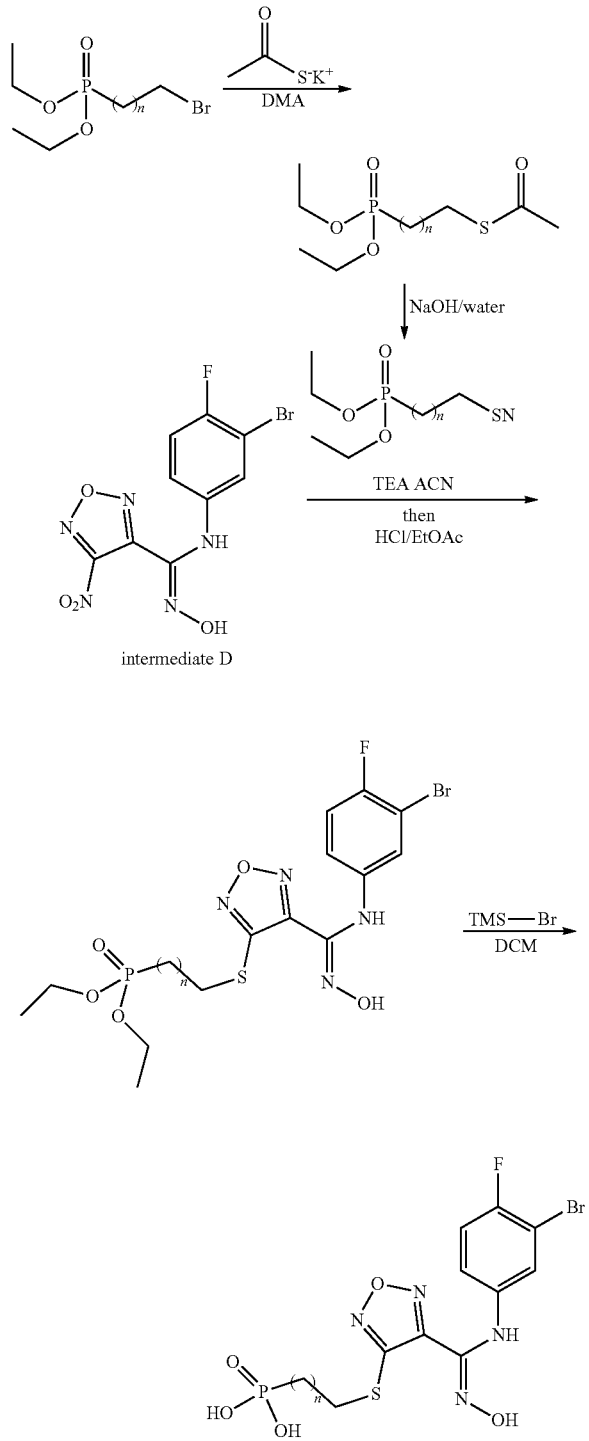

intermediate D wherein n is 0, 1, 2 or 3

In Scheme 3, processes for preparing compounds, for example those in Examples 7 and 8, are described in more detail below.

EXAMPLES

Example 1: Tert-butyl (Z)-(2-((4-(N-(3-bromo-4-fluorophenyl)-N'-hydroxycarbamimidoyl)-1,2,5-oxadiazol-3-yl)thio)ethyl)carbamate

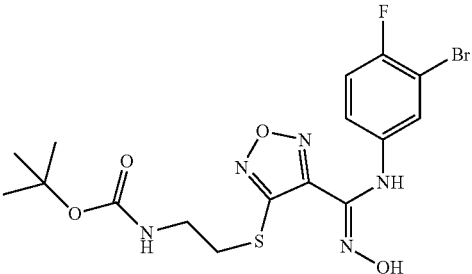 [SMILES: CC(C)(C)OC(=O)NCCSc1nonc1/C(=N/O)Nc1ccc(F)c(Br)c1]

A solution of tert-butyl (2-mercaptoethyl)carbamate (106 mg, 0.6 mmol) in ACN (0.4 mL) was added to a solution of (Z)—N-(3-bromo-4-fluorophenyl)-N'-hydroxy-4-nitro-1,2,5-oxadiazole-3-carboximidamide (70 mg, 0.202 mmol) in ACN at ambient temperature followed by the addition of TEA (0.14 mL, 1.01 mmol) and stirred for 1 h. The reaction mixture was diluted with EtOAc and water. The organics were separated, washed with brine, dried and concentrated. The resulting material was then purified by silica gel chromatography (Biotage 10 g SNAP cartridge, 0-75% ethyl acetate in hexanes) to afford the title compound. MS: 419.9 (M+1-tert-butyl). $^1$HNMR (500 MHz, DMSO-$d_6$): d 11.72 (s, 1H), 8.97 (s, 1H), 7.16 (t, J=5 Hz, 1H), 7.10 (m, 1H), 6.71 (m, 1H), 3.28 (q, J=8 Hz, 5 Hz, 2H), 3.19 (t, J=5 Hz, 2H), 1.35 (s, 9H).

Example 2: (Z)-2-((4-(N-(3-Bromo-4-fluorophenyl)-N'-hydroxycarbamimidoyl)-1,2,5-oxadiazol-3-yl)thio)ethan-1-aminium chloride

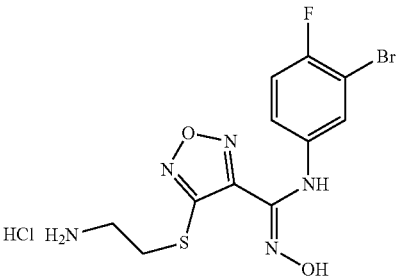

A solution of 4 M HCl in dioxane (1 mL, 12.18 mmol) was added to a solution of tert-butyl (Z)-(2-((4-(N-(3-bromo-4-fluorophenyl)-N'-hydroxycarbamimidoyl)-1,2,5-oxadiazol-3-yl)thio)ethyl)carbamate (65 mg, 0.136 mmol) in EtOAc (1 mL) and stirred at ambient temperature. The reaction mixture was concentrated, tritarated from water and ACN, and lyophilized to afford the title compound. MS: 376 (M+1). $^1$HNMR (500 MHz, DMSO-$d_6$): d 11.77 (s, 1H), 9.0 (s, 1H), 8.03 (broad s, 3H), 7.18 (t, J=10 Hz, 1H), 7.09 (m, 1H), 6.74 (m, 1H), 3.39 (t, J=5 Hz, 2H), 3.19 (m=2H).

Example 3: (Z)—N-(3-Bromo-4-fluorophenyl)-N'-hydroxy-4-((2-(sulfamoylamino)ethyl)thio)-1,2,5-oxadiazole-3-carboximidamide

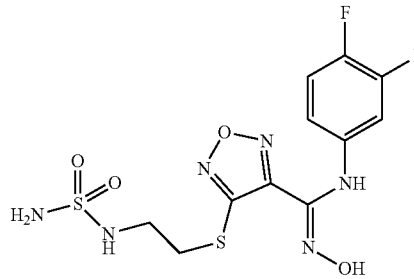

Tert-Butanol (15 mg, 0.2 mmol) in DCM (0.5 mL) was added dropwise to a solution of sulfurisocyanatidic chloride (29 mg, 0.2 mmol) in DCM (0.5 mL) cooled in an ice bath and stirred for 30 min. The resulting solution was added to (Z)-2-((4-(N-(3-bromo-4-fluorophenyl)-N'-hydroxycarbamimidoyl)-1,2,5-oxadiazol-3-yl)thio)ethan-1-aminium chloride (62 mg, 0.15 mmol) in DCM (2 mL) followed by TEA (38 mg, 0.37 mmol) in DCM (0.5 mL) and stirred at ambient temperature. The reaction mixture was diluted with DCM and water. The organics were washed with brine, dried and concentrated. The material was then purified by silica gel chromatography (Biotage 10 g SNAP cartridge, 0-80% ethyl acetate in hexanes) to afford tert-butyl (Z)—(N-(2-((4-(N-(3-bromo-4-fluorophenyl)-N'-hydroxycarbamimidoyl)-1,2,5-oxadiazol-3-yl)thio)ethyl)sulfamoyl)carbamate which was taken in EtOAc (2 mL) and to which was added 4M HCl in dioxane (1 ml, 12.18 mmol). The resulting product was concentrated, tritarated from water and ACN, and lyophilized to afford the title compound. MS: 454.9 (M+1). $^1$HNMR (500 MHz, DMSO-$d_6$): d 11.76 (s, 1H), 8.96 (s, 1H), 7.16 (t, J=10 Hz, 1H), 7.09 (m, 1H), 6.86 (t, J=5 Hz, 1H), 6.67 (m, 1H), 6.64 (s, 2H), 3.30 (m, 2H), 3.26 (t, J=6.5 Hz, 2H).

Example 4: (Z)—N-(3-Bromo-4-fluorophenyl)-N',4-dihydroxy-1,2,5-oxadiazole-3-carboximidamide

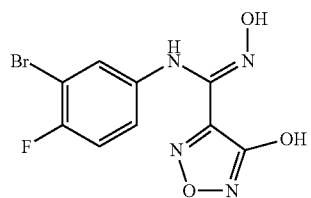 [SMILES: O/N=C(\Nc1ccc(F)c(Br)c1)c1nonc1O]

To a solution of intermediate D (586 mg, 1.69 mmol) in DMA (3.3 mL) was added potassium thioacetate (1.1 g, 9.63 mmol) and the reaction was heated to 45° C. The reaction mixture was cooled to ambient. Water (6 mL) was added and stirred. To the resulting product was extracted with EtOAc, washed with brine, dried and concentrated. The material was then purified by reverse phase chromatography (Biotage 10 g, C-18 SNAP cartridge, 5%-90% ACN in water (0.1% TFA) to afford the title compound. MS: 316.9 (M+1). $^1$HNMR (500 MHz, DMSO-$d_6$): δ 12.84 (s, 1H), 11.32 (s, 1H), 9.64 (s, 1H), 7.9 (m, 1H), 7.58 (t, J=8.5 Hz, 1H), 7.55 (m, 1H).

Example 5: N-(2-((4-(N-(3-bromo-4-fluorophenyl)-N'-hydroxycarbamimidoyl)-1,2,5-oxadiazol-3-yl)oxy)ethyl)acetamide

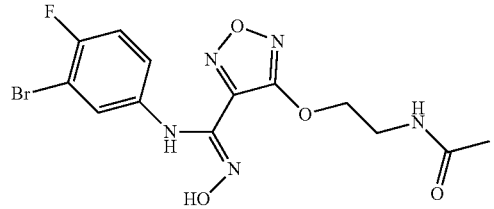 [SMILES: CC(=O)NCCOc1nonc1/C(=N/O)Nc1ccc(F)c(Br)c1]

Step 1. 3-(4-Amino-1,2,5-oxadiazol-3-yl)-4-(3-bromo-4-fluorophenyl)-1,2,4-oxadiazol-5(4H)-one

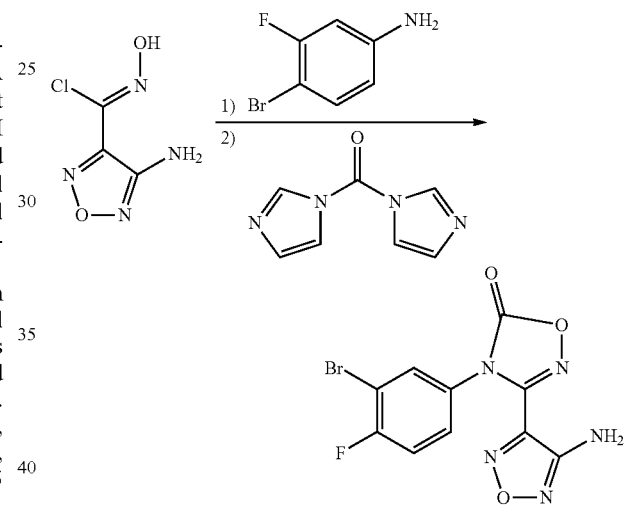

(Z)-4-Amino-N-hydroxy-1,2,5-oxadiazole-3-carbimidoyl chloride (10.2 g, 62.8 mmol) and 3-bromo-4-fluoroaniline (12.28 g, 64.6 mmol) were suspended with acetonitrile (84 mL)/water (167 mL). The reaction was warmed to 50° C. internal temperature. Potassium phosphate, dibasic (78 mL, 78 mmol) solution was added slowly over 30-40 min via dropping funnel. The reaction mixture was allowed to cool to RT, then extracted with 500 mL of EtOAc. The organic layer was washed with 100 mL of brine, dried over sodium sulfate and filtered. The solution was concentrated to ~300 mL of EtOAc before CDI (12.72 g, 78 mmol) was added in one portion, which generated slight exotherm of ~7-8° C. and then subsided. Additional EtOAc (200 mL) was added and the reaction was washed with 200 mL of 0.5M HCl (2×) followed by water and brine. The organic layer was dried over sodium sulfate, filtered and concentrated to a volume of about 100 mL. To this was then added 100 mL of hexanes and the resultant mixture was aged overnight. The precipitate was collected by filtration (washing the cake with 25 mL of 40% EtOAc/Hex) to give 3-(4-amino-1,2,5-oxadiazol-3-yl)-4-(3-bromo-4-fluorophenyl)-1,2,4-oxadiazol-5(4H)-one (18.58 g) as a solid. $^1$HNMR (500 MHz, DMSO-$d_6$): δ 8.09 (m, 1H), 7.73 (m, 1H), 7.56 (m, 1H), 6.60 (s, 2H).

Step 2. 4-(3-Bromo-4-fluorophenyl)-3-(4-nitro-1,2,5-oxadiazol-3-yl)-1,2,4-oxadiazol-5(4H)-one

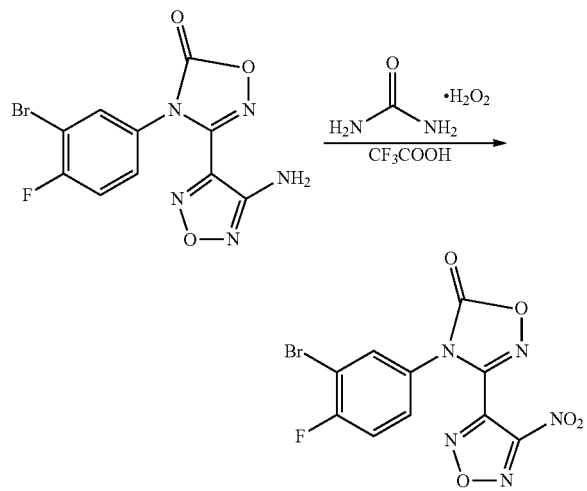

3-(4-Amino-1,2,5-oxadiazol-3-yl)-4-(3-bromo-4-fluorophenyl)-1,2,4-oxadiazol-5(4H)-one (13 g, 38.0 mmol) was dissolved in TFA (80 mL)/DCE (100 mL). Urea hydrogen peroxide (28.6 g, 304 mmol) was added in portions, and the temperature was kept at <21° C. by using a water bath. The reaction was stirred for 16 h, quenched by pouring into chilled water (100 mL), and extracted with DCM (2×100 mL). The organic layer was washed with 10% sodium thiosulfate, followed by water and brine, then dried over sodium sulfate, filtered and concentrated. Purification by flash chromatography (5-50% EtOAcf/Hex) afforded the title compound as a solid. $^1$HNMR (500 MHz, DMSO-$d_6$): δ 8.04 (m, 1H), 7.66 (m, 1H), 7.56 (m, 1H).

Step 3. N-(2-((4-(4-(3-bromo-4-fluorophenyl)-5-oxo-4,5-dihydro-1,2,4-oxadiazol-3-yl)-1,2,5-oxadiazol-3-yl)oxy)ethyl)acetamide

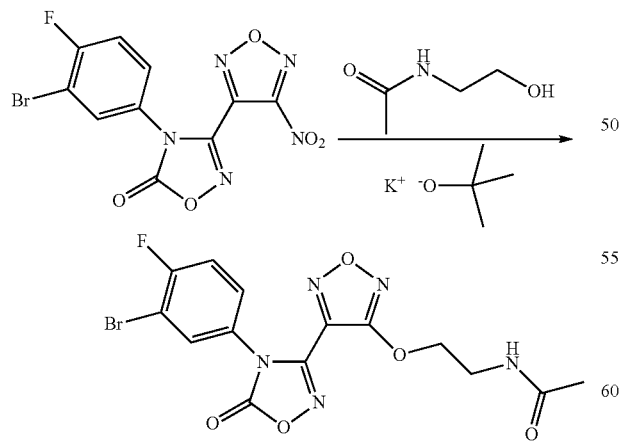

To the stirred solution of N-acetylethanolamine (94 mg, 0.908 mmol) in dry THF (7 mL) was added potassium tert-butoxide (1M in THF) (734 µL, 0.734 mmol) at RT. The mixture was stirred at RT for about 2 min before 4-(3-bromo-4-fluorophenyl)-3-(4-nitro-1,2,5-oxadiazol-3-yl)-1,2,4-oxadiazol-5(4H)-one (260 mg, 0.699 mmol) was added. The mixture was stirred at RT for about 30 min, then concentrated in vacuo. LCMass showed desired product as the major product. The mixture was used in the next step without further purification. LCMS m/z (M+H) calc'd: 427.99; found: 428.2.

Step 4. N-(2-((4-(N-(3-bromo-4-fluorophenyl)-N'-hydroxycarbamimidoyl)-1,2,5-oxadiazol-3-yl)oxy)ethyl)acetamide

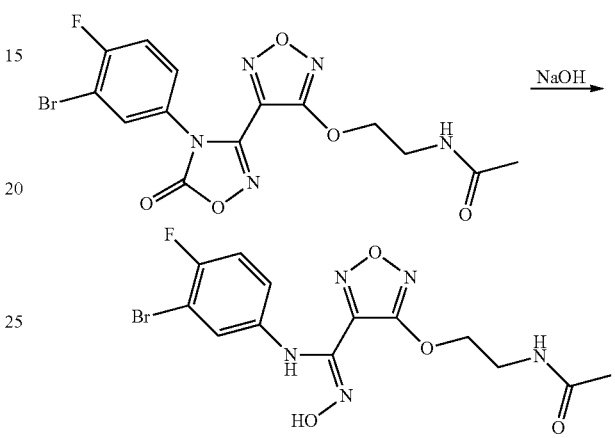

To the crude mixture of N-(2-((4-(4-(3-bromo-4-fluorophenyl)-5-oxo-4,5-dihydro-1,2,4-oxadiazol-3-yl)-1,2,5-oxadiazol-3-yl)oxy)ethyl)acetamide from the previous step (299 mg, 0.699 mmol) in THF (7 mL) were added water (2.8 mL) and NaOH (2 M in water) (1.05 mL, 2.1 mmol). The mixture was stirred at RT for about 2 h, then neutralized with addition of HCl (2 M in water) (~1 ml, ~2 mmol) to adjust the pH to 8. The mixture was partitioned between EtOAc and brine. The aqueous was extracted with EtOAc for three times (15 mL×3). Organic phases were combined, dried over $Na_2SO_4$, filtered, and concentrated in vacuo to give the crude product as an oil, which was purified by mass-directed reverse HPLC purification (5 injection on reverse HPLC on a 19×100 mm, Waters CSH C18 column, 5µ particle size, flow rate 25 ml/min, linear gradient, 5% ACN/$H_2O$ to 50% ACN/$H_2O$, total run time 15 min, buffering with 0.16% TFA) to give the desired product as a solid. LCMS m/z (M+H) calc'd: 402.01; found (M+H): 401.9; 404.2. $^1$H NMR (500 MHz, CD3OD): δ7.16-7.14 (m, 1H); 7.05-7.03 (m, 1H); 6.80-6.78 (m, 1H); 4.24 (t, J=5 Hz, 2H); 3.48 (t, J=5 Hz, 2H); 1.96 (s, 3H).

Example 6: 2-((4-(N-(3-Bromo-4-fluorophenyl)-N'-hydroxycarbamimidoyl)-1,2,5-oxadiazol-3-yl)oxy)-N-(2-hydroxyethyl)acetamide

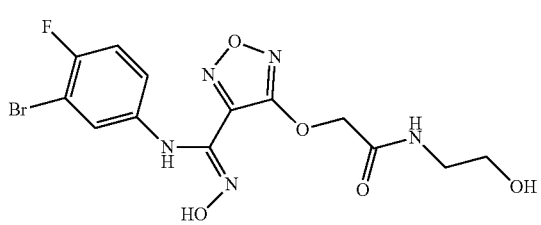 [SMILES: O=C(COc1nonc1/C(=N/O)Nc1ccc(F)c(Br)c1)NCCO]

Step 1. 2-((4-(4-(3-bromo-4-fluorophenyl)-5-oxo-4,5-dihydro-1,2,4-oxadiazol-3-yl)-1,2,5-oxadiazol-3-yl)oxy)-N-(2-hydroxyethyl)acetamide

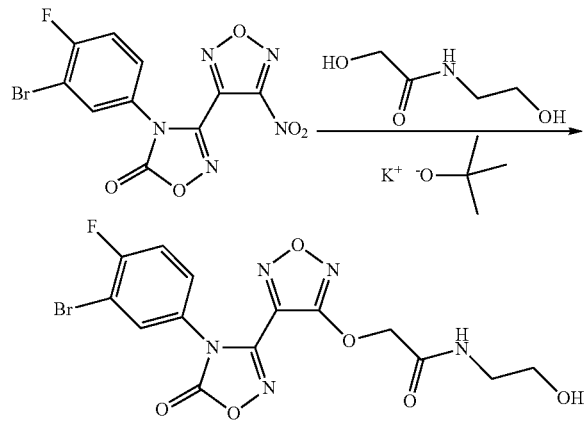

To the stirred solution of 2-hydroxy-N-(2-hydroxyethyl)acetamide (54.1 mg, 0.454 mmol) in dry THF (3.5 mL) was added potassium tert-butoxide (1M in THF, Aldrich) (367 µL, 0.367 mmol) at RT. The mixture was stirred at RT for about 2 min before 4-(3-bromo-4-fluorophenyl)-3-(4-nitro-1,2,5-oxadiazol-3-yl)-1,2,4-oxadiazol-5(4H)-one (130 mg, 0.349 mmol) was added. The mixture was stirred at RT for about 2 h. The mixture was used in the next step without further purification. LCMS m/z (M+H) calc'd: 443.99; found: M+H=444.0; 446.1.

Step 2. 2-((4-(N-(3-bromo-4-fluorophenyl)-N'-hydroxycarbamimidoyl)-1,2,5-oxadiazol-3-yl)oxy)-N-(2-hydroxyethyl)acetamide

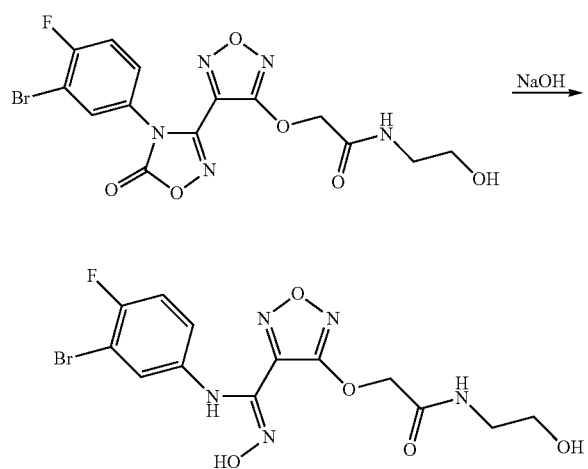

To the crude mixture of 2-((4-(4-(3-bromo-4-fluorophenyl)-5-oxo-4,5-dihydro-1,2,4-oxadiazol-3-yl)-1,2,5-oxadiazol-3-yl)oxy)-N-(2-hydroxyethyl)acetamide from the previous step were added water (1.25 mL) and NaOH (2 M in water) (0.524 mL, 1.047 mmol). The mixture was stirred at RT for about 2 h, then neutralized with addition of HCl (2 M in water) (0.524 ml, 1.047 mmol) to adjust the pH to ~8. The mixture was partitioned between EtOAc and brine. The aqueous was extracted with EtOAc for three times (10 mL×3). Organic phases were combined, dried over Na$_2$SO$_4$, filtered, and concentrated in vacuo to give the crude product as an oil, which was purified by mass-directed reverse HPLC purification (reverse HPLC on a 19×100 mm, Waters CSH C18 column, 5µ particle size, flow rate 25 ml/min, linear gradient, 15% ACN/H2O to 50% ACN/H$_2$O, total run time 8 mins, buffering with 0.16% TFA) to give the desired product as a solid. LCMS m/z (M+H) calc'd: 418.01; found (M+H): 418.0; 420.2. $^1$H NMR (500 MHz, CD3OD): δ 7.20-7.16 (m, 1H); 7.05 (t, J=10 Hz, 1H); 6.85-6.80 (m, 1H); 4.76 (s, 2H); 3.65 (t, J=5 Hz, 2H); 3.40 (t, J=5 Hz, 2H).

Example 7: Diethyl (Z)-(2-((4-(N-(3-bromo-4-fluorophenyl)-N'-hydroxycarbamimidoyl)-1,2,5-oxadiazol-3-yl)thio)ethyl)phosphonate

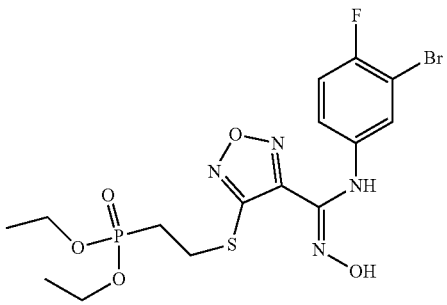 [SMILES: CCOP(=O)(CCSc1nonc1/C(=N/O)Nc1ccc(F)c(Br)c1)OCC]

Diethyl (2-bromoethyl)phosphonate (1 g, 4.08 mmol) and potassium thioacetate (0.56 g, 4.9 mmol) in ACN (5 mL) and DMA (1 mL) were heated to 45° C. for 2 h. The reaction was cooled to ambient. To the reaction mixture were added sodium hydroxide (0.2 g, 4.9 mmol) and water (3 mL) and reaction was reheated to 50° C. The reaction was cooled to ambient and diluted with EtOAc. The organics were separated, washed with brine, dried and concentrated to afford diethyl (2-mercaptoethyl)phosphonate. MS: 199.1 (M+1).

A solution of diethyl (2-mercaptoethyl)phosphonate (183 mg, 0.92 mmol) was added to a solution of (Z)—N-(3-bromo-4-fluorophenyl)-N'-hydroxy-4-nitro-1,2,5-oxadiazole-3-carboximidamide (160 mg, 0.46 mmol) in DMA (2 mL) at ambient temperature followed by the addition of TEA (94 mg, 0.92 mmol) and the mixture was stirred. The reaction mixture was diluted with EtOAc and washed with water, brine, dried and concentrated. The material was then purified by silica gel chromatography (Biotage 4 g SNAP cartridge, 0-80% ethyl acetate in hexanes) to afford the title compound. MS: 497 (M+1). $^1$HNMR (500 MHz, DMSO-d$_6$): d 11.75 (s, 1H), 8.98 (s, 1H), 7.17 (t, J=8.5 Hz, 1H), 7.08 (m, 1H), 6.69 (m, 1H), 4.00 (m, 4H), 3.28 (m, 1H), 2.93 (m, 1H), 2.61 (m, 1H), 2.53 (m, 1H), 1.22 (m, 6H).

Example 8: (Z)-(2-((4-(N-(3-Bromo-4-fluorophenyl)-N'-hydroxycarbamimidoyl)-1,2,5-oxadiazol-3-yl)thio)ethyl)phosphonic acid

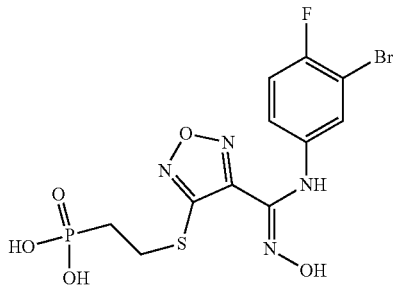 [SMILES: O=P(O)(O)CCSc1nonc1/C(=N/O)Nc1ccc(F)c(Br)c1]

To a solution of diethyl (Z)-(2-((4-(N-(3-bromo-4-fluorophenyl)-N'-hydroxycarbamimidoyl)-1,2,5-oxadiazol-3-yl)oxy)ethyl)phosphonate (120 mg, 0.24 mmol) in DCM (2 mL) cooled in an ice bath was added neat TMS-Br (2.41 mmol, 0.3 mL) and gradually warmed to ambient. At completion, MeOH was added and the reaction mixture was concentrated in vacuo. The material was then purified by reverse phase chromatography (Biotage 10 g, C-18 SNAP cartridge, 5%-90% ACN in water (0.1% TFA) to afford the title compound. MS: 440.9 (M+1). $^1$HNMR (500 MHz, DMSO-$d_6$): d 11.75 (s, 1H), 8.97 (s, 1H), 7.16 (t, J=8.5 Hz, 1H), 7.08 (m, 1H), 6.69 (m, 1H), 3.16 (m, 2H), 2.00 (m, 2H).

Example 9: (Z)-(((2-((4-(N-(3-bromo-4-fluorophenyl)-N'-hydroxycarbamimidoyl)-1,2,5-oxadiazol-3-yl)thio)ethyl)(hydroxy)phosphoryl)oxy)methyl isopropyl carbonate

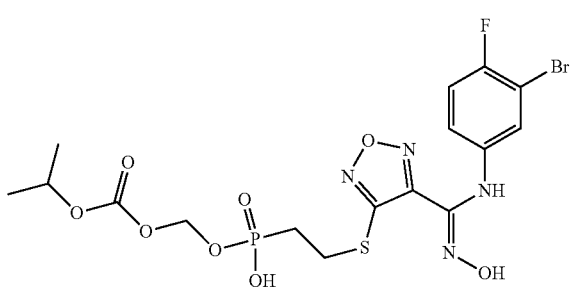 [SMILES: CC(C)OC(=O)OCOP(=O)(O)CCSc1nonc1/C(=N/O)Nc1ccc(F)c(Br)c1]

A solution of (Z)-(2-((4-(N-(3-Bromo-4-fluorophenyl)-N'-hydroxycarbamimidoyl)-1,2,5-oxadiazol-3-yl)thio)ethyl)phosphonic acid (504 mg, 0.685 mmol) in NMP (2285 µl) was heated to 45° C. for 10 min. A solution of chloromethyl isopropyl carbonate (837 mg, 5.48 mmol) and TEA (287 µl, 2.056 mmol) in 1 ml of NMP was added to the previous solution dropwise and the reaction continued to be heated at 45° C. At completion, the reaction was cooled to ambient and diluted with 1 ml of DMSO and the material was purified by reverse phase chromatography (Biotage 30 g, C-18 SNAP cartridge, 5%-90% ACN in water (0.1% TFA) to afford the title compound. MS: 557.2 (M+1). $^1$HNMR (500 MHz, DMSO-$d_6$): δ 11.75 (s, 1H), 8.98 (s, 1H), 7.16 (t, J=8.5 Hz, 1H), 7.08 (dd, J=5.7, 2.5 Hz, 1H), 6.69 (m, 1H), 5.54 (d, J=13.1 Hz, 2H), 4.80 (dt, J=12.4, 6.1 Hz, 2H), 3.30 (m, 2H), 2.43 (m, 2H), 1.22 (dq, J=10.7, 4.5 Hz, 6H).

Example 10: (Z)-(((2-((4-(N-(3-bromo-4-fluorophenyl)-N'-hydroxycarbamimidoyl)-1,2,5-oxadiazol-3-yl)thio)ethyl)phosphoryl)bis(oxy))bis(methylene) diisopropyl bis(carbonate)

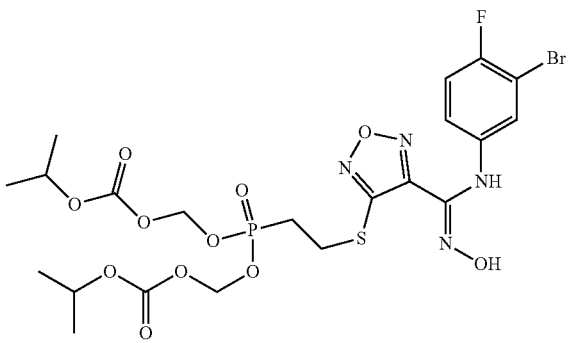 [SMILES: CC(C)OC(=O)OCOP(=O)(CCSc1nonc1/C(=N/O)Nc1ccc(F)c(Br)c1)OCOC(=O)OC(C)C]

A solution of (Z)-(2-((4-(N-(3-bromo-4-fluorophenyl)-N'-hydroxycarbamimidoyl)-1,2,5-oxadiazol-3-yl)thio)ethyl) phosphonic acid (112 mg, 0.152 mmol) and tetrabutyl ammonium bromide (49.1 mg, 0.152 mmol) in NMP (508 µl) was stirred at 45° C. for 10 min. A solution of chloromethyl isopropyl carbonate (186 mg, 1.219 mmol) and TEA (63.7 µl, 0.457 mmol) in NMP (508 µl) was added dropwise and the reaction was continually heated at 45° C. At completion, the reaction was cooled to ambient and diluted with 0.5 ml of DMSO and the material was purified by reverse phase chromatography (Biotage 30 g, C-18 SNAP cartridge, 5%-90% ACN in water (0.1% TFA) to afford the title compound. MS: 673 (M+1). $^1$HNMR (500 MHz, DMSO-$d_6$): d 11.77 (s, 1H), 8.98 (s, 1H), 7.17 (t, J=8.7 Hz, 1H), 7.09 (dd, J=6.1, 2.7 Hz, 1H), 6.76 (m, 1H), 5.61 (ddd, J=14.5, 13.0, 5.8 Hz, 4H), 4.82 (p, J=6.3 Hz, 2H), 3.30 (m, 2H), 2.43 (m, 2H), 1.23 (t, J=5.8 Hz, 12H)

Example 11: (Z)—N-(2-((4-(N-(3-Bromo-4-fluorophenyl)-N'-hydroxycarbamimidoyl)-1,2,5-oxadiazol-3-yl)thio)ethyl)acetamide

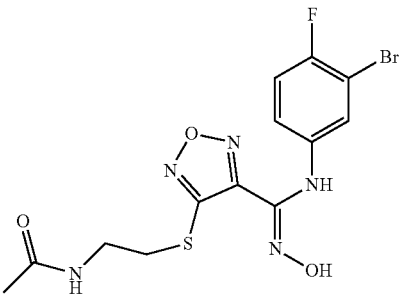 [SMILES: CC(=O)NCCSc1nonc1/C(=N/O)Nc1ccc(F)c(Br)c1]

Using the general methodology disclosed in Scheme 2, the compound of example 9 was prepared. MS: 418.0 (M+1).

Example 12: Methyl(Z)-(2-((4-(N-(3-bromo-4-fluorophenyl)-N'-hydroxycarbamimidoyl)-1,2,5-thiadiazol-3-yl)thio)ethyl)carbamate

Step 1. 4-((2-((Tert-butoxycarbonyl)amino)ethyl)thio)-1,2,5-thiadiazole-3-carboxylic acid

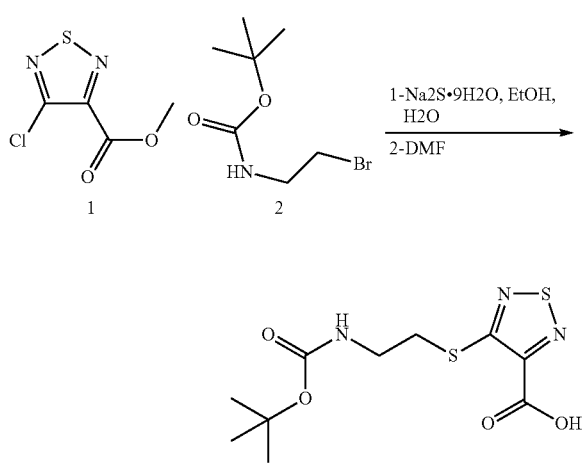

Sodium sulfide monohydrate (1614 mg, 6.72 mmol) in water (5.0 ml) was added to a solution of methyl 4-chloro-1,2,5-thiadiazole-3-carboxylate (1200.0 mg, 6.72 mmol) in ethanol (5.0 ml) and the mixture was refluxed for 24 h. The mixture was concentrated in vacuo and a solution of tert-butyl (2-bromoethyl) carbamate (4517 mg, 20.16 mmol) in DMF (5.0 ml) was added. The reaction mixture was stirred at ambient temperature for 16 hr, poured into dilute hydrochloric acid and extracted with ethyl acetate three times. The combined organic layers were dried over sodium sulfate, filtered and concentrated under vacuum. The residue was purified via flash chromatography on silica gel (Biotage silica column, 2 to 20% MeOH/DCM linear gradient). Fractions containing the product concentrated in vacuo to afford the title compound. MS (ESI) calc'd for C10H15N3O4S2 [M+H]+, 306; found, 206.

Step 2. Tert-butyl (2-((4-((3-bromo-4-fluorophenyl)carbamoyl)-1,2,5-thiadiazol-3-yl)thio)ethyl)carbamate

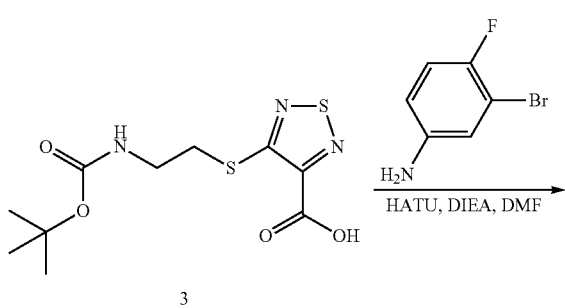

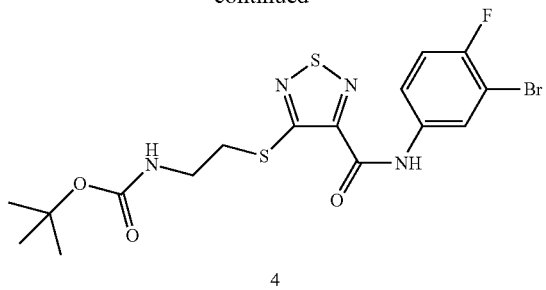

A 20 mL vial was charged with a magnetic stir bar, 4-((2-((tert-butoxycarbonyl)amino)ethyl)thio)-1,2,5-thiadiazole-3-carboxylic acid (400.0 mg, 1.310 mmol) in DMF (5.0 ml) was added with stirring HATU (598 mg, 1.572 mmol) and the reaction was stirred for a few minutes then was added 3-bromo-4-fluoroaniline (249 mg, 1.310 mmol) and DIEA (1.373 ml, 7.86 mmol). The reaction was stirred for 4 hr at room temperature. The solvent was removed by lyophilization and the crude material was purified in silica gel column chromatography 12 to 100 EtOAc/Hex to afford the title compound. MS [M+H]+, 477.

Step 3. Methyl(Z)-(2-((4-(N-(3-bromo-4-fluorophenyl)-N'-hydroxycarbamimidoyl)-1,2,5-thiadiazol-3-yl)thio)ethyl)carbamate

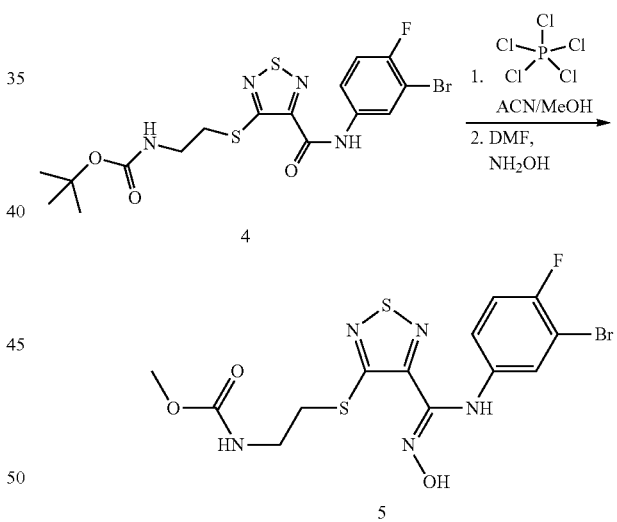

To a solution of tert-butyl (2-((4-((3-bromo-4-fluorophenyl)carbamoyl)-1,2,5-thiadiazol-3-yl)thio)ethyl)carbamate (275.0 mg, 0.729 mmol) in acetonitrile (10.0 ml) was added PCl5 (455 mg, 2.187 mmol) at 25° C. The resulting mixture was stirred at 80° C. for 15 hr. The reaction mixture was quenched with MeOH and the solvent was removed, the mixture was diluted with CH2Cl2 and washed with 1 N NaHCO3, water, and brine. The organic layer was concentrated under reduced pressure and the crude was taken to next step.

The crude was dissolved in DMF (5.0 ml) then added sodium acetate (149 mg, 1.822 mmol) and hydroxylamine hydrochloride (127 mg, 1.822 mmol). The reaction was stirred at 70° C. for 4 hr, and then cooled to room temperature. The organic layer was concentrated under reduced pressure and the residue was purified by mass-directed reverse phase chromatography (MeCN/water gradient with 0.1% TFA modifier) to afford the title compound. MS [M+H]+, 450. $^1$H NMR (600 MHz, DMSO-d$_6$) δ 11.34 (s, 1H), 8.88 (s, 1H), 7.37 (s, 1H), 7.09 (s, 1H), 6.97 (s, 1H), 6.50 (s, 1H), 3.51 (s, 3H), 3.33 (s, 2H), 3.27 (s, 2H).

Using the general methodology disclosed in the preceding schemes, examples and general knowledge in organic synthesis, compounds in the following table were prepared.

| Ex. # | Structure | Chemical Name | Mass [M + H]+ |
|---|---|---|---|
| 13 | 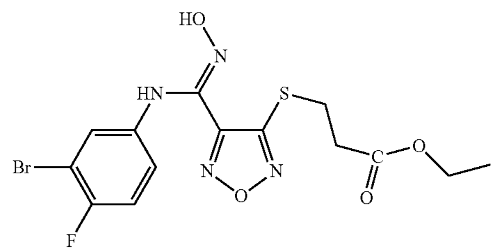 [SMILES: CCOC(=O)CCSc1nonc1/C(=N/O)Nc1ccc(F)c(Br)c1] | Ethyl (Z)-3-((4-(N-(3-bromo-4-fluorophenyl)-N'-hydroxycarbamimidoyl)-1,2,5-oxadiazol-3-yl)thio)propanoate | Calc'd 433.0, found 433.0 |
| 14 | 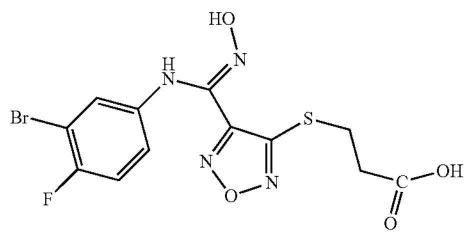 [SMILES: O=C(O)CCSc1nonc1/C(=N/O)Nc1ccc(F)c(Br)c1] | (Z)-3-((4-(N-(3-bromo-4-fluorophenyl)-N'-hydroxycarbamimidoyl)-1,2,5-oxadiazol-3-yl)thio)propanoic acid | Calc'd 405.0, found 404.9 |
| 15 | 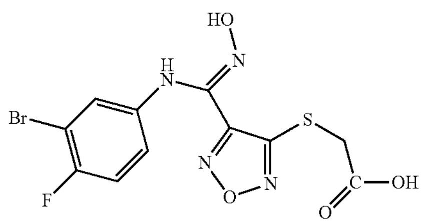 [SMILES: O=C(O)CSc1nonc1/C(=N/O)Nc1ccc(F)c(Br)c1] | (Z)-2-((4-(N-(3-bromo-4-fluorophenyl)-N'-hydroxycarbamimidoyl)-1,2,5-oxadiazol-3-yl)thio)acetic acid | Calc'd 391.0, found 390.9 |
| 16 | 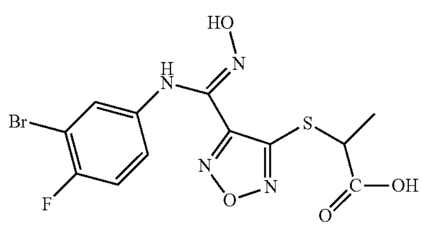 [SMILES: CC(Sc1nonc1/C(=N/O)Nc1ccc(F)c(Br)c1)C(=O)O] | (Z)-2-((4-(N-(3-bromo-4-fluorophenyl)-N'-hydroxycarbamimidoyl)-1,2,5-oxadiazol-3-yl)thio)propanoic acid | Calc'd 405.0, found 404.9 |
| 17 | 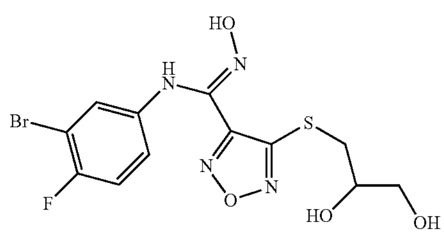 [SMILES: OCC(O)CSc1nonc1/C(=N/O)Nc1ccc(F)c(Br)c1] | (Z)-N-(3-bromo-4-fluorophenyl)-4-((2,3-dihydroxypropyl)thio)-N'-hydroxy-1,2,5-oxadiazole-3-carboximidamide | Calc'd 407.0, found 407.0 |
| 18 | 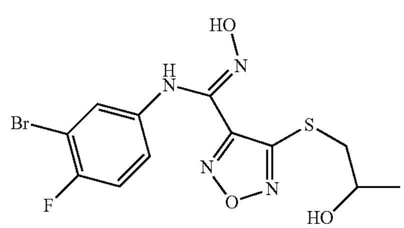 [SMILES: CC(O)CSc1nonc1/C(=N/O)Nc1ccc(F)c(Br)c1] | (Z)-N-(3-bromo-4-fluorophenyl)-N'-hydroxy-4-((2-hydroxypropyl)thio)-1,2,5-oxadiazole-3-carboximidamide | Calc'd 391.0, found 391.0 |

| Ex. # | Structure | Chemical Name | Mass [M + H]+ |
|---|---|---|---|
| 19 | 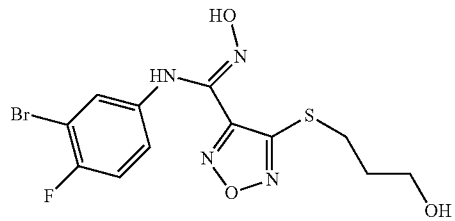 [SMILES: OCCCSc1nonc1/C(=N/O)Nc1ccc(F)c(Br)c1] | (Z)-N-(3-bromo-4-fluorophenyl)-N'-hydroxy-4-((3-hydroxypropyl)thio)-1,2,5-oxadiazole-3-carboximidamide | Calc'd 391.0, found 391.0 |
| 20 | 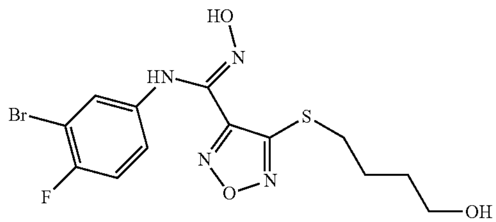 [SMILES: OCCCCSc1nonc1/C(=N/O)Nc1ccc(F)c(Br)c1] | (Z)-N-(3-bromo-4-fluorophenyl)-N'-hydroxy-4-((4-hydroxybutyl)thio)-1,2,5-oxadiazole-3-carboximidamide | Calc'd 405.0, found 405.0 |
| 21 | 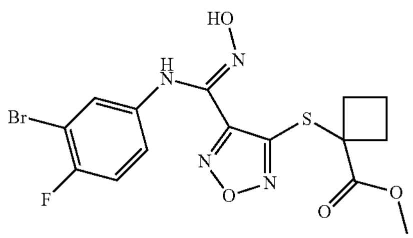 [SMILES: COC(=O)C1(Sc2nonc2/C(=N/O)Nc2ccc(F)c(Br)c2)CCC1] | Methyl (Z)-1-((4-(N-(3-bromo-4-fluorophenyl)-N'-hydroxycarbamimidoyl)-1,2,5-oxadiazol-3-yl)thio)cyclobutane-1-carboxylate | Calc'd 445.0, found 445.0 |
| 22 | 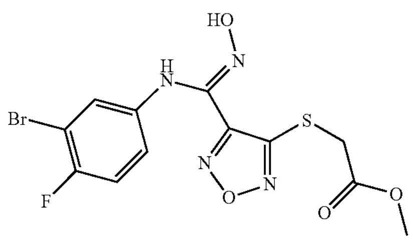 [SMILES: COC(=O)CSc1nonc1/C(=N/O)Nc1ccc(F)c(Br)c1] | Methyl (Z)-2-((4-(N-(3-bromo-4-fluorophenyl)-N'-hydroxycarbamimidoyl)-1,2,5-oxadiazol-3-yl)thio)acetate | Calc'd 405.0, found 404.9 |
| 23 | 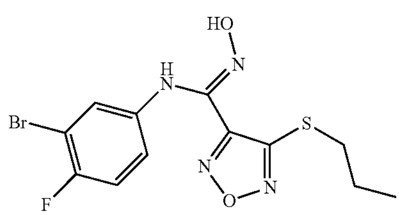 [SMILES: CCCSc1nonc1/C(=N/O)Nc1ccc(F)c(Br)c1] | (Z)-N-(3-bromo-4-fluorophenyl)-N'-hydroxy-4-(propylthio)-1,2,5-oxadiazole-3-carboximidamide | Calc'd 375.0, found 375.0 |
| 24 | 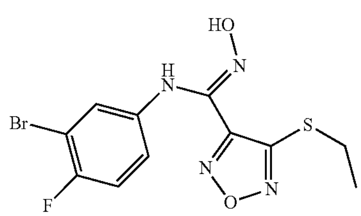 [SMILES: CCSc1nonc1/C(=N/O)Nc1ccc(F)c(Br)c1] | (Z)-N-(3-bromo-4-fluorophenyl)-4-(ethylthio)-N'-hydroxy-1,2,5-oxadiazole-3-carboximidamide | Calc'd 361.0, found 361.0 |
| 25 | 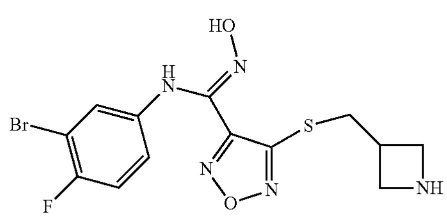 [SMILES: O/N=C(\Nc1ccc(F)c(Br)c1)c1nonc1SCC1CNC1] | (Z)-4-((azetidin-3-ylmethyl)thio)-N-(3-bromo-4-fluorophenyl)-N'-hydroxy-1,2,5-oxadiazole-3-carboximidamide | Calc'd 402.0, found 402.0 |

| Ex. # | Structure | Chemical Name | Mass [M + H]+ |
|---|---|---|---|
| 26 | 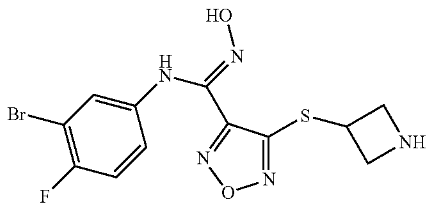 [SMILES: O/N=C(\Nc1ccc(F)c(Br)c1)c1nonc1SC1CNC1] | (Z)-4-(azetidin-3-ylthio)-N-(3-bromo-4-fluorophenyl)-N'-hydroxy-1,2,5-oxadiazole-3-carboximidamide | Calc'd 388.0, found 388.0 |

Example 27: 2-((4-(N-(3-bromo-4-fluorophenyl)-N'-hydroxycarbamimidoyl)-1,2,5-oxadiazol-3-yl)thio)-N-(1-hydroxy-2-methylpropan-2-yl)acetamide Step 1: N-(1-hydroxy-2-methylpropan-2-yl)-2-mercaptoacetamide

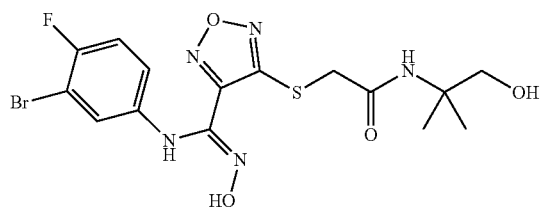 [SMILES: CC(C)(CO)NC(=O)CSc1nonc1/C(=N/O)Nc1ccc(F)c(Br)c1]

A mixture of methyl 2-mercaptoacetate (2 mL, 22.4 mmol) and 2-amino-2-methylpropan-1-ol (2.99 g, 33.5 mmol) was stirred at 26° C. for 15 h, then concentrated in vacuo to give the crude title compound (3.65 g) as an oil, which was used in the next step without further purification. $^1$H NMR (400 MHz, CD$_3$OD) δ 3.54 (s, 2H), 3.09 (s, 2H), 1.25 (s, 6H)

Step 2: 2-((4-(N-(3-bromo-4-fluorophenyl)-N'-hydroxycarbamimidoyl)-1,2,5-oxadiazol-3-yl)thio)-N-(1-hydroxy-2-methylpropan-2-yl)acetamide

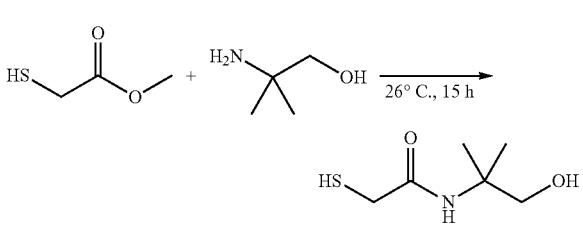

To a solution of N-(3-bromo-4-fluorophenyl)-N'-hydroxy-4-nitro-1,2,5-oxadiazole-3-carboximidamide (106 mg, 0.306 mmol) in MeCN (1 mL) were added TEA (0.1 mL, 0.717 mmol) and N-(1-hydroxy-2-methylpropan-2-yl)-2-mercaptoacetamide (50 mg, 0.306 mmol) drop-wise at room temperature. The reaction mixture was stirred at 26° C. for 1 h, then concentrated in vacuo. The residue was purified by prep-HPLC to afford the title compound (28 mg, 0.059 mmol) as a solid. $^1$H NMR (400 MHz, CD$_3$OD) δ 7.12 (dd, J=6.4, 2.4 Hz, 1H), 7.07 (t, J=8.8 Hz, 1H), 6.78 (dd, J=8.0, 2.8 Hz, 1H), 3.93 (s, 2H), 3.59 (s, 2H), 1.30 (s, 6H). ESI MS m/z 463.9 [M+H]$^+$ Example 28: 2-((4-(N-(3-bromo-4-fluorophenyl)-N'-hydroxycarbamimidoyl)-1,2,5-oxadiazol-3-yl)thio)-N-(2-hydroxy-2-methylpropyl)acetamide

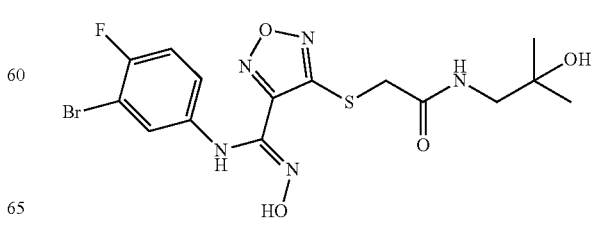

Step 1:
N-(2-hydroxy-2-methylpropyl)-2-mercaptoacetamide

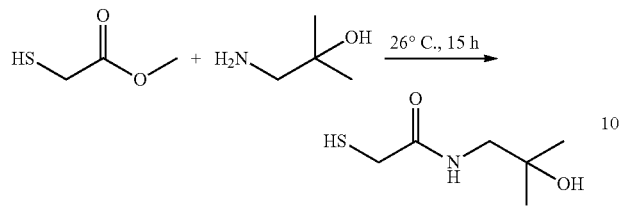

A mixture of methyl 2-mercaptoacetate (1.1 mL, 12.30 mmol) and 1-amino-2-methylpropan-2-ol (1.096 g, 12.30 mmol) was stirred at 26° C. for 15 h, then concentrated in vacuo to give the crude title compound (1.85 g, 11.33 mmol) as an oil, which was used in the next step without further purification. $^1$H NMR (400 MHz, CD$_3$OD) δ 3.35 (s, 2H), 3.21 (s, 2H), 1.19 (s, 6H)

Step 2. 2-((4-(N-(3-bromo-4-fluorophenyl)-N'-hydroxycarbamimidoyl)-1,2,5-oxadiazol-3-yl)thio)-N-(2-hydroxy-2-methylpropyl)acetamide

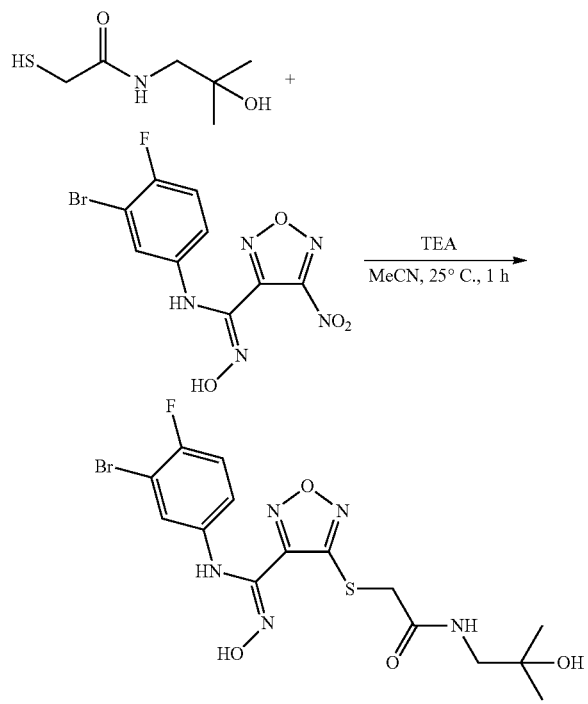

To a solution of N-(3-bromo-4-fluorophenyl)-N'-hydroxy-4-nitro-1,2,5-oxadiazole-3-carboximidamide (100 mg, 0.289 mmol) in acetonitrile (5 mL) were added N-(2-hydroxy-2-methylpropyl)-2-mercaptoacetamide (50 mg, 0.306 mmol) and Et$_3$N (0.1 mL, 0.717 mmol). The reaction was stirred at 25° C. for 1 h, and concentrated in vacuo. The residue was purified by HPLC on a GILSON 281 instrument fitted with a phenomenex Synergi C18 (150*30 mm*4 um) using water (0.225% formic acid) and acetonitrile as eluent. The solvent was lyophilized to give the title compound (40.24 mg, 0.086 mmol) as a solid. $^1$H NMR (400 MHz, CD$_3$OD) δ 7.11 (dd, J=6.0, 2.8 Hz, 1H), 7.03 (t, J=8.8 Hz, 1H), 6.78 (ddd, J=8.8, 4.0, 2.8 Hz, 1H), 3.97 (s, 2H), 3.23 (s, 2H), 1.15 (s, 6H). ESI MS m/z 462.1 [M+H]$^+$

Examples 29 and 30: (R)/(S)—N-(3-bromo-4-fluorophenyl)-4-((2,3-dihydroxy-3-methylbutyl)thio)-N'-hydroxy-1,2,5-oxadiazole-3-carboximidamide

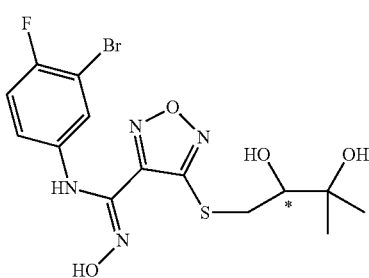 [SMILES: CC(C)(O)C(O)CSc1nonc1/C(=N/O)Nc1ccc(F)c(Br)c1]

Step 1: N-(3-bromo-4-fluorophenyl)-4-((2,3-dihydroxy-3-methylbutyl)thio)-N'-hydroxy-1,2,5-oxadiazole-3-carboximidamide

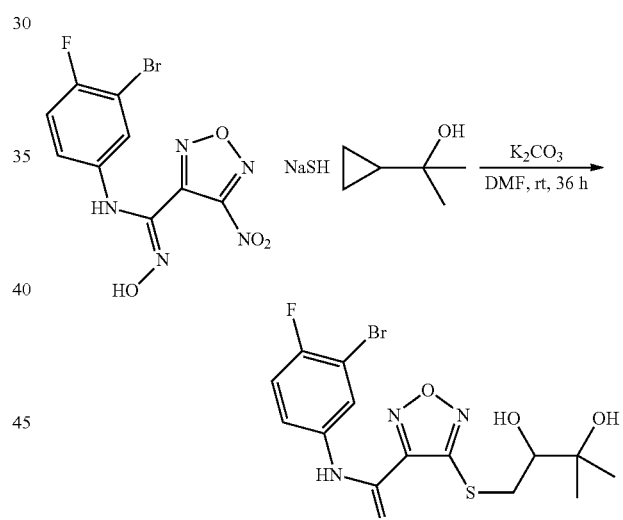

To a solution of N-(3-bromo-4-fluorophenyl)-N'-hydroxy-4-nitro-1,2,5-oxadiazole-3-carboximidamide (120 mg, 0.347 mmol) in DMF (8 mL) at 25° C. was added NaSH (30 mg, 0.535 mmol). The mixture was stirred at 25° C. for 30 min before K$_2$CO$_3$ (120 mg, 0.867 mmol) and 2-(oxiran-2-yl)propan-2-ol (40 mg, 0.392 mmol) were added. The mixture was stirred at 25° C. for 36 h. The insoluble salts were removed by filtration and the filtrate was purified by reverse phase HPLC on a GILSON 281 instrument fitted with a Phenomenex Synergi C18 (250*21.2 mm*4 m) using water (0.2% formic acid) and acetonitrile as eluents (Mobile phase A water (0.2% Formic acid), Mobile phase B acetonitrile, Detective wavelength: 220 nm), followed by concentration in vacuo to afford the title compound (30 mg, 0.065 mmol) as a solid. ESI MS m/z: 436.9 [M+H]$^+$ Step 2: N-(3-bromo-4-fluorophenyl)-4-((2,3-dihydroxy-3-methylbutyl)thio)-N'-hydroxy-1,2,5-oxadiazole-3-carboximidamide

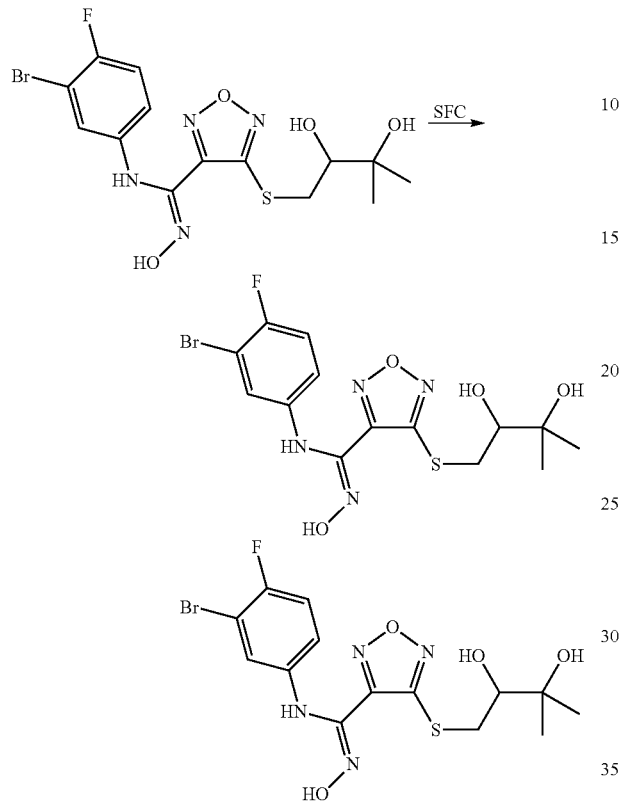

After SFC separation, two enantiomers were obtained as solids.

Column: ChiralPak AD-3 150×4.6 mm I.D., 3 um. Column temperature: 40° C.

Mobile phase: A: CO$_2$; B: Ethanol (0.05% DEA); Flow rate: 2.5 mL/min

Gradient: from 5% to 40% of B in 5.5 min and hold 40% for 3 min, then 5% of B for 1.5 min $^1$H NMR_P1 (400 MHz, CD3OD) δ 7.06-7.11 (m, 1H), 7.00-7.06 (m, 1H), 6.73-6.80 (m, 1H), 3.60-3.67 (m, 2H), 3.00-3.11 (m, 1H), 1.22 (d, J=8.16 Hz, 6H). ESI MS m/z: 436.9 [M+H]$^+$ Example 31: N-(3-bromo-4-fluorophenyl)-N'-hydroxy-4-((2-((N-(2-methoxyethyl) sulfamoyl)-ethyl)thio)-1,2,5-oxadiazole-3-carboximidamide

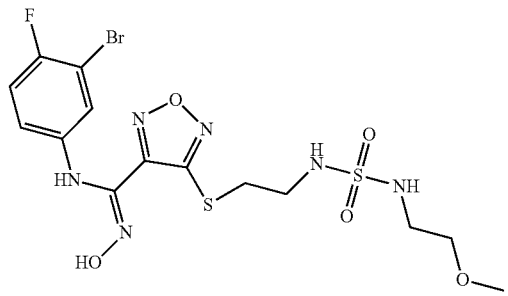 [SMILES: COCCNS(=O)(=O)NCCSc1nonc1/C(=N/O)Nc1ccc(F)c(Br)c1]

Step 1: Tert-butyl(2-((4-(4-(3-bromo-4-fluorophenyl)-5-oxo-4,5-dihydro-1,2,4-oxadiazol-3-yl)-1,2,5-oxadiazol-3-yl)thio)ethyl)carbamate

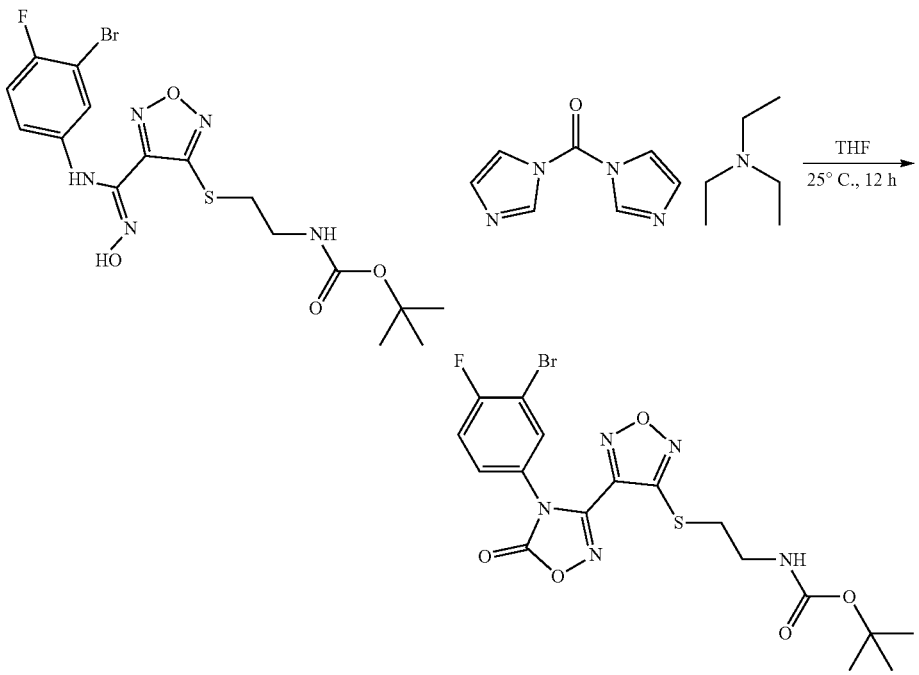

To a solution of tert-butyl (2-((4-(N-(3-bromo-4-fluorophenyl)-N'-hydroxycarbamimid-oyl)-1,2,5-oxadiazol-3-yl)thio)ethyl)carbamate (325 mg, 0.546 mmol) in THF (10 mL) was added CDI (177 mg, 1.092 mmol). The reaction mixture was stirred at 25° C. for 12 h, and concentrated in vacuo. The residue was purified by pre-TLC (SiO$_2$, DCM:MeOH=3:1 as eluent) to give the title compound (332 mg, 0.496 mmol) as a solid. $^1$H NMR (400 MHz, CDCl$_3$) δ 7.65 (dd, J=2.5, 5.6 Hz, 1H), 7.33-7.38 (m, 1H), 7.30 (d, J=7.9 Hz, 1H), 3.51-3.56 (m, 2H), 3.38-3.42 (m, 2H), 1.43 (s, 9H).

Step 2: 3-(4-((2-Aminoethyl)thio)-1,2,5-oxadiazol-3-yl)-4-(3-bromo-4-fluorophenyl)-1,2,4-oxadiazol-5(4H)-one, HCl

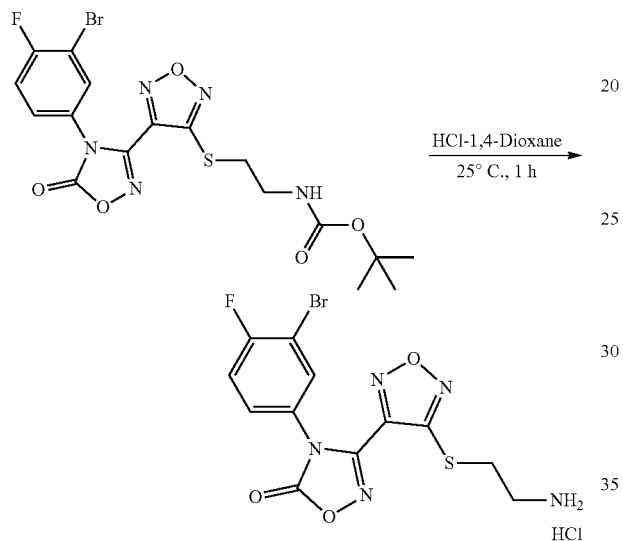

To a solution of tert-butyl (2-((4-(4-(3-bromo-4-fluorophenyl)-5-oxo-4,5-dihydro-1,2,4-oxadiazol-3-yl)-1,2,5-oxadiazol-3-yl)thio)ethyl)carbamate (332 mg, 0.496 mmol) in 1,4-dioxane (5 mL) was added 4N HCl-dioxane (1.4 mL, 5.60 mmol). The reaction mixture was stirred at 25° C. for 1 h, concentrated in vacuo to give the title compound. ESI MS m/z: 404.0 [M+H]$^+$ Step 3: (2-Methoxyethyl)sulfamoyl chloride

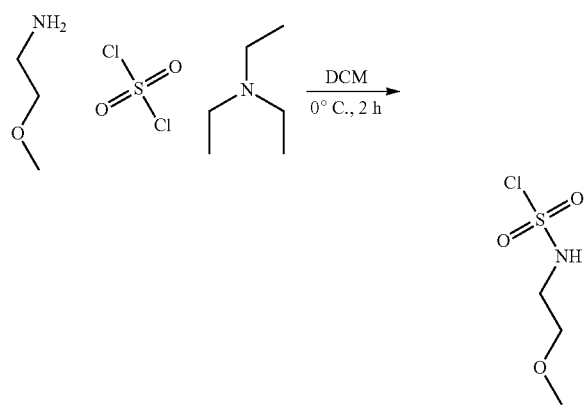

A premixed solution of 2-methoxyethanamine (1 g, 13.31 mmol) and triethylamine (2.8 mL, 20.09 mmol) was added dropwise to a solution of sulfuryl dichloride (1.6 mL, 19.80 mmol) in DCM (20 mL) at 0° C. under N$_2$ atmosphere. The reaction mixture was continually stirred at 0° C. for 2 h, then poured into ice and extracted with DCM (3*20 mL). The combined organic extracts were washed with brine (20 ml), the organic layer was dried over anhydrous Na$_2$SO$_4$, filtered and the filtrate was concentrated under vacuum to afford the title compound (1.1 g, 5.07 mmol) as an oil, which was used without further purification in the next step. $^1$H NMR (400 MHz, DMSO-d6) δ 10.10 (br s, 1H), 3.52-3.57 (m, 2H), 3.24 (s, 3H), 3.16 (t, J=5.67 Hz, 2H).

Step 4: N-(3-bromo-4-fluorophenyl)-N'-hydroxy-4-((2-((N-(2-methoxyethyl) sulfamoyl)amino)ethyl)thio)-1,2,5-oxadiazole-3-yl)-1,2,4-oxadiazol-5(4H)-one

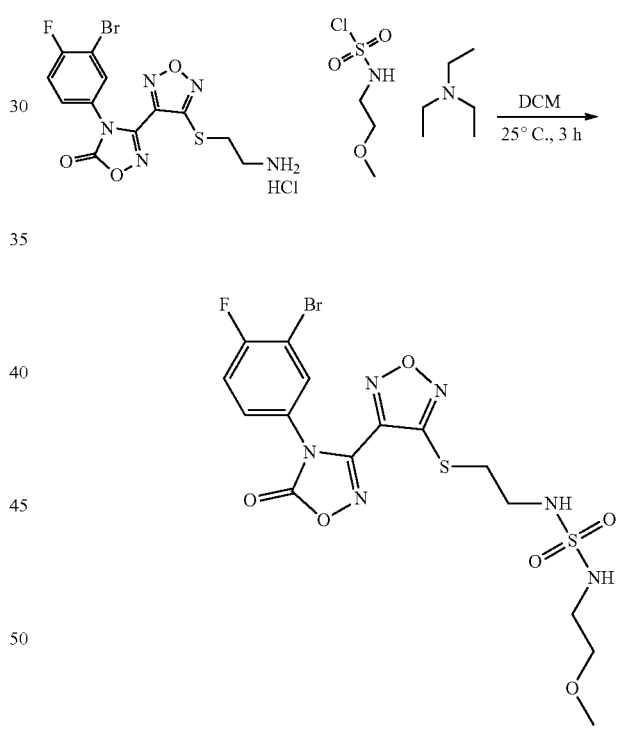

To a solution of 3-(4-((2-aminoethyl)thio)-1,2,5-oxadiazol-3-yl)-4-(3-bromo-4-fluorophenyl)-1,2,4-oxadiazol-5(4H)-one HCL salt (332 mg, 0.413 mmol) in DCM (15 mL) was added Et$_3$N (4.0 mL), followed by addition of (2-methoxyethyl)sulfamoyl chloride (960 mg, 4.42 mmol) dropwise at 0° C. After 3 h at 25° C., the reaction was quenched by adding MeOH (3 mL), then concentrated in vacuo to give the crude title compound as a yellow solid which was used in the next step without further purification. ESI MS m/z: 539.0 [M+H]$^+$ Step 5: N-(3-bromo-4-fluorophenyl)-N'-hydroxy-4-((2-((N-(2-methoxyethyl)sulfamoyl)amino)ethyl)thio)-1,2,5-oxadiazole-3-carboximidamide

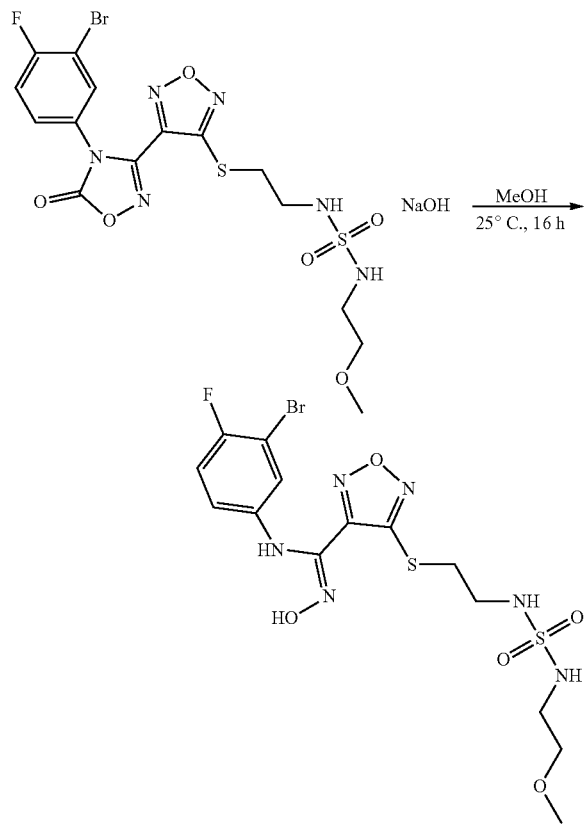

To a solution of N-(3-bromo-4-fluorophenyl)-N'-hydroxy-4-((2-((N-(2-methoxyethyl)sulfamoyl)amino)ethyl)thio)-1,2,5-oxadiazole-3-yl)-1,2,4-oxadiazol-5(4H)-one (1.433 g, 0.425 mmol) in MeOH (10 mL) was added NaOH (1.1 mL, 2.2 mmol) at 25° C. The reaction mixture was stirred for 16 h at 25° C., concentrated in vacuo, purified by prep-HPLC (Column: Agela ASB 150*25 mm*5 um; Condition: water (0.1% TFA)-ACN; Begin B/End B: 33/63; Gradient Time (min): 10; FlowRate(ml/min): 25) to give the title compound (41.45 mg, 0.079 mmol) as an oil. ¹H NMR (400 MHz, CD₃OD) δ 7.05 (dd, J=2.6, 6.0 Hz, 1H), 7.00 (t, J=8.6 Hz, 1H), 6.74 (ddd, J=2.8, 4.08, 8.82 Hz, 1H), 3.46 (t, J=5.51 Hz, 2H), 3.31-3.35 (m, 2H), 3.31 (s, 3H), 3.28 (td, J=1.6, 3.3 Hz, 2H), 3.11 (t, J=5.6 Hz, 2H). ESI MS m/z 513.1 [M+H]⁺

Example 32: (R)—N-(3-chloro-4-fluorophenyl)-4-(((1,1-dioxido-1,2,5-thiadiazolidin-3-yl)methyl)thio)-N'-hydroxy-1,2,5-oxadiazole-3-carboximidamide

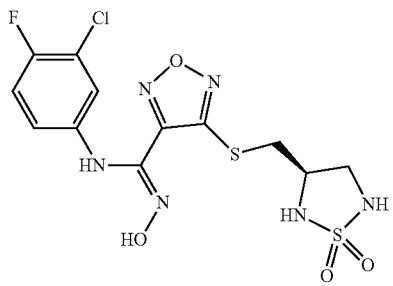 [SMILES: O=S1(=O)NC[C@H](CSc2nonc2/C(=N/O)Nc2ccc(F)c(Cl)c2)N1]

Step 1: (R)-methyl 2-((tert-butoxycarbonyl)amino)-3-((4-(N-(3-chloro-4-fluorophenyl)-N'-hydroxycarbamimidoyl)-1,2,5-oxadiazol-3-yl)thio)propanoate

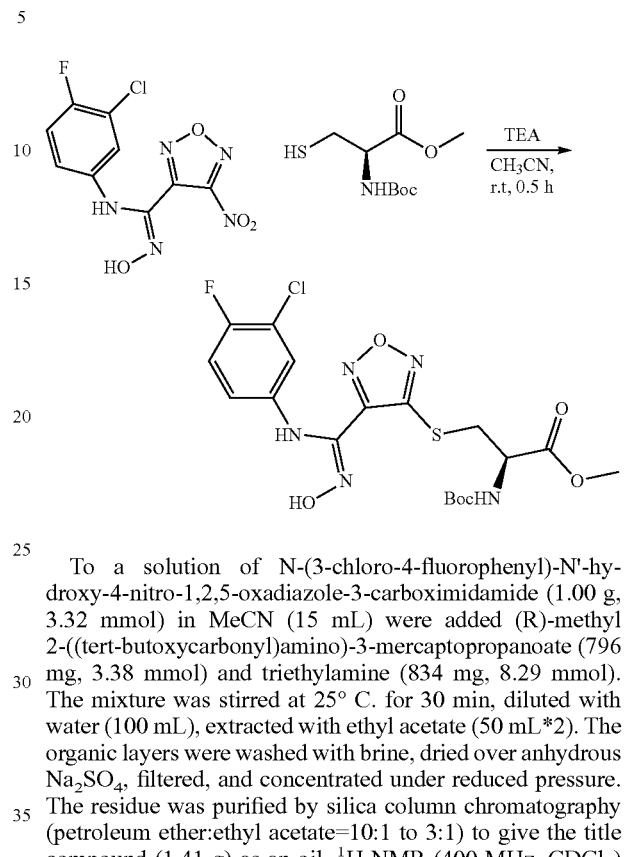

To a solution of N-(3-chloro-4-fluorophenyl)-N'-hydroxy-4-nitro-1,2,5-oxadiazole-3-carboximidamide (1.00 g, 3.32 mmol) in MeCN (15 mL) were added (R)-methyl 2-((tert-butoxycarbonyl)amino)-3-mercaptopropanoate (796 mg, 3.38 mmol) and triethylamine (834 mg, 8.29 mmol). The mixture was stirred at 25° C. for 30 min, diluted with water (100 mL), extracted with ethyl acetate (50 mL*2). The organic layers were washed with brine, dried over anhydrous Na₂SO₄, filtered, and concentrated under reduced pressure. The residue was purified by silica column chromatography (petroleum ether:ethyl acetate=10:1 to 3:1) to give the title compound (1.41 g) as an oil. ¹H NMR (400 MHz, CDCl₃) δ 6.97-7.03 (2H, m), 6.70-6.78 (1H, m), 3.72-3.77 (5H, m), 1.41 (9H, s). ESI MS m/z=490.1 [M+H]⁺

Step 2: (R)-methyl 2-amino-3-((4-(N-(3-chloro-4-fluorophenyl)-N'-hydroxycarbamimidoyl)-1,2,5-oxadiazol-3-yl)thio)propanoate hydrochloride

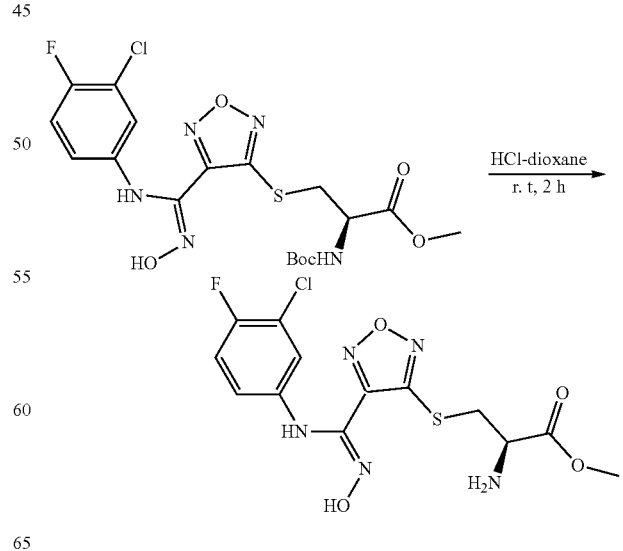

A solution of (R)-methyl 2-((tert-butoxycarbonyl)amino)-3-((4-(N-(3-chloro-4-fluorophenyl)-N'-hydroxycarbamimidoyl)-1,2,5-oxadiazol-3-yl)thio)propanoate (1.41 mg, 2.88 mmol) in 4N HCl-dioxane (10 mL) was stirred at 25° C. for 2 h. The solvent was removed under reduced pressure to give the crude title compound (1.23 g) as a solid. $^1$H NMR (400 MHz, CD$_3$OD) δ 7.10 (1H, t, J=8.9 Hz), 6.99 (1H, dd, J=6.4, 2.7 Hz), 6.79 (1H, ddd, J=8.8, 4.02, 2.8 Hz), 3.84-3.93 (5H, m). ESI MS m/z=390.0 [M+H]$^+$ Step 3: (R)-methyl 3-((4-(N-(3-chloro-4-fluorophenyl)-N'-hydroxycarbamimidoyl)-1,2,5-oxadiazol-3-yl)thio)-2-(sulfamoylamino)propanoate

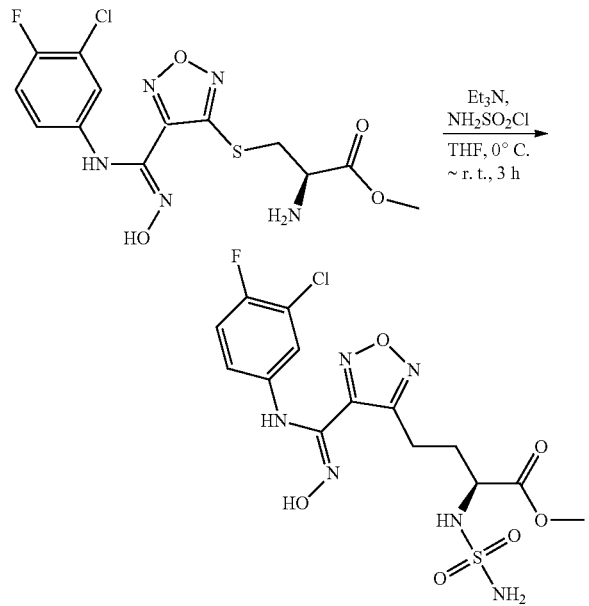

To a solution of sulfamoyl chloride (228 mg, 1.97 mmol) in THF (5 mL) were added (R)-methyl 2-amino-3-((4-(N-(3-chloro-4-fluorophenyl)-N'-hydroxycarbamimidoyl)-1,2,5-oxadiazol-3-yl)thio)propanoate hydrochloride (700 mg, 1.64 mmol) and triethylamine (415 mg, 4.11 mmol) in THF (5.0 mL) at 0° C. The mixture was stirred at 30° C. for 3 h, cooled to room temperature, diluted with water (100 mL), extracted with ethyl acetate (50 mL*2). The organic layers were washed with brine, dried over anhydrous Na$_2$SO$_4$, then concentrated under reduced pressure. The residue was purified by prep-TLC to give the title compound (420 mg) as an oil. ESI MS m/z=469.0 [M+H]$^+$ Step 4: (R)—N-(3-chloro-4-fluorophenyl)-4-(((1,1-dioxido-4-oxo-1,2,5-thiadiazolidin-3-yl)methyl)thio)-N'-hydroxy-1,2,5-oxadiazole-3-carboximidamide

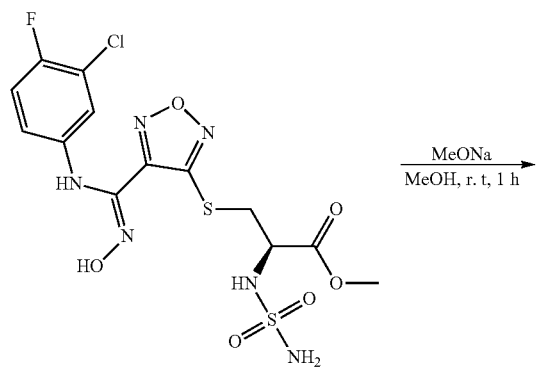

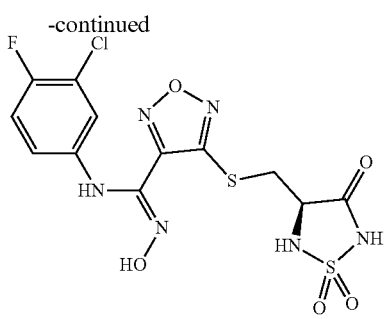

NaH (60 mg, 1.49 mmol) was added to anhydrous MeOH (3 mL), after stirring for 5 min, a clear solution was obtained. (R)-methyl 3-((4-(N-(3-chloro-4-fluorophenyl)-N'-hydroxycarbamimidoyl)-1,2,5-oxadiazol-3-yl)thio)-2-(sulfamoylamino)propanoate (200 mg, 0.43 mmol) was then added. The reaction mixture was stirred at 30° C. for 1 h, cooled to RT, diluted with water (100 mL), and extracted with ethyl acetate (50 mL*2). The organic layers were washed with brine, dried over anhydrous Na$_2$SO$_4$, then concentrated under reduced pressure to give the title compound (145 mg) as an oil. ESI MS m/z=436.9 [M+H]$^+$ Step 5: (R)—N-(3-chloro-4-fluorophenyl)-4-(((1,1-dioxido-1,2,5-thiadiazolidin-3-yl)methyl)thio)-N'-hydroxy-1,2,5-oxadiazole-3-carboximidamide

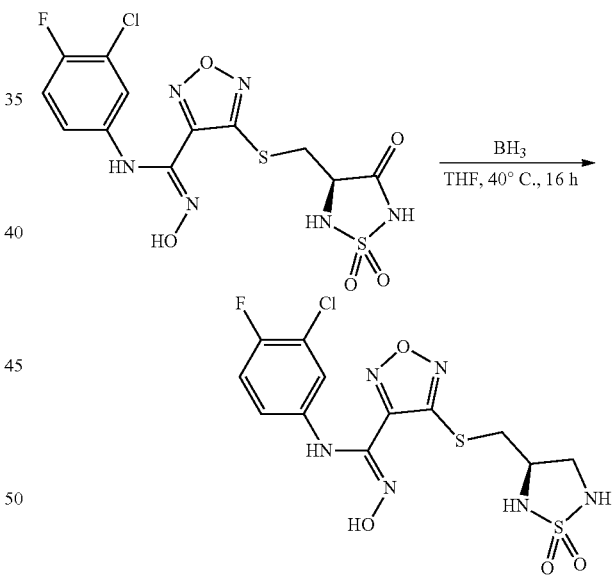

To a solution of (R)—N-(3-chloro-4-fluorophenyl)-4-(((1,1-dioxido-4-oxo-1,2,5-thiadiazolidin-3-yl)methyl)thio)-N'-hydroxy-1,2,5-oxadiazole-3-carboximidamide (145 mg, 331.94 mmol) in THF (3 mL) was added borane (1.0 mL, 1 mmol) at 0° C. The mixture was stirred at 40° C. for 32 h, cooled to room temperature, and quenched with water (100 mL). After adjusting the pH to 4 by adding 4N aqueous HCl, the mixture was extracted with ethyl acetate (50 mL*2). The organic layers were washed with brine, dried over anhydrous Na$_2$SO$_4$, then concentrated under reduced pressure. The residue was purified by reverse phase HPLC on a GILSON 281 instrument fitted with a Phenomenex Synergi C18 (250*21.2 mm*4 μm) using water (0.2% formic acid) and acetonitrile as eluents (Mobile phase A water (0.2% formic acid), Mobile phase B acetonitrile, Detective wavelength: 220 nm) followed by concentration to give the title compound (8.04 mg) as an oil. $^1$H NMR (400 MHz, CD$_3$OD) δ 7.08 (1H, t, J=8.9 Hz), 6.96 (1H, dd, J=6.4, 2.64 Hz), 6.74 (1H, ddd, J=8.8, 4.0, 2.8 Hz), 4.05-4.17 (1H, m), 3.62 (1H, dd, J=11.8, 6.6 Hz), 3.38 (2H, d, J=7.0 Hz), 3.27-3.32 (1H, m). ESI MS m/z=422.9 [M+H]$^+$ Example 33: (R)—N-(3-bromo-4-fluorophenyl)-4-(((1,1-dioxido-1,2,5-thiadiazolidin-3-yl)methyl)thio)-N'-hydroxy-1,2,5-oxadiazole-3-carboximidamide

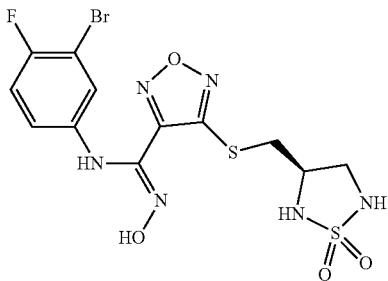 [SMILES: O=S1(=O)NC[C@H](CSc2nonc2/C(=N/O)Nc2ccc(F)c(Br)c2)N1]

Following the procedures described in Example 32, the title compound was obtained as a solid. $^1$H NMR (400 MHz, CD$_3$OD) δ 7.0-7.1 (m, 2H), 6.7 (ddd, J=8.8, 4.1, 2.8 Hz, 1H), 4.0-4.1 (m, 1H), 3.6 (dd, J=11.7, 6.6 Hz, 1H), 3.3 (d, J=7.1 Hz, 2H), 3.2 (br d, J=4.6 Hz, 1H). ESI MS m/z 468.7 [M+H]$^+$ Example 34: N-(3-bromo-4-fluorophenyl)-N'-hydroxy-4-(((5-oxo-4,5-dihydro-1H-1,2,4-triazol-3-yl)methyl)thio)-1,2,5-oxadiazole-3-carboximidamide

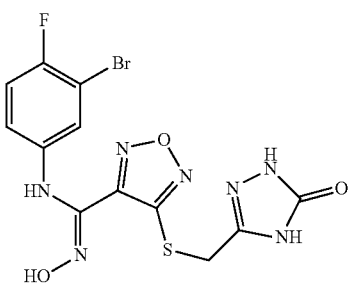 [SMILES: O=c1[nH]nc(CSc2nonc2/C(=N/O)Nc2ccc(F)c(Br)c2)[nH]1]

Step 1: 3-((benzyloxy)methyl)-1H-1,2,4-triazol-5(4H)-one

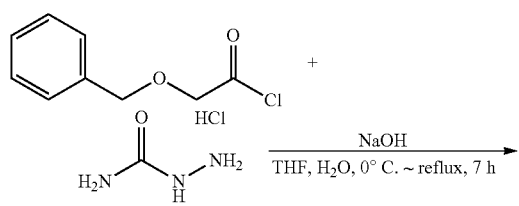

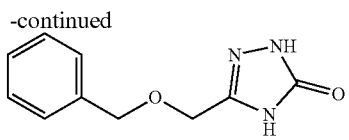

NaOH (1.44 g, 36.0 mmol) was added to a suspension of hydrazinecarboxamide hydrochloride (2.00 g, 17.93 mmol) in THF (6.5 mL) and water (1.5 mL) at 0° C. under nitrogen atmosphere. The mixture was stirred at 0° C. for 10 min before a solution of 2-(benzyloxy)acetyl chloride (3.31 g, 17.93 mmol) in THF (12 mL) was added dropwise. The reaction mixture was stirred at 0° C. for another 2 h before THF was removed in vacuo. After 2 M NaOH (8.0 mL) was added, the reaction mixture was refluxed for 5 h, cooled to room temperature and neutralized with conc. HCl (2 mL). The slurry was cooled to 0° C. for 1 h, filtered and washed with cold water to give the crude title compound (3.60 g) as a solid which was used in next step without further purification. $^1$H NMR (400 MHz, CD$_3$OD) δ 7.16-7.40 (m, 5H), 4.50 (s, 2H), 4.31 (s, 2H). ESI MS m/z 205.8 [M+H]$^+$ Step 2: 3-(hydroxymethyl)-1H-1,2,4-triazol-5(4H)-one

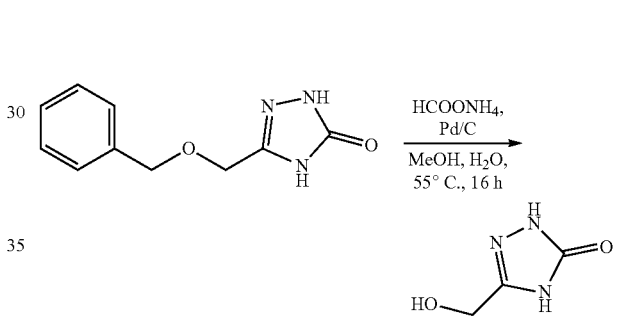

3-((Benzyloxy)methyl)-1H-1,2,4-triazol-5(4H)-one (3.10 g, 15.11 mmol) and 10% Pd—C (1.00 g, 0.940 mmol) were slurried in MeOH (30.0 mL) under a nitrogen atmosphere. A solution of ammonium formate (4.76 g, 76 mmol) in water (6.0 mL) was added and the mixture was vigorously stirred at 60° C. for 16 h. The reaction mixture was filtered through celite. The filtrate was evaporated under reduced pressure to low volume and filtered to remove the excess ammonium formate. The filtrate was concentrated in vacuo to give the crude title compound (1.70 g) as a solid which was used in the next step without further purification. $^1$H NMR (400 MHz, DMSO-d$_6$) δ 4.18 (s, 2H).

Step 3: 3-(chloromethyl)-1H-1,2,4-triazol-5(4H)-one

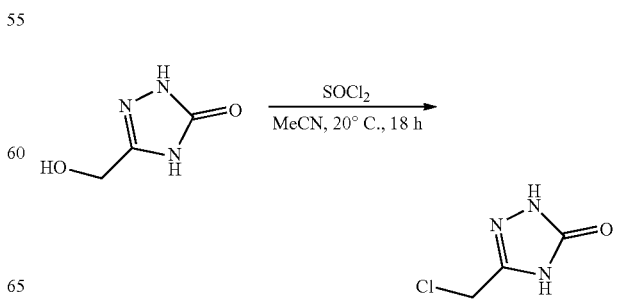

To a suspension of 3-(hydroxymethyl)-1H-1,2,4-triazol-5(4H)-one (850 mg, 7.39 mmol) in MeCN (10.0 mL) was added thionyl chloride (0.647 mL, 8.86 mmol) at 20° C. under a nitrogen atmosphere. The reaction mixture was stirred at 20° C. for 18 hours, and concentrated in vacuo. The residue was partitioned between ethyl acetate (20.0 mL) and water (10.0 mL). The organic layer was washed with saturated NaHCO$_3$ (10.0 mL, aq) and brine (10.0 mL), and concentrated in vacuo. The residue was triturated with petroleum ether (20.0 mL), filtered, and washed with petroleum ether several times to give the crude title compound (900 mg) as a solid which was used in the next step without further purification. $^1$H NMR (400 MHz, DMSO-d$_6$) δ 11.73 (br. s., 1H), 11.49-11.62 (m, 1H), 4.50 (s, 2H). ESI MS m/z 134 [M+H]$^+$ Step 4: N-(3-bromo-4-fluorophenyl)-N'-hydroxy-4-(((5-oxo-4,5-dihydro-1H-1,2,4-triazol-3-yl)methyl)thio)-1,2,5-oxadiazole-3-carboximidamide

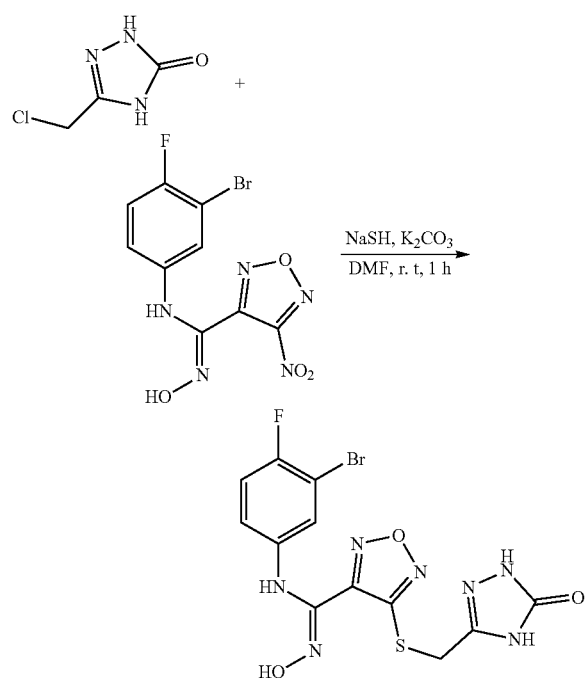

To a solution of N-(3-bromo-4-fluorophenyl)-N'-hydroxy-4-nitro-1,2,5-oxadiazole-3-carboximidamide (100 mg, 0.289 mmol) in DMF (2.0 mL) at 25° C. was added NaSH (25 mg, 0.446 mmol). The mixture was stirred at 25° C. for 30 min. Then K$_2$CO$_3$ (40 mg, 0.289 mmol) and 3-(chloromethyl)-1H-1,2,4-triazol-5(4H)-one (58 mg, 0.434 mmol) were added. The mixture was stirred at 25° C. for 30 min, diluted with sat. NaHCO$_3$ (10.0 mL, aq), and extracted with ethyl acetate (10.0 mL). The organic layer was washed with brine (5.0 mL), dried over MgSO$_4$, and concentrated. The residue was purified by reverse phase HPLC on a GILSON 281 instrument fitted with a Phenomenex Synergi C18 (250*21.2 mm*4 μm) using water (0.2% formic acid) and acetonitrile as eluents (Mobile phase A water (0.2% Formic acid), Mobile phase B acetonitrile, Detective wavelength: 220 nm) followed by freeze-drying to give the title compound (40 mg) as a solid. $^1$H NMR (400 MHz, CD3OD) δ 7.09 (dd, J=5.8, 2.5 Hz, 1H), 7.04 (t, J=8.7 Hz, 1H), 6.73-6.81 (m, 1H), 4.27 (s, 2H). ESI MS m/z 430 [M+H]$^+$ Example 35: (3-bromo-4-fluorophenyl)-N'-hydroxy-4-(((6-oxo-1,6-dihydropyridazin-3-yl)methyl)thio)-1,2,5-oxadiazole-3-carboximidamide

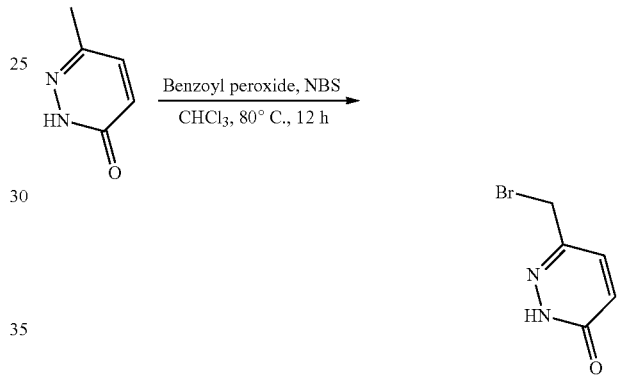

Step 1: 6-(Bromomethyl)pyridazin-3(2H)-one

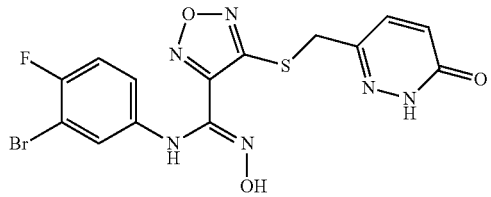 [SMILES: O=c1ccc(CSc2nonc2/C(=N/O)Nc2ccc(F)c(Br)c2)n[nH]1]

To a solution of 6-methylpyridazin-3(2H)-one (6.0 g, 54.5 mmol) in CHCl$_3$ (150 mL) were added NBS (10.67 g, 59.9 mmol) and benzoyl peroxide (6.60 g, 27.2 mmol). The mixture was stirred at 80° C. for 12 h, cooled to room temperature, and concentrated in vacuo. The residue was purified by column chromatography (petroleum ether:ethyl acetate=5:1 to 1:1) to give the title compound (4.1 g) as a solid which was used directly in the next step. $^1$H NMR (400 MHz, DMSO-d$_6$) δ 11.06 (br. s., 1H), 7.55-7.49 (m, 1H), 6.93-6.87 (m, 1H), 4.54 (s, 1H), 4.29 (s, 1H).

Step 2: N-(3-bromo-4-fluorophenyl)-N'-hydroxy-4-(((6-oxo-1,6-dihydropyridazin-3-yl)methyl)thio)-1,2,5-oxadiazole-3-carboximidamide

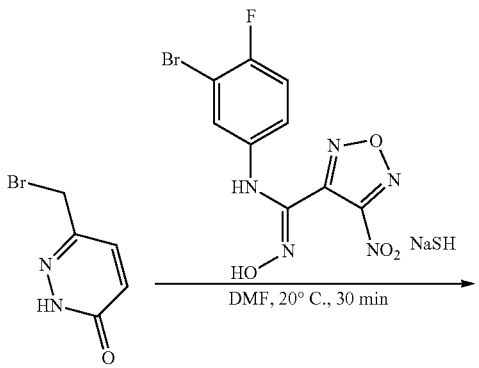

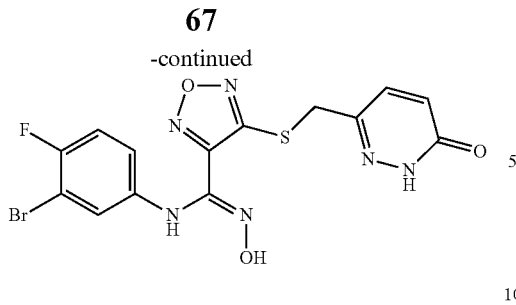

To a solution of N-(3-bromo-4-fluorophenyl)-N'-hydroxy-4-nitro-1,2,5-oxadiazole-3-carboximidamide (50 mg, 0.144 mmol) in DMF (2 mL) at 20° C. was added NaHS (12.15 mg, 0.217 mmol). The mixture was stirred at 20° C. for 30 min. Then K$_2$CO$_3$ (19.97 mg, 0.144 mmol) and 6-(bromomethyl)pyridazin-3(2H)-one (41.0 mg, 0.217 mmol) was added. The mixture was stirred at 20° C. for 30 min, diluted with sat. NaHCO$_3$ (30 mL), and extracted with ethyl acetate (50 mL). The organic layer was washed with brine, dried over MgSO$_4$, and concentrated. The residue was purified by reverse phase HPLC on a Phenomenex Synergi C18 150*30 mm*4 um using water (0.1% TFA) and acetonitrile as the eluents (Mobile phase A water ((0.1% TFA)), Mobile phase B acetonitrile, Detective wavelength: 220 nm) followed by lyophilization to give the title compound (20 mg) as a solid. $^1$H NMR (400 MHz, CD$_3$OD) δ 7.59 (d, J=9.9 Hz, 1H), 7.07-6.99 (m, 2H), 6.94 (d, J=9.7 Hz, 1H), 6.75 (td, J=3.4, 8.7 Hz, 1H), 4.36 (s, 2H). ESI MS m/z 443.0[M+H]$^+$ Example 36: N-(3-bromo-4-fluorophenyl)-N'-hydroxy-4-((2-((2-(methylamino)-3,4-dioxocyclobut-1-en-1-yl)amino)ethyl)thio)-1,2,5-oxadiazole-3-carboximidamide

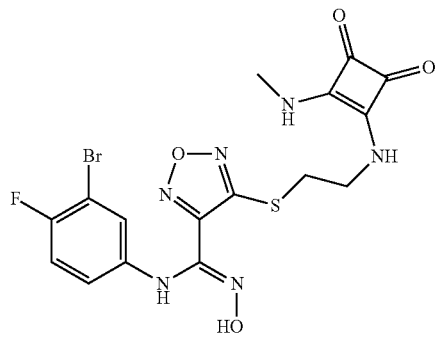 [SMILES: CNc1c(NCCSc2nonc2/C(=N/O)Nc2ccc(F)c(Br)c2)c(=O)c1=O]

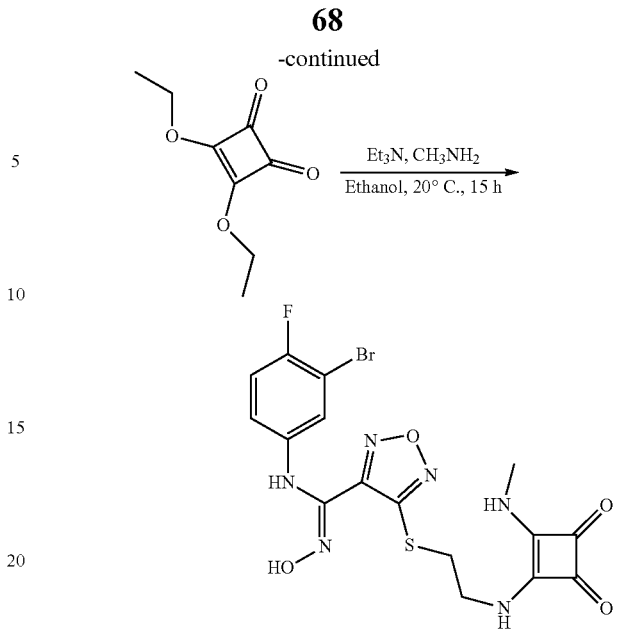

To a solution of 2-((4-(N-(3-bromo-4-fluorophenyl)-N'-hydroxycarbamimidoyl)-1,2,5-oxadiazol-3-yl)thio)ethan-1-aminium chloride (80 mg, 0.213 mmol) in ethanol (5 mL) was added triethylamine (0.148 mL, 1.063 mmol). The mixture was stirred at 20° C. for 5 min before a mixture of 3,4-diethoxycyclobut-3-ene-1,2-dione (40.5 mg, 0.238 mmol) in ethanol (5 mL) was added dropwise. After stirring at 20° C. for 3 h, methanamine (9.91 mg, 0.319 mmol) was added and the reaction mixture was stirred at 20° C. for another 15 h. The reaction mixture was concentrated in vacuo. The residue was purified by reverse phase HPLC on a GILSON 281 instrument fitted with a Phenomenex Synergi C18 (250*21.2 mm*4 μm) using water (0.225% FA)-MeCN, Mobile phase B acetonitrile, Detective wavelength: 220 nm) followed by concentration to give N-(3-bromo-4-fluorophenyl)-N'-hydroxy-4-((2-((2-(methylamino)-3,4-dioxocyclobut-1-en-1-yl)amino)ethyl)thio)-1,2,5-oxadiazole-3-carboximidamide (35 mg) as a solid. $^1$H NMR (400 MHz, CD$_3$OD) δ 7.09 (dd, J=5.8, 2.5 Hz, 1H), 7.04 (t, J=8.6 Hz, 1H), 6.70-6.76 (m, 1H), 3.96 (br. s., 2H), 3.41 (t, J=6.2 Hz, 2H), 3.23 (br. s., 3H), ESI MS m/z 487.4 [M+H]$^+$ Example 37: N-(2-((4-(N-(3-cyano-4-fluorophenyl)-N'-hydroxycarbamimidoyl)-1,2,5-oxadiazol-3-yl)thio)ethyl)acetamide

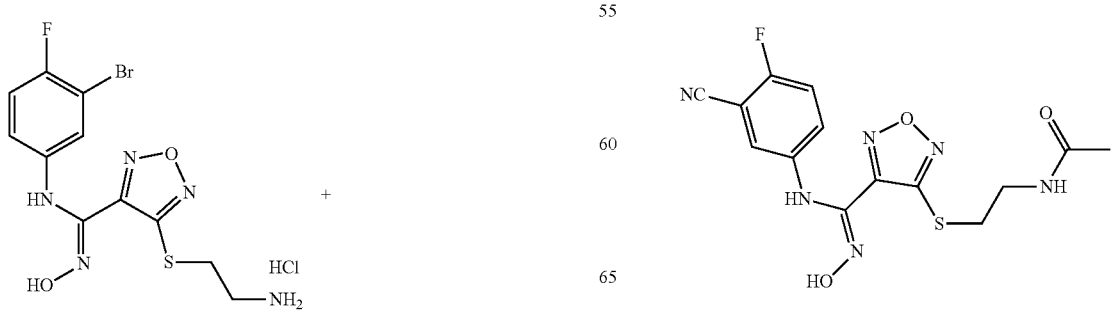

Step 1. N-(2-((4-Cyano-1,2,5-oxadiazol-3-yl)thio)ethyl)acetamide

Step 3. 4-((2-Acetamidoethyl)thio)-N-hydroxy-1,2,5-oxadiazole-3-carbimidoyl chloride

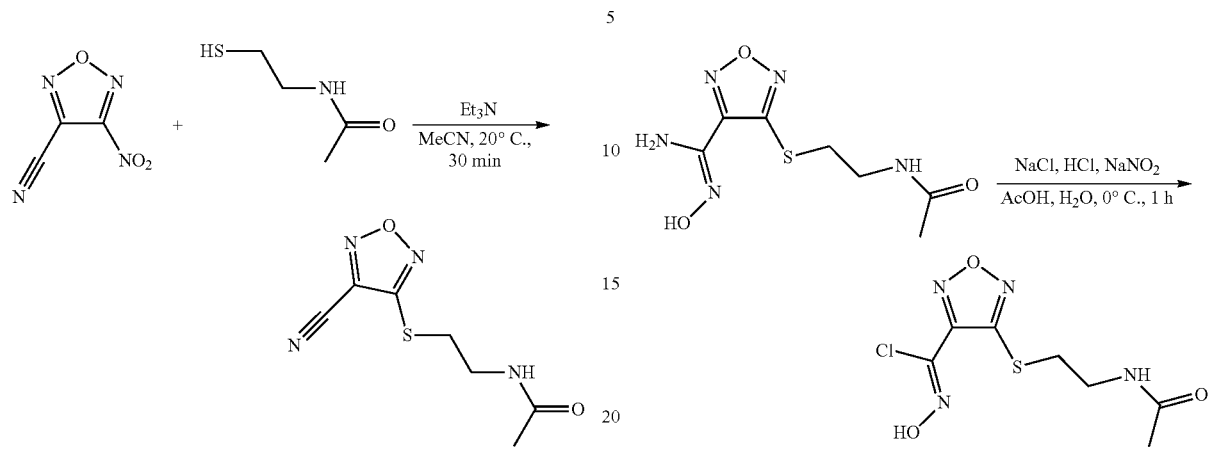

To a solution of 4-nitro-1,2,5-oxadiazole-3-carbonitrile (200 mg, 1.428 mmol) in $CH_3CN$ (5 mL) were added $Et_3N$ (289 mg, 2.86 mmol) and N-(2-mercaptoethyl)acetamide (170 mg, 1.428 mmol). The mixture was stirred at 20° C. for 30 min, concentrated under reduced pressure. The residue was purified by column chromatography ($CH_3OH/CH_2Cl_2$ 1:30-1:20 as eluent) to give the title compound (112 mg, 0.475 mmol) as a solid.

Step 2. N-(2-((4-(N-Hydroxycarbamimidoyl)-1,2,5-oxadiazol-3-yl)thio)ethyl)acetamide

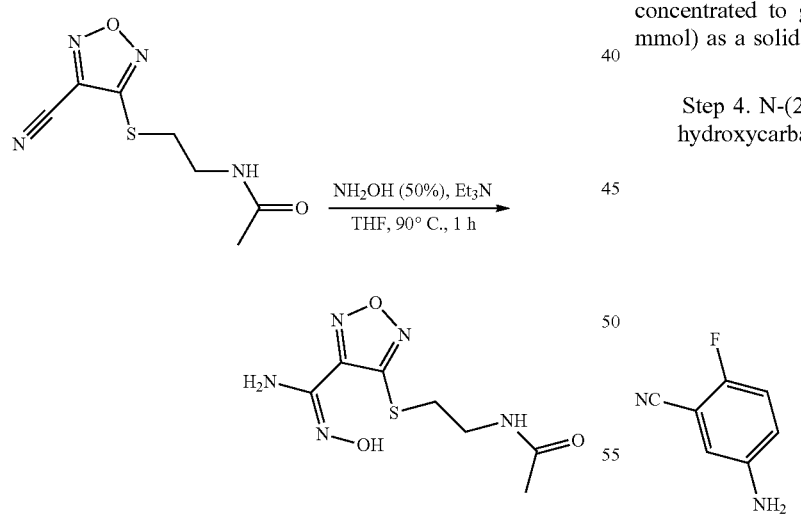

To a solution of N-(2-((4-cyano-1,2,5-oxadiazol-3-yl)thio)ethyl)acetamide (112 mg, 0.528 mmol) in THF (10 mL) were added $Et_3N$ (0.79 mL, 5.68 mmol) and 50% aqueous $NH_2OH$ (0.14 mL, 2.285 mmol). The mixture was stirred at 90° C. for 1 h, cooled to RT, concentrated under reduced pressure. The residue was purified by column chromatography ($CH_3OH/CH_2Cl_2$ 1:10 as eluent) to give the title compound (117 mg, 0.429 mmol) as a solid.

N-(2-((4-(N-hydroxycarbamimidoyl)-1,2,5-oxadiazol-3-yl)thio)ethyl)acetamide (117 mg, 0.477 mmol) was added to a mixture of water (2.0 mL), AcOH (1.0 mL) and 6 M HCl (0.24 mL, 1.440 mmol). The suspension was stirred at 45° C. until a clear solution was achieved. NaCl (84 mg, 1.431 mmol) was then added. The reaction was cooled using an ice/water/methanol bath before a solution of sodium nitrite (33 mg, 0.478 mmol) in water (10 mL) was added over 10 min while maintaining the temperature below 0° C. After stirring for another 1.5 h, the reaction mixture was allowed to warm to RT. The precipitate was collected by filtration, washed well with water (10 mL), taken in ethyl acetate (30 mL×2), treated with anhydrous sodium sulfate. This suspension was filtered through sodium sulfate and the filtrate was concentrated to give the title compound (100 mg, 0.340 mmol) as a solid.

Step 4. N-(2-((4-(N-(3-cyano-4-fluorophenyl)-N'-hydroxycarbamimidoyl)-1,2,5-oxadiazol-3-yl)thio)ethyl)acetamide

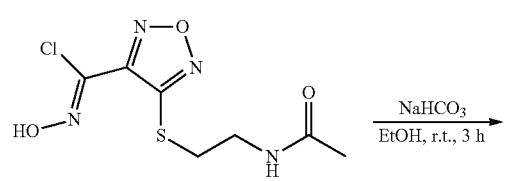

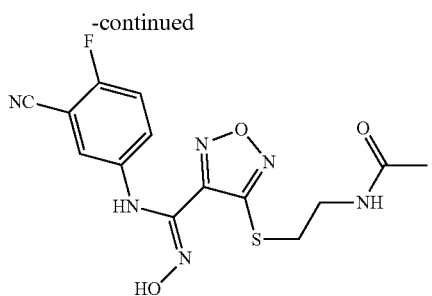

To a solution of 4-((2-acetamidoethyl)thio)-N-hydroxy-1,2,5-oxadiazole-3-carbimidoyl chloride (80 mg, 0.30 mmol) in EtOH (10 mL) at 20° C. were added 5-amino-2-fluorobenzonitrile (62 mg, 0.46 mmol) and NaHCO$_3$ (64 mg, 0.76 mmol). The mixture was warmed to 60° C. After 1 h, the reaction mixture was cooled to room temperature, concentrated in vacuo. The residue was purified by reverse phase HPLC on a GILSON 281 instrument fitted with a Phenomenex Synergi C18 (250*21.2 mm*4 μm) using water (0.225% FA)-MeCN, Mobile phase B acetonitrile, Detective wavelength: 220 nm) followed by concentration to give the title compound (60 mg) as a white solid. $^1$H NMR (400 MHz, CD$_3$OD) δ 7.12-7.22 (m, 2H), 7.05-7.11 (m, 1H), 3.56 (t, J=6.4 Hz, 2H), 3.26-3.30 (m, 2H), 1.94 (s, 3H). ESI MS m/z 365.1 [M+H]$^+$ Examples 38 and 39: (R)—N-(3-cyano-4-fluorophenyl)-4-((2,3-dihydroxy-3-methylbutyl)thio)-N'-hydroxy-1,2,5-oxadiazole-3-carboximidamide and (S)—N-(3-cyano-4-fluorophenyl)-4-((2,3-dihydroxy-3-methylbutyl)thio)-N'-hydroxy-1,2,5-oxadiazole-3-carboximidamide

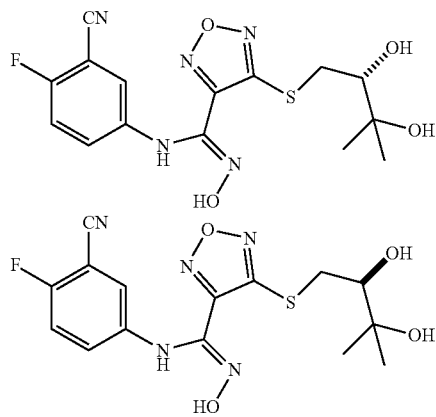

Step 1. 2-(Oxiran-2-yl)propan-2-ol

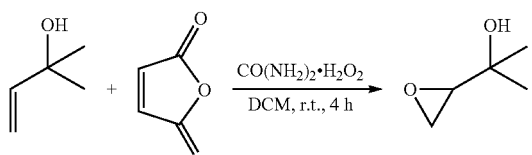

To a solution of urea hydrogen peroxide (49.1 g, 522 mmol) in CH$_2$Cl$_2$ (200 ml) was added furan-2,5-dione (25.6 g, 261 mmol). The mixture was stirred at 25° C. for 5 min before 2-methylbut-3-en-2-ol (15 g, 174 mmol) in CH$_2$Cl$_2$ (30 mL) was added dropwise. The mixture was stirred at 25° C. for 4 h. The mixture was filtered, NaHCO$_3$ (30 g) was added to the filtrate, filtered again. The filtrate was concentrated in vacuo to give 2-(oxiran-2-yl)propan-2-ol (11.2 g) as an oil which was used in the next step without further purification. $^1$H NMR (400 MHz, CDCl$_3$) δ 2.94 (dd, J=4.2, 2.8 Hz, 1H), 2.80 (dd, J=4.8, 2.8 Hz, 1H), 2.70-2.75 (m, 1H), 1.32 (s, 3H), 1.22 (s, 3H)

Step 2. 1-Mercapto-3-methylbutane-2,3-diol

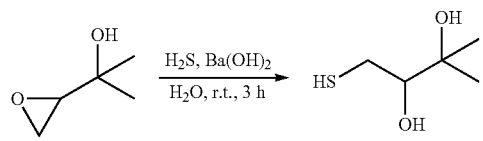

Into a solution of barium hydroxide (5.03 g, 29.4 mmol) in water (60 mL) was passed hydrogen sulfide gas (excess) for 90 minutes at RT, followed by the addition of 2-(oxiran-2-yl)propan-2-ol (3.0 g, 29.4 mmol) in methanol (4 mL) slowly. After the addition was finished, hydrogen sulfide gas was passed through the reaction mixture for another 90 min. CO$_2$ was then bubbled through the mixture with stirring for 20 min. The resultant white suspension was filtered, and the filtrate was concentrated in vacuo to give the crude 1-mercapto-3-methylbutane-2,3-diol (4.00 g) as a solid which was used in the next step directly. $^1$H NMR (400 MHz, CD$_3$OD) δ 3.36-3.36 (m, 1H), 2.75 (dd, J=13.6, 1.8 Hz, 1H), 2.47 (dd, J=13.6, 10.4 Hz, 1H), 1.2 (s, 3H), 1.13 (s, 3H).

Step 3. 4-((2,3-Dihydroxy-3-methylbutyl)thio)-1,2,5-oxadiazole-3-carbonitrile

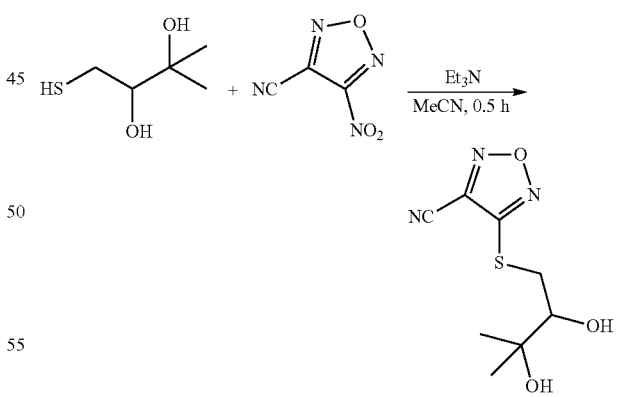

To a solution of 4-nitro-1,2,5-oxadiazole-3-carbonitrile (510 mg, 3.64 mmol) in MeCN (3 mL) was added 1-mercapto-3-methylbutane-2,3-diol (450 mg, 3.30 mmol) and Et$_3$N (1.1 mL, 7.89 mmol) and the mixture was stirred at 0° C. for 0.5 h under N$_2$ atmosphere. Then the solvent was removed in vacuo to give the crude 4-((2,3-dihydroxy-3-methylbutyl)thio)-1,2,5-oxadiazole-3-carbonitrile (530 mg) as an oil which was used in the next step directly without further purification. ESI MS m/z 271.2 [M+CH3CN]$^+$

Step 4. 4-((2,3-Dihydroxy-3-methylbutyl)thio)-N'-hydroxy-1,2,5-oxadiazole-3-carboximidamide

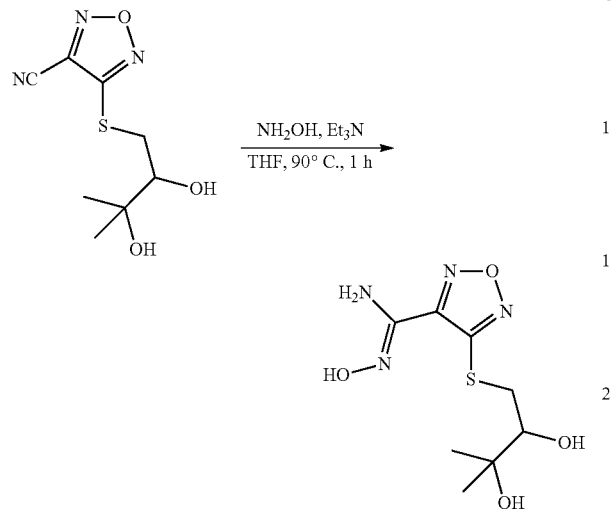

To a solution of 4-((2,3-dihydroxy-3-methylbutyl)thio)-1,2,5-oxadiazole-3-carbonitrile (530 mg, 2.312 mmol) in THF (3 mL) were added hydroxylamine (0.3 mL, 4.54 mmol) and Et$_3$N (2.5 mL, 17.94 mmol). The mixture was stirred at 80° C. for 1 h under N$_2$ atmosphere, cooled to RT, concentrated in vacuo. The residue was purified by prep-TLC (DCM:MeOH=10:1) to give the title compound (330 mg) as a solid. ESI MS m/z 263.1 [M+H]$^+$

Step 5. 4-((2,3-Dihydroxy-3-methylbutyl)thio)-N-hydroxy-1,2,5-oxadiazole-3-carbimidoyl chloride

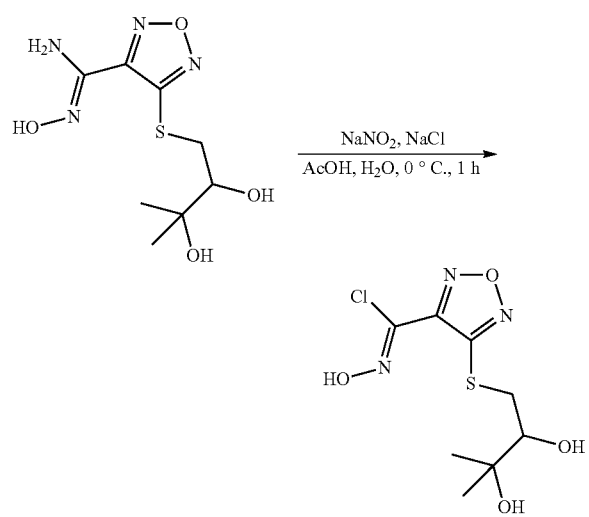

A solution of 4-((2,3-dihydroxy-3-methylbutyl)thio)-N-hydroxy-1,2,5-oxadiazole-3-carboximidamide (330 mg, 1.258 mmol) in a mixture of water (2 mL), AcOH (3 mL) and 6 M HCl (0.4 mL, 2.40 mmol) was stirred at 30° C. for 20 min before sodium chloride (177 mg, 3.03 mmol) was added. The mixture was cooled using an ice/water/methanol bath. A solution of sodium nitrite (97 mg, 1.406 mmol) in water (0.3 mL) was added slowly while maintaining the temperature below 0° C. The mixture was stirred for 1.5 in the ice bath, warmed to RT, and stirred for another 2 h. The precipitate was collected by filtration, washed with water (10 mL), taken in DCM (30 mL*2), treated with anhydrous sodium sulfate, filtered through sodium sulfate and the filtrate was concentrated in vacuo to give the title compound (335 mg) as a white solid which was used in the next step directly without further purification.

Step 6. N-(3-Cyano-4-fluorophenyl)-4-((2,3-dihydroxy-3-methylbutyl)thio)-N'-hydroxy-1,2,5-oxadiazole-3-carboximidamide

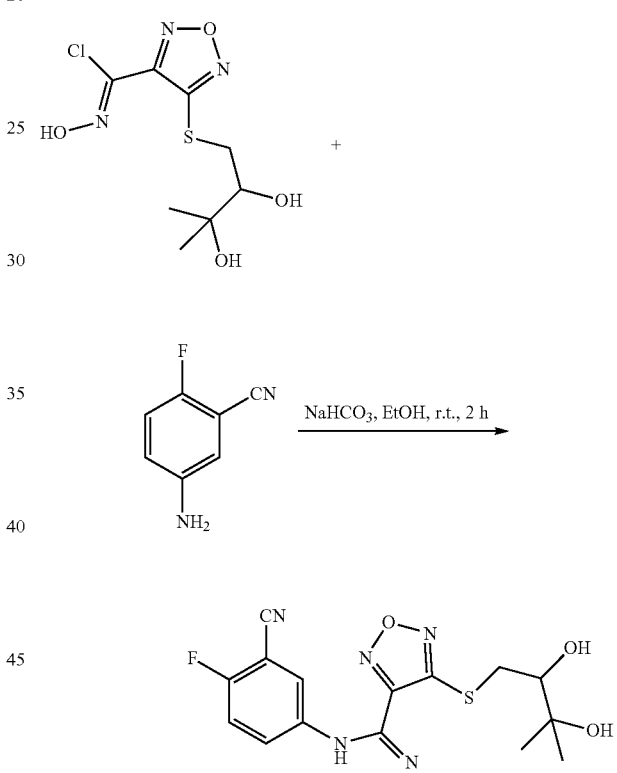

To a solution of 4-((2,3-dihydroxy-3-methylbutyl)thio)-N-hydroxy-1,2,5-oxadiazole-3-carbimidoyl chloride (270 mg, 0.958 mmol) in EtOH (3 mL) were added 5-amino-2-fluorobenzonitrile (157 mg, 1.150 mmol) and sodium bicarbonate (161 mg, 1.917 mmol). The mixture was stirred at RT for 2 h under N$_2$ atmosphere, quenched with water (10 mL) at 28° C., extracted with EtOAc (20 mL*3) and the organic layer was concentrated under the reduced pressure. The residue was purified by Pre-TLC (SiO$_2$, DCM:MeOH=10:1 as eluent) to give the title compound (140 mg) as a white solid. $^1$H NMR (400 MHz, CD$_3$OD) δ 7.05-7.22 (m, 3H), 3.59-3.67 (m, 2H), 3.04 (dd, J=13.6, 11.2 Hz, 1H), 1.23 (d, J=7.6 Hz, 6H) ESI m/z: 403.9 [M+Na]$^+$ Step 7. (R)—N-(3-cyano-4-fluorophenyl)-4-((2,3-dihydroxy-3-methylbutyl)thio)-N'-hydroxy-1,2,5-oxadiazole-3-carboximidamide and (S)—N-(3-cyano-4-fluorophenyl)-4-((2,3-dihydroxy-3-methylbutyl)thio)-N'-hydroxy-1,2,5-oxadiazole-3-carboximidamide

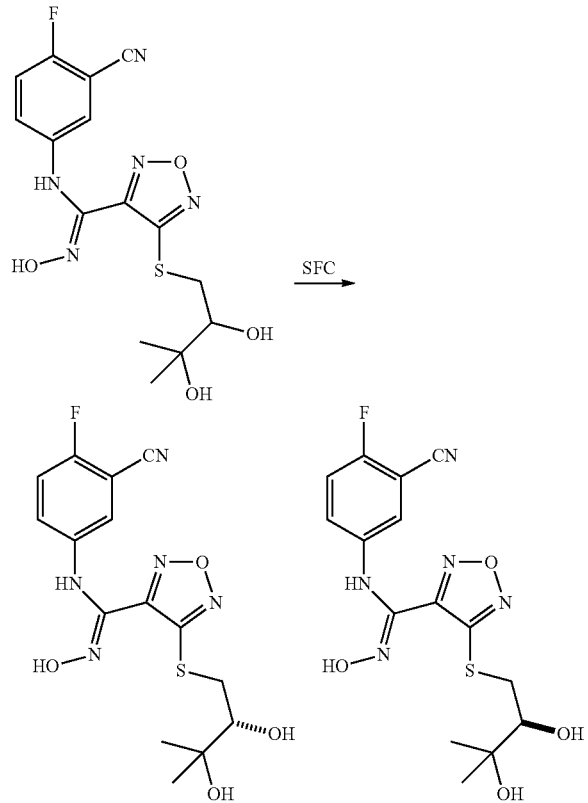

Two chiral isomers were obtained after SFC separation of 140 mg racemate compound above. AD(250 mm*30 mm, 5 um); 0.1% NH$_3$H$_2$O EtOH Begin B 40% End B 40% FlowRate(ml/min) 60

Example 38

(Peak 1): $^1$H NMR (400 MHz, CD$_3$OD) δ 7.05-7.22 (m, 3H), 3.59-3.67 (m, 2H), 3.04 (dd, J=13.6, 11.2 Hz, 1H), 1.23 (d, J=7.6 Hz, 6H) ESI m/z: 403.9 [M+Na]$^+$ Example 39

(Peak 2): $^1$H NMR (400 MHz, CD$_3$OD) δ 7.05-7.22 (m, 3H), 3.59-3.67 (m, 2H), 3.04 (dd, J=13.6, 11.2 Hz, 1H), 1.23 (d, J=7.6 Hz, 6H) ESI m/z: 403.9 [M+Na]$^+$ Example 40. N-(2-((4-(N-(3-cyano-4-fluorophenyl)-N'-hydroxycarbamimidoyl)-1,2,5-oxadiazol-3-yl)thio)ethyl)cyclopropanecarboxamide

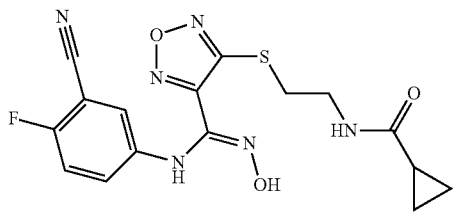 [SMILES: N#Cc1cc(N/C(=N\O)c2nonc2SCCNC(=O)C2CC2)ccc1F]

Step 1. Tert-butyl (2-((4-(N-(3-cyano-4-fluorophenyl)-N'-hydroxycarbamimidoyl)-1,2,5-oxadiazol-3-yl)thio)ethyl)carbamate

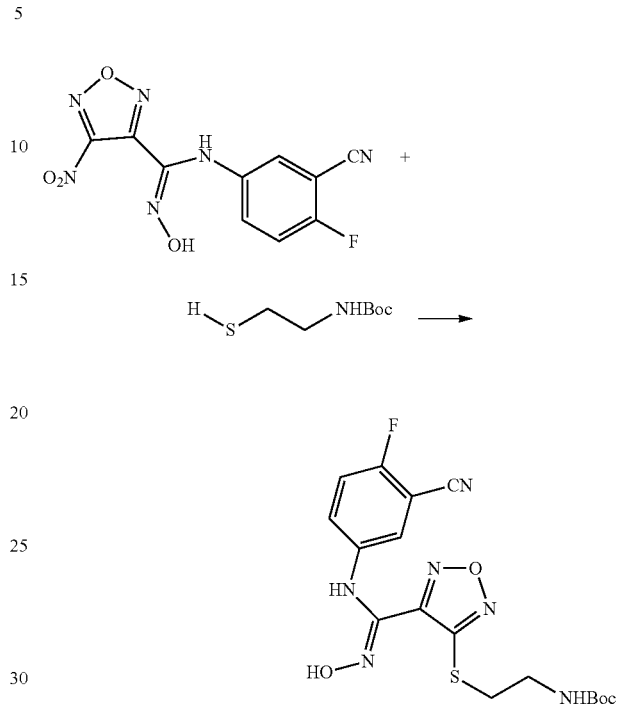

To a solution of N-(3-cyano-4-fluorophenyl)-N'-hydroxy-4-nitro-1,2,5-oxadiazole-3-carboximidamide (1.11 g, 3.81 mmol) in 6 mL of MeCN at 0° C. was added Et$_3$N (1.59 mL, 11.43 mmol), followed by the addition of a solution of tert-butyl (2-mercaptoethyl)carbamate (675 mg, 3.81 mmol) in 1.6 mL of MeCN. The mixture was stirred at 0° C. for 30 min, then partitioned between EtOAc and sat. NaHCO$_3$ solution. The organic layer was washed with brine, dried over MgSO$_4$, and concentrated. The residue was purified by silica gel chromatography (RediSepRf 40 g column, 0-50% ethyl acetate in hexanes) to afford tert-butyl (2-((4-(N-(3-cyano-4-fluorophenyl)-N'-hydroxycarbamimidoyl)-1,2,5-oxadiazol-3-yl)thio)ethyl)carbamate (370 mg, 0.876 mmol) as a solid.

Step 2. Tert-butyl (2-((4-(4-(3-cyano-4-fluorophenyl)-5-oxo-4,5-dihydro-1,2,4-oxadiazol-3-yl)-1,2,5-oxadiazol-3-yl)thio)ethyl)carbamate

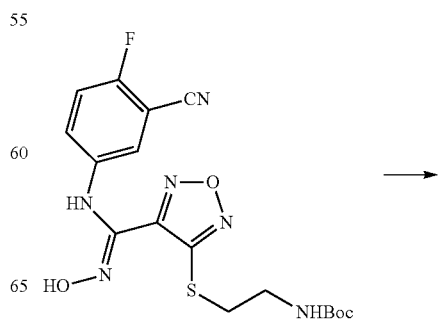

-continued

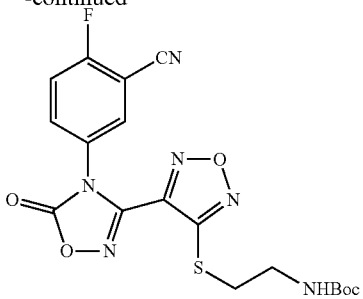

To a solution of tert-butyl (2-((4-(N-(3-cyano-4-fluorophenyl)-N'-hydroxycarbamimidoyl)-1,2,5-oxadiazol-3-yl)thio)ethyl)carbamate (364 mg, 0.862 mmol) in THF (4.3 mL) was added CDI (168 mg, 1.034 mmol). The resulting solution was stirred at 70° C. for 1 h. The reaction mixture was concentrated in vacuo. The residue was purified by silica gel chromatography (RediSepRf 24 g column, 0-60% ethyl acetate in hexanes) to afford tert-butyl (2-((4-(4-(3-cyano-4-fluorophenyl)-5-oxo-4,5-dihydro-1,2,4-oxadiazol-3-yl)-1,2,5-oxadiazol-3-yl)thio)ethyl)carbamate (312 mg, 0.696 mmol) as a solid.

Step 3. 5-(3-(4-((2-Aminoethyl)thio)-1,2,5-oxadiazol-3-yl)-5-oxo-1,2,4-oxadiazol-4(5H)-yl)-2-fluorobenzonitrile hydrochloride

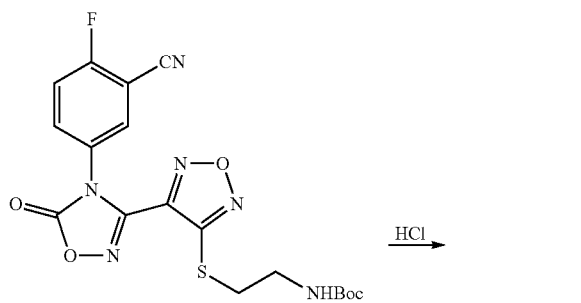

To a solution of tert-butyl (2-((4-(4-(3-cyano-4-fluorophenyl)-5-oxo-4,5-dihydro-1,2,4-oxadiazol-3-yl)-1,2,5-oxadiazol-3-yl)thio)ethyl)carbamate (310 mg, 0.691 mmol) in dioxane (2.3 mL) was added HCl (4M in dioxane, 0.86 mL, 3.44 mmol) at RT for 16 h. The reaction mixture was concentrated in vacuo to afford 5-(3-(4-((2-aminoethyl)thio)-1,2,5-oxadiazol-3-yl)-5-oxo-1,2,4-oxadiazol-4(5H)-yl)-2-fluorobenzonitrile hydrochloride (270 mg, 0.702 mmol) as a solid.

Step 4. N-(2-((4-(4-(3-Cyano-4-fluorophenyl)-5-oxo-4,5-dihydro-1,2,4-oxadiazol-3-yl)-1,2,5-oxadiazol-3-yl)thio)ethyl)cyclopropanecarboxamide

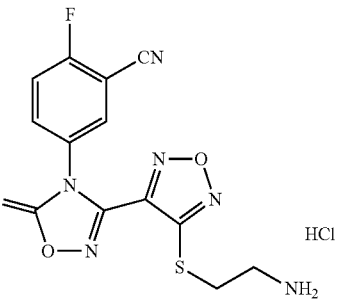

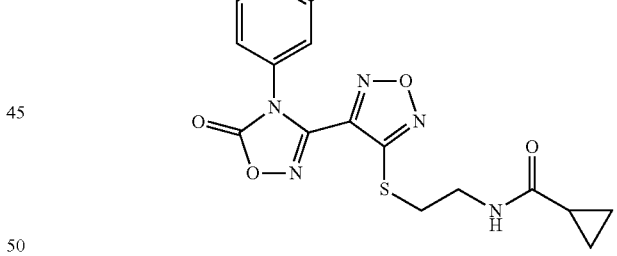

To a mixture of 5-(3-(4-((2-aminoethyl)thio)-1,2,5-oxadiazol-3-yl)-5-oxo-1,2,4-oxadiazol-4(5H)-yl)-2-fluorobenzonitrile hydrochloride (45 mg, 0.117 mmol), cyclopropanecarboxylic acid (15.10 mg, 0.175 mmol) and N-ethyl-N-isopropylpropan-2-amine (63.0 µl, 0.351 mmol) in DMF (234 µl) was added HATU (66.7 mg, 0.175 mmol) at RT. After addition the mixture was stirred at RT overnight. The resulting mixture was diluted with water and extracted with EA twice. The combined organic layers were washed with brine, dried over MgSO$_4$ and concentrated to afford crude N-(2-((4-(4-(3-cyano-4-fluorophenyl)-5-oxo-4,5-dihydro-1,2,4-oxadiazol-3-yl)-1,2,5-oxadiazol-3 yl)thio)ethyl)cyclopropanecarboxamide as a solid, which was used without further purification.

Step 5. N-(2-((4-(N-(3-cyano-4-fluorophenyl)-N'-hydroxycarbamimidoyl)-1,2,5-oxadiazol-3-yl)thio)ethyl)cyclopropanecarboxamide

Step 1. 2-((4-(N-(3-Bromo-4-fluorophenyl)-N'-hydroxycarbamimidoyl)-1,2,5-oxadiazol-3-yl)thio)acetic acid

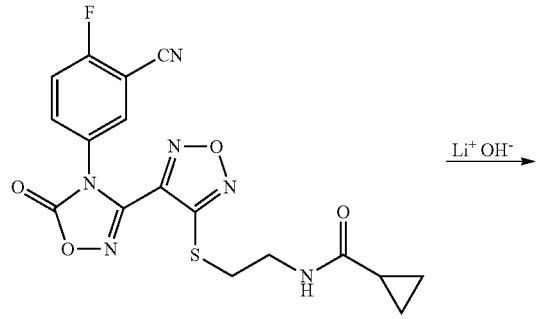

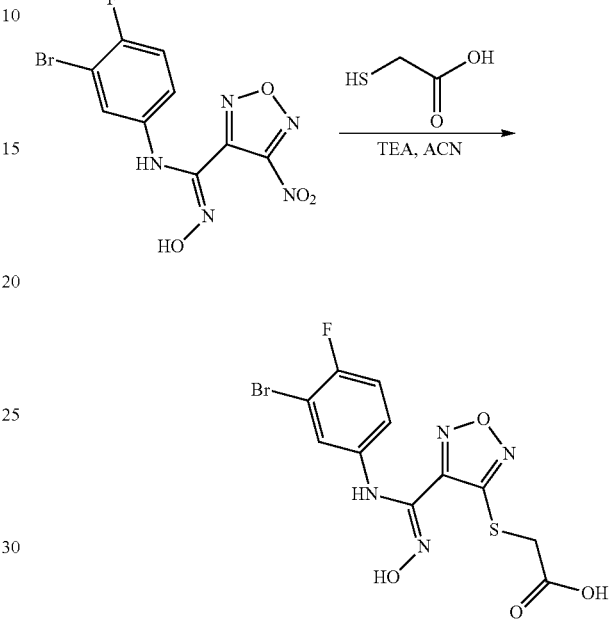

To the solution of N-(2-((4-(4-(3-cyano-4-fluorophenyl)-5-oxo-4,5-dihydro-1,2,4-oxadiazol-3-yl)-1,2,5-oxadiazol-3-yl)thio)ethyl)cyclopropanecarboxamide (48 mg, 0.115 mmol) in MeOH (1.2 mL) and THF (1.2 mL) was added aqueous LiOH solution (1.0 M, 346 µL, 0.346 mmol). The resulting reaction mixture was stirred at RT overnight, concentrated in vacuo. The residue was purified by reverse phase HPLC (H₂O/CH₃CN containing 0.1% TFA) to afford (N-2-((4-(N-(3-cyano-4-fluorophenyl)-N'-hydroxycarbamimidoyl)-1,2,5-oxadiazol-3-yl)thio)ethyl)cyclopropanecarboxamide (16 mg, 0.032 mmol) as a solid. MS: 391.0 (M+1). ¹HNMR (600 MHz, DMSO-d₆): δ 11.84 (s, 1H), 9.09 (s, 1H), 8.31 (t, J=6 Hz, 1H), 7.30 (t, J=12 Hz, 1H), 7.21 (m, 1H), 7.10 (m, 1H) 3.42 (m, 2H), 3.21 (m, 2H), 1.48 (m, 1H), 0.61 (m, 4H).

Example 41. 2-((4-(N-(3-bromo-4-fluorophenyl)-N'-hydroxycarbamimidoyl)-1,2,5-oxadiazol-3-yl)thio)-N-methylacetamide

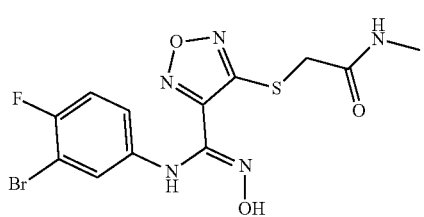 [SMILES: CNC(=O)CSc1nonc1/C(=N/O)Nc1ccc(F)c(Br)c1]

To a solution of N-(3-bromo-4-fluorophenyl)-N'-hydroxy-4-nitro-1,2,5-oxadiazole-3-carboximidamide (200 mg, 0.578 mmol) in acetonitrile (4 mL) were added 2-mercaptoacetic acid (160 mg, 1.734 mmol) and Et₃N (161 µl, 1.156 mmol). The mixture was stirred at RT for 18 h, concentrated in vacuo. The residue was purified by reversed phase HPLC (ACN/water, 0.1% TFA) to afford 2-((4-(N-(3-bromo-4-fluorophenyl)-N'-hydroxycarbamimidoyl)-1,2,5-oxadiazol-3-yl)thio)acetic acid (61.2 mg). MS: 393 (M+1).

Step 2. 2-((4-(N-(3-Bromo-4-fluorophenyl)-N'-hydroxycarbamimidoyl)-1,2,5-oxadiazol-3-yl)thio)-N-methylacetamide

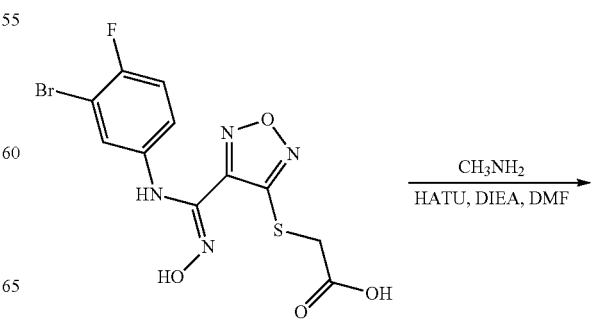

-continued

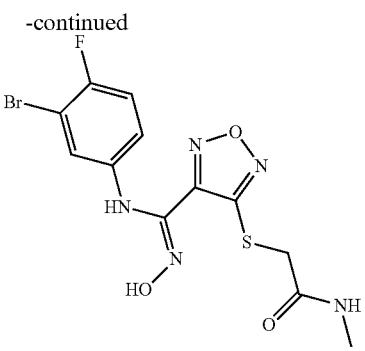

To a vial were added 2-((4-(N-(3-bromo-4-fluorophenyl)-N'-hydroxycarbamimidoyl)-1,2,5-oxadiazol-3-yl)thio)acetic acid (20 mg, 0.051 mmol), HATU (23.33 mg, 0.061 mmol), DMF (250 μL), methylamine in THF (300 μL, 0.600 mmol) and DIEA (50 μL, 0.286 mmol). The mixture was stirred at RT for 16 h. The mixture was filtered and purified by reversed phase HPLC (ACN/water, 0.1% TFA) to afford 2-((4-(N-(3-bromo-4-fluorophenyl)-N'-hydroxycarbamimidoyl)-1,2,5-oxadiazol-3-yl)thio)-N-methylacetamide (7.7 mg). MS: 404 (M+1). $^1$HNMR (600 MHz, DMSO-d$_6$): δ 11.76 (s, 1H), 8.93 (s, 1H), 8.20-8.14 (m, 1H), 7.14 (t, J=6 Hz, 1H), 7.08-7.03 (m, 1H), 6.72-6.66 (m, 1H), 3.91 (s, 2H), 2.58 (d, J=4.5 Hz, 3H).

Example 42. (R)-2-((4-(N-(3-bromo-4-fluorophenyl)-N'-hydroxycarbamimidoyl)-1,2,5-oxadiazol-3-yl)thio)-N-(2,3-dihydroxypropyl)acetamide

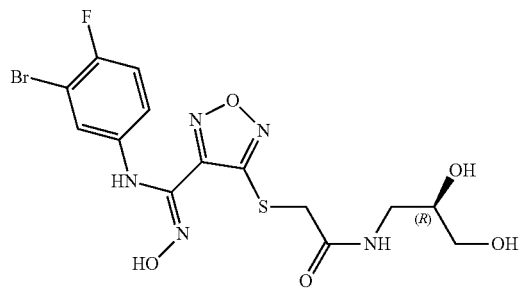

Step 1. Methyl 2-((4-(N-(3-bromo-4-fluorophenyl)-N'-hydroxycarbamimidoyl)-1,2,5-oxadiazol-3-yl)thio)acetate

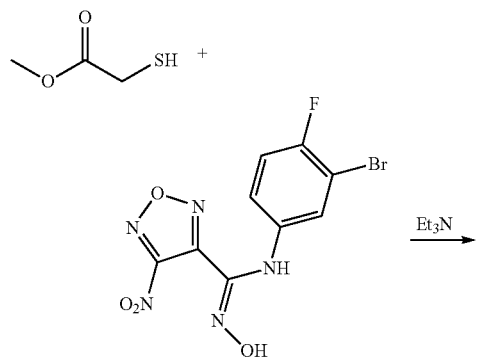

-continued

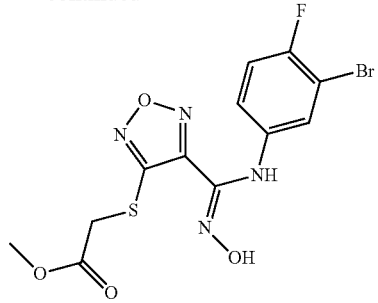

To a solution of N-(3-bromo-4-fluorophenyl)-N'-hydroxy-4-nitro-1,2,5-oxadiazole-3-carboximidamide (5800 mg, 1.68 mmol) in MeCN (6 mL) were added methyl 2-mercaptoacetate (300 μL, 3.35 mmol) and TEA (0.6 mL, 4.3 mmol). The reaction mixture was stirred for 2 h, concentrated in vacuo. The residue was purified by silica gel chromatography (EtOAc/hexanes 1/1) to afford methyl 2-((4-(N-(3-bromo-4-fluorophenyl)-N'-hydroxycarbamimidoyl)-1,2,5-oxadiazol-3-yl)thio)acetate (580 mg) as an oil. MS: 405 (M+H).

Step 2. (R)-2-((4-(N-(3-bromo-4-fluorophenyl)-N'-hydroxycarbamimidoyl)-1,2,5-oxadiazol-3-yl)thio)-N-(2,3-dihydroxypropyl)acetamide

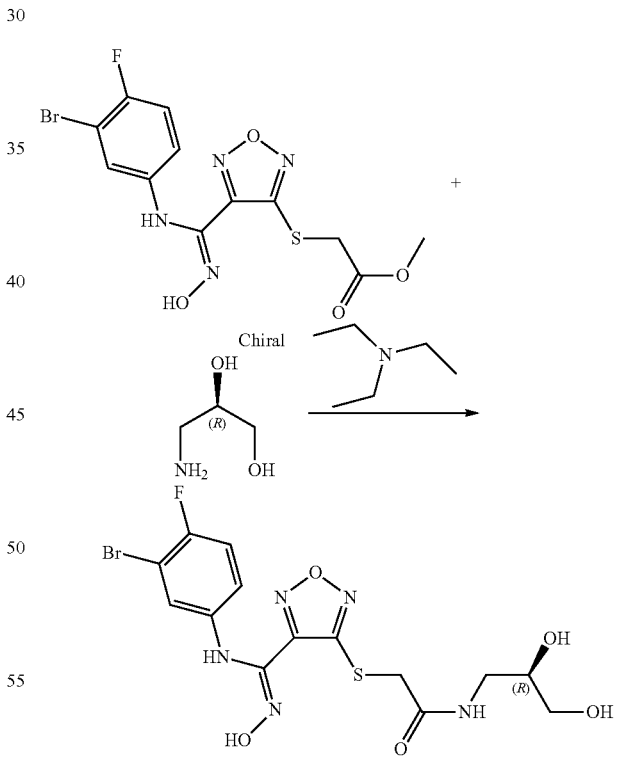

A mixture of methyl 2-((4-(N-(3-bromo-4-fluorophenyl)-N'-hydroxycarbamimidoyl)-1,2,5-oxadiazol-3-yl)thio)acetatate (1.50 g, 3.70 mmol), (R)-3-amino-1,2-propanediol (3.37 g, 37.0 mmol) in MeOH (10.0 mL) was heated at 150° C. in a microwave oven for 60 minutes. The reaction mixture was cooled to RT, concentrated in vacuo. The residual was purified by mass-directed reverse phase chromatography (MeCN/water gradient with 0.1% TFA modifier) to give (R)-2-((4-(N-(3-bromo-4-fluorophenyl)-N'-hydroxycarbamimidoyl)-1,2,5-oxadiazol-3-yl)thio)-N-(2,3-dihydroxypropyl)acetamide. $^1$H NMR (600 MHz, DMSO-d$_6$) δ 11.79 (s, 1H), 8.97 (s, 1H), 8.24 (s, 1H), 7.16 (s, 1H), 7.10 (s, 1H), 6.73 (s, 1H), 4.76 (s, 1H), 4.53 (s, 1H), 4.00 (s, 2H), 3.50 (s, 1H), 3.28 (m, 3H), 3.00 (m, 1H). ESI MS m/z 464 [M+H]$^+$ Example 43. (R)—N-(3-bromo-4-fluorophenyl)-N'-hydroxy-4-(((3-methyl-2-oxoimidazolidin-4-yl)methyl)thio)-1,2,5-oxadiazole-3-carboximidamide

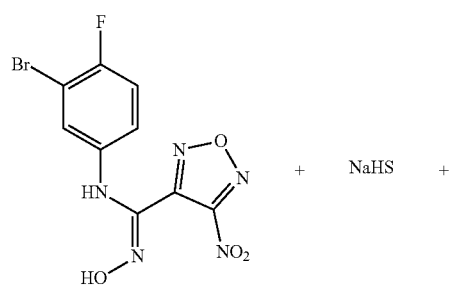

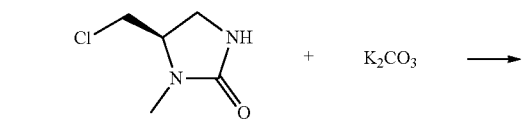

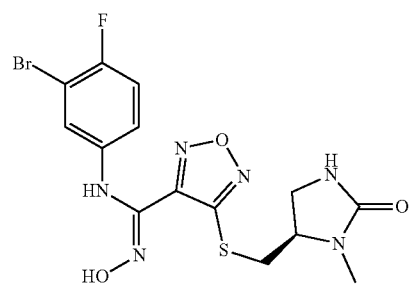

To a solution of N-(3-bromo-4-fluorophenyl)-N'-hydroxy-4-nitro-1,2,5-oxadiazole-3-carboximidamide (0.4 g, 1.16 mmol) in DMF (3 mL) at 0° C. was added sodium hydrogen sulfide (0.078 g, 1.39 mmol) in DMF (1 mL). The mixture was gradually warmed up to RT. To this reaction mixture, (R)-5-(chloromethyl)-1-methylimidazolidin-2-one (0.172 g, 1.16 mmol) was added, followed by potassium carbonate (0.319 g, 2.312 mmol). The reaction mixture was stirred at RT overnight. Ethyl acetate was added to the reaction mixture. The formed mixture was filtered through celite and was concentrated. The residue was purified using prep-HPLC to give (R)—N-(3-bromo-4-fluorophenyl)-N'-hydroxy-4-(((3-methyl-2-oxoimidazolidin-4-yl)methyl)thio)-1,2,5-oxadiazole-3-carboximidamide (68 mg). MS: 445 (M+1). $^1$HNMR (500 MHz, DMSO-d$_6$): δ 11.8 (s, 1H), 11.43 (s, 1H), 8.98 (s, 1H), 7.17 (t, J=5 Hz, 1H), 7.10 (m, 1H), 6.69 (m, 1H), 6.20 (m, 1H), 3.95 (t, 1H), 3.22-3.80 (m, 4H), 2.50 (s, 3H).

Example 44. Dimethyl 2,2'-(((2-((4-(N-(3-bromo-4-fluorophenyl)-N'-hydroxycarbamimidoyl)-1,2,5-oxadiazol-3-yl)thio)ethyl)phosphoryl)bis(azanediyl)) (Z)-diacetate

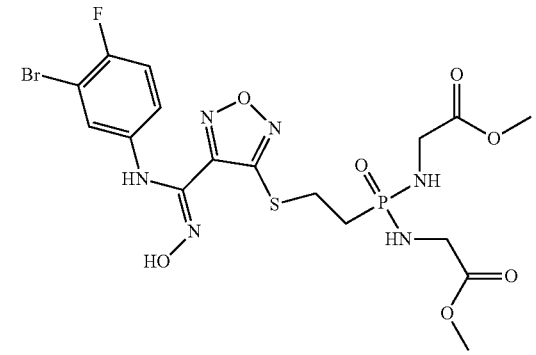 [SMILES: COC(=O)CNP(=O)(CCSc1nonc1/C(=N/O)Nc1ccc(F)c(Br)c1)NCC(=O)OC]

Step 1. Dimethyl 2,2'-(((2-chloroethyl)phosphoryl)bis(azanediyl))diacetate

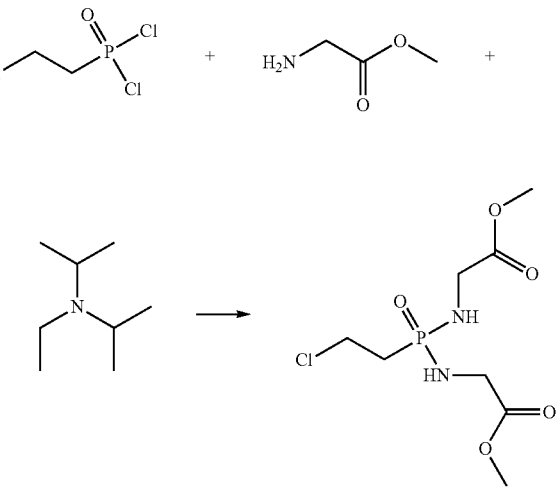

To a solution of methyl 2-aminoacetate (150 mg, 1.686 mmol) and DIEA (295 µL, 1.686 mmol) in dichloromethane (5 mL) was added 2-chloroethyl)phosphonic dichloride at 0° C. The mixture was stirred for 20 min, partitioned between dichloromethane (15 mL) and water (10 mL). The organic layer was washed with sodium bicarbonate (saturated, 2 mL) and water (10 ml), dried over anhydrous sodium sulfate, filtered, and concentrated in vacuo to afford the crude product (181 mg), which was used directly in the next step.

Step 2. Dimethyl 2,2'-(((2-((4-(N-(3-bromo-4-fluorophenyl)-N'-hydroxycarbamimidoyl)-1,2,5-oxadiazol-3-yl)thio)ethyl)phosphoryl)bis(azanediyl))(Z)-diacetate

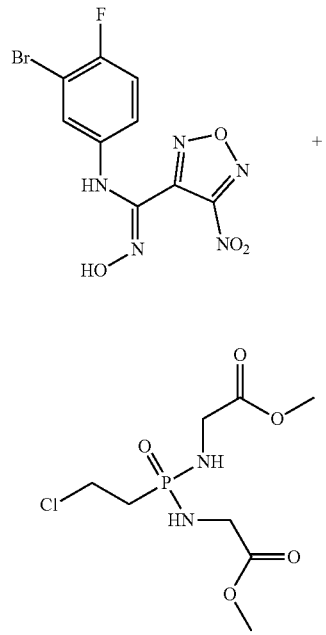

To a solution of (Z)—N-(3-bromo-4-fluorophenyl)-N'-hydroxy-4-nitro-1,2,5-oxadiazole-3-carboximidamide (0.4 g, 1.156 mmol) in DMF (3 mL) at 0° C. was added sodium hydrogen sulfide (0.078 g, 1.387 mmol) in DMF (1 mL). The mixture was gradually warmed up to RT. To this reaction mixture, the crude intermediate from the previous step was added, followed by potassium carbonate (0.319 g, 2.312 mmol). The reaction mixture was stirred at RT overnight. Ethyl acetate was added to the reaction mixture. The formed mixture was filtered through celite and was concentrated. The residue was purified using prep-HPLC to give dimethyl 2,2'-(((2-((4-(N-(3-bromo-4-fluorophenyl)-N'-hydroxycarbamimidoyl)-1,2,5-oxadiazol-3-yl)thio)ethyl)phosphoryl)bis(azanediyl))(Z)-diacetate (60 mg). MS: 583 (M+1). $^1$HNMR (500 MHz, DMSO-d$_6$): δ 11.73 (s, 1H), 9.01 (s, 1H), 7.17 (t, J=5 Hz, 1H), 7.06 (m, 1H), 6.69 (m, 1H), 6.20 (m, 1H), 4.86 (m, 2H), 4.76 (1H, t, J=8 Hz), 4.61 (1H, t, J=8 Hz), 3.95 (t, 1H), 3.80 (m, 4H), 2.50 (s, 3H).

Example 45. N-(3-bromo-4-fluorophenyl)-N'-hydroxy-4-((2-(3-methylureido)ethyl)thio)-1,2,5-oxadiazole-3-carboximidamide

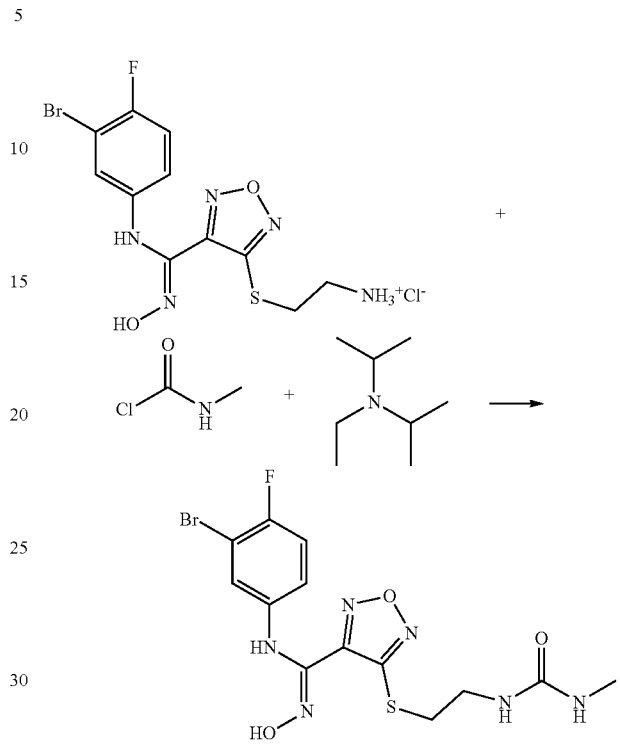

To a suspension of 4-((2-aminoethyl)thio)-N-(3-bromo-4-fluorophenyl)-N'-hydroxy-1,2,5-oxadiazole-3-carboximidamide hydrochloride (32 mg, 0.078 mmol) in DCM (0.5 mL) was added DIEA (0.041 mL, 0.23 mmol). The mixture was cooled to −5° C. and methylcarbamic chloride (7.25 mg, 0.078 mmol) in DCM (0.3 mL) was added. The reaction was stirred for 10 min at RT and LCMS showed that the reaction was completed. The reaction mixture was purified with prep-HPLC to give N-(3-bromo-4-fluorophenyl)-N'-hydroxy-4-((2-(3-methylureido)ethyl)thio)-1,2,5-oxadiazole-3-carboximidamide (12 mg). MS: 433 (M+1). $^1$HNMR (500 MHz, DMSO-d$_6$): δ 11.73 (s, 1H), 8.98 (s, 1H), 7.17 (t, J=5 Hz, 1H), 7.10 (m, 1H), 6.69 (m, 1H), 6.20 (m, 1H), 5.83 (s, 1H), 3.34 (q, J=8 Hz, 5 Hz, 2H), 3.21 (t, J=5 Hz, 2H), 2.54 (d, J=5 Hz, 3H).

Example 46. N-(3-Bromo-4-fluorophenyl)-N'-hydroxy-4-((2-ureidoethyl)thio)-1,2,5-oxadiazole-3-carboximidamide

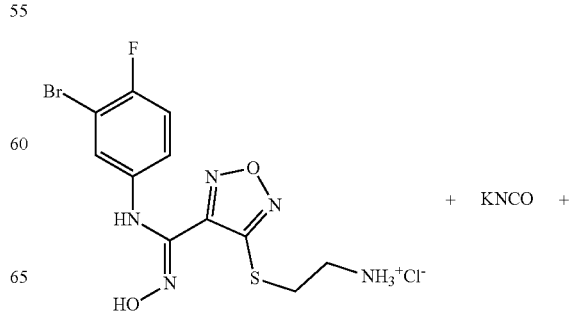

87
-continued

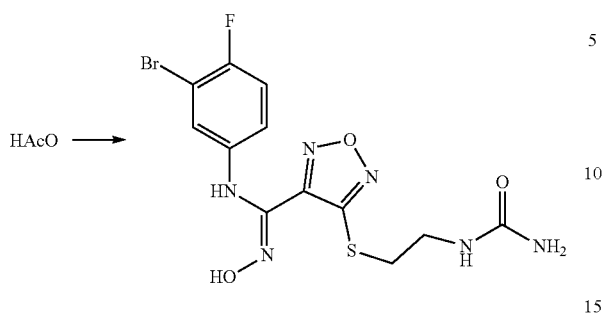

HAcO →

To a solution of 2-((4-(N-(3-bromo-4-fluorophenyl)-N'-hydroxycarbamimidoyl)-1,2,5-oxadiazol-3-yl)thio)ethan-1-aminium chloride (2.1 g, 5.09 mmol) in water (30 mL) and acidic acid (0.29 mL, 5.09 mml) was added potassium cyanate (0.454 g, 5.6 mmol) in water (5 mL) dorpwise. The mixture was stirred for 1 h at RT and was heated up to 100° C. for 2 h. Solid formed during the reaction and it was collected by filtration, washed with water and purified using silica gel chromatography (Biotage 10 g SNAP cartridge, 0-75% ethyl acetate/ethanol (3:1) in hexanes) to provide N-(3-bromo-4-fluorophenyl)-N'-hydroxy-4-((2-ureidoethyl)

88 thio)-1,2,5-oxadiazole-3-carboximidamide. MS: 419 (M+1). $^1$HNMR (500 MHz, DMSO-d$_6$): δ 11.72 (s, 1H), 8.97 (s, 1H), 7.16 (t, J=5 Hz, 1H), 7.10 (m, 1H), 6.67 (m, 1H), 6.23 (m, 1H), 5.54 (s, 2H), 3.34 (q, J=8 Hz, 5 Hz, 2H), 3.21 (t, J=5 Hz, 2H).

Example 47. N-(3-bromo-4-fluorophenyl)-N'-hydroxy-4-((2-(sulfamoylamino)ethyl) thio)-1,2,5-thiadiazole-3-carboximidamide

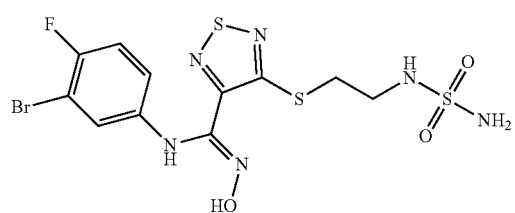 [SMILES: NS(=O)(=O)NCCSc1nsnc1/C(=N/O)Nc1ccc(F)c(Br)c1]

Step 1. N-(3-bromo-4-fluorophenyl)-4-chloro-1,2,5-thiadiazole-3-carboxamide

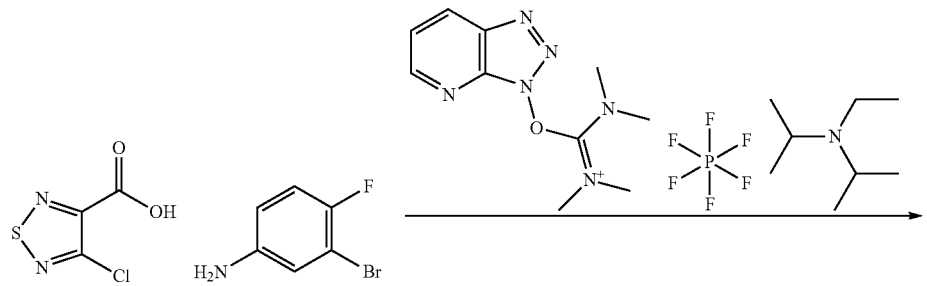

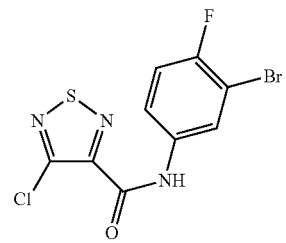

To a solution of 4-chloro-1,2,5-thiadiazole-3-carboxylic acid (3.55 g, 21.57 mmol) in DMF (15.0 mL) was added HATU (8.22 g, 21.57 mmol). After 5 min, 3-bromo-4-fluoroaniline (4.1 g, 21.57 mmol) and DIEA (11.30 mL, 64.7 mmol) were added. The reaction was stirred for 4 h at RT, then concentrated in vacuo. The residue was purified by silica gel column chromatography to afford N-(3-bromo-4-fluorophenyl)-4-chloro-1,2,5-thiadiazole-3-carboxamide. MS (ESI), 336 [M+1].

Step 2. N-(3-bromo-4-fluorophenyl)-4-chloro-N'-hydroxy-1,2,5-thiadiazole-3-carboximidamide

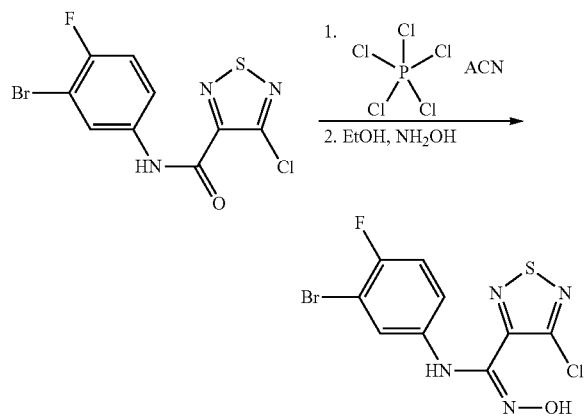

To a solution of N-(3-bromo-4-fluorophenyl)-4-chloro-1,2,5-thiadiazole-3-carboxamide in acetonitrile (10.0 mL) was added PCl$_5$ (742 mg, 3.57 mmol) at 25° C. and the resulting mixture was stirred at 80° C. for 5 h. The solvent was concentrated under reduced pressure. The residue was dissolved in ethanol (5.0 mL). Sodium acetate (244 mg, 2.97 mmol) and hydroxylamine hydrochloride (206 mg, 2.97 mmol) were added. The reaction mixture was stirred at 70° C. for 4 h, cooled to RT, concentrated in vacuo. The residue was purified by column chromatography (silica gel, 2 to 20% MeOH/DCM to afford N-(3-bromo-4-fluorophenyl)-4-chloro-N'-hydroxy-1,2,5-thiadiazole-3-carboximidamide. MS (ESI) 351 [M+1].

Step 3. Tert-butyl (N-(2-bromoethyl)sulfamoyl)carbamate

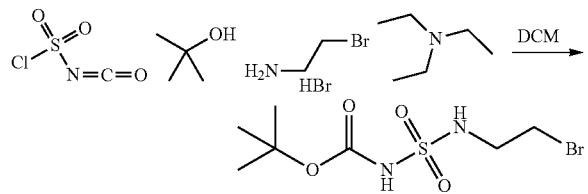

A solution of tert-butanol (1.03 mL, 10.8 mmol) in 5 mL of DCM was added to a solution of sulfurisocyanatidic chloride (1.27 g, 8.99 mmol) in 5 mL of DCM dropwise at 0° C. After 30 min, 2-bromoethanamine hydrobromide (2.21 g, 10.79 mmol) in 10 mL of DCM was added dropwise, followed by Et$_3$N (5.01 mL, 36.0 mmol) in 5 mL of DCM. The reaction mixture was stirred for 30 min, then concentrated in vacuo. The residue was purified by column chromatography (2 to 20% MeOH/DCM on silica gel) to afford (tert-butyl (N-(2-bromoethyl)sulfamoyl)carbamate. MS (ESI) 303 [M+1].

Step 4. Tert-butyl (N-(2-((4-(N-(3-bromo-4-fluorophenyl)-N'-hydroxycarbamimidoyl)-1,2,5-thiadiazol-3-yl)thio)ethyl)sulfamoyl)carbamate

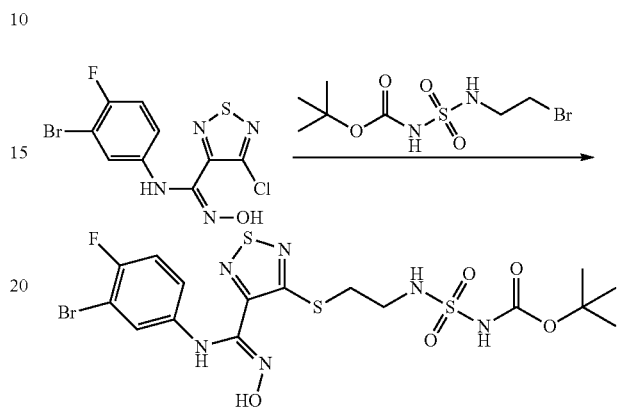

Sodium sulfide nonahydrate (273 mg, 1.138 mmol) in water (3.0 ml) was added to a solution of N-(3-bromo-4-fluorophenyl)-4-chloro-N'-hydroxy-1,2,5-thiadiazole-3-carboximidamide (400 mg, 1.138 mmol) in ethanol (8.0 mL). The mixture was refluxed for 24 h, cooled to RT, and concentrated in vacuo. A solution of tert-butyl (N-(2-bromoethyl)sulfamoyl)carbamate (517 mg, 1.71 mmol) in DMF (5 mL) was added, followed by potassium carbonate (472 mg, 3.41 mmol). The reaction mixture was stirred at ambient temperature for 16 h, poured into dilute hydrochloric acid and extracted with ethyl acetate three times. The combined organic layers were dried over sodium sulfate, filtered and concentrated in vacuo to give crude tert-butyl (N-(2-((4-(N-(3-bromo-4-fluorophenyl)-N'-hydroxycarbamimidoyl)-1,2,5-thiadiazol-3-yl)thio)ethyl)sulfamoyl)carbamate, which was used in the next step without further purification. MS (ESI) 571 [M+1].

Step 5. N-(3-bromo-4-fluorophenyl)-N'-hydroxy-4-((2-(sulfamoylamino)ethyl)thio)-1,2,5-thiadiazole-3-carboximidamide

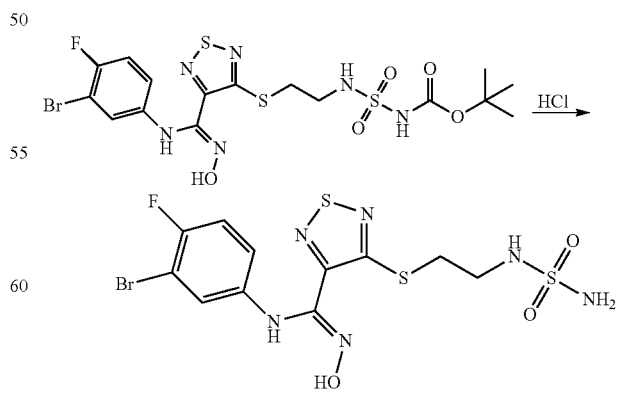

4N HCl in dioxane (3.0 mL) was added to a solution of tert-butyl (N-(2-((4-(N-(3-bromo-4-fluorophenyl)-N'-hydroxycarbamimidoyl)-1,2,5-thiadiazol-3-yl)thio)ethyl)sulfamoyl)carbamate (200 mg, 0.35 mmol) in dichloromethane (8.0 mL). After 2 h, the reaction mixture was concentrated under reduced pressure and the residue was purified by mass-directed reverse phase chromatography (MeCN/water gradient with 0.1% TFA modifier) to afford N-(3-bromo-4-fluorophenyl)-N'-hydroxy-4-((2-(sulfamoylamino)ethyl)thio)-1,2,5-thiadiazole-3-carboximidamide. $^1$H NMR (600 MHz, DMSO-d6) δ 11.32 (s, 1H), 8.85 (s, 1H), 7.06 (t, J=8.7 Hz, 1H), 6.91 (dd, J=6.2, 2.8 Hz, 1H), 6.79 (t, J=5.9 Hz, 1H), 6.57 (s, 2H), 6.44 (dt, J=7.6, 3.4 Hz, 1H), 3.31 (t, J=7.1 Hz, 3H), 3.19 (q, J=6.7 Hz, 2H). MS (ESI) 471[M+1].

Using the general methodology disclosed in the preceding schemes, examples and general knowledge in organic synthesis, compounds in the following table were prepared.

| Ex # | Structure | Chemical Name | Mass [M + H]+ |
|---|---|---|---|
| 48 | 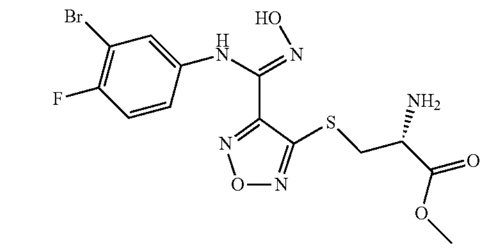 [SMILES: COC(=O)[C@@H](N)CSc1nonc1/C(=N/O)Nc1ccc(F)c(Br)c1] | methyl S-{4-[N-(3-bromo-4-fluorophenyl)-N'-hydroxycarbamimidoyl]-1,2,5-oxadiazol-3-yl}-L-cisteinate | Calc'd 434.0, found 434.0 |
| 49 | 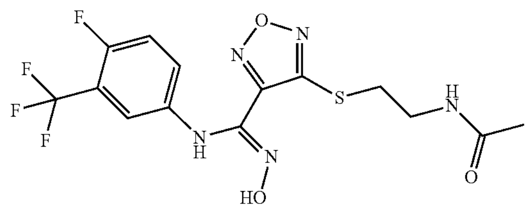 [SMILES: CC(=O)NCCSc1nonc1/C(=N/O)Nc1ccc(F)c(C(F)(F)F)c1] | N-{2-[(4-{N-[4-fluoro-3-(trifluoromethyl)phenyl]-N'-hydroxycarbamimidoyl}-1,2,5-oxadiazol-3-yl)sulfanyl]ethyl}acetamide | Calc'd 408.0, found 408.0 |
| 50 | 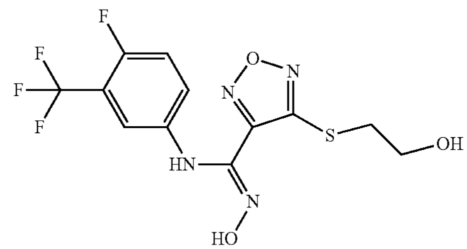 [SMILES: OCCSc1nonc1/C(=N/O)Nc1ccc(F)c(C(F)(F)F)c1] | N-[4-fluoro-3-(trifluoromethyl)phenyl]-N'-hydroxy-4-[(2-hydroxyethyl)sulfanyl]-1,2,5-oxadiazole-3-carboximidamide | Calc'd 367.0, found 367.0 |
| 51 | 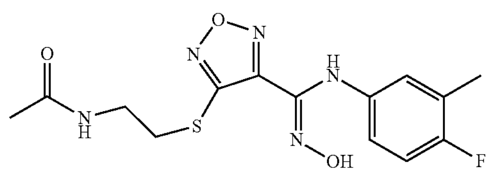 [SMILES: CC(=O)NCCSc1nonc1/C(=N/O)Nc1ccc(F)c(C)c1] | N-[2-({4-[N-(4-fluoro-3-methylphenyl)-N'-hydroxycarbamimidoyl]-1,2,5-oxadiazol-3-yl}sulfanyl)ethyl]acetamide | Calc'd 354.0, found 354.0 |
| 52 | 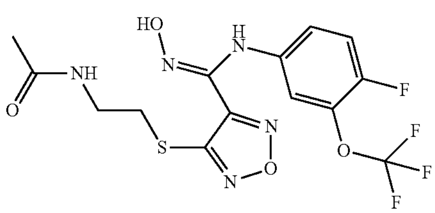 [SMILES: CC(=O)NCCSc1nonc1/C(=N/O)Nc1ccc(F)c(OC(F)(F)F)c1] | N-{2-[(4-{N-[4-fluoro-3-(trifluoromethoxy)phenyl]-N'-hydroxycarbamimidoyl}-1,2,5-oxadiazol-3-yl)sulfanyl]ethyl}acetamide | Calc'd 424.0, found 424.0 |
| 53 | 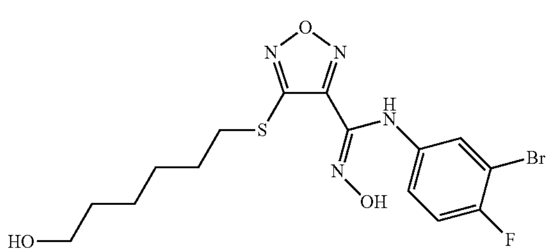 [SMILES: OCCCCCCSc1nonc1/C(=N/O)Nc1ccc(F)c(Br)c1] | N-(3-bromo-4-fluorophenyl)-N'-hydroxy-4-[(6-hydroxyhexyl)sulfanyl]-1,2,5-oxadiazole-3-carboximidamide | Calc'd 433.0, found 433.0 |

-continued

| Ex # | Structure | Chemical Name | Mass [M + H]+ |
|---|---|---|---|
| 54 | 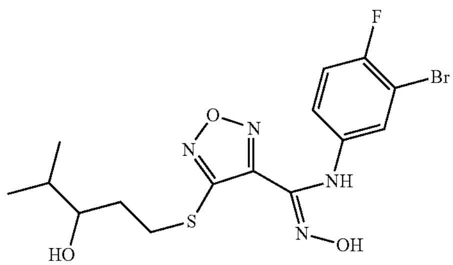 [SMILES: CC(C)C(O)CCSc1nonc1/C(=N/O)Nc1ccc(F)c(Br)c1] | N-(3-bromo-4-fluorophenyl)-N'-hydroxy-4-[(3-hydroxy-4-methylpentyl)sulfanyl]-1,2,5-oxadiazole-3-carboximidamide | Calc'd 433.0, found 433.0 |
| 55 | 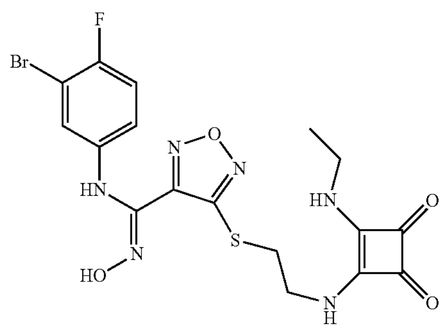 [SMILES: CCNc1c(NCCSc2nonc2/C(=N/O)Nc2ccc(F)c(Br)c2)c(=O)c1=O] | N-(3-bromo-4-fluorophenyl)-4-[(2-{[2-(ethylamino)-3,4-dioxocyclobut-1-en-1-yl]amino}ethyl)sulfanyl]-N'-hydroxy-1,2,5-oxadiazole-3-carboximidamide | Calc'd 499.0, found 499.0 |
| 56 | 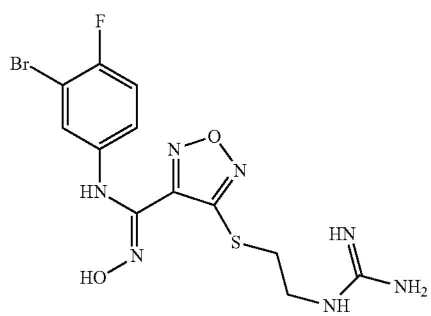 [SMILES: N=C(N)NCCSc1nonc1/C(=N/O)Nc1ccc(F)c(Br)c1] | N-(3-bromo-4-fluorophenyl)-4-[(2-carbamimidamidoethyl)sulfanyl]-N'-hydroxy-1,2,5-oxadiazole-3-carboximidamide | Calc'd 418.0, found 418.0 |
| 57 | 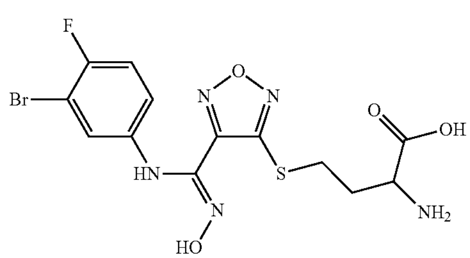 [SMILES: NC(CCSc1nonc1/C(=N/O)Nc1ccc(F)c(Br)c1)C(=O)O] | S-{4-[N-(3-bromo-4-fluorophenyl)-N'-hydroxycarbamimidoyl]-1,2,5-oxadiazol-3-yl}homocysteine | Calc'd 434.0, found 434.1 |
| 58 | 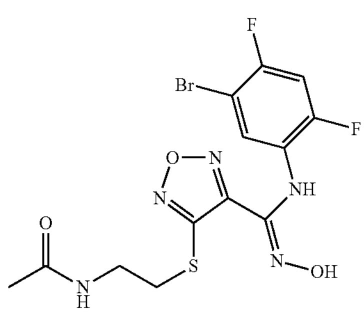 [SMILES: CC(=O)NCCSc1nonc1/C(=N/O)Nc1cc(Br)c(F)cc1F] | N-[2-({4-[N-(5-bromo-2,4-difluorophenyl)-N'-hydroxycarbamimidoyl]-1,2,5-oxadiazol-3-yl}sulfanyl)ethyl]acetamide | Calc'd 436.0, found 436.0 |

| Ex # | Structure | Chemical Name | Mass [M + H]+ |
|---|---|---|---|
| 59 | 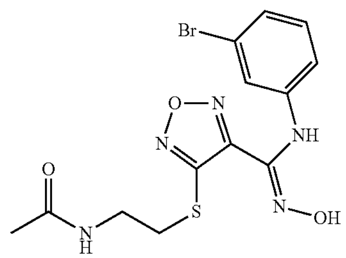 [SMILES: CC(=O)NCCSc1nonc1/C(=N/O)Nc1cccc(Br)c1] | N-[2-({4-[N-(3-bromophenyl)-N'-hydroxycarbamimidoyl]-1,2,5-oxadiazol-3-yl}sulfanyl)ethyl]acetamide | Calc'd 400.0, found 400.0 |
| 60 | 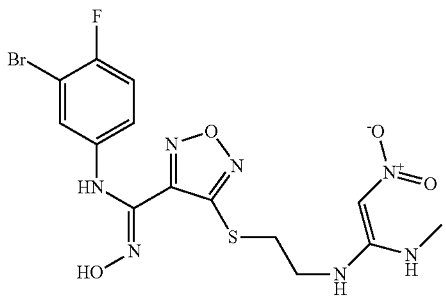 | N-(3-bromo-4-fluorophenyl)-N'-hydroxy-4-[(2-{[(E)-1-(methylamino)-2-nitroethenyl]amino}ethyl)sulfanyl]-1,2,5-oxadiazole-3-carboximidamide | Calc'd 476.0, found 476.1 |
| 61 | 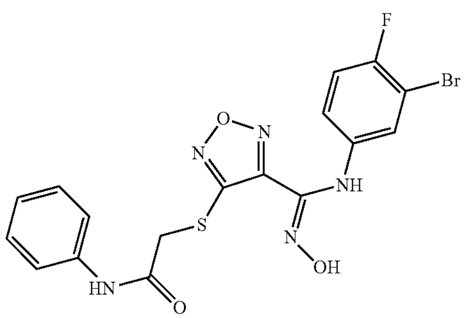 [SMILES: O=C(CSc1nonc1/C(=N/O)Nc1ccc(F)c(Br)c1)Nc1ccccc1] | 2-({4-[N-(3-bromo-4-fluorophenyl)-N'-hydroxycarbamimidoyl]-1,2,5-oxadiazol-3-yl}sulfanyl)-N-phenylacetamide | Calc'd 466.0, found 466.1 |
| 62 | 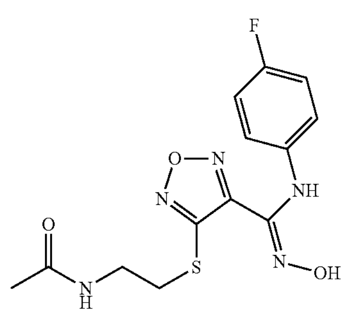 [SMILES: CC(=O)NCCSc1nonc1/C(=N/O)Nc1ccc(F)cc1] | N-[2-({4-[N-(4-fluorophenyl)-N'-hydroxycarbamimidoyl]-1,2,5-oxadiazol-3-yl}sulfanyl)ethyl]acetamide | Calc'd 340.0, found 340.0 |
| 63 | 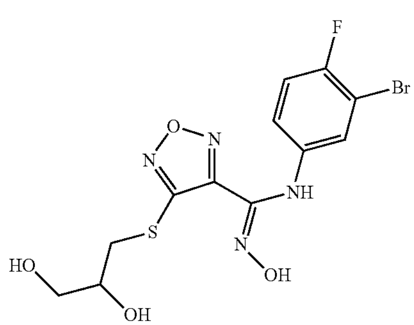 [SMILES: OCC(O)CSc1nonc1/C(=N/O)Nc1ccc(F)c(Br)c1] | N-(3-bromo-4-fluorophenyl)-4-[(2,3-dihydroxypropyl)sulfanyl]-N'-hydroxy-1,2,5-oxadiazole-3-carboximidamide (peak 1) | Calc'd 407.0, found 407.0 |

-continued

| Ex # | Structure | Chemical Name | Mass [M + H]+ |
|---|---|---|---|
| 64 | 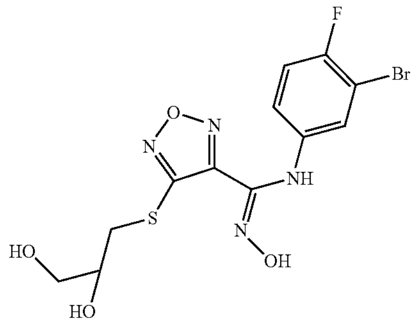 [SMILES: OCC(O)CSc1nonc1/C(=N/O)Nc1ccc(F)c(Br)c1] | N-(3-bromo-4-fluorophenyl)-4-[(2,3-dihydroxypropyl)sulfanyl]-N'-hydroxy-1,2,5-oxadiazole-3-carboximidamide (peak 2 | Calc'd 407.0, found 407.0 |
| 65 | 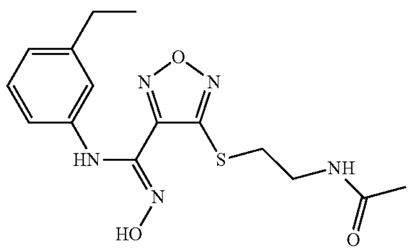 [SMILES: CCc1cccc(N/C(=N\O)c2nonc2SCCNC(C)=O)c1] | N-[2-({4-[N-(3-ethylphenyl)-N'-hydroxycarbamimidoyl]-1,2,5-oxadiazol-3-yl}sulfanyl)ethyl]acetamide | Calc'd 350.0, found 350.0 |
| 66 | 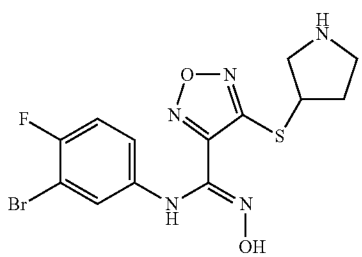 [SMILES: O/N=C(\Nc1ccc(F)c(Br)c1)c1nonc1SC1CCNC1] | N-(3-bromo-4-fluorophenyl)-N'-hydroxy-4-(pyrrolidin-3-ylsulfanyl)-1,2,5-oxadiazole-3-carboximidamide | Calc'd 402.0, found 402.0 |
| 67 | 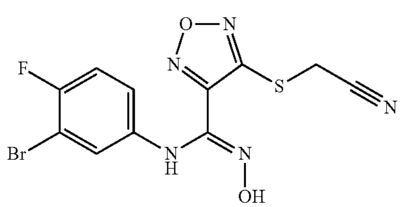 [SMILES: N#CCSc1nonc1/C(=N/O)Nc1ccc(F)c(Br)c1] | N-(3-bromo-4-fluorophenyl)-4-[(cyanomethyl)sulfanyl]-N'-hydroxy-1,2,5-oxadiazole-3-carboximidamide | Calc'd 372.0, found 372.1 |
| 68 | 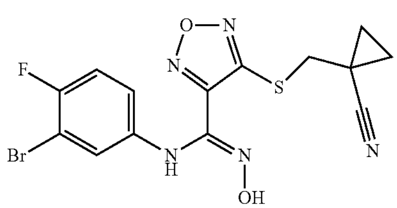 [SMILES: N#CC1(CSc2nonc2/C(=N/O)Nc2ccc(F)c(Br)c2)CC1] | N-(3-bromo-4-fluorophenyl)-4-{[(1-cyanocyclopropyl)methyl]sulfanyl}-N'-hydroxy-1,2,5-oxadiazole-3-carboximidamide | Calc'd 412.0, found 412.1 |
| 69 | 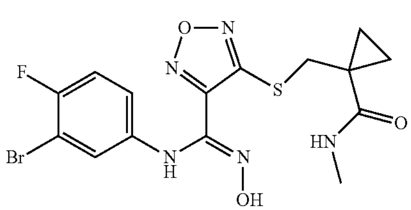 [SMILES: CNC(=O)C1(CSc2nonc2/C(=N/O)Nc2ccc(F)c(Br)c2)CC1] | 1-[({4-[N-(3-bromo-4-fluorophenyl)-N'-hydroxycarbamimidoyl]-1,2,5-oxadiazol-3-yl}sulfanyl)methyl]-N-methylcyclopropanecarboxamide | Calc'd 444.0, found 444.0 |

| Ex # | Structure | Chemical Name | Mass [M + H]+ |
|---|---|---|---|
| 70 | 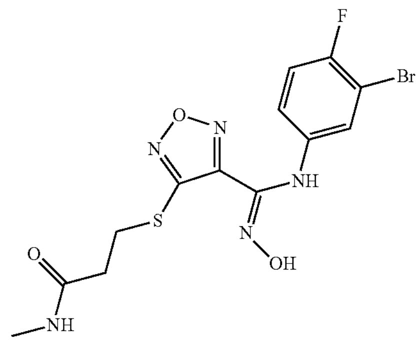 [SMILES: CNC(=O)CCSc1nonc1/C(=N/O)Nc1ccc(F)c(Br)c1] | 3-({4-[N-(3-bromo-4-fluorophenyl)-N'-hydroxycarbamimidoyl]-1,2,5-oxadiazol-3-yl}sulfanyl)-N-methylpropanamide | Calc'd 418.0, found 418.0 |
| 71 | 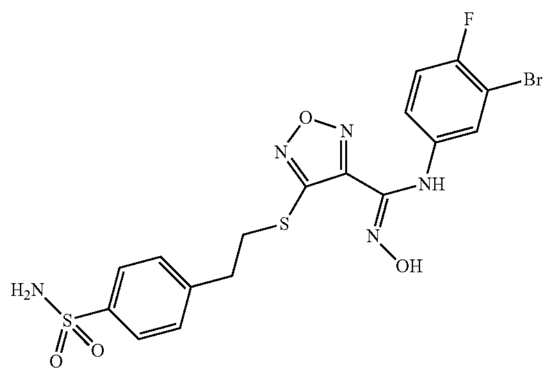 [SMILES: NS(=O)(=O)c1ccc(CCSc2nonc2/C(=N/O)Nc2ccc(F)c(Br)c2)cc1] | N-(3-bromo-4-fluorophenyl)-N'-hydroxy-4-{[2-(4-sulfamoylphenyl)ethyl]sulfanyl}-1,2,5-oxadiazole-3-carboximidamide | Calc'd 516.0, found 516.0 |
| 72 | 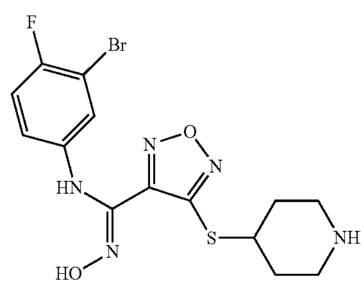 [SMILES: O/N=C(\Nc1ccc(F)c(Br)c1)c1nonc1SC1CCNCC1] | N-(3-bromo-4-fluorophenyl)-N'-hydroxy-4-(piperidin-4-ylsulfanyl)-1,2,5-oxadiazole-3-carboximidamide | Calc'd 416.0, found 415.9 |
| 73 | 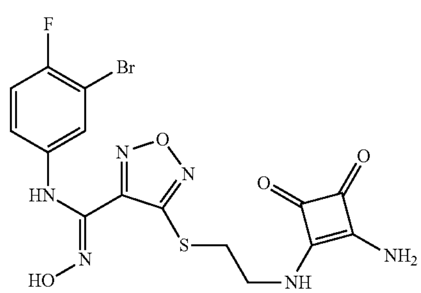 [SMILES: Nc1c(NCCSc2nonc2/C(=N/O)Nc2ccc(F)c(Br)c2)c(=O)c1=O] | 4-({2-[(2-amino-3,4-dioxocyclobut-1-en-1-yl)amino]ethyl}sulfanyl)-N-(3-bromo-4-fluorophenyl)-N'-hydroxy-1,2,5-oxadiazole-3-carboximidamide | Calc'd 471.0, found 470.9 |
| 74 | 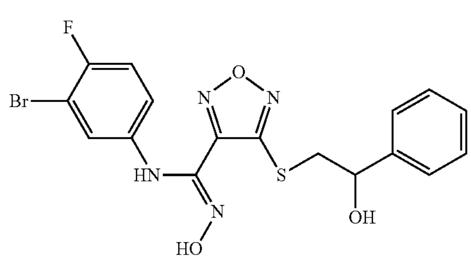 [SMILES: O/N=C(\Nc1ccc(F)c(Br)c1)c1nonc1SCC(O)c1ccccc1] | N-(3-bromo-4-fluorophenyl)-N'-hydroxy-4-[(2-hydroxy-2-phenylethyl)sulfanyl]-1,2,5-oxadiazole-3-carboximidamide | Calc'd 453.0, found 453.0 |

-continued

| Ex # | Structure | Chemical Name | Mass [M + H]+ |
|---|---|---|---|
| 75 | 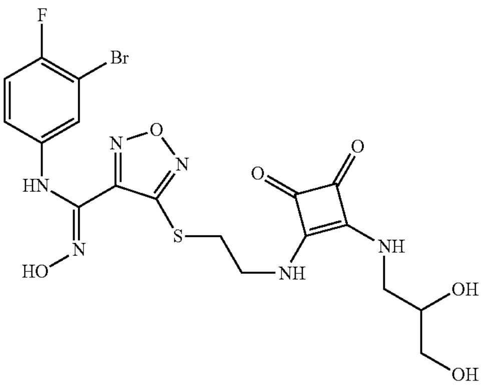 [SMILES: O=c1c(NCCSc2nonc2/C(=N/O)Nc2ccc(F)c(Br)c2)c(NCC(O)CO)c1=O] | N-(3-bromo-4-fluorophenyl)-4-{[2-({2-[(2,3-dihydroxypropyl)amino]-3,4-dioxocyclobut-1-en-1-yl}amino)ethyl]sulfanyl}-N'-hydroxy-1,2,5-oxadiazole-3-carboximidamide | Calc'd 545.0, found 545.0 |
| 76 | 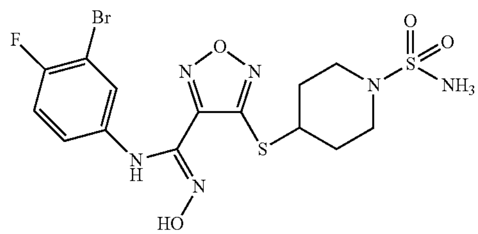 [SMILES: NS(=O)(=O)N1CCC(Sc2nonc2/C(=N/O)Nc2ccc(F)c(Br)c2)CC1] | N-(3-bromo-4-fluorophenyl)-N'-hydroxy-4-[(1-sulfamoylpiperidin-4-yl)sulfanyl]-1,2,5-oxadiazole-3-carboximidamide | Calc'd 495.0, found 495.0 |
| 77 | 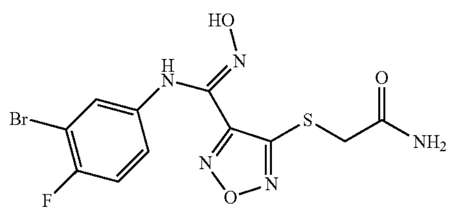 [SMILES: NC(=O)CSc1nonc1/C(=N/O)Nc1ccc(F)c(Br)c1] | 2-({4-[N-(3-bromo-4-fluorophenyl)-N'-hydroxycarbamimidoyl]-1,2,5-oxadiazol-3-yl}sulfanyl)acetamide | Calc'd 390.0, found 390.0 |
| 78 | 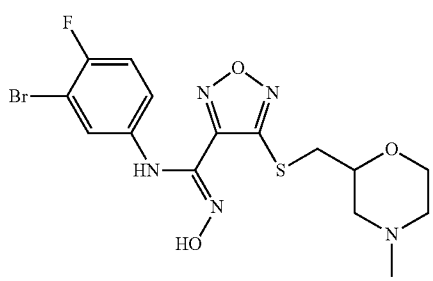 [SMILES: CN1CCOC(CSc2nonc2/C(=N/O)Nc2ccc(F)c(Br)c2)C1] | N-(3-bromo-4-fluorophenyl)-N'-hydroxy-4-{[(4-methylmorpholin-2-yl)methyl]sulfanyl}-1,2,5-oxadiazole-3-carboximidamide | Calc'd 446.0, found 446.0 |
| 79 | 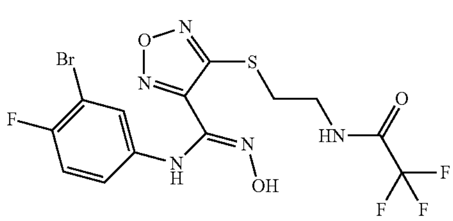 [SMILES: O=C(NCCSc1nonc1/C(=N/O)Nc1ccc(F)c(Br)c1)C(F)(F)F] | N-[2-({4-[N-(3-bromo-4-fluorophenyl)-N'-hydroxycarbamimidoyl]-1,2,5-oxadiazol-3-yl}sulfanyl)ethyl]-2,2,2-trifluoroacetamide | Calc'd 472.0, found 472.0 |
| 80 | 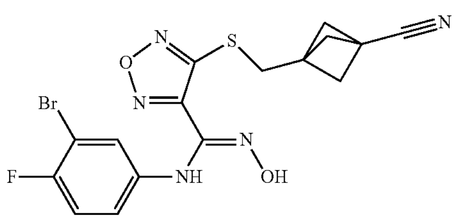 [SMILES: N#CC12CC(CSc3nonc3/C(=N/O)Nc3ccc(F)c(Br)c3)(C1)C2] | N-(3-bromo-4-fluorophenyl)-4-{[(3-cyanobicyclo[1.1.1]pent-1-yl)methyl]sulfanyl}-N'-hydroxy-1,2,5-oxadiazole-3-carboximidamide | Calc'd 438.0, found 438.0 |

| Ex # | Structure | Chemical Name | Mass [M + H]+ |
|---|---|---|---|
| 81 | 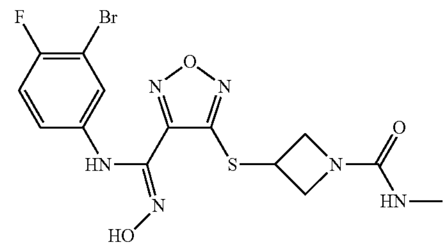 [SMILES: CNC(=O)N1CC(Sc2nonc2/C(=N/O)Nc2ccc(F)c(Br)c2)C1] | 3-({4-[N-(3-bromo-4-fluorophenyl)-N'-hydroxycarbamimidoyl]-1,2,5-oxadiazol-3-yl}sulfanyl)-N-methylazetidine-1-carboxamide | Calc'd 445.0, found 445.0 |
| 82 | 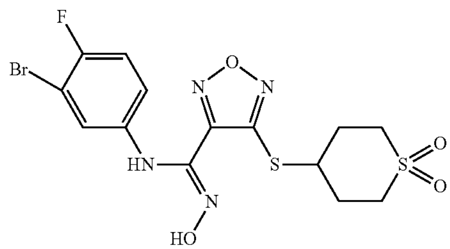 [SMILES: O=S1(=O)CCC(Sc2nonc2/C(=N/O)Nc2ccc(F)c(Br)c2)CC1] | N-(3-bromo-4-fluorophenyl)-4-[(1,1-dioxidotetrahydro-2H-thiopyran-4-yl)sulfanyl]-N'-hydroxy-1,2,5-oxadiazole-3-carboximidamide | Calc'd 465.0, found 465.0 |
| 83 | 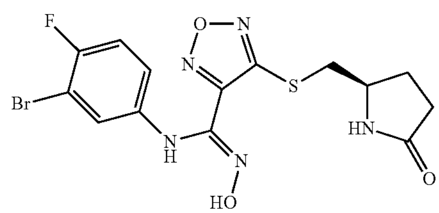 [SMILES: O=C1CC[C@H](CSc2nonc2/C(=N/O)Nc2ccc(F)c(Br)c2)N1] | N-(3-bromo-4-fluorophenyl)-N'-hydroxy-4-({[(2R)-5-oxopyrrolidin-2-yl]methyl}sulfanyl)-1,2,5-oxadiazole-3-carboximidamide | Calc'd 430.0, found 430.0 |
| 84 | 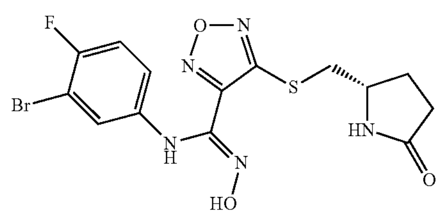 [SMILES: O=C1CC[C@@H](CSc2nonc2/C(=N/O)Nc2ccc(F)c(Br)c2)N1] | N-(3-bromo-4-fluorophenyl)-N'-hydroxy-4-({[(2S)-5-oxopyrrolidin-2-yl]methyl}sulfanyl)-1,2,5-oxadiazole-3-carboximidamide | Calc'd 430.0, found 430.0 |
| 85 | 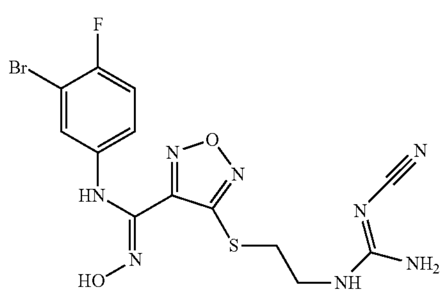 [SMILES: N#C/N=C(\N)NCCSc1nonc1/C(=N/O)Nc1ccc(F)c(Br)c1] | N-(3-bromo-4-fluorophenyl)-4-{[2-(N''-cyanocarbamimidamido)ethyl]sulfanyl}-N'-hydroxy-1,2,5-oxadiazole-3-carboximidamide | Calc'd 443.0, found 443.0 |
| 86 | 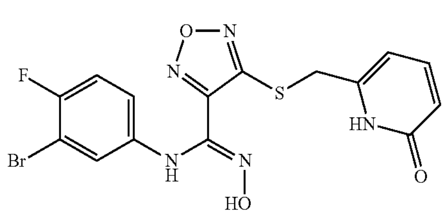 [SMILES: O=c1cccc(CSc2nonc2/C(=N/O)Nc2ccc(F)c(Br)c2)[nH]1] | N-(3-bromo-4-fluorophenyl)-N'-hydroxy-4-{[(6-oxo-1,6-dihydropyridin-2-yl)methyl]sulfanyl}-1,2,5-oxadiazole-3-carboximidamide | Calc'd 440.0, found 440.0 |

-continued

| Ex # | Structure | Chemical Name | Mass [M + H]+ |
|---|---|---|---|
| 87 | 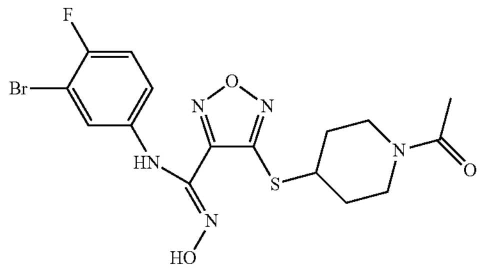 [SMILES: CC(=O)N1CCC(Sc2nonc2/C(=N/O)Nc2ccc(F)c(Br)c2)CC1] | 4-[(1-acetylpiperidin-4-yl)sulfanyl]-N-(3-bromo-4-fluorophenyl)-N'-hydroxy-1,2,5-oxadiazole-3-carboximidamide | Calc'd 458.0, found 458.0 |
| 88 | 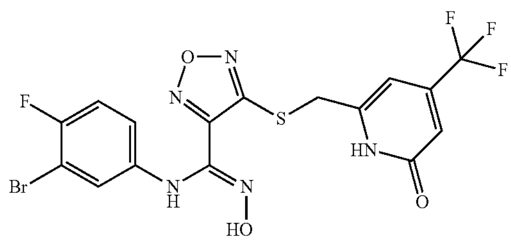 [SMILES: O=c1cc(C(F)(F)F)cc(CSc2nonc2/C(=N/O)Nc2ccc(F)c(Br)c2)[nH]1] | N-(3-bromo-4-fluorophenyl)-N'-hydroxy-4-({[6-oxo-4-(trifluoromethyl)-1,6-dihydropyridin-2-yl]methyl}sulfanyl)-1,2,5-oxadiazole-3-carboximidamide | Calc'd 508.0, found 508.0 |
| 89 | 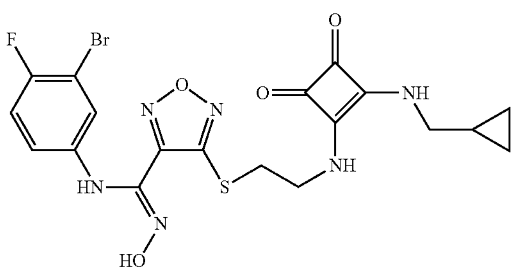 [SMILES: O=c1c(NCCSc2nonc2/C(=N/O)Nc2ccc(F)c(Br)c2)c(NCC2CC2)c1=O] | N-(3-bromo-4-fluorophenyl)-4-{[2-({2-[(cyclopropylmethyl)amino]-3,4-dioxocyclobut-1-en-1-yl}amino)ethyl]sulfanyl}-N'-hydroxy-1,2,5-oxadiazole-3-carboximidamide | Calc'd 525.0, found 525.0 |
| 90 | 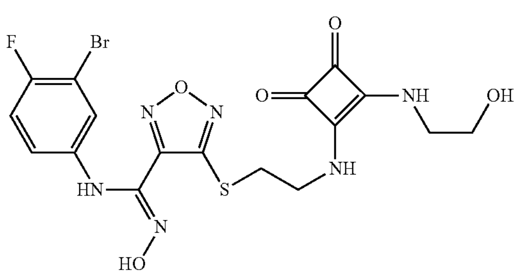 [SMILES: O=c1c(NCCO)c(NCCSc2nonc2/C(=N/O)Nc2ccc(F)c(Br)c2)c1=O] | N-(3-bromo-4-fluorophenyl)-N'-hydroxy-4-{[2-({2-[(2-hydroxyethyl)amino]-3,4-dioxocyclobut-1-en-1-yl}amino)ethyl]sulfanyl}-1,2,5-oxadiazole-3-carboximidamide | Calc'd 515.0, found 515.0 |
| 91 | 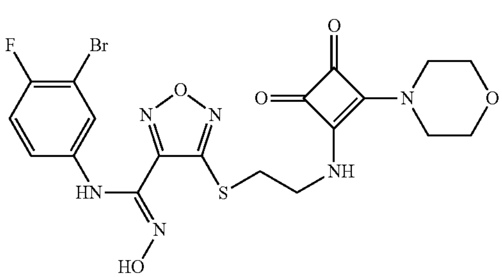 [SMILES: O=c1c(NCCSc2nonc2/C(=N/O)Nc2ccc(F)c(Br)c2)c(N2CCOCC2)c1=O] | N-(3-bromo-4-fluorophenyl)-N'-hydroxy-4-({2-[(2-morpholin-4-yl-3,4-dioxocyclobut-1-en-1-yl)amino]ethyl}sulfanyl)-1,2,5-oxadiazole-3-carboximidamide | Calc'd 541.0, found 541.0 |

-continued

| Ex # | Structure | Chemical Name | Mass [M + H]+ |
|---|---|---|---|
| 92 | 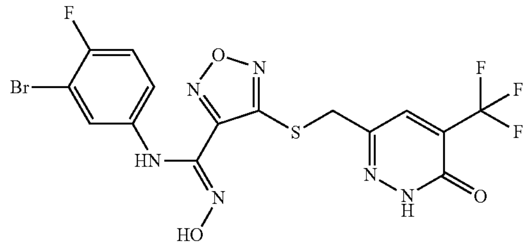 [SMILES: O=c1[nH]nc(CSc2nonc2/C(=N/O)Nc2ccc(F)c(Br)c2)cc1C(F)(F)F] | N-(3-bromo-4-fluorophenyl)-N'-hydroxy-4-({[6-oxo-5-(trifluoromethyl)-1,6-dihydropyridazin-3-yl]methyl}sulfanyl)-1,2,5-oxadiazole-3-carboximidamide | Calc'd 509.0, found 509.0 |
| 93 | 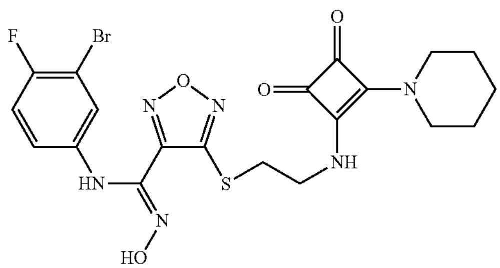 [SMILES: O=c1c(NCCSc2nonc2/C(=N/O)Nc2ccc(F)c(Br)c2)c(N2CCCCC2)c1=O] | N-(3-bromo-4-fluorophenyl)-4-({2-[(3,4-dioxo-2-piperidin-1-ylcyclobut-1-en-1-yl)amino]ethyl}sulfanyl)-N'-hydroxy-1,2,5-oxadiazole-3-carboximidamide | Calc'd 539.0, found 539.0 |
| 94 | 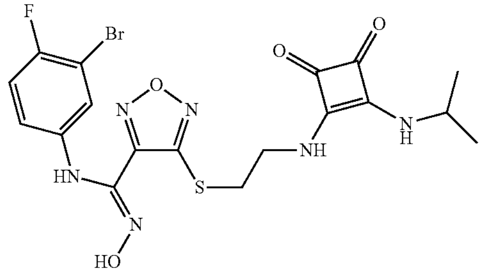 [SMILES: CC(C)Nc1c(NCCSc2nonc2/C(=N/O)Nc2ccc(F)c(Br)c2)c(=O)c1=O] | N-(3-bromo-4-fluorophenyl)-N'-hydroxy-4-{[2-({2-[(1-methylethyl)amino]-3,4-dioxocyclobut-1-en-1-yl}amino)ethyl]sulfanyl}-1,2,5-oxadiazole-3-carboximidamide | Calc'd 513.0, found 513.0 |
| 95 | 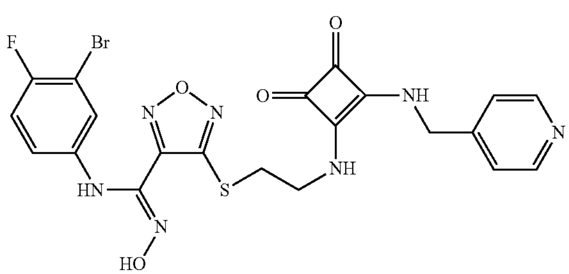 [SMILES: O=c1c(NCCSc2nonc2/C(=N/O)Nc2ccc(F)c(Br)c2)c(NCc2ccncc2)c1=O] | N-(3-bromo-4-fluorophenyl)-4-{[2-({3,4-dioxo-2-[(pyridin-4-ylmethyl)amino]cyclobut-1-en-1-yl}amino)ethyl]sulfanyl}-N'-hydroxy-1,2,5-oxadiazole-3-carboximidamide | Calc'd 562.0, found 562.0 |
| 96 | 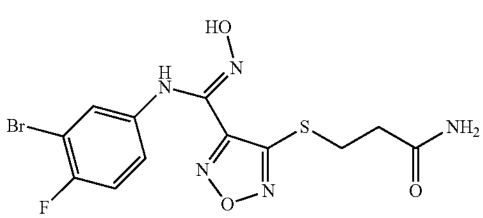 [SMILES: NC(=O)CCSc1nonc1/C(=N/O)Nc1ccc(F)c(Br)c1] | 3-({4-[N-(3-bromo-4-fluorophenyl)-N'-hydroxycarbamimidoyl]-1,2,5-oxadiazol-3-yl}sulfanyl)propanamide | Calc'd 404.0, found 404.0 |

-continued

| Ex # | Structure | Chemical Name | Mass [M + H]+ |
|---|---|---|---|
| 97 | 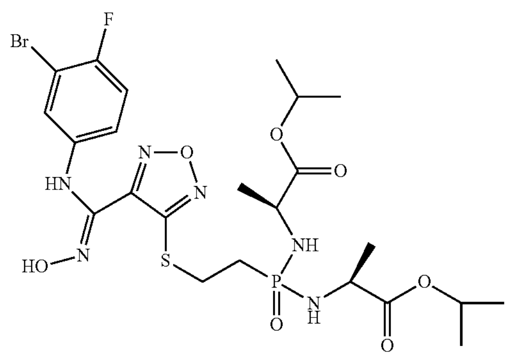 [SMILES: CC(C)OC(=O)[C@H](C)NP(=O)(CCSc1nonc1/C(=N/O)Nc1ccc(F)c(Br)c1)N[C@@H](C)C(=O)OC(C)C] | 1-methylethyl (2S,6S)-4-[2-({4-[N-(3-bromo-4-fluorophenyl)-N'-hydroxycarbamimidoyl]-1,2,5-oxadiazol-3-yl}sulfanyl)ethyl]-2,6,9-trimethyl-7-oxo-8-oxa-3,5-diaza-4-phosphadecan-1-oate 4-oxide (non-preferred name) | Calc'd 667.0, found 667.0 |
| 98 | 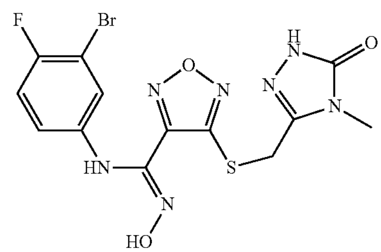 [SMILES: Cn1c(CSc2nonc2/C(=N/O)Nc2ccc(F)c(Br)c2)n[nH]c1=O] | N-(3-bromo-4-fluorophenyl)-N'-hydroxy-4-{[(4-methyl-5-oxo-4,5-dihydro-1H-1,2,4-triazol-3-yl)methyl]sulfanyl}-1,2,5-oxadiazole-3-carboximidamide | Calc'd 444.0, found 444.0 |
| 99 | 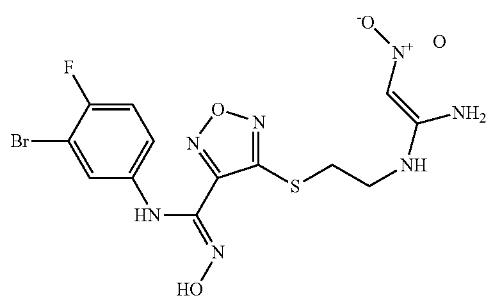 | 4-[(2-{[(E)-1-amino-2-nitroethenyl]amino}ethyl)sulfanyl]-N-(3-bromo-4-fluorophenyl)-N'-hydroxy-1,2,5-oxadiazole-3-carboximidamide | Calc'd 462.0, found 462.0 |
| 100 | 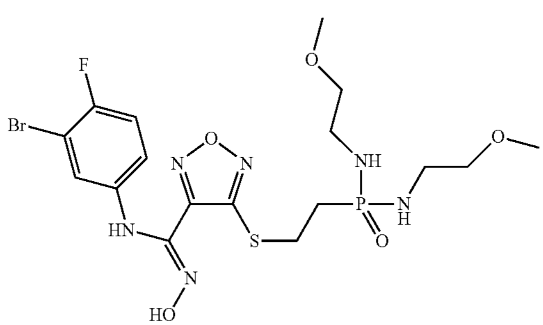 [SMILES: COCCNP(=O)(CCSc1nonc1/C(=N/O)Nc1ccc(F)c(Br)c1)NCCOC] | 4-[(2-{bis[(2-methoxyethyl)amino]phosphoryl}ethyl)sulfanyl]-N-(3-bromo-4-fluorophenyl)-N'-hydroxy-1,2,5-oxadiaxole-3-carboximidamide | Calc'd 555.0, found 555.0 |
| 101 | 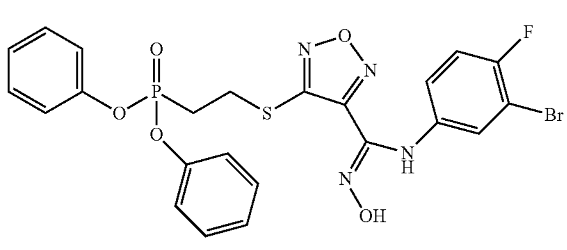 [SMILES: O=P(CCSc1nonc1/C(=N/O)Nc1ccc(F)c(Br)c1)(Oc1ccccc1)Oc1ccccc1] | diphenyl [2-({4-[N-(3-bromo-4-fluorophenyl)-N'-hydroxycarbamimidoyl]-1,2,5-oxadiazol-3-yl}sulfanyl)ethyl]phosphonate | Calc'd 593.0, found 593.0 |

-continued

| Ex # | Structure | Chemical Name | Mass [M + H]+ |
|---|---|---|---|
| 102 | 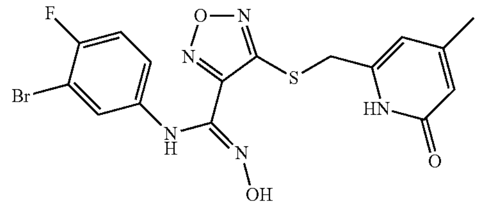 [SMILES: Cc1cc(CSc2nonc2/C(=N/O)Nc2ccc(F)c(Br)c2)[nH]c(=O)c1] | N-(3-bromo-4-fluorophenyl)-N'-hydroxy-4-{[(4-methyl-6-oxo-1,6-dihydropyridin-2-yl)methyl]sulfanyl}-1,2,5-oxadiazole-3-carboximidamide | Calc'd 454.0, found 454.0 |
| 103 | 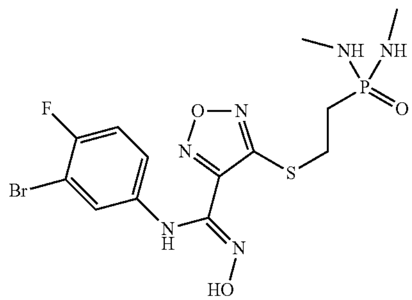 [SMILES: CNP(=O)(CCSc1nonc1/C(=N/O)Nc1ccc(F)c(Br)c1)NC] | 4-({2-[bis(methylamino)phosphoryl]ethyl}sulfanyl)-N-(3-bromo-4-fluorophenyl)-N'-hydroxy-1,2,5-oxadiazole-3-carboximidamide | Calc'd 467.0, found 467.1 |
| 104 | 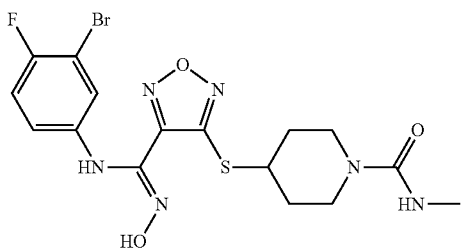 [SMILES: CNC(=O)N1CCC(Sc2nonc2/C(=N/O)Nc2ccc(F)c(Br)c2)CC1] | 4-({4-[N-(3-bromo-4-fluorophenyl)-N'-hydroxycarbamimidoyl]-1,2,5-oxadiazol-3-yl}sulfanyl)-N-methylpiperidine-1-carboxamide | Calc'd 473.0, found 473.0 |
| 105 | 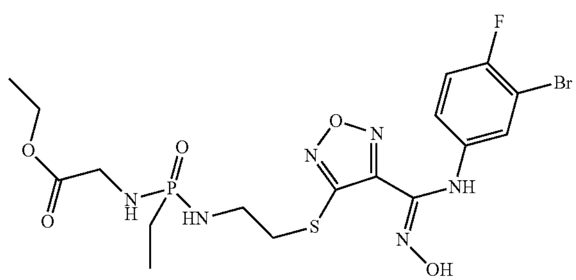 [SMILES: CCOC(=O)CNP(=O)(CC)NCCSc1nonc1/C(=N/O)Nc1ccc(F)c(Br)c1] | ethyl N-[{[2-({4-[N-(3-bromo-4-fluorophenyl)-N'-hydroxycarbamimidoyl]-1,2,5-oxadiazol-3-yl}sulfanyl)ethyl]amino}(ethyl)phosphoryl]glycinate | Calc'd 553.0, found 553.0 |
| 106 | 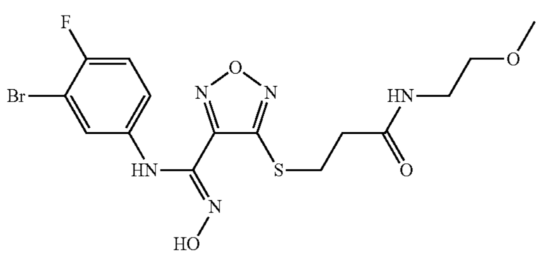 [SMILES: COCCNC(=O)CCSc1nonc1/C(=N/O)Nc1ccc(F)c(Br)c1] | 3-({4-[N-(3-bromo-4-fluorophenyl)-N'-hydroxycarbamimidoyl]-1,2,5-oxadiazol-3-yl}sulfanyl)-N-(2-methoxyethyl)propanamide | Calc'd 462.0, found 462.0 |
| 107 | 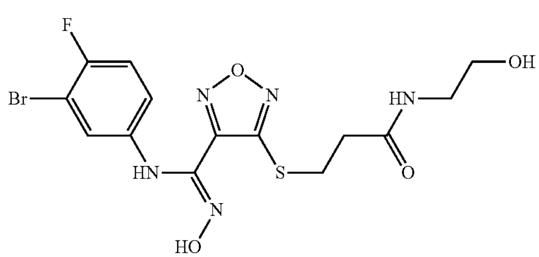 [SMILES: O=C(CCSc1nonc1/C(=N/O)Nc1ccc(F)c(Br)c1)NCCO] | 3-({4-[N-(3-bromo-4-fluorophenyl)-N'-hydroxycarbamimidoyl]-1,2,5-oxadiazol-3-yl}sulfanyl)-N-(2-hydroxyethyl)propanamide | Calc'd 448.0, found 448.0 |

-continued

| Ex # | Structure | Chemical Name | Mass [M + H]+ |
|---|---|---|---|
| 108 | 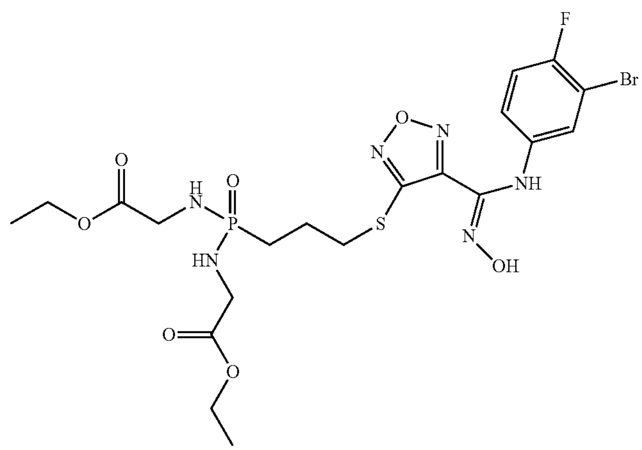 [SMILES: CCOC(=O)CNP(=O)(CCCSc1nonc1/C(=N/O)Nc1ccc(F)c(Br)c1)NCC(=O)OCC] | ethyl 4-[3-({4-[N-(3-bromo-4-fluorophenyl)-N'-hydroxycarbamimidoyl]-1,2,5-oxadiazol-3-yl}sulfanyl)propyl]-7-oxo-8-oxa-3,5-diaza-4-phosphadecan-1-oate 4-oxide (non-preferred name) | Calc'd 625.0, found 625.0 |
| 109 | 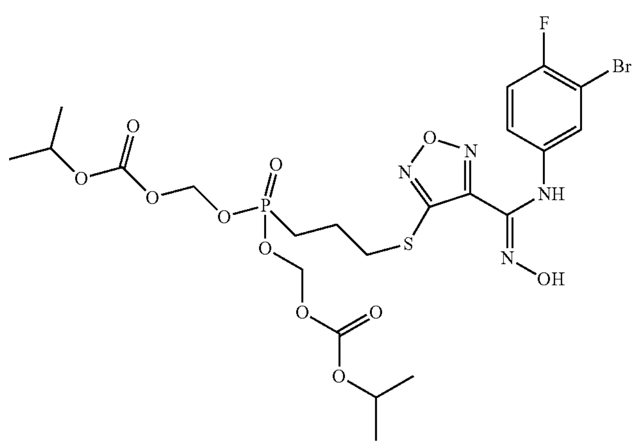 [SMILES: CC(C)OC(=O)OCOP(=O)(CCCSc1nonc1/C(=N/O)Nc1ccc(F)c(Br)c1)OCOC(=O)OC(C)C] | bis({[(1-methylethoxy)carbonyl]oxy}methyl) [3-({4-[N-(3-bromo-4-fluorophenyl)-N'-hydroxycarbamimidoyl]-1,2,5-oxadiazol-3-yl}sulfanyl)propyl]phosphonate | Calc'd 687.0, found 687.0 |
| 110 | 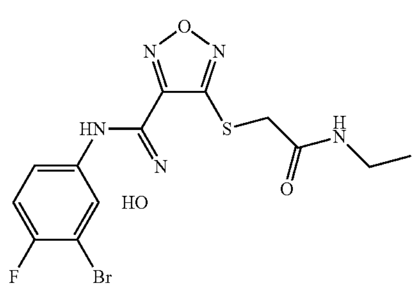 | 2-({4-[N-(3-bromo-4-fluorophenyl)-N'-hydroxycarbamimidoyl]-1,2,5-oxadiazol-3-yl}sulfanyl)-N-ethylacetamide | Calc'd 418.0, found 417.8 |
| 111 | 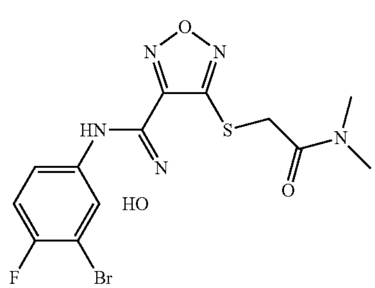 | 2-({4-[N-(3-bromo-4-fluorophenyl)-N'-hydroxycarbamimidoyl]-1,2,5-oxadiazol-3-yl}sulfanyl)-N,N-dimethylacetamide | Calc'd 418.0, found 417.9 |

-continued

| Ex # | Structure | Chemical Name | Mass [M + H]+ |
|---|---|---|---|
| 112 | 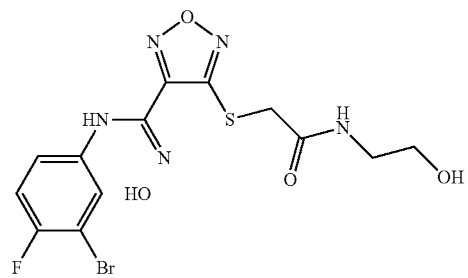 | 2-({4-[N-(3-bromo-4-fluorophenyl)-N'-hydroxycarbamimidoyl]-1,2,5-oxadiazol-3-yl}sulfanyl)-N-(2-hydroxyethyl)acetamide | Calc'd 434.0, found 433.9 |
| 113 | 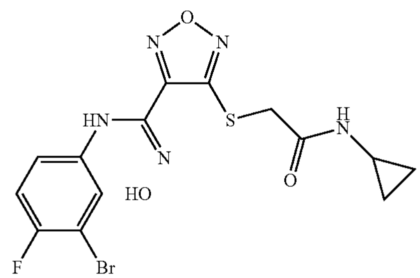 | 2-({4-[N-(3-bromo-4-fluorophenyl)-N'-hydroxycarbamimidoyl]-1,2,5-oxadiazol-3-yl}sulfanyl)-N-cyclopropylacetamide | Calc'd 430.0, found 429.8 |
| 114 | 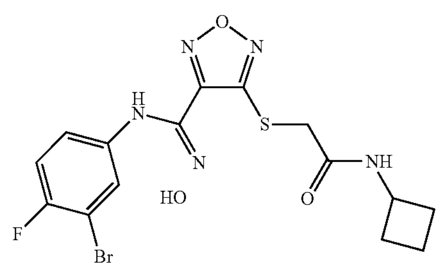 | 2-({4-[N-(3-bromo-4-fluorophenyl)-N'-hydroxycarbamimidoyl]-1,2,5-oxadiazol-3-yl}sulfanyl)-N-cyclobutylacetamide | Calc'd 444.0, found 443.8 |
| 115 | 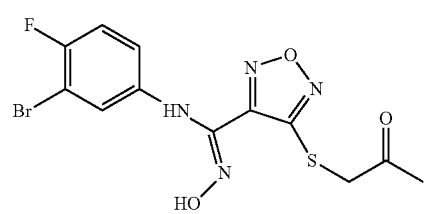 [SMILES: CC(=O)CSc1nonc1/C(=N/O)Nc1ccc(F)c(Br)c1] | N-(3-bromo-4-fluorophenyl)-N'-hydroxy-4-[(2-oxopropyl)sulfanyl]-1,2,5-oxadiazole-3-carboximidamide | Calc'd 389.0, found 389.0 |
| 116 | 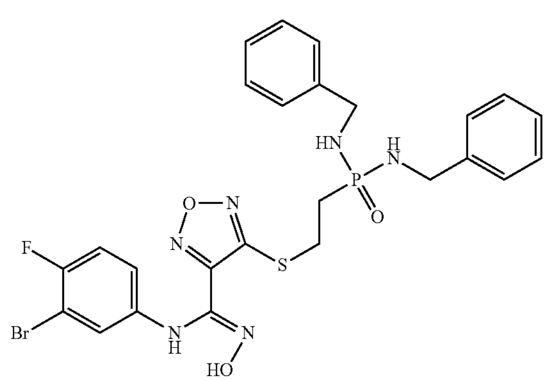 [SMILES: O=P(CCSc1nonc1/C(=N/O)Nc1ccc(F)c(Br)c1)(NCc1ccccc1)NCc1ccccc1] | 4-({2-[bis(benzylamino)phosphoryl]ethyl}sulfanyl)-N-(3-bromo-4-fluorophenyl)-N'-hydroxy-1,2,5-oxadiazole-3-carboximidamide | Calc'd 619.0, found 619.0 |

-continued

| Ex # | Structure | Chemical Name | Mass [M + H]+ |
|---|---|---|---|
| 117 | 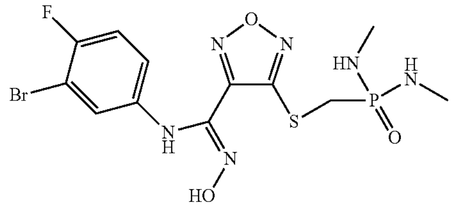 [SMILES: CNP(=O)(CSc1nonc1/C(=N/O)Nc1ccc(F)c(Br)c1)NC] | 4-({[bis(methylamino)phosphoryl]methyl}sulfanyl)-N-(3-bromo-4-fluorophenyl)-N'-hydroxy-1,2,5-oxadiazole-3-carboximidamide | Calc'd 453.0, found 453.0 |
| 118 | 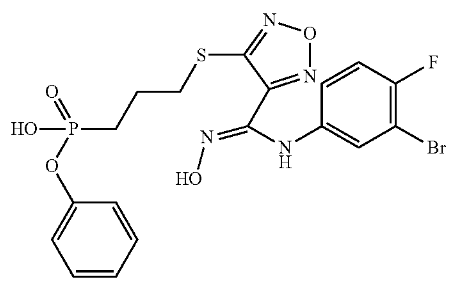 [SMILES: O=P(O)(CCCSc1nonc1/C(=N/O)Nc1ccc(F)c(Br)c1)Oc1ccccc1] | phenyl hydrogen [3-({4-[N-(3-bromo-4-fluorophenyl)-N'-hydroxycarbamimidoyl]-1,2,5-oxadiazol-3-yl}sulfanyl)propyl]phosphonate | Calc'd 531.0, found 531.0 |
| 119 | 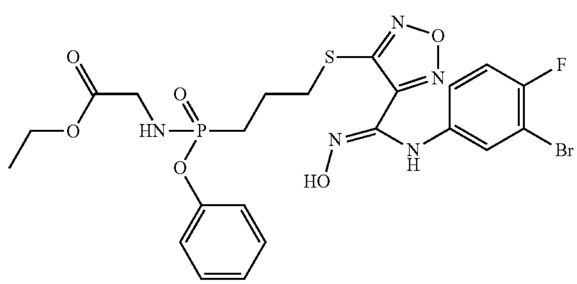 [SMILES: CCOC(=O)CNP(=O)(CCCSc1nonc1/C(=N/O)Nc1ccc(F)c(Br)c1)Oc1ccccc1] | ethyl N-{[3-({4-[N-(3-bromo-4-fluorophenyl)-N'-hydroxyarbamimidoyl]-1,2,5-oxadiazol-3-yl}sulfanyl)propy](phenoxy)phosphoryl]glycinate | Calc'd 616.0, found 616.0 |
| 120 | 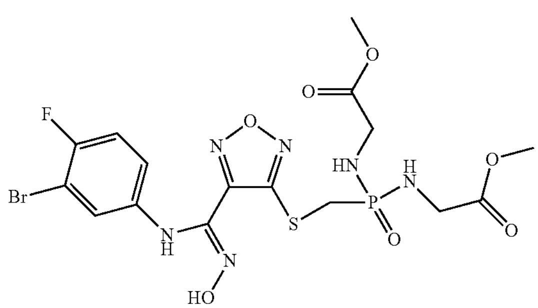 [SMILES: COC(=O)CNP(=O)(CSc1nonc1/C(=N/O)Nc1ccc(F)c(Br)c1)NCC(=O)OC] | methyl 6-[({4-[N-(3-bromo-4-fluorophenyl)-N'-hydroxycarbamimidoyl]-1,2,5-oxadiazol-3-yl}sulfanyl)methyl]-3-oxo-2-oxa-5,7-diaza-6-phosphanonan-9-oate 6-oxide | Calc'd 569.0, found 569.0 |
| 121 | 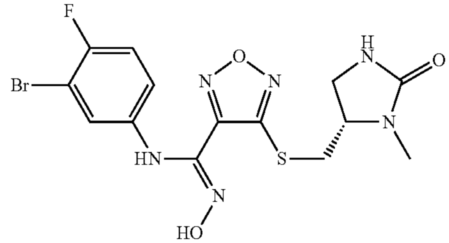 [SMILES: CN1C(=O)NC[C@H]1CSc1nonc1/C(=N/O)Nc1ccc(F)c(Br)c1] | N-(3-bromo-4-fluorophenyl)-N'-hydroxy-4-({[(4S)-3-methyl-2-oxoimidazolidin-4-yl]methyl}sulfanyl)-1,2,5-oxadiazole-3-carboximidamide | Calc'd 445.0, found 445.0 |

| Ex # | Structure | Chemical Name | Mass [M + H]+ |
|---|---|---|---|
| 122 | 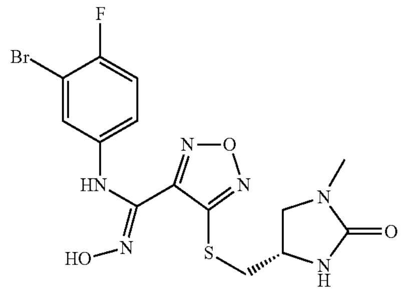 [SMILES: CN1C[C@@H](CSc2nonc2/C(=N/O)Nc2ccc(F)c(Br)c2)NC1=O] | N-(3-bromo-4-fluorophenyl)-N'-hydroxy-4-({[(4S)-1-methyl-2-oxoimidazolidin-4-yl]methyl}sulfanyl)-1,2,5-oxadiazole-3-carboximidamide | Calc'd 445.0, found 445.0 |
| 123 | 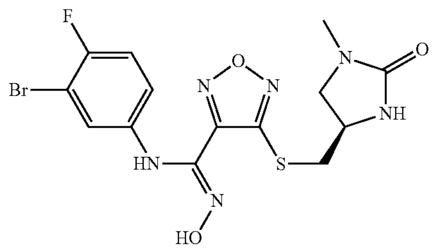 [SMILES: CN1C[C@H](CSc2nonc2/C(=N/O)Nc2ccc(F)c(Br)c2)NC1=O] | N-(3-bromo-4-fluorophenyl)-N'-hydroxy-4-({[(4R)-1-methyl-2-oxoimidazolidin-4-yl]methyl}sulfanyl)-1,2,5-oxadiazole-3-carboximidamide | Calc'd 445.0, found 445.0 |
| 124 | 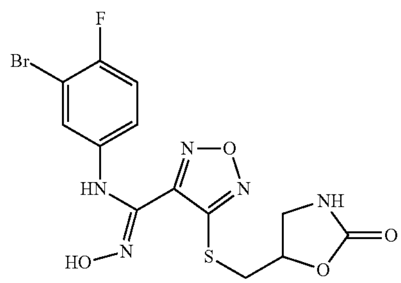 [SMILES: O=C1NCC(CSc2nonc2/C(=N/O)Nc2ccc(F)c(Br)c2)O1] | N-(3-bromo-4-fluorophenyl)-N'-hydroxy-4-{[(2-oxo-1,3-oxazolidin-5-yl)methyl]sulfanyl}-1,2,5-oxadiazole-3-carboximidamide | Calc'd 432.0, found 432.0 |
| 125 | 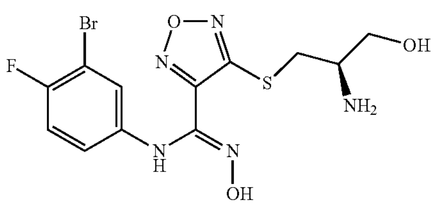 [SMILES: N[C@H](CO)CSc1nonc1/C(=N/O)Nc1ccc(F)c(Br)c1] | 4-{[(2R)-2-amino-3-hydroxypropyl]sulfanyl}-N-(3-bromo-4-fluorophenyl)-N'-hydroxy-1,2,5-oxadiazole-3-carboximidamide | Calc'd 406.0, found |
| 126 | 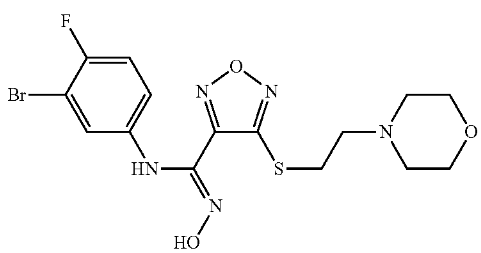 [SMILES: O/N=C(\Nc1ccc(F)c(Br)c1)c1nonc1SCCN1CCOCC1] | N-(3-bromo-4-fluorophenyl)-N'-hydroxy-4-[(2-morpholin-4-ylethyl)sulfanyl]-1,2,5-oxadiazole-3-carboximidamide | Calc'd 446.0, found 446.1 |
| 127 | 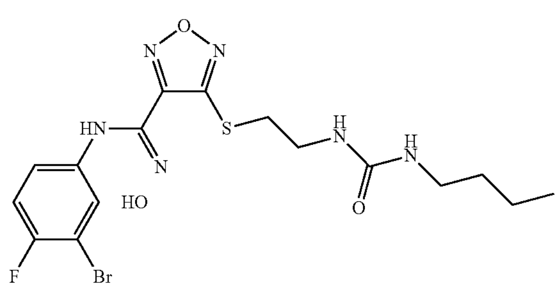 | N-(3-bromo-4-fluorophenyl)-4-({2-[(butylcarbamoyl)amino]ethyl}sulfanyl)-N'-hydroxy-1,2,5-oxadiazole-3-carboximidamide | Calc'd 475.0, found 475.0 |

-continued

| Ex # | Structure | Chemical Name | Mass [M + H]+ |
|---|---|---|---|
| 128 | 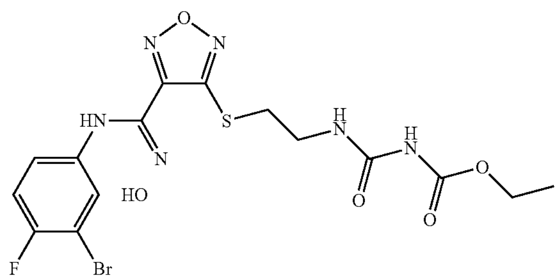 | ethyl {[2-({4-[N-(3-bromo-4-fluorophenyl)-N'-hydroxycarbamimidoyl]-1,2,5-oxadiazol-3-yl}sulfanyl)ethyl]carbamoyl} carbamate | Calc'd 491.0, found 491.0 |
| 129 | 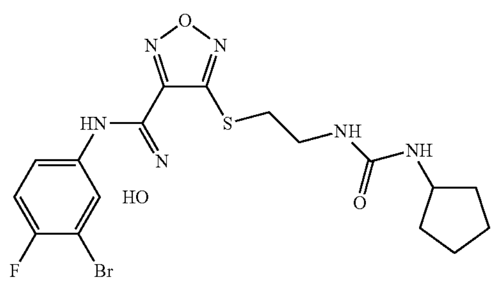 | N-(3-bromo-4-fluorophenyl)-4-({2-[(cyclopentylcarbamoyl)amino]ethyl}sulfanyl)-N'-hydroxy-1,2,5-oxadiazole-3-carboximidamide | Calc'd 487.0, found 487.0 |
| 130 | 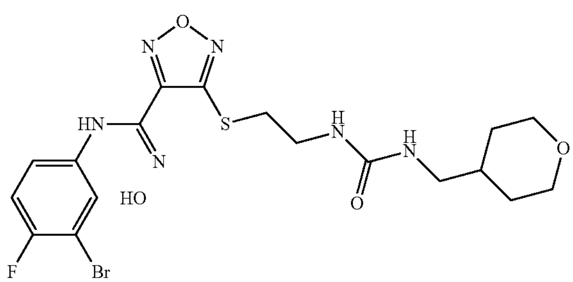 | N-(3-bromo-4-fluorophenyl)-N'-hydroxy-4-[(2-{[(tetrahydro-2H-pyran-4-ylmethyl)carbamoyl]amino}ethyl)sulfanyl]-1,2,5-oxadiaxole-3-carboximidamide | Calc'd 517.0, found 517.0 |
| 131 | 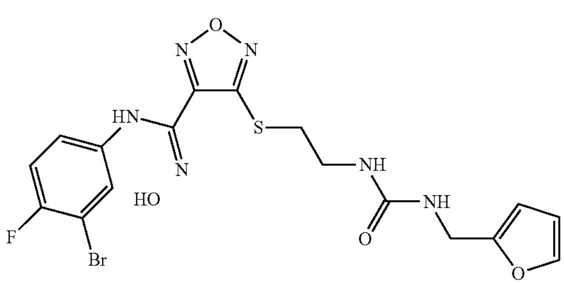 | N-(3-bromo-4-fluorophenyl)-4-[(2-{[(furan-2-ylmethyl)carbamoyl]amino}ethyl)sulfanyl]-N'-hydroxy-1,2,5-oxadiazole-3-carboximidamide | Calc'd 499.0, found 499.0 |
| 132 | 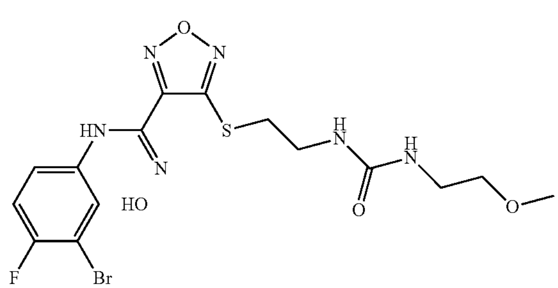 | N-(3-bromo-4-fluorophenyl)-N'-hydroxy-4-[(2-{[(2-methoxyethyl)carbamoyl]amino}ethyl)sulfanyl]-1,2,5-oxadiazole-3-carboximidamide | Calc'd 477.0, found 477.0 |

-continued

| Ex # | Structure | Chemical Name | Mass [M + H]+ |
|---|---|---|---|
| 133 | 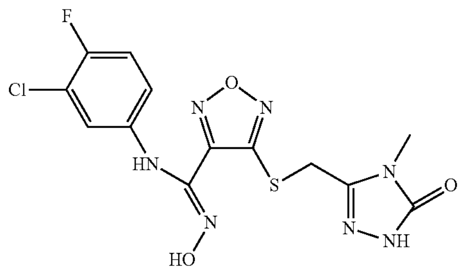 [SMILES: Cn1c(CSc2nonc2/C(=N/O)Nc2ccc(F)c(Cl)c2)n[nH]c1=O] | N-(3-chloro-4-fluorophenyl)-N'-hydroxy-4-{[(4-methyl-5-oxo-4,5-dihydro-1H-1,2,4-triazol-3-yl)methyl]sulfanyl}-1,2,5-oxadiazole-3-carboximidamide | Calc'd 400.0, found 400.1 |
| 134 | 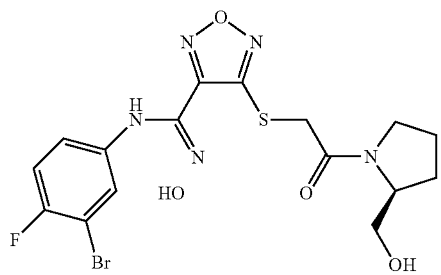 | N-(3-bromo-4-fluorophenyl)-N'-hydroxy-4-({2-[(2S)-2-(hydroxymethyl)pyrrolidin-1-yl]-2-oxoethyl}sulfanyl)-1,2,5-oxadiazole-3-carboximidamide | Calc'd 474.0, found 474.0 |
| 135 | 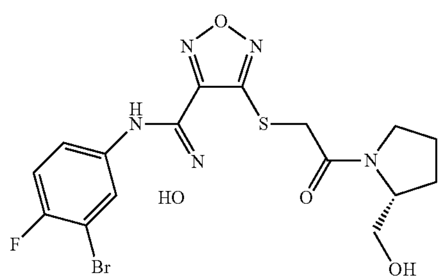 | N-(3-bromo-4-fluorophenyl)-N'-hydroxy-4-({2-[(2R)-2-(hydroxymethyl)pyrrolidin-1-yl]-2-oxoethyl}sulfanyl)-1,2,5-oxadiazole-3-carboximidamide | Calc'd 474.0, found 474.1 |
| 136 | 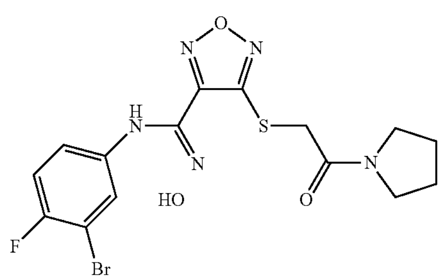 | N-(3-bromo-4-fluorophenyl)-N'-hydroxy-4-[(2-oxo-2-pyrrolidin-1-ylethyl)sulfanyl]-1,2,5-oxadiazole-3-carboximidamide | Calc'd 444.0, found 444.1 |
| 137 | 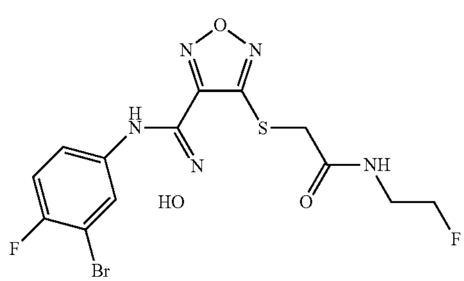 | 2-({4-[N-(3-bromo-4-fluorophenyl)-N'-hydroxycarbamimidoyl]-1,2,5-oxadiazol-3-yl}sulfanyl)-N-(2-fluoroethyl)acetamide | Calc'd 436.0, found 436.0 |

-continued

| Ex # | Structure | Chemical Name | Mass [M + H]+ |
|---|---|---|---|
| 138 | 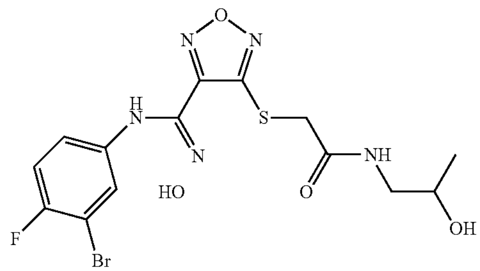 | 2-({4-[N-(3-bromo-4-fluorophenyl)-N'-hydroxycarbamimidoyl]-1,2,5-oxadiazol-3-yl}sulfanyl)-N-(2-hydroxypropyl)acetamide | Calc'd 448.0, found 448.1 |
| 139 | 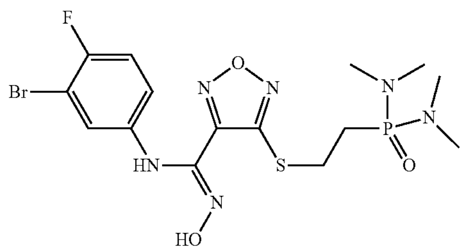 [SMILES: CN(C)P(=O)(CCSc1nonc1/C(=N/O)Nc1ccc(F)c(Br)c1)N(C)C] | 4-({2-[bis(dimethylamino)phosphoryl]ethyl}sulfanyl)-N-(3-bromo-4-fluorophenyl)-N'-hydroxy-1,2,5-oxadiazole-3-carboximidamide | Calc'd 495.0, found 495.0 |
| 140 | 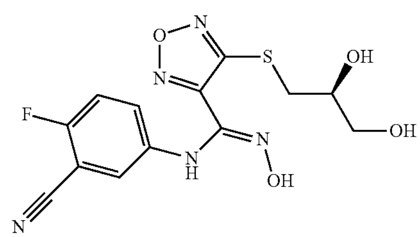 [SMILES: N#Cc1cc(N/C(=N\O)c2nonc2SC[C@@H](O)CO)ccc1F] | N-(3-cyano-4-fluorophenyl)-4-{[(2S)-2,3-dihydroxypropyl]sulfanyl}-N'-hydroxy-1,2,5-oxadiazole-3-carboximidamide | Calc'd 354.0, found 354.0 |
| 141 | 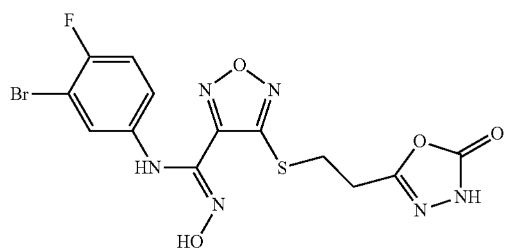 [SMILES: O=c1[nH]nc(CCSc2nonc2/C(=N/O)Nc2ccc(F)c(Br)c2)o1] | N-(3-bromo-4-fluorophenyl)-N'-hydroxy-4-{[2-(5-oxo-4,5-dihydro-1,3,4-oxadiazol-2-yl)ethyl]sulfanyl}-1,2,5-oxadiazole-3-carboximidamide | Calc'd 445.0, found 445.0 |
| 142 | 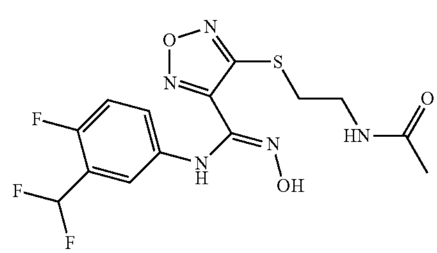 [SMILES: CC(=O)NCCSc1nonc1/C(=N/O)Nc1ccc(F)c(C(F)F)c1] | N-{2-[(4-{N-[3-(difluoromethyl)-4-fluorophenyl]-N'-hydroxycarbamimidoyl}-1,2,5-oxadiazol-3-yl)sulfanyl]ethyl}acetamide | Calc'd 390.0, found 390.0 |
| 143 | 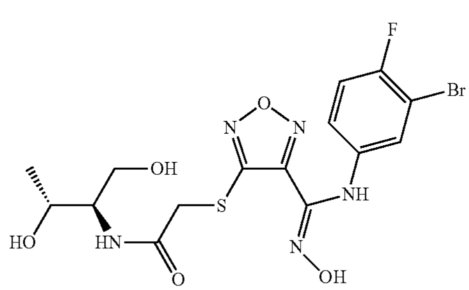 [SMILES: C[C@@H](O)[C@@H](CO)NC(=O)CSc1nonc1/C(=N/O)Nc1ccc(F)c(Br)c1] | 2-({4-[N-(3-bromo-4-fluorophenyl)-N'-hydroxycarbamimidoyl]-1,2,5-oxadiazol-3-yl}sulfanyl)-N-[(1R,2R)-2-hydroxy-1-(hydroxymethyl)propyl]acetamide | Calc'd 478.0, found 478.0 |

-continued

| Ex # | Structure | Chemical Name | Mass [M + H]+ |
|---|---|---|---|
| 144 | 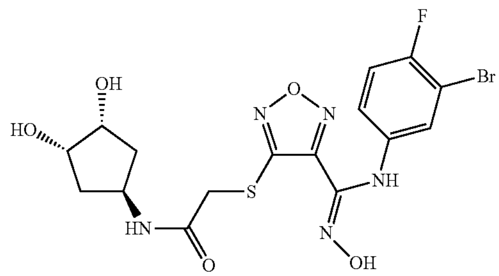 [SMILES: O=C(CSc1nonc1/C(=N/O)Nc1ccc(F)c(Br)c1)N[C@@H]1C[C@@H](O)[C@@H](O)C1] | 2-({4-[N-(3-bromo-4-fluorophenyl)-N'-hydroxycarbamimidoyl]-1,2,5-oxadiazol-3-yl}sulfanyl)-N-[(1s,3R,4S)-3,4-dihydroxycyclopentyl]acetamide | Calc'd 490.0, found 490.0 |
| 145 | 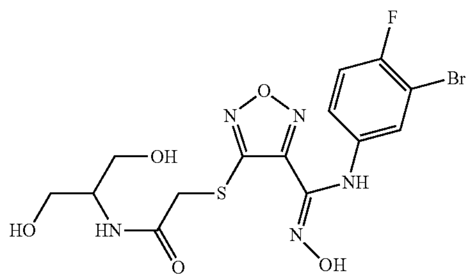 [SMILES: O=C(CSc1nonc1/C(=N/O)Nc1ccc(F)c(Br)c1)NC(CO)CO] | 2-({4-[N-(3-bromo-4-fluorophenyl)-N'-hydroxycarbamimidoyl]-1,2,5-oxadiazol-3-yl}sulfanyl)-N-[2-hydroxy-1-(hydroxymethyl)ethyl]acetamide | Calc'd 464.0, found 464.0 |
| 146 | 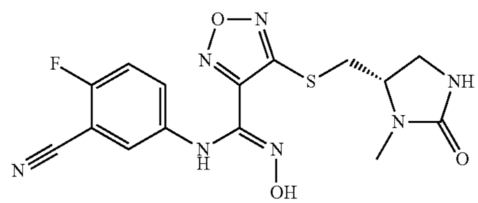 [SMILES: CN1C(=O)NC[C@H]1CSc1nonc1/C(=N/O)Nc1ccc(F)c(C#N)c1] | N-(3-cyano-4-fluorophenyl)-N'-hydroxy-4-({[(4S)-3-methyl]-2-oxoimidazolidin-4-yl]methyl}sulfanyl)-1,2,5-oxadiazole-3-carboximidamide | Calc'd 392.0, found 392.0 |
| 147 | 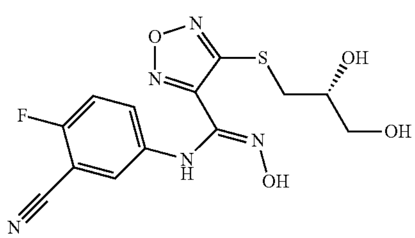 [SMILES: N#Cc1cc(N/C(=N\O)c2nonc2SC[C@H](O)CO)ccc1F] | N-(3-cyano-4-fluorophenyl)-4-{[(2R)-2,3-dihydroxypropyl]sulfanyl}-N'-hydroxy-1,2,5-oxadiazole-3-carboximidamide | Calc'd 354.0, found 354.0 |
| 148 | 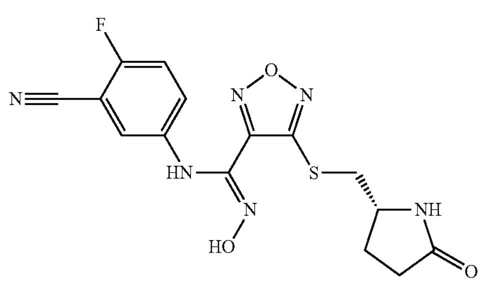 [SMILES: N#Cc1cc(N/C(=N\O)c2nonc2SC[C@H]2CCC(=O)N2)ccc1F] | N-(3-cyano-4-fluorophenyl)-N'-hydroxy-4-({[(2R)-5-oxopyrrolidin-2-yl]methyl}sulfanyl)-1,2,5-oxadiazole-3-carboximidamide | Calc'd 377.0, found 377.0 |
| 149 | 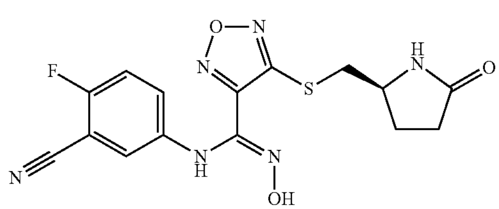 [SMILES: N#Cc1cc(N/C(=N\O)c2nonc2SC[C@@H]2CCC(=O)N2)ccc1F] | N-(3-cyano-4-fluorophenyl)-N'-hydroxy-4-({[(2S)-5-oxopyrrolidin-2-yl]methyl}sulfanyl)-1,2,5-oxadiazole-3-carboximidamide | Calc'd 377.0, found 377.0 |

-continued

| Ex # | Structure | Chemical Name | Mass [M + H]+ |
|---|---|---|---|
| 150 | 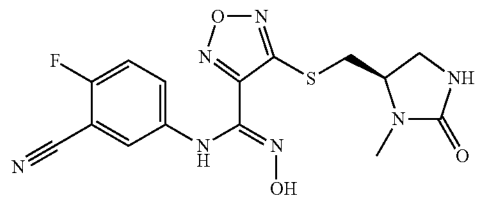 [SMILES: CN1C(=O)NC[C@@H]1CSc1nonc1/C(=N/O)Nc1ccc(F)c(C#N)c1] | N-(3-cyano-4-fluorophenyl)-N'-hydroxy-4-({[(4R)-3-methyl-2-oxoimidazolidin-4-yl]methyl}sulfanyl)-1,2,5-oxadiazole-3-carboximidamide | Calc'd 392.0, found 392.0 |
| 151 | 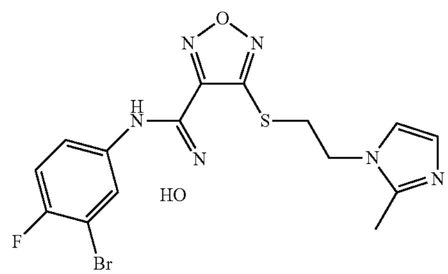 | N-(3-bromo-4-fluorophenyl)-N'-hydroxy-4-{[2-(2-methyl-1H-imidazol-1-yl)ethyl]sulfanyl}-1,2,5-oxadiazole-3-carboximidamide | Calc'd 441.0, found 441.0 |
| 152 | 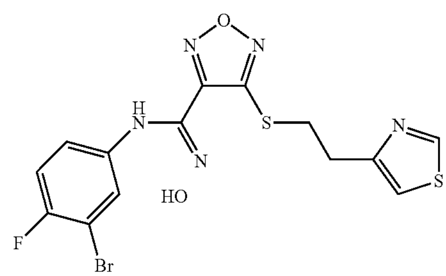 | N-(3-bromo-4-fluorophenyl)-N'-hydroxy-4-{[2-(1,3-thiazol-4-yl)ethyl]sulfanyl}-1,2,5-oxadiazole-3-carboximidamide | Calc'd 444.0, found 444.1 |
| 153 | 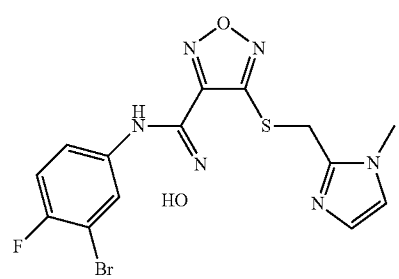 | N-(3-bromo-4-fluorophenyl)-N'-hydroxy-4-{[(1-methyl-1H-imidazol-2-yl)methyl]sulfanyl}-1,2,5-oxadiazole-3-carboximidamide | Calc'd 427.0, found 427.0 |
| 154 | 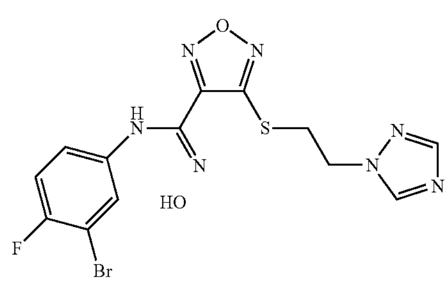 | N-(3-bromo-4-fluorophenyl)-N'-hydroxy-4-{[2-(1H-1,2,4-triazol-1-yl)ethyl]sulfanyl}-1,2,5-oxadiazole-3-carboximidamide | Calc'd 428.0, found 428.0 |

-continued

| Ex # | Structure | Chemical Name | Mass [M + H]+ |
|---|---|---|---|
| 155 | 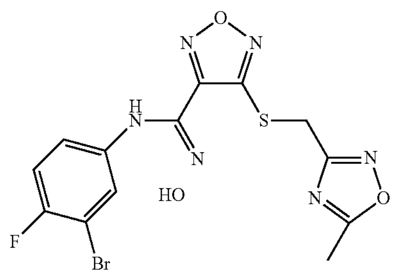 | N-(3-bromo-4-fluorophenyl)-N'-hydroxy-4-{[(5-methyl-1,2,4-oxadiazol-3-yl)methyl]sulfanyl}-1,2,5-oxadiazole-3-carboximidamide | Calc'd 429.0, found 429.0 |
| 156 | 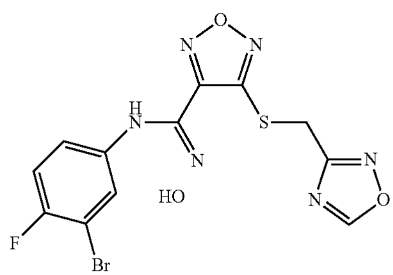 | N-(3-bromo-4-fluorophenyl)-N'-hydroxy-4-[(1,2,4-oxadiazol-3-ylmethyl)sulfanyl]-1,2,5-oxadiazole-3-carboximidamide | Calc'd 415.0, found 415.0 |
| 157 | 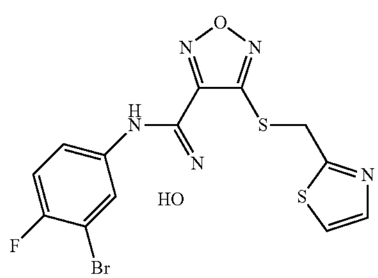 | N-(3-bromo-4-fluorophenyl)-N'-hydroxy-4-[(1,3-thiazol-2-ylmethyl)sulfanyl]-1,2,5-oxadiazole-3-carboximidamide | Calc'd 430.0, found 430.0 |
| 158 | 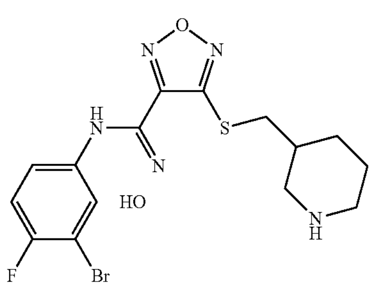 | N-(3-bromo-4-fluorophenyl)-N'-hydroxy-4-[(piperidin-3-ylmethyl)sulfanyl]-1,2,5-oxadiazole-3-carboximidamide | Calc'd 430.0, found 430.0 |
| 159 | 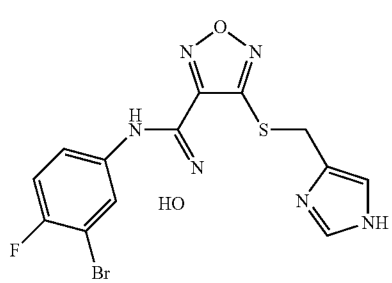 | N-(3-bromo-4-fluorophenyl)-N'-hydroxy-4-[(1H-imidazol-4-ylmethyl)sulfanyl]-1,2,5-oxadiazole-3-carboximidamide | Calc'd 413.0, found 413.0 |

| Ex # | Structure | Chemical Name | Mass [M + H]+ |
|---|---|---|---|
| 160 | 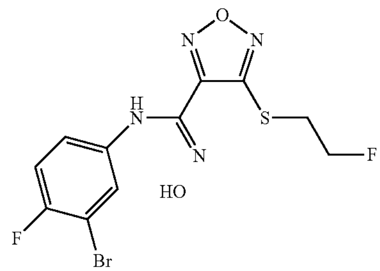 | N-(3-bromo-4-fluorophenyl)-4-[(2-fluoroethyl)sulfanyl]-N'-hydroxy-1,2,5-oxadiazole-3-carboximidamide | Calc'd 379.0, found 379.0 |
| 161 | 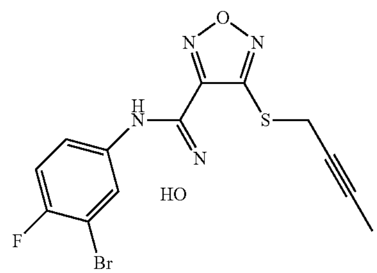 | N-(3-bromo-4-fluorophenyl)-4-(but-2-yn-1-ylsulfanyl)-N'-hydroxy-1,2,5-oxadiazole-3-carboximidamide | Calc'd 385.0, found 385.0 |
| 162 | 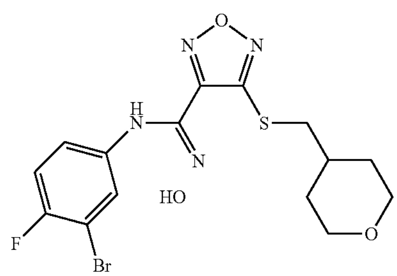 | N-(3-bromo-4-fluorophenyl)-N'-hydroxy-4-[(tetrahydro-2H-pyran-4-ylmethyl)sulfanyl]-1,2,5-oxadiazole-3-carboximidamide | Calc'd 431.0, found 431.0 |
| 163 | 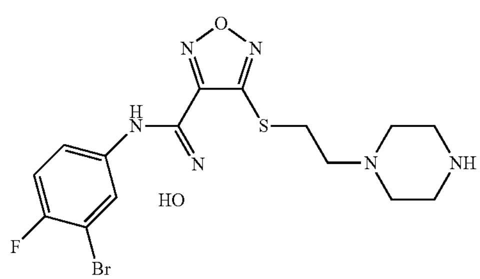 | N-(3-bromo-4-fluorophenyl)-N'-hydroxy-4-[(2-piperazin-1-ylethyl)sulfanyl]-1,2,5-oxadiazole-3-carboximidamide | Calc'd 445.0, found 445.0 |
| 164 | 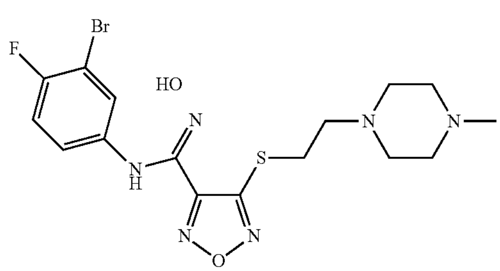 | N-(3-bromo-4-fluorophenyl)-N'-hydroxy-4-{[2-(4-methylpiperazin-1-yl)ethyl]sulfanyl}-1,2,5-oxadiazole-3-carboximidamide | Calc'd 459.0, found 459.0 |

-continued

| Ex # | Structure | Chemical Name | Mass [M + H]+ |
|---|---|---|---|
| 165 | 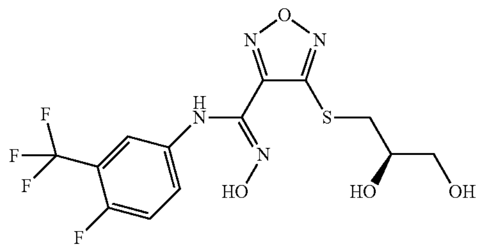 [SMILES: OC[C@@H](O)CSc1nonc1/C(=N/O)Nc1ccc(F)c(C(F)(F)F)c1] | 4-{[(2R)-2,3-dihydroxypropyl]sulfanyl}-N-[4-fluoro-3-(trifluoromethyl)phenyl]-N'-hydroxy-1,2,5-oxadiazole-3-carboximidamide | Calc'd 397.0, found 397.0 |
| 166 | 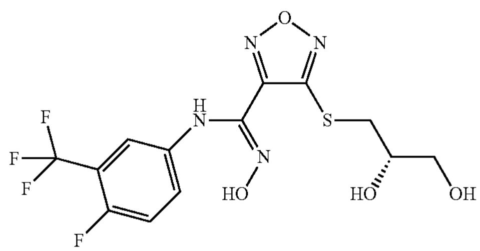 [SMILES: OC[C@H](O)CSc1nonc1/C(=N/O)Nc1ccc(F)c(C(F)(F)F)c1] | 4-{[(2S)-2,3-dihydroxypropyl]sulfanyl}-N-[4-fluoro-3-(trifluoromethyl)phenyl]-N'-hydroxy-1,2,5-oxadiazole-3-carboximidamide | Calc'd 397.0, found 397.0 |
| 167 | 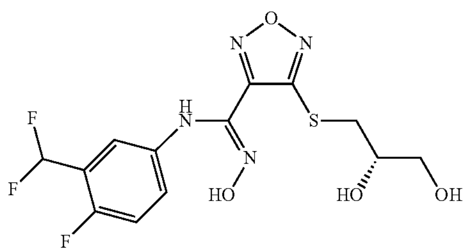 [SMILES: OC[C@H](O)CSc1nonc1/C(=N/O)Nc1ccc(F)c(C(F)F)c1] | N-[3-(difluoromethyl)-4-fluorophenyl]-4-{[(2S)-2,3-dihydroxypropyl]sulfanyl}-N'-hydroxy-1,2,5-oxadiazole-3-carboximidamide | Calc'd 379.0, found 379.0 |
| 168 | 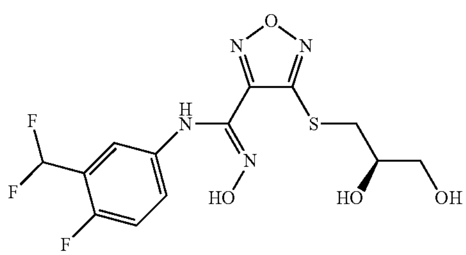 [SMILES: OC[C@@H](O)CSc1nonc1/C(=N/O)Nc1ccc(F)c(C(F)F)c1] | N-[3-(difluoromethyl)-4-fluorophenyl]-4-{[(2R)-2,3-dihydroxypropyl]sulfanyl}-N'-hydroxy-1,2,5-oxadiazole-3-carboximidamide | Calc'd 379.0, found 379.0 |
| 169 | 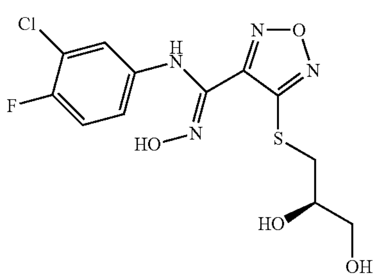 [SMILES: OC[C@@H](O)CSc1nonc1/C(=N/O)Nc1ccc(F)c(Cl)c1] | N-(3-chloro-4-fluorophenyl)-4-{[(2R)-2,3-dihydroxypropyl]sulfanyl}-N'-hydroxy-1,2,5-oxadiazole-3-carboximidamide | Calc'd 363.0, found 363.0 |
| 170 | 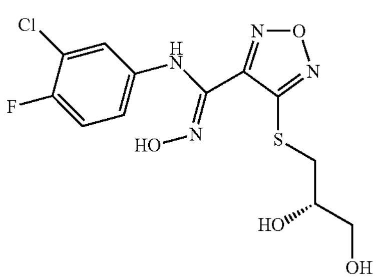 [SMILES: OC[C@H](O)CSc1nonc1/C(=N/O)Nc1ccc(F)c(Cl)c1] | N-(3-chloro-4-fluorophenyl)-4-{[(2S)-2,3-dihydroxypropyl]sulfanyl}-N'-hydroxy-1,2,5-oxadiazole-3-carboximidamide | Calc'd 363.0, found 363.0 |

| Ex # | Structure | Chemical Name | Mass [M + H]+ |
|---|---|---|---|
| 171 | 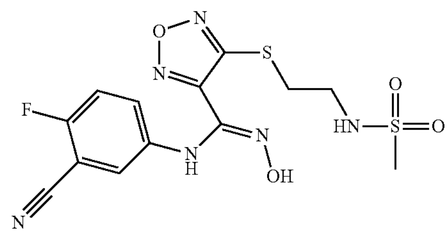 [SMILES: CS(=O)(=O)NCCSc1nonc1/C(=N/O)Nc1ccc(F)c(C#N)c1] | N-(3-cyano-4-fluorophenyl)-N'-hydroxy-4-({2-[(methylsulfonyl)amino]ethyl}sulfanyl)-1,2,5-oxadiazole-3-carboximidamide | Calc'd 401.0, found 401.0 |
| 172 | 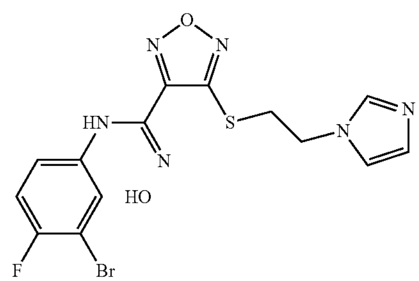 | N-(3-bromo-4-fluorophenyl)-N'-hydroxy-4-{[2-(1H-imidazol-1-yl)ethyl]sulfanyl}-1,2,5-oxadiazole-3-carboximidamide | Calc'd 427.0, found 427.0 |
| 173 | 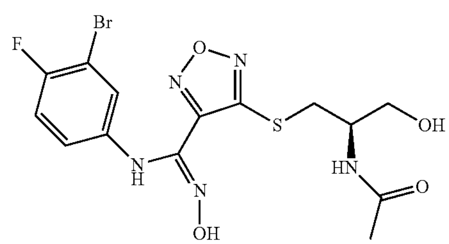 [SMILES: CC(=O)N[C@H](CO)CSc1nonc1/C(=N/O)Nc1ccc(F)c(Br)c1] | N-[(1R)-2-({4-[N-(3-bromo-4-fluorophenyl)-N'-hydroxycarbamimidoyl]-1,2,5-oxadiazol-3-yl}sulfanyl)-1-(hydroxymethyl)ethyl]acetamide | Calc'd 448.0, found 448.0 |
| 174 | 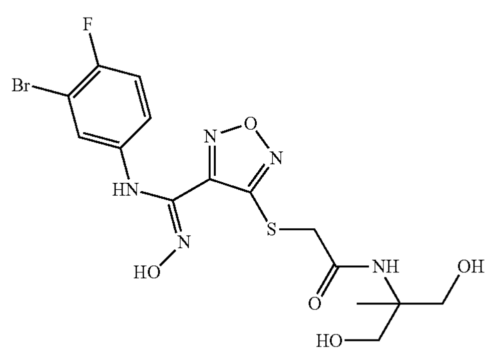 [SMILES: CC(CO)(CO)NC(=O)CSc1nonc1/C(=N/O)Nc1ccc(F)c(Br)c1] | 2-({4-[N-(3-bromo-4-fluorophenyl)-N'-hydroxycarbamimidoyl]-1,2,5-oxadiazol-3-yl}sulfanyl)-N-[2-hydroxy-1-(hydroxymethyl)-1-methylethyl]acetamide | Calc'd 478.0, found 478.0 |
| 175 | 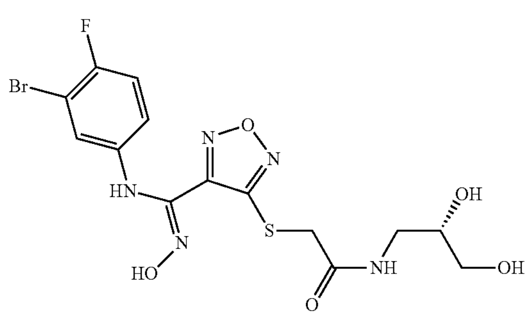 [SMILES: O=C(CSc1nonc1/C(=N/O)Nc1ccc(F)c(Br)c1)NC[C@H](O)CO] | 2-({4-[N-(3-bromo-4-fluorophenyl)-N'-hydroxycarbamimidoyl]-1,2,5-oxadiaxol-3-yl}sulfanyl)-N-[(2S)-2,3-dihydroxypropyl]acetamide | Calc'd 464.0, found 464.0 |

-continued

| Ex # | Structure | Chemical Name | Mass [M + H]+ |
|---|---|---|---|
| 176 | 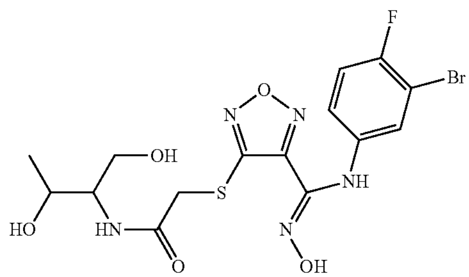 [SMILES: CC(O)C(CO)NC(=O)CSc1nonc1/C(=N/O)Nc1ccc(F)c(Br)c1] | 2-({4-[N-(3-bromo-4-fluorophenyl)-N'-hydroxycarbamimidoyl]-1,2,5-oxadiazol-3-yl}sulfanyl)-N-[2-hydroxy-1-(hydroxymethyl)propyl]acetamide | Calc'd 478.0, found 478.0 |
| 177 | 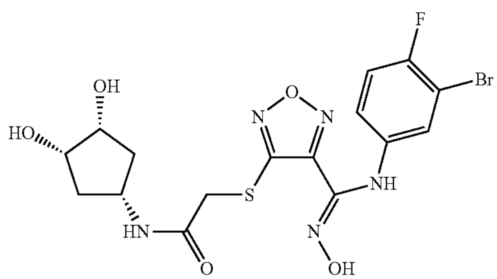 [SMILES: O=C(CSc1nonc1/C(=N/O)Nc1ccc(F)c(Br)c1)N[C@H]1C[C@@H](O)[C@@H](O)C1] | 2-({4-[N-(3-bromo-4-fluorophenyl)-N'-hydroxycarbamimidoyl]-1,2,5-oxadiazol-3-yl}sulfanyl)-N-[(1r,3R,4S)-3,4-dihydroxycyclopentyl]acetamide | Calc'd 490.0, found 490.0 |
| 178 | 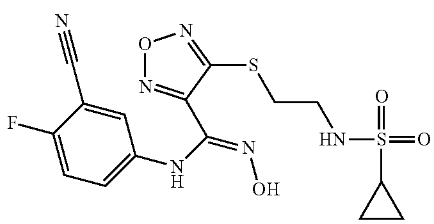 [SMILES: N#Cc1cc(N/C(=N\O)c2nonc2SCCNS(=O)(=O)C2CC2)ccc1F] | N-(3-cyano-4-fluorophenyl)-4-({2-[(cyclopropylsulfonyl)amino]ethyl}sulfanyl)-N'-hydroxy-1,2,5-oxadiazole-3-carboximidamide | Calc'd 427.0, found 427.1 |
| 179 | 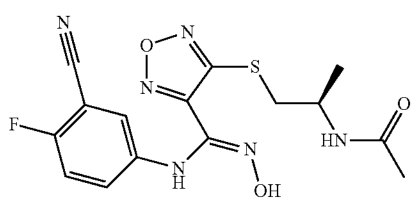 [SMILES: CC(=O)N[C@H](C)CSc1nonc1/C(=N/O)Nc1ccc(F)c(C#N)c1] | N-[(1R)-2-({4-[N-(3-cyano-4-fluorophenyl)-N'-hydroxycarbamimidoyl]-1,2,5-oxadiazol-3-yl}sulfanyl)-1-methylethyl]acetamide | Calc'd 379.0, found 379.1 |
| 180 | 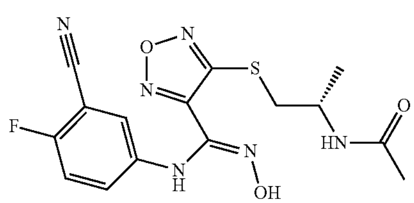 [SMILES: CC(=O)N[C@@H](C)CSc1nonc1/C(=N/O)Nc1ccc(F)c(C#N)c1] | N-[(1S)-2-({4-[N-(3-cyano-4-fluorophenyl)-N'-hydroxycarbamimidoyl]-1,2,5-oxadiazol-3-yl}sulfanyl)-1-methylethyl]acetamide | Calc'd 379.0, found 379.1 |
| 181 | 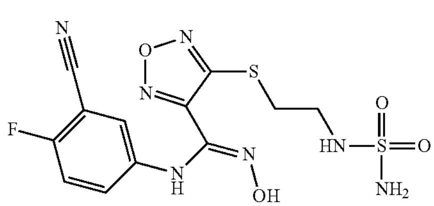 [SMILES: N#Cc1cc(N/C(=N\O)c2nonc2SCCNS(N)(=O)=O)ccc1F] | N-(3-cyano-4-fluorophenyl)-N'-hydroxy-4-{[2-(sulfamoylamino)ethyl]sulfanyl}-1,2,5-oxadiazole-3-carboximidamide | Calc'd 402.0, found 402.0 |

-continued

| Ex # | Structure | Chemical Name | Mass [M + H]+ |
|---|---|---|---|
| 182 | 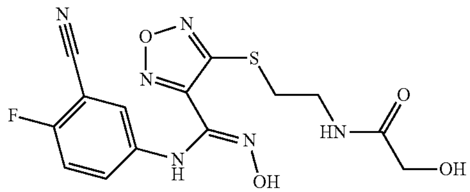 [SMILES: N#Cc1cc(N/C(=N\O)c2nonc2SCCNC(=O)CO)ccc1F] | N-[2-({4-[N-(3-cyano-4-fluorophenyl)-N'-hydroxycarbamimidoyl]-1,2,5-oxadiazol-3-yl}sulfanyl)ethyl]-2-hydroxyacetamide | Calc'd 381.0, found 381.0 |
| 183 | 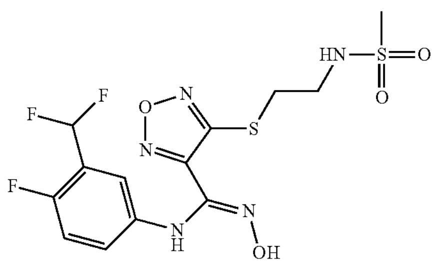 [SMILES: CS(=O)(=O)NCCSc1nonc1/C(=N/O)Nc1ccc(F)c(C(F)F)c1] | N-[3-(difluoromethyl)-4-fluorophenyl]-N'-hydroxy-4-({2-[(methylsulfonyl)amino]ethyl}sulfanyl)-1,2,5-oxadiazole-3-carboximidamide | Calc'd 426.0, found 426.0 |
| 184 | 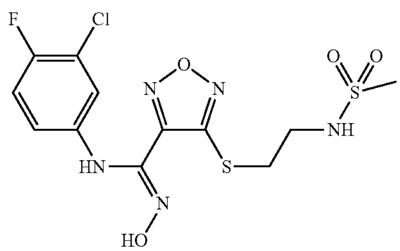 [SMILES: CS(=O)(=O)NCCSc1nonc1/C(=N/O)Nc1ccc(F)c(Cl)c1] | N-(3-chloro-4-fluorophenyl)-N'-hydroxy-4-({2-[(methylsulfonyl)amino]ethyl}sulfanyl)-1,2,5-oxadiazole-3-carboximidamide | Calc'd 410.0, found 410.0 |
| 185 | 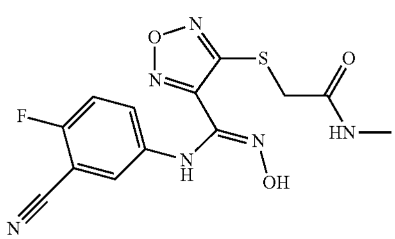 [SMILES: CNC(=O)CSc1nonc1/C(=N/O)Nc1ccc(F)c(C#N)c1] | 2-({4-[N-(3-cyano-4-fluorophenyl)-N'-hydroxycarbamimidoyl]-1,2,5-oxadiazol-3-yl}sulfanyl)-N-methylacetamide | Calc'd 351.0, found 351.0 |
| 186 | 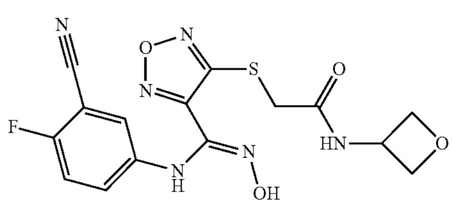 [SMILES: N#Cc1cc(N/C(=N\O)c2nonc2SCC(=O)NC2COC2)ccc1F] | 2-({4-[N-(3-cyano-4-fluorophenyl)-N'-hydroxycarbamimidoyl]-1,2,5-oxadiazol-3-yl}sulfanyl)-N-oxetan-3-ylacetamide | Calc'd 393.0, found 393.0 |
| 187 | 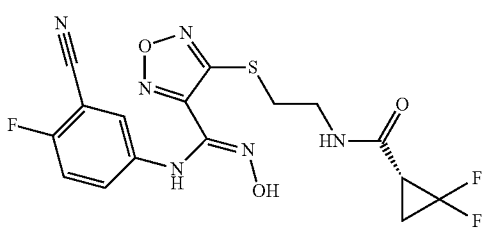 [SMILES: N#Cc1cc(N/C(=N\O)c2nonc2SCCNC(=O)[C@H]2CC2(F)F)ccc1F] | (1R)-N-[2-({4-[N-(3-cyano-4-fluorophenyl)-N'-hydroxycarbamimidoyl]-1,2,5-oxadiazol-3-yl}sulfanyl)ethyl]-2,2-difluorocyclopropanecarboxamide | Calc'd 427.0, found 427.1 |

| Ex # | Structure | Chemical Name | Mass [M + H]+ |
|---|---|---|---|
| 188 | 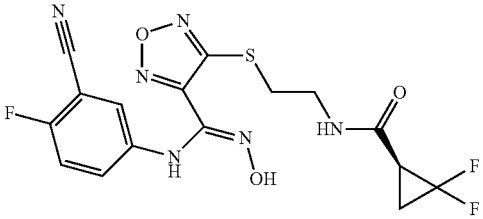 [SMILES: N#Cc1cc(N/C(=N\O)c2nonc2SCCNC(=O)[C@@H]2CC2(F)F)ccc1F] | (1S)-N-[2-({4-[N-(3-cyano-4-fluorophenyl)-N'-hydroxycarbamimidoyl]-1,2,5-oxadiazol-3-yl}sulfanyl)ethyl]-2,2-difluorocyclopropanecarboxamide | Calc'd 427.0, found 427.1 |
| 189 | 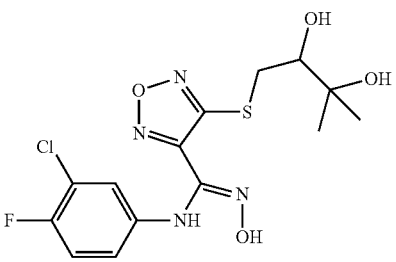 [SMILES: CC(C)(O)C(O)CSc1nonc1/C(=N/O)Nc1ccc(F)c(Cl)c1] | N-(3-chloro-4-fluorophenyl)-4-[(2,3-dihydroxy-3-methylbutyl)sulfanyl]-N'-hydroxy-1,2,5-oxadiazole-3-carboximidamide (peak 1) | Calc'd 391.0, found 391.0 |
| 190 | 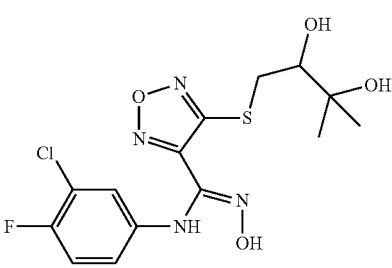 [SMILES: CC(C)(O)C(O)CSc1nonc1/C(=N/O)Nc1ccc(F)c(Cl)c1] | N-(3-chloro-4-fluorophenyl)-4-[(2,3-dihydroxy-3-methylbutyl)sulfanyl]-N'-hydroxy-1,2,5-oxadiazole-3-carboximidamide (peak 2) | Calc'd 391.0, found 391.0 |
| 191 | 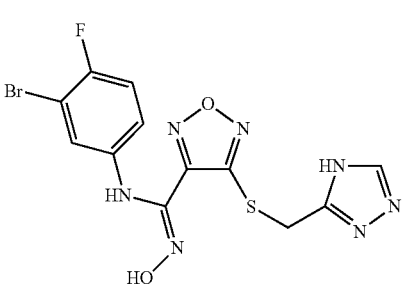 [SMILES: O/N=C(\Nc1ccc(F)c(Br)c1)c1nonc1SCc1nnc[nH]1] | N-(3-bromo-4-fluorophenyl)-N'-hydroxy-4-[(4H-1,2,4-triazol-3-ylmethyl)sulfanyl]-1,2,5-oxadiazole-3-carboximidamide | Calc'd 414.0, found 414.0 |
| 192 | 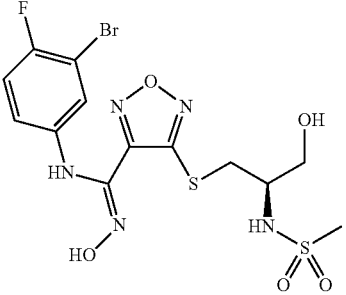 [SMILES: CS(=O)(=O)N[C@H](CO)CSc1nonc1/C(=N/O)Nc1ccc(F)c(Br)c1] | N-(3-bromo-4-fluorophenyl)-N'-hydroxy-4-({(2R)-3-hydroxy-2-[(methylsulfonyl)amino]propyl}sulfanyl)-1,2,5-oxadiazole-3-carboximidamide | Calc'd 484.0, found 484.0 |

-continued

| Ex # | Structure | Chemical Name | Mass [M + H]+ |
|---|---|---|---|
| 193 | 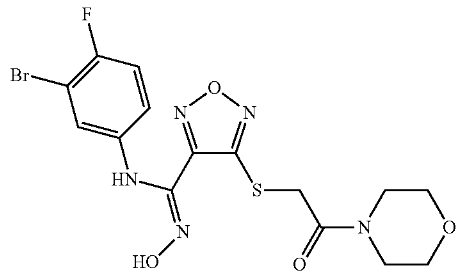 [SMILES: O=C(CSc1nonc1/C(=N/O)Nc1ccc(F)c(Br)c1)N1CCOCC1] | N-(3-bromo-4-fluorophenyl)-N'-hydroxy-4-[(2-morpholin-4-yl-2-oxoethyl)sulfanyl]-1,2,5-oxadiazole-3-carboximidamide | Calc'd 460.0, found 460.0 |
| 194 | 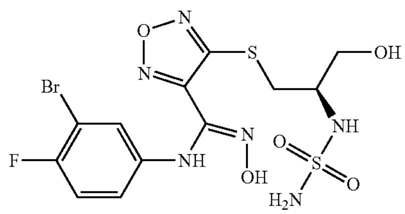 [SMILES: NS(=O)(=O)N[C@H](CO)CSc1nonc1/C(=N/O)Nc1ccc(F)c(Br)c1] | N-(3-bromo-4-fluorophenyl)-N'-hydroxy-4-{[(2R)-3-hydroxy-2-(sulfamoylamino)propyl]sulfanyl}-1,2,5-oxadiazole-3-carboximidamide | Calc'd 485.0, found 485.0 |
| 195 | 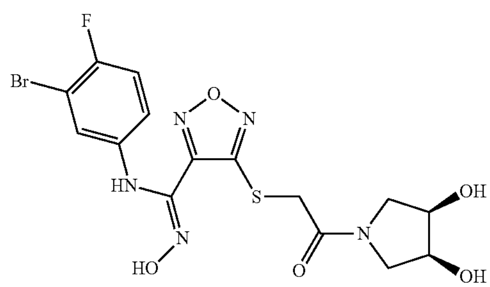 [SMILES: O=C(CSc1nonc1/C(=N/O)Nc1ccc(F)c(Br)c1)N1C[C@@H](O)[C@@H](O)C1] | N-(3-bromo-4-fluorophenyl)-4-((2-((3S,4R)-3,4-dihydroxypyrrolidin-1-yl)-2-oxoethyl)thio)-N'-hydroxy-1,2,5-oxadiazole-3-carboximidamide | Calc'd 476.0, found 476.0 |
| 196 | 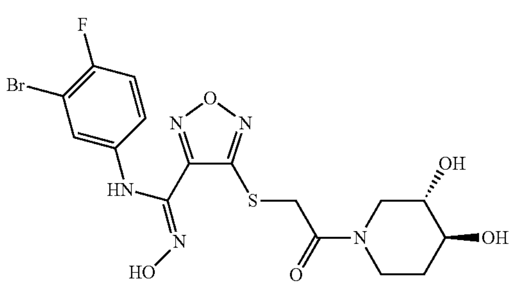 [SMILES: O=C(CSc1nonc1/C(=N/O)Nc1ccc(F)c(Br)c1)N1CC[C@H](O)[C@@H](O)C1] | N-(3-bromo-4-fluorophenyl)-4-((2-((3S,4S)-3,4-dihydroxypiperidin-1-yl)-2-oxoethyl)thio)-N'-hydroxy-1,2,5-oxadiazole-3-carboximidamide | Calc'd 490.0, found 490.0 |
| 197 | 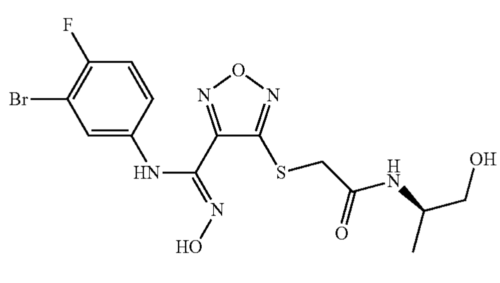 [SMILES: C[C@H](CO)NC(=O)CSc1nonc1/C(=N/O)Nc1ccc(F)c(Br)c1] | (R)-2-((4-(N-(3-bromo-4-fluorophenyl)-N'-hydroxycarbamimidoyl)-1,2,5-oxadiazol-3-yl)thio)-N-(1-hydroxypropan-2-yl)acetamide | Calc'd 448.0, found 448.0 |

| Ex # | Structure | Chemical Name | Mass [M + H]+ |
|---|---|---|---|
| 198 | 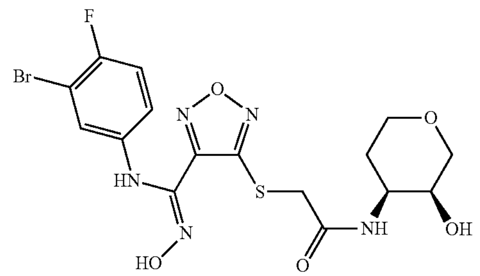 [SMILES: O=C(CSc1nonc1/C(=N/O)Nc1ccc(F)c(Br)c1)N[C@H]1CCOC[C@H]1O] | 2-((4-(N-(3-bromo-4-fluorophenyl)-N'-hydroxycarbamimidoyl)-1,2,5-oxadiazol-3-yl)thio)-N-((3S,4S)-3-hydroxytetrahydro-2H-pyran-4-yl)acetamide | Calc'd 490.0, found 490.0 |
| 199 | 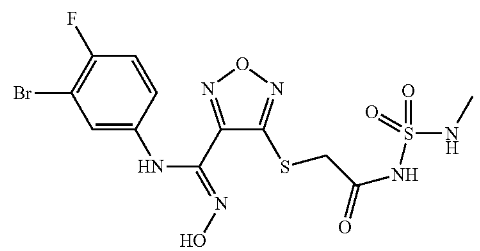 [SMILES: CNS(=O)(=O)NC(=O)CSc1nonc1/C(=N/O)Nc1ccc(F)c(Br)c1] | 2-((4-(N-(3-bromo-4-fluorophenyl)-N'-hydroxycarbamimidoyl)-1,2,5-oxadiazol-3-yl)thio)-N-(N-methylsulfamoyl)acetamide | Calc'd 483.0, found 483.0 |
| 200 | 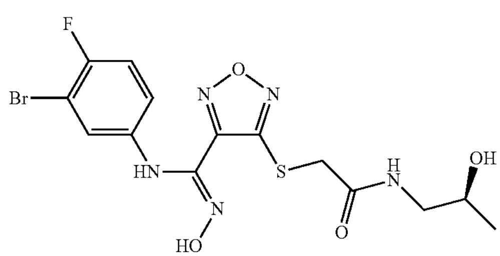 [SMILES: C[C@H](O)CNC(=O)CSc1nonc1/C(=N/O)Nc1ccc(F)c(Br)c1] | (S)-2-((4-(N-(3-bromo-4-fluorophenyl)-N'-hydroxycarbamimidoyl)-1,2,5-oxadiazol-3-yl)thio)-N-(2-hydroxypropyl)acetamide | Calc'd 448.0, found 448.0 |
| 201 | 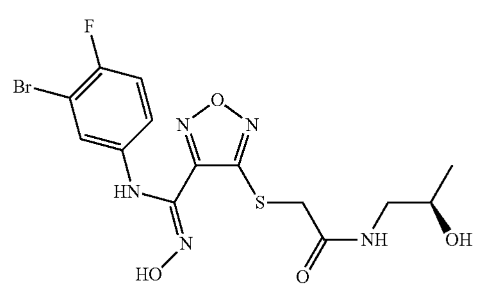 [SMILES: C[C@@H](O)CNC(=O)CSc1nonc1/C(=N/O)Nc1ccc(F)c(Br)c1] | (R)-2-((4-(N-(3-bromo-4-fluorophenyl)-N'-hydroxycarbamimidoyl)-1,2,5-oxadiazol-3-yl)thio)-N-(2-hydroxypropyl)acetamide | Calc'd 448.0, found 448.0 |
| 202 | 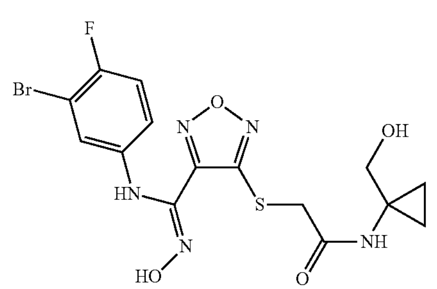 [SMILES: O=C(CSc1nonc1/C(=N/O)Nc1ccc(F)c(Br)c1)NC1(CO)CC1] | 2-((4-(N-(3-bromo-4-fluorophenyl)-N'-hydroxycarbamimidoyl)-1,2,5-oxadiazol-3-yl)thio)-N-(1-(hydroxymethyl)cyclopropyl)acetamide | Calc'd 460.0, found 460.0 |

-continued

| Ex # | Structure | Chemical Name | Mass [M + H]+ |
|---|---|---|---|
| 203 | 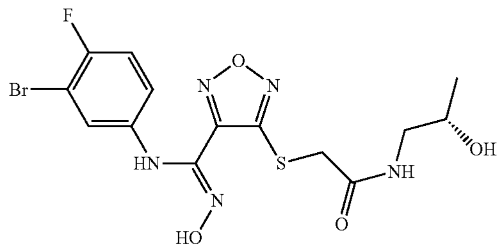 [SMILES: C[C@H](O)CNC(=O)CSc1nonc1/C(=N/O)Nc1ccc(F)c(Br)c1] | (S)-2-((4-(N-(3-bromo-4-fluorophenyl)-N'-hydroxycarbamimidoyl)-1,2,5-oxadiazol-3-yl)thio)-N-(2-hydroxypropyl)acetamide | Calc'd 448.0, found 448.0 |
| 204 | 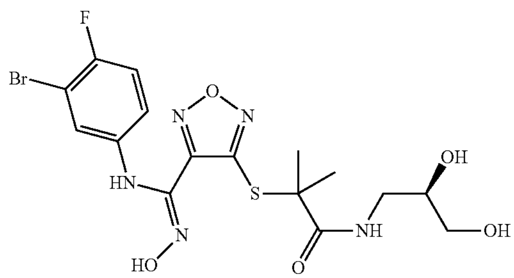 [SMILES: CC(C)(Sc1nonc1/C(=N/O)Nc1ccc(F)c(Br)c1)C(=O)NC[C@@H](O)CO] | (R)-2-((4-(N-(3-bromo-4-fluorophenyl)-N'-hydroxycarbamimidoyl)-1,2,5-oxadiazol-3-yl)thio)-N-(2,3-dihydroxypropyl)-2-methylpropanamide | Calc'd 492.0, found 492.0 |
| 205 | 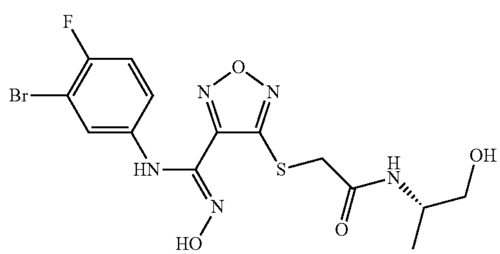 [SMILES: C[C@@H](CO)NC(=O)CSc1nonc1/C(=N/O)Nc1ccc(F)c(Br)c1] | (S)-2-((4-(N-(3-bromo-4-fluorophenyl)-N'-hydroxycarbamimidoyl)-1,2,5-oxadiazol-3-yl)thio)-N-(1-hydroxypropan-2-yl)acetamide | Calc'd 448.0, found 448.0 |
| 206 | 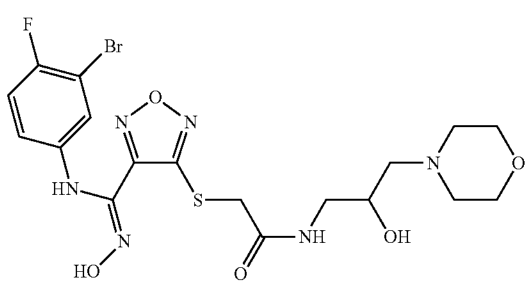 [SMILES: O=C(CSc1nonc1/C(=N/O)Nc1ccc(F)c(Br)c1)NCC(O)CN1CCOCC1] | 2-((4-(N-(3-bromo-4-fluorophenyl)-N'-hydroxycarbamimidoyl)-1,2,5-oxadiazol-3-yl)thio)-N-(2-hydroxy-3-morpholinopropyl)acetamide (peak 1) | Calc'd 533.0, found 533.0 |
| 207 | 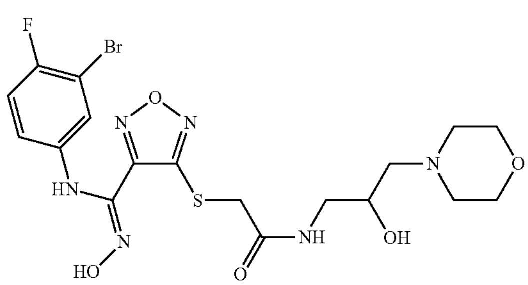 [SMILES: O=C(CSc1nonc1/C(=N/O)Nc1ccc(F)c(Br)c1)NCC(O)CN1CCOCC1] | 2-((4-(N-(3-bromo-4-fluorophenyl)-N'-hydroxycarbamimidoyl)-1,2,5-oxadiazol-3-yl)thio)-N-(2-hydroxy-3-morpholinopropyl)acetamide (peak 2) | Calc'd 533.0, found 533.0 |

-continued

| Ex # | Structure | Chemical Name | Mass [M + H]+ |
|---|---|---|---|
| 208 | 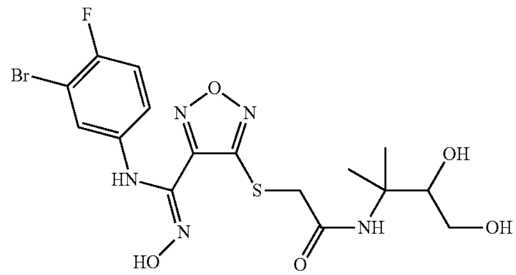 [SMILES: CC(C)(NC(=O)CSc1nonc1/C(=N/O)Nc1ccc(F)c(Br)c1)C(O)CO] | 2-((4-(N-(3-bromo-4-fluorophenyl)-N'-hydroxycarbamimidoyl)-1,2,5-oxadiazol-3-yl)thio)-N-(3,4-dihydroxy-2-methylbutan-2-yl)acetamide | Calc'd 492.0, found 492.0 |
| 209 | 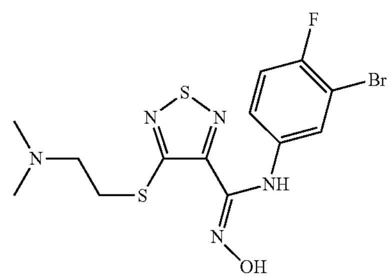 [SMILES: CN(C)CCSc1nsnc1/C(=N/O)Nc1ccc(F)c(Br)c1] | N-(3-bromo-4-fluorophenyl)-4-{[2-(dimethylamino)ethyl]sulfanyl}-N'-hydroxy-1,2,5-thiadiazole-3-carboximidamide | Calc'd 420.0, found 420.0 |
| 210 | 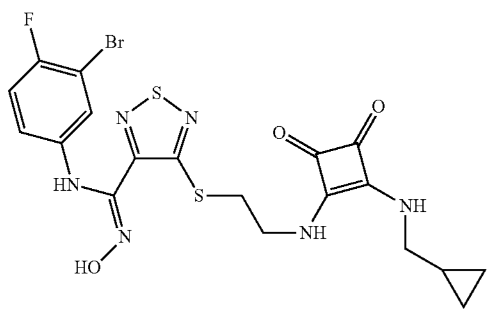 [SMILES: O=c1c(NCCSc2nsnc2/C(=N/O)Nc2ccc(F)c(Br)c2)c(NCC2CC2)c1=O] | N-(3-bromo-4-fluorophenyl)-4-{[2-({2-[(cyclopropylmethyl)amino]-3,4-dioxocyclobut-1-en-1-yl}amino)ethyl]sulfanyl}-N'-hydroxy-1,2,5-thiadiazole-3-carboximidamide | Calc'd 541.0, found 541.0 |
| 211 | 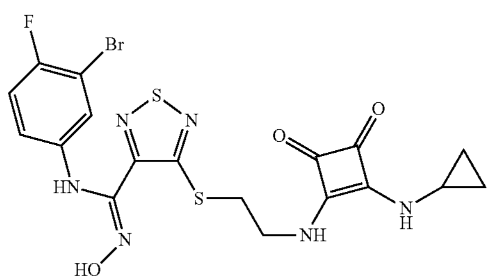 [SMILES: O=c1c(NCCSc2nsnc2/C(=N/O)Nc2ccc(F)c(Br)c2)c(NC2CC2)c1=O] | N-(3-bromo-4-fluorophenyl)-4-[(2-{[2-(cyclopropylamino)-3,4-dioxocyclobut-1-en-1-yl]amino}ethyl)sulfanyl]-N'-hydroxy-1,2,5-thiadiazole-3-carboximidamide | Calc'd 527.0, found 527.0 |

Example 212: N-(3-bromo-4-fluorophenyl)-N'-hydroxy-4-(2-(sulfamoylamino)ethoxy)-1,2,5-oxadiazole-3-carboximidamide

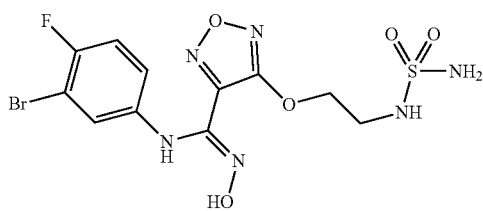 [SMILES: NS(=O)(=O)NCCOc1nonc1/C(=N/O)Nc1ccc(F)c(Br)c1]

Step 1. N-(2-((4-(4-(3-bromo-4-fluorophenyl)-5-oxo-4,5-dihydro-1,2,4-oxadiazol-3-yl)-1,2,5-oxadiazol-3-yl)oxy)ethyl)acetamide

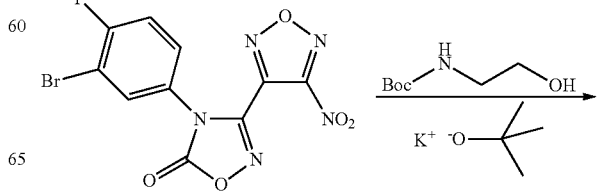

-continued

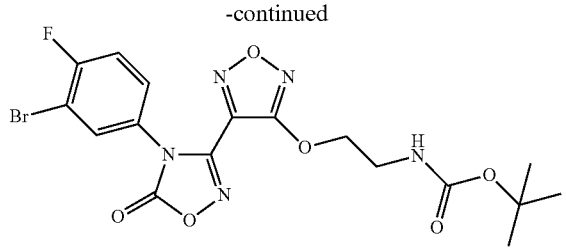

To the stirred solution of tert-butyl (2-hydroxyethyl)carbamate (39.4 mg, 0.245 mmol) in dry THF (1881 μL) was added potassium tert-butoxide (1M in THF, 198 μL, 0.198 mmol) at RT. The mixture was stirred at RT for about 2 min before 4-(3-bromo-4-fluorophenyl)-3-(4-nitro-1,2,5-oxadiazol-3-yl)-1,2,4-oxadiazol-5(4H)-one (70 mg, 0.188 mmol) was added. The mixture was stirred at RT for about 2.5 h, then quenched with addition of HCl (1 M in water) (188 μL, 0.188 mmol). The mixture was partitioned between EtOAc and brine, and the aqueous was extracted with EtOAc for three times. The organic phases were combined, dried over Na$_2$SO$_4$, filtered, and concentrated in vacuo. The residue was purified by chromatography (Isco CombiFlash, 24 g RediSep silica gel gold column, and 0-60% EtOAc in hexane as eluent) to give the desired product as a solid. LCMS m/z (M+H) calc'd: 486.03; found (M+H): 486.0; 488.2.

Step 2. 3-(4-(2-Aminoethoxy)-1,2,5-oxadiazol-3-yl)-4-(3-bromo-4-fluorophenyl)-1,2,4-oxadiazol-5(4H)-one HCl

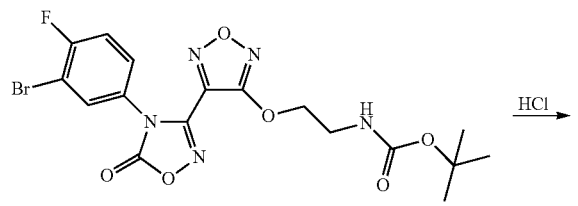

A mixture of tert-butyl (2-((4-(4-(3-bromo-4-fluorophenyl)-5-oxo-4,5-dihydro-1,2,4-oxadiazol-3-yl)-1,2,5-oxadiazol-3-yl)oxy)ethyl)carbamate (62 mg, 0.128 mmol) in HCl (4 M in dioxane, 3188 μl, 12.75 mmol) was stirred at RT for about 1 h, then concentrated in vacuo to give the product as a solid, which was taken to next step without further purification. LCMS m/z (M+H) calc'd: 385.98; found (M+H): 386.1; 388.1.

Step 3. Tert-butyl (N-(2-((4-(4-(3-bromo-4-fluorophenyl)-5-oxo-4,5-dihydro-1,2,4-oxadiazol-3-yl)-1,2,5-oxadiazol-3-yl)oxy)ethyl)sulfamoyl)carbamate

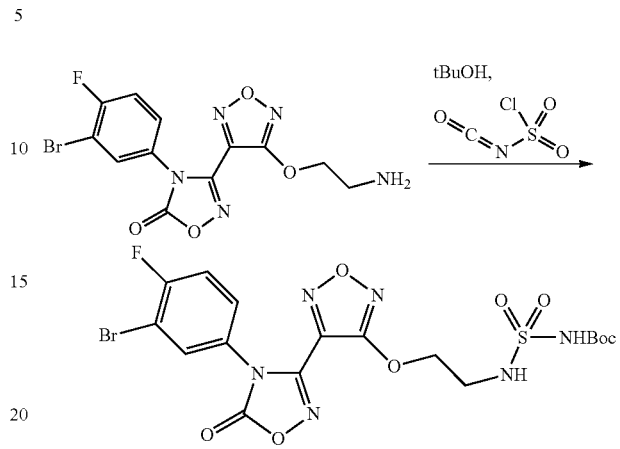

To the stirred solution of chlorosulfonyl isocyanate (25.4 mg, 0.179 mmol) in DCM (640 μL) was added tert-butanol (17.14 μL, 0.179 mmol) at 0° C. The mixture was stirred at 0° C. for 30 min before the premixed solution of 3-(4-(2-aminoethoxy)-1,2,5-oxadiazol-3-yl)-4-(3-bromo-4-fluorophenyl)-1,2,4-oxadiazol-5(4H)-one, HCl (54.1 mg, 0.128 mmol) and DIEA (67.1 μl, 0.384 mmol) in DCM (640 μL) was added. The reaction mixture was stirred at RT for about 2 h, then diluted with DCM (~5 mL), and partitioned between DCM and brine (5 mL). The aqueous was extracted with DCM. Organic phases were combined, dried over Na$_2$SO$_4$, filtered, and concentrated in vacuo. The residue was purified by chromatography (Isco CombiFlash system, using 24 g RediSep silica gel gold column, and 0-60% EtOAc in hexane as eluenting solvent) to give the desired product as a solid. LCMS m/z (M+H) calc'd: 565.01; found (M+H): 565.2; 567.2.

Step 4. Tert-butyl (N-(2-((4-(N-(3-bromo-4-fluorophenyl)-N'-hydroxycarbamimidoyl)-1,2,5-oxadiazol-3-yl)oxy)ethyl)sulfamoyl)carbamate

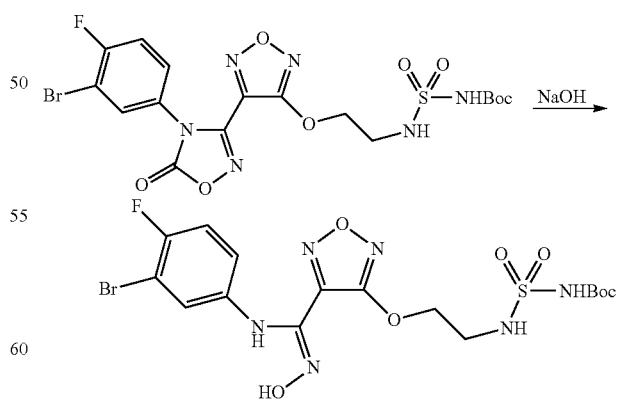

To the stirred solution of tert-butyl N-(2-((4-(4-(3-bromo-4-fluorophenyl)-5-oxo-4,5-dihydro-1,2,4-oxadiazol-3-yl)-1,2,5-oxadiazol-3-yl)oxy)ethyl)sulfamoylcarbamate (0.062 g, 0.11 mmol) in THF (941 μL) were added water (471 μL) and NaOH (2 M in water) (165 µL, 0.329 mmol). The mixture was stirred at RT for 2 h. Aqueous HCl (2 M in water) (165 µL, 0.329 mmol) was added to adjust the pH~8. The mixture was partitioned between EtOAc (5 mL) and brine (5 mL). The aqueous was extracted with EtOAc (3×5 mL). The organic phases were combined, dried over Na$_2$SO$_4$, filtered, and concentrated to give the product as a solid, which was used in the next step without further purification. LCMS m/z (M+H) calc'd: 539.03; found (M+H): 539.2.

Step 5. N-(3-bromo-4-fluorophenyl)-N'-hydroxy-4-(2-(sulfamoylamino)ethoxy)-1,2,5-oxadiazole-3-carboximidamide

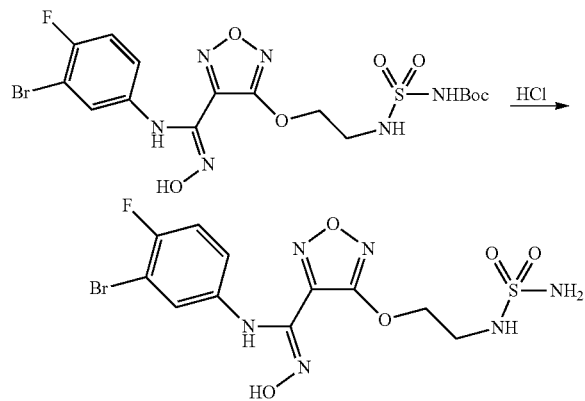

To the stirred solution of tert-butyl N-(2-((4-(N-(3-bromo-4-fluorophenyl)-N'-hydroxycarbamimidoyl)-1,2,5-oxadiazol-3-yl)oxy)ethyl)sulfamoylcarbamate (48 mg, 0.089 mmol) in EtOAc (1.0 mL) was added HCl (4 M in dioxane, Aldrich) (2.23 mL, 8.90 mmol). The mixture was stirred at RT for 1.5 h, then was concentrated and purified by prep. TLC using one 2000 microns (20×20 cm) silica gel plate (Analtech), and 10% MeOH in DCM as eluting solvent. The major band (middle band) was cut and scraped off the plate, and the collected silica gel was soaked in 20% MeOH in DCM (50 mL) and stirred at RT for 10 min, then filtered. The solid was washed with MeOH (~10 mL). The combined filtrate was concentrated in vacuo. The residue was then lyophlized from HPLC grade acetonitrile-water (4:1, 5 ml) to give the desired product as a solid. LCMS m/z (M+H) calc'd: 438.98; found (M+H): 439.0; 441.0. $^1$H NMR (500 MHz, CD$_3$OD): δ 7.16-7.12 (m, 1H); 7.06 (t, J=10 Hz, 1H); 6.86-6.81 (m, 1H); 4.35 (t, J=5 Hz, 2H); 3.37 (t, J=5 Hz, 2H)

Example 213: 4-(2-aminoethoxy)-N-(3-bromo-4-fluorophenyl)-N'-hydroxy-1,2,5-oxadiazole-3-carboximidamide

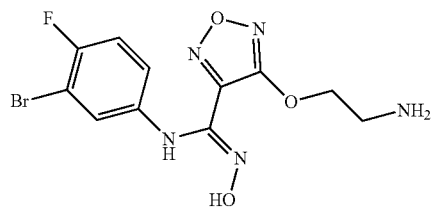 [SMILES: NCCOc1nonc1/C(=N/O)Nc1ccc(F)c(Br)c1]

Following the procedure described in Example 212 (Step 4), basic hydrolysis of 3-(4-(2-aminoethoxy)-1,2,5-oxadiazol-3-yl)-4-(3-bromo-4-fluorophenyl)-1,2,4-oxadiazol-5(4H)-one HCl (Step 2 in Example 212), followed by reverse phase HPLC purification, afford the title compound as a solid after lyophilization. LCMS m/z (M+H) calc'd: 360.0; found (M+H): 360.0; 361.9. $^1$H NMR (500 MHz, CD$_3$OD): δ 7.19-7.15 (m, 1H); 7.10-7.04 (m, 1H); 6.85-6.80 (m, 1H); 4.57-4.51 (m, 2H); 3.42-3.35 (m, 2H)

Example 214: N-(3-bromo-4-fluorophenyl)-N'-hydroxy-4-(2-(methylsulfonamido)ethoxy)-1,2,5-oxadiazole-3-carboximidamide

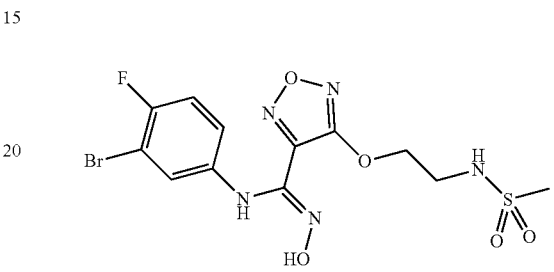

The title compound was synthesized following the procedures described in Example 212. LCMS m/z (M+H) calc'd: 437.98; found (M+H): 438.0; 439.9 $^1$H NMR (500 MHz, CD$_3$OD): δ 7.16-7.13 (m, 1H); 7.06 (t, J 8.5 Hz, 1H); 6.83-6.80 (m, 1H); 4.28 (t, J 5 Hz, 2H); 3.39 (t, J 5 Hz, 2H); 2.98 (s, 3H)

Biological Assays
IDO1 Enzyme Assay

Compounds to be tested were serially diluted in ten 3-fold steps in DMSO starting from 10 mM DMSO stocks. Compound dilutions or DMSO alone were then dispensed from the dilution plate into a Greiner black 384-well assay plate (catalog #781086) using an Echo 555 acoustic liquid handler (Labcyte).

HIS-tagged IDO1 protein was recombinantly expressed in *Escherichia coli* using ZYP5052 autoinduction media supplemented with 500 µM delta aminolevulinic acid for 48 h at 16° C. IDO1 protein was purified using Ni$^{2+}$-affinity resin and size exclusion chromatography. Purified protein was then diluted in assay buffer (50 mM Tris pH 7.0, 1% glycerol, 20 µM methylene blue, 0.05% Tween-20, 20 mM sodium ascorbate, 100 units/mL catalase to obtain a final IDO1 concentration of 40 nM. IDO1 solution (30 µM) or buffer alone (30 µM) were dispensed to wells of the assay plate using a BioRAPTR liquid dispenser (Beckman Coulter). Assay plates containing compound and IDO1 enzyme were incubated at RT for 30 min. Afterwards, 10 µL of 400 µM tryptophan in assay buffer were added to each well of the assay plate using a BioRAPTR liquid dispenser. Plates were incubated at RT for 60 min and reactions were quenched by addition of 10 µL of 0.5 M methyl isonipecotate in dimethyl sulfoxide. Plates were sealed and incubated at 37° C. for 4 h or 50° C. for 2 h. The plates are allowed to cool and then centrifuged for 1 min at 1000×g. The resulting fluorescence was measured in an Envision plate reader (Perkin Elmer) with a 400/25 nm excitation filter and an 510/20 nm emission filter.

The fluorescence intensity of each well was corrected for the background observed in wells that did not receive IDO1 and was expressed as a fraction of the intensity observed in wells that received IDO1 enzyme and DMSO only. Potencies were calculated by linear least squares fit to the four parameter logistic $IC_{50}$ equation.

IDO1 Cellular Assay in Frozen HEK293 Cells Transiently Transfected with Human IDO1

HEK293 cells were cultured in complete HEK293 culture medium (90% DMEM, 10% heat-inactivated fetal bovine serum). When reaching sub-confluent, the cells were trypsinized and neutralized with complete medium. After spinning down, the cells were washed once with MaxCyte's EP buffer, and then resuspend in MaxCyte's EP buffer at 1×108 cells/ml. Flag-IDO1 plasmid was added to the cell suspension at a concentration of 100 μg/mL. The cell-plasmid solutions were transferred to the OC-400 processing assembly (Maxcyte), 400 l/unit and the units were placed in a Maxcyte instrument to carry out flow electroporation for transfection. The cells were then transferred to a sterile 24-well cell culture plate to recover for 20-30 min at 37° C. in an incubator with 5% $CO_2$. After recovery, the cells were suspended in complete culture medium at 1×106/mL and plated in cell culture flasks for 24 h in a 37 OC/5% $CO_2$ incubator. The cells were then collected and frozen down at 20×106 cells/vial in 1 mL frozen medium (90% complete HEK293 culture medium, 10% DMSO). Untransfected HREK293 WT cells were also frozen down at 5×106/vial similarly to serve as the Max-E control.

Compounds to be tested were serially diluted in ten 3-fold steps in DMSO starting from 10 mM DMSO stocks in Echo low volume plate(s). Compound dilutions or DMSO alone were then dispensed from the dilution plate(s) into the Greiner black 384-well assay plate(s) (catalog #781086, 50 nL/well) using an Echo 550 acoustic liquid handler (Labcyte).

Frozen HEK293/IDO1 and HEK293 WT cells were thawed and transferred into HEK293 assay medium (99% complete HEK293 culture medium, 1% Pen/Strep) with 20 mL medium/vial of cells. The cells were spun down at 250 g in a table top centrifuge for 5 min and suspended in same volume of HEK293 assay medium. The cells were counted and adjusted to density of 2×105 cells/ml in HEK293 assay medium. Sterile L-tryptophan were added to the cells with final concentration of 300 μM.

HEK293/IDO1 and HEK293 WT cells were dispensed to the respective wells of 384-well assay plates containing the compounds. The plates were incubated for about 28-30 h at a 37° C., 5% $CO_2$ incubator. Afterwards, 12 μL of 0.5 M methyl isonipecotate in dimethyl sulfoxide were added into each well and the plates were sealed and incubated at 37° C. without $CO_2$ overnight. The plates were centrifuged for 1 min at 200×g. The resulting fluorescence was measured in a Spectramax plate reader (Molecular Devices) with a 400 nm excitation filter and a 510 nm emission filter.

The fluorescence intensity of each well was corrected for the background observed in wells with untransfected cells and was expressed as a fraction of the intensity observed in wells of IDO1 transfected cells and DMSO only. Potencies were calculated by linear least squares fit to the four parameter logistic $IC_{50}$ equation.

IDO1 Cellular Assay in Hela Cells Stimulated with IFNγ

Hela cells were cultured in complete Hela culture medium (90% EMEM, 10% heat-inactivated fetal bovine serum) and expanded to about 1×109 cells. The cells were then collected and frozen down at 10×106 cells/vial in 1 mL frozen medium (90% complete Hela culture medium, 10% DMSO)

Compounds to be tested were serially diluted in ten 3-fold steps in DMSO starting from 10 mM DMSO stocks in Echo low volume plate(s). Compound dilutions or DMSO alone were then dispensed from the dilution plate(s) into Greiner black 384-well assay plate(s) (catalog #781086, 50 nL/well) using an Echo 550 acoustic liquid handler (Labcyte).

Frozen Hela cells were thawed and transferred into Hela assay medium (99% complete Hela culture medium, 1% Pen/Strep) with 20 mL medium/vial of cells. The cells were spun down at 250 g in a table top centrifuge for 5 min and suspended in same volume of Hela assay medium. The cells were then counted and adjusted to a density of 2×105 cells/ml in Hela assay medium. Sterile L-tryptophan were added to the cells with final concentration of 300 uM L-tryptophan. A small aliquot (2 mL/plate) of Hela cells were set aside and were not treated with IFNγ, to serve as the Max-E control. The rest of Hela cells were added with sterile IFNγ (Cat #285-IF, R & D systems) with a final concentration of 100 ng/mL.

Hela cells with and without IFNγ were dispensed to the respective wells of 384-well assay plates containing the compounds. The plates were incubated for about 48 hours at a 37° C., 5% $CO_2$ incubator. Afterwards, 12 μL of 0.5 M methyl isonipecotate in dimethyl sulfoxide were added into each well and the plates were sealed and incubated at 37° C. without $CO_2$ overnight. The plates were centrifuged for 1 min at 200×g. The resulting fluorescence was measured in a Spectramax plate reader (Molecular Devices) with a 400 nm excitation filter and a 510 nm emission filter.

The fluorescence intensity of each well was corrected for the background observed in wells with non-IFNγ-treated cells and was expressed as a fraction of the intensity observed in wells of IFNγ-treated cells and DMSO only. Potencies were calculated by linear least squares fit to the four parameter logistic $IC_{50}$ equation.

The biological activity data using the IDO1 enzyme assay and IDO1 cellular assay described above are summarized in the table below. Compounds disclosed herein generally have $IC_{50}$ of about 0.1 nM to about 20,000 nM, or more specifically, about 1 nM to about 10,000 nM, or more specifically, about 5 nM to about 5,000 nM, or more specifically, about 10 nM to about 1,000 nM, or still more specifically, about 10 nM to about 500 nM. Such a result is indicative of the intrinsic activity of the compounds in use as an inhibitor of an IDO enzyme. Specific $IC_{50}$ activity data for the exemplified compounds disclosed herein is provided in the following table.

| Ex. No. | IDO1 Enzyme Assay, $IC_{50}$, nM | IDO1 HEK293 Cell Assay, $IC_{50}$, nM | IDO1 HELA Cell Assay, $IC_{50}$, nM |
| --- | --- | --- | --- |
| 1 | 270.7 | 740.1 | |
| 2 | 48.1 | 215.9 | 77.5 |
| 3 | 79.5 | 56.9 | 72.4 |
| 4 | >10,000 | 3,703 | |
| 5 | 47.59 | | 94.0 |
| 6 | 44 | | 143.8 |
| 7 | 40.9 | 137.8 | 63.8 |
| 8 | 106.7 | 6,358.0 | 7948 |
| 9 | 196.9 | 5,116 | 5,064 |
| 10 | 136.5 | >10,000 | 4,164 |
| 11 | 27.7 | 22.2 | 9.3 |
| 12 | 616 | 1,461 | |
| 13 | 86.1 | 4,486.0 | 6,118 |
| 14 | 48.2 | >10,000 | |
| 15 | 105.0 | >10,000 | >10,000 |
| 16 | 148.8 | >10,000 | |
| 17 | 34.8 | 42.5 | 39.5 |
| 18 | 58.4 | 64.2 | 87.9 |
| 19 | 71.9 | 39.7 | 39.7 |
| 20 | 67.7 | 56.0 | 65.3 |
| 21 | 5.9.5 | 523.8 | 242.2 |
| 22 | 35.7 | 1,222.0 | |
| 23 | 187.4 | 262.9 | 154 |

-continued

| Ex. No. | IDO1 Enzyme Assay, IC$_{50}$, nM | IDO1 HEK293 Cell Assay, IC$_{50}$, nM | IDO1 HELA Cell Assay, IC$_{50}$, nM |
|---|---|---|---|
| 24 | 153.6 | 132.6 | 62.8 |
| 25 | 92.2 | 152.0 | 149.6 |
| 26 | 74.8 | 174.3 | 103.5 |
| 27 | 29.81 | | 17.6 |
| 28 | 38.05 | | 65.9 |
| 29 | 81.28 | 23.6 | 61.04 |
| 30 | 85.33 | 29.4 | 84.2 |
| 31 | 43.43 | 10.2 | 37.4 |
| 32 | 32.01 | | 13.1 |
| 33 | 53.55 | | 26.3 |
| 34 | 64.89 | 187.7 | 40.2 |
| 35 | 34.94 | 77.7 | 64.6 |
| 36 | 22.6 | 205.7 | 94.8 |
| 37 | 104.5 | 83.1 | 59.4 |
| 38 | 143.5 | | 118.4 |
| 39 | 117.6 | | 87.6 |
| 40 | 76.23 | 92.1 | 181.8 |
| 41 | 43.11 | 22.2 | 17.6 |
| 42 | 47.69 | 59.6 | 34.3 |
| 43 | 53.32 | 78.5 | 117.8 |
| 44 | 18.07 | 17.5 | 8.6 |
| 45 | 22.53 | 24.3 | 47.7 |
| 46 | 33.93 | 16.9 | 13.5 |
| 47 | 439 | 289.6 | 245.1 |
| 48 | 170.4 | 226.3 | 647.6 |
| 49 | 65.31 | 31.7 | 11.9 |
| 50 | 99.49 | 67.5 | 45.7 |
| 51 | 112.8 | 105.7 | 48.1 |
| 52 | 355.6 | 177.2 | 144.4 |
| 53 | 98.53 | 785.8 | 683 |
| 54 | 329.8 | 204.1 | 200.3 |
| 55 | 20.25 | 261.3 | 67.8 |
| 56 | 41.45 | 211.8 | 94.27 |
| 57 | 29.38 | 361.1 | 131.1 |
| 58 | 136.1 | 289.8 | 153.5 |
| 59 | 23.18 | 20.6 | 22.4 |
| 60 | 36.45 | 175.7 | 152.6 |
| 61 | 94.3 | 170.9 | 77.5 |
| 62 | 1032 | 1792 | |
| 63 | 46.08 | 53.2 | 37.5 |
| 64 | 49.11 | 75.9 | 44.1 |
| 65 | 59.43 | 74.53 | 52.6 |
| 66 | 28.31 | 67.7 | 92.3 |
| 67 | 39.32 | 17.7 | 14.5 |
| 68 | 96.15 | 107.1 | 77.2 |
| 69 | 81.23 | 103.3 | 90.8 |
| 70 | 27.88 | 26.2 | 20.9 |
| 71 | 406.6 | 108.9 | 91.2 |
| 72 | 87.75 | 231.2 | 282.7 |
| 73 | 27.22 | 376.2 | 106 |
| 74 | 502.9 | 579.3 | 387.8 |
| 75 | 23.04 | 1135 | |
| 76 | 97.25 | 114.2 | 43.8 |
| 77 | 51.78 | 36.4 | 43.5 |
| 78 | 90.89 | 100.7 | 57.7 |
| 79 | 61.59 | 27.5 | 24.1 |
| 80 | 124.8 | 78.1 | 37.9 |
| 81 | 41.76 | 36.9 | 42.9 |
| 82 | 102.1 | 78.1 | 40.6 |
| 83 | 22.77 | 11.5 | 75.93 |
| 84 | 37.55 | 33.1 | 27.2 |
| 85 | 39.27 | 35.7 | 16.9 |
| 86 | 32.32 | 41.6 | 15.7 |
| 87 | 99.73 | 132.6 | 70.0 |
| 88 | 173.3 | | 174.2 |
| 89 | 38.96 | | |
| 90 | 29.31 | | |
| 91 | 57.41 | 366.7 | 356.7 |
| 92 | 99.53 | 363.8 | 145.3 |
| 93 | 38.97 | 403.6 | 248.7 |
| 94 | 26.79 | 193.3 | 73.0 |
| 95 | 27.76 | 723.2 | |
| 96 | 36.9 | 32.9 | 24.7 |
| 97 | 131.9 | 745.2 | 380.5 |
| 98 | 37.82 | 83.0 | 57.1 |
| 99 | 84.03 | 230.5 | 194.9 |
| 100 | 98.84 | 581.6 | 342.2 |
| 101 | 764.5 | 2240 | |
| 102 | 72.38 | 44.4 | 81.8 |
| 103 | 48.52 | 84.5 | 32.3 |
| 104 | 169.2 | 268.6 | 352.8 |
| 105 | 2681 | 1146 | |
| 106 | 30.02 | 78.7 | 557.8 |
| 107 | 30.15 | 43.1 | 48.3 |
| 108 | 131.1 | 838.1 | |
| 109 | 705.8 | 2429 | |
| 110 | 48.54 | 25.6 | 54.3 |
| 111 | 59.57 | 445.6 | 684.6 |
| 112 | 54.18 | 39.97 | 40.8 |
| 113 | 47.31 | 35.4 | 76.5 |
| 114 | 36.94 | 97.0 | 147.9 |
| 115 | 51.02 | 105.3 | 168.5 |
| 116 | 154.4 | 705.8 | |
| 117 | 558 | 485.4 | 309.9 |
| 118 | 34.08 | 8154 | |
| 119 | 99.9 | 983.5 | |
| 120 | 14.03 | 13.4 | 28.4 |
| 121 | 47.69 | 45.8 | 39.7 |
| 122 | 37.69 | 23.3 | 26.7 |
| 123 | 44.23 | 37.8 | 75.7 |
| 124 | 34.45 | 65.6 | 56.2 |
| 125 | 51.89 | 45.0 | 131 |
| 126 | 57.5 | 52.9 | 92.6 |
| 127 | 33.49 | 114.6 | 219.2 |
| 128 | 110.2 | 148.7 | 169.1 |
| 129 | 35.33 | 258.1 | 702.4 |
| 130 | 37.05 | 206.2 | 370.7 |
| 131 | 34.09 | 66.7 | 167.1 |
| 132 | 32.13 | 33.1 | 31.7 |
| 133 | 71.48 | 226.5 | 235.2 |
| 134 | 119.6 | | |
| 135 | 105.6 | | |
| 136 | 111.6 | | |
| 137 | 34.94 | | |
| 138 | 38.74 | 60.0 | 54.7 |
| 139 | 117.4 | 551 | |
| 140 | 96.67 | 269.3 | 245 |
| 141 | 72.25 | 131.3 | 111.6 |
| 142 | 54.01 | 46.9 | 57.2 |
| 143 | 53.94 | 65.1 | 34.8 |
| 144 | 75.76 | 549 | |
| 145 | 50.85 | 77.1 | 68.0 |
| 146 | 155.3 | 221.7 | 398 |
| 147 | 153.9 | 373.4 | 494 |
| 148 | 172.5 | 208.9 | 303.5 |
| 149 | 109.9 | 119.9 | 285.3 |
| 150 | 172.7 | 421.7 | 820.5 |
| 151 | 96.26 | 79.3 | 155.6 |
| 152 | 97.63 | 165.8 | 331.1 |
| 153 | 85.41 | 65.72 | 69.4 |
| 154 | 31.44 | 26.1 | 41.0 |
| 155 | 77.74 | 217.5 | 300.9 |
| 156 | 58.82 | 46.9 | 113.7 |
| 157 | 63.79 | 103.7 | 112.7 |
| 158 | 95.71 | 72.0 | 232.6 |
| 159 | 104.5 | 81.7 | 153.4 |
| 160 | 65.74 | 61.0 | 126.1 |
| 161 | 168.8 | 188.2 | 340.9 |
| 162 | 111.2 | 166.7 | 321.6 |
| 163 | 161.1 | 181.2 | 405.5 |
| 164 | 62.2 | 91.5 | 246.5 |
| 165 | 126.3 | 129.9 | 159.4 |
| 166 | 126.4 | 114 | 137.6 |
| 167 | 142.5 | 110.2 | 97.3 |
| 168 | 69.08 | 55.1 | 110.7 |
| 169 | 52.76 | 93.7 | 191.4 |
| 170 | 68.41 | 132.4 | 110.3 |
| 171 | 110.1 | 30.8 | 120.3 |
| 172 | 78.56 | 47.5 | 43.4 |
| 173 | 93.65 | 154.7 | 245.6 |
| 174 | 82.66 | 113 | 63.6 |
| 175 | 124.9 | 280.5 | 222.8 |

-continued

| Ex. No. | IDO1 Enzyme Assay, IC$_{50}$, nM | IDO1 HEK293 Cell Assay, IC$_{50}$, nM | IDO1 HELA Cell Assay, IC$_{50}$, nM |
|---|---|---|---|
| 176 | 115.5 | 182.5 | 127 |
| 177 | 97.27 | 411 | 469.4 |
| 178 | 60.81 | 35.5 | 57.2 |
| 179 | 218 | 685.7 | |
| 180 | 195.6 | 309.1 | 425.5 |
| 181 | 119.1 | 136.5 | 260.5 |
| 182 | 135 | 186.4 | 320.6 |
| 183 | 52.52 | 25.6 | 58.2 |
| 184 | 50.87 | 16.1 | 47.4 |
| 185 | 87.98 | 65.4 | 166.3 |
| 186 | 179.6 | 412 | 321.8 |
| 187 | 85.95 | 140.5 | 272.1 |
| 188 | 87.88 | 87.7 | 173.4 |
| 189 | 69.41 | 39.9 | 66.0 |
| 190 | 79.13 | 56.8 | 110.7 |
| 191 | 43.74 | 10.0 | 22.6 |
| 192 | | | |
| 193 | 73.83 | | 143.1 |
| 194 | 51.01 | | 47.1 |
| 195 | 92.54 | | 341.8 |
| 196 | 62.27 | | 131.7 |
| 197 | 44.85 | | 15.3 |
| 198 | 55.99 | | 149.5 |
| 199 | 57.78 | | 508 |
| 200 | 29.94 | | 14.9 |
| 201 | 22.38 | | 26.8 |
| 202 | 20.24 | | 12.2 |
| 203 | 14.54 | | 11.6 |
| 204 | 82.63 | | 144.2 |
| 205 | 12.43 | | 11.7 |
| 206 | 39.31 | | 110.8 |
| 207 | 43.11 | | 140.3 |
| 208 | 26.63 | | 37.5 |
| 209 | 1280 | 770.2 | 967.9 |
| 210 | 166 | 1413 | |
| 211 | 297.1 | 1315 | |
| 212 | 51.97 | | 111.2 |
| 213 | 130 | | 607.2 |
| 214 | 205 | | 44.4 |

IDO1 Human Whole Blood Assay

Compounds to be tested were serially diluted in ten 3-fold steps in DMSO starting from 10 mM. 3 μL of compound dilutions or DMSO alone were then dispensed from the dilution plate into a polypropylene 96-well assay plate containing 97 μL of RPMI using an Echo 555 acoustic liquid handler (Labcyte). LPS and IFNγ was prepared in in RPMI to a 10× of final conc. (1000 ng/mL), final concentration is 100 ng/mL.

Human whole blood was drawn in sodium heparin coated tubes from healthy internal donors. Two hundred fourty μL of blood was transferred to each of the wells of a v-bottom 96 well plate. Thirty μL of compound was transferred from intermediate dilution plate, and incubated for 15 min. Thirty L from stimulants was then transferred to blood and mixed thoroughly. Plate was covered with breathable membrane and incubated at 37° C. for overnight (18 h).

On day 2 isotope labeled standard of kunurenine and tryptophan was made in water at 10× concentration and 30 μL was added to the blood at 3 μM final concentration. The assay plates were centrifuged at 300×G for 10 min with no brake to separate plasma from red blood cells. Sixty μL of plasma samples was removed without disturbing red blood cells. Plasma was diluted with RPMI in 1:1 ratio and proteins were precipitated out with two volume of Acetonitrile. The plates was centrifuged at 4000×G for 60 min. Twenty μL of supernatant was carefully transferred to a 384 well plate contain 40 μL of 0.1% formic acid in water and analysed by LC/MS/MS.

LC/MS/MS analyses were performed using Thermo Fisher's LX4-TSQ Quantum Ultra system. This system consists of four Agilent binary high-performance liquid chromatography (HPLC) pumps and a TSQ Quantum Ultra triple quadrupole MS/MS instrument. For each sample, 5 μL were injected onto an Atlantis T3 column column (2.1 mm×150 mm, 3 μm particle size) from Waters. The mobile phase gradient pumped at 0.8 mL/min was used to elute the analytes from the column at 25° C. The elution started at 0% B increasing linearly to 25% B at 6.5 min, holding at 25% for 1 min, re-equilibrating to 10 min. Mobile phase A consisted of 0.1% formic acid in water. Mobile phase B consisted of 0.1% of formic acid in acetonitrile. Data was acquired in positive mode using a HESI interface. The operational parameters for the TSQ Quantum Ultra instrument were a spray voltage of 4000 V, capillary temperature of 380° C., vaporizer temperature 400° C., shealth gas 60 arbitrary units, Aux gas 20 arbitrary units, tube lens 85 and collision gas 1.2 mTorr. SRM chromatograms of kynurenine (Q1: 209.2>Q3:94.0) and internal standard (Q1: 215.3>Q3: 98.2) were collected for 90 sec. The peak area was integrated by Xcalibur Quan software. The ratios between the kynurenine generated in the reaction and 2D6-Kynurenine spiked-in internal standard were used to generate percentage inhibition and IC$_{50}$ values. Compounds were titrated and IC$_{50}$'s were calculated by 4 parameter sigmoidal curve fitting formula.

The biological activity data of selective compounds using the IDO1 human whole blood assay described above are summarized in the table below.

| Ex. No. | IDO1 human whole blood assay, IC$_{50}$, nM |
|---|---|
| 17 | 441.4 |
| 29 | 784.1 |
| 30 | 890.8 |
| 31 | 642.9 |
| 35 | 922.5 |
| 36 | 7,109 |
| 37 | 468.8 |
| 40 | 1,674 |
| 41 | 150 |
| 42 | 518.8 |
| 44 | 129.9 |
| 45 | 405.1 |
| 46 | 239.3 |
| 84 | 184.1 |
| 86 | 4,119 |
| 98 | 634.9 |
| 102 | >10,000 |
| 120 | 154.9 |
| 125 | 745.5 |
| 140 | 384 |
| 144 | 3,995 |
| 145 | 1,271 |
| 146 | 1,398 |
| 147 | 1,206 |
| 148 | 1,761 |
| 149 | 1,051 |
| 168 | 474.5 |
| 169 | 1,289 |
| 171 | 660.3 |
| 173 | 827.3 |
| 175 | 1,722 |
| 178 | 1,082 |
| 181 | 3,241 |
| 182 | 525.6 |
| 185 | 395.3 |
| 189 | 703.9 |
| 190 | 1,395 |
| 191 | 902.7 |

IDO1 In Vivo Assay hIDO1-CT26, a murine cell line generated in house to constitutively express the human IDO1 protein, was cultured in RPMI-1640+10% FBS+500 µM L-tryptophan in a standard cell incubator (37° C., 5% $CO_2$). At 80% confluency, cells are rinsed in TrypLE, then incubated with TrypLE until fully detached (usually 1-5 min), resuspended in complete media, spun down (1000 rpm, 4° C., 5 min), and resuspended in phenol red-free RPMI-1640 before counting.

Two millions hIDO1-CT26 cells (20×10E6 cells/ml) in 50% phenol red-free RPMI-1640/50% Matrigel (growth factor reduced, GFR) are implanted subcutaneously in the right flank of anesthetized immunocompromised animals (CD-1 Nu/Nu, Charles River Labs). Ten days following implantation, tumors reach an average volume of 180 $mm^3$ at which point animals are randomized into treatment groups.

Animals are treated with IDO1 inhibitors by oral gavage (PO) every 12 h (BID dosing). Based on experimental design, animals will receive a minimum of 1 dose. At various times following the last dose, animals will be euthanized ($CO_2$ asphyxiation), blood will be collected via cardiac puncture for plasma, and tumors will be resected. For plasma preparation, whole blood is transferred to plasma tube, and stored on ice prior to centrifugation. For tumor preparation, tumors are weighed, and artificial plasma (4% BSA in PBS) will be added (3× tumor weights) prior to liquid nitrogen freezing.

A Hamilton Star liquid handling system was programmed for preparing (with suitable dilutions) calibration standards in control plasma, QCs, and biological samples, and for adding the internal standard to the samples in a 96-well destination plate. Two different working solutions containing the analyte were prepared by diluting a suitable amount of the stock solution (10 or 50 mM) with acetonitrile/water (50/50) for the calibration standards (STD) and quality control (QC) samples preparation, respectively.

The standard solutions and quality control samples were prepared in a 96 well plate by transferring the working solutions, standard and QC, respectively, into the wells assigned. Different standard levels from 0.0001 to 10 µM for Kynurenine and from 0.01 to 1000 M for Tryptophan were prepared by diluting the appropriate volume of working solution with a diluent consisting of acetonitrile/water (50/50). Six quality control (QC) levels were prepared by adding the appropriate volume of the QC working solution into acetonitrile/water (50/50). After preparation, an aliquot of 10 µL of each calibration standards (STD) and QC solutions was transferred in a new 96-well plate for plasma sample pretreatment and added each of 50 µL of artificial plasma (4 g of bovine albumine in 100 mL PBS) used as surrogate matrix. Three replicates for each QC concentration were prepared.

Unknown plasma samples obtained from dosed animals were prepared for analysis in a 96-well plate format. An aliquot (50 µL) of individual subject samples was disposed into the well assigned and then added of 10 µL of acetonitrile/water (50/50).

A single step protein precipitation technique was used for sample preparation. A 200 µL aliquot of acetonitrile containing the following IS mix (labetalol, imipramine and diclofenac) was added to each sample (standard, QCs and biological samples) in order to precipitate the proteins. Plates were mixed by vortex for homogeneity, and then subjected to centrifugation at 4000 rpm (1950 g) for 15 min. The supernatant (200 µL) was transferred into a clean 96 deep well plates and injected into the LC-MS/MS system.

For blood samples where samples are generally collected by adding 30 µL of 0.1M sodium citrate to 10 µL of whole blood the following surrogate matrix is used: Artificial plasma dilute with 3 volumes of 0.1M sodium citrate. Tumor and other tissue samples are homogenized by adding 3 volumes of artificial plasma per g of tissue. STD and QC are then prepared in artificial plasma.

LC analysis was carried out on an LX-2 system using Allegros Pumps (ThermoFisher) equipped with a dual arm HTC PAL autosampler system refrigerated at 4° C. during analysis. Chromatography was performed on a Waters Acquity HSS T3 (2.1 mm×50 mm, 1.8 µm) column at RT with an injection volume of 5 µL. The mobile phase consisting of a solvent A (0.1% formic acid in water) and solvent B (0.1% formic acid in acetonitrile) was delivered at a flow rate of 750 µL/min.

Detection was carried out using a triple quadrupole tandem mass spectrometer (API5000 Applied Biosystems) equipped with an electrospray interface (ESI). Ions were created in the positive ion mode setting the sprayer voltage at 5.0 kV and the ion source temperature at 500° C. The common parameters and the nitrogen flow values for nebulizer gas (Gas 1), auxiliary gas (Gas 2), curtain gas and the gas for collision-activated dissociation (CAD) were set at 50, 60, 40 and 6, respectively. Detection of the ions was performed in the multiple reaction-monitoring (MRM) mode. MRM chromatograms of kynurenine (Q1: 209.2>Q3: 192.1, Q1: 209.2>Q3:146.0) and tryptophan (Q1: 205.1>Q3:146.1) were collected.

Chromagraphic data were collected and integrated by MultiQuant 2.1.1 data analysis program. Peak area ratios of the analyte to IS were utilized for construction of the calibration curve. A weighting of $1/x2$ (least-squares linear regression analysis, where x is the concentration of a given standard) was used for curve fit. Concentrations in unknown samples were calculated from the best-fit equation (y=mx+b) where y is the peak area ratio. The regression equation for the calibration curve was also used to back-calculate the measured concentration at each quality control level, and the results were compared with the theoretical concentration to obtain the accuracy expressed as a percentage of the theoretical value. Accuracy was defined as the degree of deviation of the determined value from the nominal value: [(measured value−nominal value)/nominal value]×100.

In the hIDO1-CT26 murine model described above, oral administration of Examples 42 and 46 at 100 and 300 mg/kg dosages produced a dose-dependent reduction of kynurenine levels in both plasma and tumor.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of Formula (I), or a pharmaceutically acceptable salt thereof:

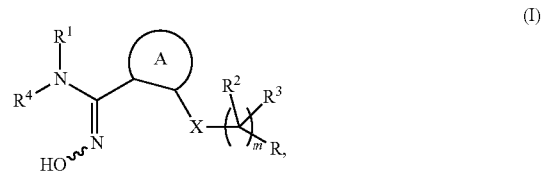

(I)

wherein:

m is 0, 1, 2, 3, 4, 5 or 6;

X is O or S;

ring A is a 5-membered heterocyclyl selected from 1,2,5-oxadiazolyl and 1,2,5-thiadiazolyl; each of which is optionally substituted with:
(i) halogen,
(ii) $C_{1-6}$ alkyl, optionally substituted with one to four halogens,
(iii) $C_{3-6}$ cycloalkyl,
(iv) $C_{2-6}$ alkenyl,
(v) $C_{2-6}$ alkynyl,
(vi) aryl,
(vii) heteroaryl,
(viii) CN,
(ix) $NO_2$,
(x) $OR^4$,
(xi) $SR^4$,
(xii) $C(O)R^4$,
(xiii) $NR^4R^4$,
(xiv) $S(O)R^4$, and
(xv) $S(O)_2R^4$;

R is selected from:
(a) hydrogen,
(b) $OR^a$,
(c) $C_{3-6}$cycloalkyl, optionally substituted with one to four substituents independently selected from:
  (i) $C_{1-6}$alkyl,
  (ii) CN, and
  (iii) —(C=O)—O—$C_{1-6}$alkyl,
(d) aryl, optionally substituted with one to four substituents independently selected from:
  (i) halogen,
  (ii) $C_{1-6}$alkyl, optionally substituted with one to three halogens,
  (iii) oxo, and
  (iv) —$S(O)_2$—NH—$R^4$,
(e) a 4-, 5- or 6-membered heterocyclyl, optionally substituted with one to four substituents independently selected from:
  (i) halogen,
  (ii) $C_{1-6}$alkyl, optionally substituted with one to three halogens,
  (iii) oxo,
  (iv) —$S(O)_2$—NH—$R^4$,
  (v) —(C=O)—$C_{1-6}$alkyl, and
  (vi) —(C=O)NH—$R^4$,
(f) CN,
(g) —(C=O)—$R^a$,
(h) —(C=O)NH—$R^a$,
(i) —$P(O)(OR^a)_2$,
(j) —$P(O)(NHR^a)(OR^a)$,
(k) —$P(O)(NR^4R^a)_2$,
(l) $C_{2-4}$alkynyl,
(m) —$NR^xR^y$, wherein each of $R^x$ and $R^y$ is independently selected from:
  (i) hydrogen,
  (ii) $C_{1-6}$alkyl, optionally substituted with a 4-, 5- or 6-membered heterocyclyl,
  (iii) $C_{3-6}$cycloalkenyl, optionally substituted with one to four substituents independently selected from NH—$R^a$, oxo, and 4-, 5- or 6-membered heterocyclyl,
  (iv) $C_{2-4}$alkenyl, optionally substituted with one to four substituents independently selected from $NR^4$ and $NO_2$,
  (v) —(C=O)—$R^a$,
  (vi) —(C=O)—$C_{3-6}$cycloalkyl,
  (vii) —(C=O)—$NR^4R^a$,
  (viii) aryl,
  (ix) heteroaryl,
  (x) —(C=NH)($NH_2$)—CN,
  (xi) —$S(O)_2$—$R^a$, and
  (xii) —$S(O)_2$—NH—$R^a$;

$R^1$ is aryl, optionally substituted with one to four substituents independently selected from:
(a) halogen,
(b) $C_{1-6}$ alkyl, optionally substituted with one to four halogens,
(c) CN,
(d) $C_{2-6}$ alkenyl,
(e) $C_{2-6}$ alkynyl,
(f) $C_{3-6}$cycloalkyl,
(g) $OR^4$,
(h) $SR^4$,
(i) $C(O)R^4$,
(j) $C(O)NR^4R^4$,
(k) $S(O)R^4$,
(l) $S(O)_2R^4$, and
(m) $S(O)_2NR^4R^4$;

each occurrence of $R^2$ and $R^3$ is independently selected from:
(a) $R^4$,
(b) OH,
(c) NH—$R^4$,
(d) NH—(C=O)—$R^4$,
(e) halogen,
(f) $C_{3-6}$cycloalkyl, and
(g) $C_{1-6}$alkoxy;
or $R^2$ and $R^3$ together form an oxo group;
or $R^2$ and $R^3$ together with the carbon to which they are attached form a $C_{3-6}$cycloalkyl group;

each occurrence of $R^4$ is independently selected from hydrogen and $C_{1-6}$ alkyl; and each occurrence of $R^a$ is independently selected from the group consisting of:
(a) hydrogen,
(b) $C_{1-6}$alkyl, optionally substituted with one or three substituents independently selected from halogen, $OR^4$, —O—(C=O)—O—$C_{1-6}$alkyl, —(C=O)—O—$C_{1-6}$alkyl, aryl, and 4-, 5- or 6-membered heterocyclyl,
(c) $C_{3-6}$cycloalkyl, optionally substituted with one or three substituents independently selected from halogen, $C_{1-6}$alkyl and $OR^4$,
(d) —O—$C_{1-6}$alkyl,
(e) —(C=O)—O—$C_{1-6}$alkyl,
(f) aryl, optionally substituted with $C_{1-6}$alkyl, and
(g) 4, 5- or 6-membered heterocyclyl, optionally substituted with —$C_{1-6}$alkyl or —$C_{1-6}$alkyl-$OR^4$.

2. The compound of claim 1 of Formula (Ia), or a pharmaceutically acceptable salt thereof:

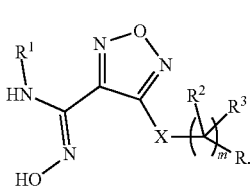

(Ia)

3. The compound of claim 1, or a pharmaceutically acceptable salt thereof, wherein:
$R^1$ is aryl, optionally substituted with one to four substituents independently selected from:
  (a) halogen,
  (b) $C_{1-6}$ alkyl, optionally substituted with one to four halogens, and
  (c) CN; and
each occurrence of $R^2$ and $R^3$ is independently selected from:
  (a) $R^4$,
  (b) $OR^4$,
  (c) NH—$R^4$,
  (d) halogen, and
  (e) $C_{3-6}$cycloalkyl;
or alternatively, $R^2$ and $R^3$ together form an oxo group;
or alternatively, $R^2$ and $R^3$ together with the carbon to which they are attached form a $C_{3-6}$cycloalkyl group.

4. The compound of claim 1, wherein:
X is S,
$R^1$ is phenyl, optionally substituted with one to four substituents independently selected from:
  (a) halogen,
  (b) $C_{1-6}$ alkyl, optionally substituted with one to four halogens, and
  (c) CN; and
each occurrence of $R^2$ and $R^3$ is independently selected from:
  (a) $R^4$,
  (b) OH,
  (c) NH—$R^4$, and
  (d) halogen;
or alternatively, $R^2$ and $R^3$ together form an oxo group.

5. The compound of claim 1, wherein:
each occurrence of aryl is phenyl; and
each occurrence of the 4-, 5- or 6-membered heterocyclyl is independently selected from: azetidinyl, 1,2,5-thiadiazolidinyl, imidazolidinyl, oxazolidinyl, oxetanyl, pyrrolidinyl, piperidinyl, piperazinyl, morpholinyl, tetrahydropyranyl, tetrahydro-2H-thiopyranyl, 4,5-dihydro-1H-1,2,4-triazolyl, dihydropyridazinyl, dihydropyridinyl, furanyl, imidazolyl, dihydro-oxadiazolyl, oxadiazolyl, pyridinyl, thiazolyl, and triazolyl.

6. The compound of claim 1, wherein:
R is selected from:
  (a) hydrogen,
  (b) $OR^a$,
  (c) $C_{3-6}$cycloalkyl, optionally substituted with one to four substituents independently selected from:
    (i) $C_{1-6}$alkyl, and
    (ii) CN,
  (d) phenyl, optionally substituted with one to four substituents independently selected from:
    (i) halogen,
    (ii) $C_{1-6}$alkyl, and
    (iii) —S(O)$_2$—NH—$R^4$,
  (e) a 4-, 5- or 6-membered heterocyclyl selected from azetidinyl, 1,2,5-thiadiazolidinyl, imidazolidinyl, oxazolidinyl, oxetanyl, pyrrolidinyl, piperidinyl, piperazinyl, morpholinyl, tetrahydropyranyl, tetrahydro-2H-thiopyranyl, 4,5-dihydro-1H-1,2,4-triazolyl, dihydropyridazinyl, dihydropyridinyl, furanyl, imidazolyl, dihydro-oxadiazolyl, pyridinyl, thiazolyl, and triazolyl; each of which is optionally substituted with one to four substituents independently selected from:
    (i) halogen,
    (ii) $C_{1-6}$alkyl, optionally substituted with one to three halogens,
    (iii) oxo,
    (iv) —S(O)$_2$—NH—$R^4$, and
    (v) —(C=O)—$C_{1-6}$alkyl,
  (f) CN,
  (g) —(C=O)—$R^a$,
  (h) —(C=O)NH—$R^a$,
  (i) —P(O)(O$R^a$)$_2$,
  (j) —P(O)(NH$R^a$)(O$R^a$),
  (k) $C_{2-4}$alkynyl,
  (m) —N$R^x R^y$, wherein each of $R^x$ and $R^y$ is independently selected from:
    (i) hydrogen,
    (ii) $C_{1-6}$alkyl, optionally substituted with a 4-, 5- or 6-membered heterocyclyl,
    (iii) $C_{3-6}$cycloalkenyl, optionally substituted with one to four substituents independently selected from NH—$R^a$, oxo, and 4-, 5- or 6-membered heterocyclyl,
    (iv) $C_{2-4}$alkenyl, optionally substituted with one to four substituents independently selected from N$R^4$ and NO$_2$,
    (v) —(C=O)—$R^a$,
    (vi) —(C=O)—$C_{3-6}$cycloalkyl,
    (vii) —(C=O)—N$R^4 R^a$,
    (viii) aryl,
    (ix) heteroaryl,
    (x) —(C=NH)(NH$_2$)—CN,
    (xi) —S(O)$_2$—$R^a$, and
    (xii) —S(O)$_2$—NH—$R^a$.

7. The compound of claim 1, wherein:
R is selected from:
  (a) $R^4$,
  (b) $OR^4$,
  (c) $C_{4-6}$cycloalkyl, optionally substituted with one to three substituents independently selected from (i) $C_{1-4}$alkyl and (ii) —(C=O)—O—$C_{1-4}$alkyl,
  (d) phenyl, optionally substituted with one to three halogens,
  (e) a 4-, 5- or 6-membered heterocyclyl independently selected from: azetidinyl, 1,2,5-thiadiazolidinyl, imidazolidinyl, oxazolidinyl, oxetanyl, pyrrolidinyl, piperidinyl, piperazinyl, morpholinyl, tetrahydropyranyl, tetrahydro-2H-thiopyranyl, 4,5-dihydro-1H-1,2,4-triazolyl, dihydropyridazinyl, dihydropyridinyl, furanyl, imidazolyl, dihydro-oxadiazolyl, oxadiazolyl, pyridinyl, thiazolyl, and triazolyl each of which is optionally substituted with one to three substituents independently selected from (i) $C_{1-6}$alkyl and (ii) halogen,
  (f) —(C=O)—$R^a$,
  (g) —P(O)(O$R^a$)$_2$, wherein each $R^a$ is independently selected from (i) hydrogen, (ii) $C_{1-4}$alkyl, and (iii) C—O—C(O)—O-iPr, and
  (h) —N$R^x R^y$, wherein each of $R^x$ and $R^y$ is independently selected from (i) $R^4$, (ii) —(C=O)—O—$R^4$, (iii) —(C=O)—$R^4$, (iv) aryl, (v) heteroaryl, and (vii) —S(O)$_2$—NH$_2$.

8. The compound of claim 1, wherein:
R is selected from:
  (a) hydrogen,
  (b) hydroxyl,
  (c) $C_{4-6}$cycloalkyl, optionally substituted with —(C=O)—O—$C_{1-4}$alkyl,
  (d) —P(O)(O—$C_{1-4}$alkyl)$_2$,
  (e) —P(O)(O—C—O—C(O)—O-iPr)$_2$, (f) —P(O)H(O—C—O—C(O)—O-iPr),
(g) —P(O)(OH)$_2$,
(h) —NH—C(O)—O—C$_{1-4}$alkyl,
(i) —NH—C(O)—C$_{1-4}$alkyl and
(j) a 4- or 5-membered heterocyclyl containing one ring nitrogen atom, optionally B substituted with a halogen or —C$_{1-4}$alkyl.

9. The compound of claim 1, wherein:
each of R$^2$ and R$^3$ is independently selected from (i) R$^4$, (ii) OH and (iii) halogen;
or R$^2$ and R$^3$ together form an oxo group.

10. The compound of claim 1, wherein:
each occurrence of R$^a$ is independently selected from the group consisting of:
(a) hydrogen,
(b) C$_{1-6}$alkyl, optionally substituted with one or three substituents independently selected from halogen, OR$^4$, —O—(C=O)—O—C$_{1-6}$alkyl, —(C=O)—O—C$_{1-6}$alkyl, aryl, and 4-, 5- or 6-membered heterocyclyl,
(c) C$_{3-6}$cycloalkyl, optionally substituted with one or three substituents independently selected from halogen, C$_{1-6}$alkyl and OR$^4$,
(d) —O—C$_{1-6}$alkyl,
(e) —(C=O)—O—C$_{1-6}$alkyl,
(f) phenyl, optionally substituted with one or three substituents independently selected from C$_{1-6}$alkyl and halogen, and
(g) a 4, 5- or 6-membered heterocyclyl independently selected from: azetidinyl, 1,2,5-thiadiazolidinyl, imidazolidinyl, oxazolidinyl, oxetanyl, pyrrolidinyl, piperidinyl, piperazinyl, morpholinyl, tetrahydropyranyl, tetrahydro-2H-thiopyranyl, 4,5-dihydro-1H-1,2,4-triazolyl, dihydropyridazinyl, dihydropyridinyl, furanyl, imidazolyl, dihydro-oxadiazolyl, oxadiazolyl, pyridinyl, thiazolyl, and triazolyl; each of which is optionally substituted with —C$_{1-6}$alkyl or —C$_{1-6}$alkyl-OR$^4$.

11. The compound of claim 1 of formula (Ib), or a pharmaceutically acceptable salt thereof:

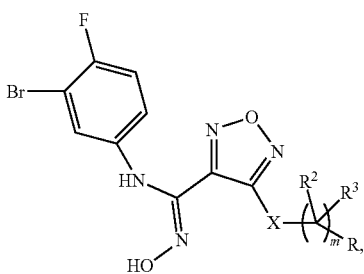

(Ib)

wherein:
m is 0, 1, 2, 3, 4, 5 or 6;
X is S or O;
each occurrence of R$^2$ and R$^3$ is independently selected from:
(a) hydrogen,
(b) hydroxyl,
(c) halogen and
(d) C$_{1-4}$alkyl;
or R$^2$ and R$^3$ together form an oxo group; and R is selected from:
(a) R$^4$,
(b) OR$^4$,
(c) C$_{4-6}$cycloalkyl, optionally substituted with one to three substituents independently selected from (a) C$_{1-4}$alkyl and (b) —(C=O)—O—C$_{1-4}$alkyl,
(d) a 4-, 5- or 6-membered heterocyclyl,
(e) —(C=O)—R$^a$,
(f) —P(O)(OR$^a$)$_2$, and
(g) —NR$^x$R$^y$, wherein each of R$^x$ and R$^y$ is independently selected from (i) hydrogen, (ii) C$_{1-4}$alkyl, (iii) —(C=O)—O—C$_{1-4}$alkyl, (iv) —(C=O)—C$_{1-4}$alkyl, (v) aryl, (vi) heteroaryl, and (vii) —S(O)$_2$—NH$_2$.

12. The compound of claim 11, wherein each occurrence of R$^2$ and R$^3$ is independently selected from:
(a) R$^4$,
(b) OR$^4$, and
(c) halogen.

13. The compound of claim 11, wherein R is selected from:
(a) hydrogen,
(b) hydroxyl,
(c) cyclobutyl substituted with —(C=O)—O—CH$_3$,
(d) —P(O)(O—CH$_2$CH$_3$)$_2$,
(e) —P(O)(O—C—O—C(O)—O-iPr)$_2$,
(f) —P(O)H(O—C—O—C(O)—O-iPr),
(g) —P(O)(OH)$_2$,
(h) —NH—C(O)—O—CH$_3$,
(i) —NH—C(O)—CH$_3$ and
(j) azetidinyl.

14. The compound of claim 1 selected from:
tert-butyl (Z)-(2-((4-(N-(3-bromo-4-fluorophenyl)-N'-hydroxycarbamimidoyl)-1,2,5-oxadiazol-3-yl)thio)ethyl)carbamate,
(Z)-2-((4-(N-(3-bromo-4-fluorophenyl)-N'-hydroxycarbamimidoyl)-1,2,5-oxadiazol-3-yl)thio)ethan-1-aminium chloride,
(Z)—N-(3-bromo-4-fluorophenyl)-N'-hydroxy-4-((2-(sulfamoylamino)ethyl)thio)-1,2,5-oxadiazole-3-carboximidamide,
(Z)—N-(3-bromo-4-fluorophenyl)-N',4-dihydroxy-1,2,5-oxadiazazole-3-carboximidamide,
(Z)—N-(3-bromo-4-fluorophenyl)-4-ethoxy-N'-hydroxy-1,2,5-oxadiazole-3-carboximidamide,
(Z)-2-((4-(N-(3-Bromo-4-fluorophenyl)-N'-hydroxycarbamimidoyl)-1,2,5-oxadiazol-3-yl)oxy)ethan-1-aminium chloride,
diethyl (Z)-(2-((4-(N-(3-bromo-4-fluorophenyl)-N'-hydroxycarbamimidoyl)-1,2,5-oxadiazol-3-yl)thio)ethyl)phosphonate,
(Z)-(2-((4-(N-(3-bromo-4-fluorophenyl)-N'-hydroxycarbamimidoyl)-1,2,5-oxadiazol-3-yl)thio)ethyl)phosphonic acid,
(Z)—N-(2-((4-(N-(3-bromo-4-fluorophenyl)-N'-hydroxycarbamimidoyl)-1,2,5-oxadiazol-3-yl)thio)ethyl)acetamide,
ethyl (Z)-3-((4-(N-(3-bromo-4-fluorophenyl)-N'-hydroxycarbamimidoyl)-1,2,5-oxadiazol-3-yl)thio)propanoate,
(Z)-3-((4-(N-(3-bromo-4-fluorophenyl)-N'-hydroxycarbamimidoyl)-1,2,5-oxadiazol-3-yl)thio)propanoic acid,
(Z)-2-((4-(N-(3-bromo-4-fluorophenyl)-N'-hydroxycarbamimidoyl)-1,2,5-oxadiazol-3-yl)thio)acetic acid,
(Z)-2-((4-(N-(3-bromo-4-fluorophenyl)-N'-hydroxycarbamimidoyl)-1,2,5-oxadiazol-3-yl)thio)propanoic acid,
(Z)—N-(3-bromo-4-fluorophenyl)-4-((2,3-dihydroxypropyl)thio)-N'-hydroxy-1,2,5-oxadiazole-3-carboximidamide, (Z)—N-(3-bromo-4-fluorophenyl)-N'-hydroxy-4-((2-hydroxypropyl)thio)-1,2,5-oxadiazole-3-carboximidamide,
(Z)—N-(3-bromo-4-fluorophenyl)-N'-hydroxy-4-((3-hydroxypropyl)thio)-1,2,5-oxadiazazole-3-carboximidamide,
(Z)—N-(3-bromo-4-fluorophenyl)-N'-hydroxy-4-((4-hydroxybutyl)thio)-1,2,5-oxadiazole-3-carboximidamide,
methyl (Z)-1-((4-(N-(3-bromo-4-fluorophenyl)-N'-hydroxycarbamimidoyl)-1,2,5-oxadiazol-3-yl)thio)cyclobutane-1-carboxylate,
methyl (Z)-2-((4-(N-(3-bromo-4-fluorophenyl)-N'-hydroxycarbamimidoyl)-1,2,5-oxadiazol-3-yl)thio)acetate,
(Z)—N-(3-bromo-4-fluorophenyl)-N'-hydroxy-4-(propylthio)-1,2,5-oxadiazole-3-carboximidamide,
(Z)—N-(3-bromo-4-fluorophenyl)-4-(ethylthio)-N'-hydroxy-1,2,5-oxadiazole-3-carboximidamide,
(Z)-4-((azetidin-3-ylmethyl)thio)-N-(3-bromo-4-fluorophenyl)-N'-hydroxy-1,2,5-oxadiazole-3-carboximidamide,
(Z)-4-(azetidin-3-ylthio)-N-(3-bromo-4-fluorophenyl)-N'-hydroxy-1,2,5-oxadiazole-3-carboximidamide,
(Z)-(((2-((4-(N-(3-bromo-4-fluorophenyl)-N'-hydroxycarbamimidoyl)-1,2,5-oxadiazol-3-yl)thio)ethyl)(hydroxy)phosphoryl)oxy)methyl isopropyl carbonate,
(Z)-(((2-((4-(N-(3-bromo-4-fluorophenyl)-N'-hydroxycarbamimidoyl)-1,2,5-oxadiazol-3-yl)thio)ethyl)phosphoryl)bis(oxy))bis(methylene) diisopropyl bis(carbonate),
(Z)—N-(2-((4-(N-(3-Bromo-4-fluorophenyl)-N'-hydroxycarbamimidoyl)-1,2,5-oxadiazol-3-yl)thio)ethyl) acetamide,
methyl(Z)-(2-((4-(N-(3-bromo-4-fluorophenyl)-N'-hydroxycarbamimidoyl)-1,2,5-thiadiazol-3-yl)thio)ethyl) carbamate,
2-((4-(N-(3-bromo-4-fluorophenyl)-N'-hydroxycarbamimidoyl)-1,2,5-oxadiazol-3-yl)thio)-N-(1-hydroxy-2-methylpropan-2-yl)acetamide,
2-((4-(N-(3-bromo-4-fluorophenyl)-N'-hydroxycarbamimidoyl)-1,2,5-oxadiazol-3-yl)thio)-N-(2-hydroxy-2-methylpropyl)acetamide,
(R)—N-(3-bromo-4-fluorophenyl)-4-((2,3-dihydroxy-3-methylbutyl)thio)-N'-hydroxy-1,2,5-oxadiazole-3-carboximidamide,
(S)—N-(3-bromo-4-fluorophenyl)-4-((2,3-dihydroxy-3-methylbutyl)thio)-N'-hydroxy-1,2,5-oxadiazole-3-carboximidamide,
N-(3-bromo-4-fluorophenyl)-N'-hydroxy-4-((2-((N-(2-methoxyethyl) sulfamoyl)-ethyl)thio)-1,2,5-oxadiazole-3-carboximidamide,
(R)—N-(3-chloro-4-fluorophenyl)-4-(((1,1-dioxido-1,2,5-thiadiazolidin-3-yl)methyl)thio)-N'-hydroxy-1,2,5-oxadiazole-3-carboximidamide,
(R)—N-(3-bromo-4-fluorophenyl)-4-(((1,1-dioxido-1,2,5-thiadiazolidin-3-yl)methyl)thio)-N'-hydroxy-1,2,5-oxadiazole-3-carboximidamide,
N-(3-bromo-4-fluorophenyl)-N'-hydroxy-4-(((5-oxo-4,5-dihydro-1H-1,2,4-triazol-3-yl)methyl)thio)-1,2,5-oxadiazole-3-carboximidamide,
(3-bromo-4-fluorophenyl)-N'-hydroxy-4-(((6-oxo-1,6-dihydropyridazin-3-yl)methyl)thio)-1,2,5-oxadiazole-3-carboximidamide,
N-(3-bromo-4-fluorophenyl)-N'-hydroxy-4-((2-((2-(methylamino)-3,4-dioxocyclobut-1-en-1-yl)amino)ethyl)thio)-1,2,5-oxadiazole-3-carboximidamide,
N-(2-((4-(N-(3-cyano-4-fluorophenyl)-N'-hydroxycarbamimidoyl)-1,2,5-oxadiazol-3-yl)thio)ethyl)acetamide,
(R)—N-(3-cyano-4-fluorophenyl)-4-((2,3-dihydroxy-3-methylbutyl)thio)-N'-hydroxy-1,2,5-oxadiazole-3-carboximidamide,
(S)—N-(3-cyano-4-fluorophenyl)-4-((2,3-dihydroxy-3-methylbutyl)thio)-N'-hydroxy-1,2,5-oxadiazole-3-carboximidamide,
N-(2-((4-(N-(3-cyano-4-fluorophenyl)-N'-hydroxycarbamimidoyl)-1,2,5-oxadiazol-3-yl)thio)ethyl)cyclopropanecarboxamide,
2-((4-(N-(3-bromo-4-fluorophenyl)-N'-hydroxycarbamimidoyl)-1,2,5-oxadiazol-3-yl)thio)-N-methylacetamide,
(R)-2-((4-(N-(3-bromo-4-fluorophenyl)-N'-hydroxycarbamimidoyl)-1,2,5-oxadiazol-3-yl)thio)-N-(2,3-dihydroxypropyl)acetamide,
(R)—N-(3-bromo-4-fluorophenyl)-N'-hydroxy-4-(((3-methyl-2-oxoimidazolidin-4-yl)methyl)thio)-1,2,5-oxadiazole-3-carboximidamide,
Dimethyl 2,2'-(((2-((4-(N-(3-bromo-4-fluorophenyl)-N'-hydroxycarbamimidoyl)-1,2,5-oxadiazol-3-yl)thio) ethyl)phosphoryl)bis(azanediyl))(Z)-diacetate,
N-(3-bromo-4-fluorophenyl)-N'-hydroxy-4-((2-(3-methylureido)ethyl)thio)-1,2,5-oxadiazole-3-carboximidamide,
N-(3-Bromo-4-fluorophenyl)-N'-hydroxy-4-((2-ureidoethyl)thio)-1,2,5-oxadiazole-3-carboximidamide,
N-(3-bromo-4-fluorophenyl)-N'-hydroxy-4-((2-(sulfamoylamino)ethyl)thio)-1,2,5-thiadiazole-3-carboximidamide,
methyl S-{4-[N-(3-bromo-4-fluorophenyl)-N'-hydroxycarbamimidoyl]-1,2,5-oxadiazol-3-yl}-L-cysteinate,
N-{2-[(4-{N-[4-fluoro-3-(trifluoromethyl)phenyl]-N'-hydroxycarbamimidoyl}-1,2,5-oxadiazol-3-yl)sulfanyl]ethyl}acetamide,
N-[4-fluoro-3-(trifluoromethyl)phenyl]-N'-hydroxy-4-[(2-hydroxyethyl)sulfanyl]-1,2,5-oxadiazole-3-carboximidamide,
N-[2-({4-[N-(4-fluoro-3-methylphenyl)-N'-hydroxycarbamimidoyl]-1,2,5-oxadiazol-3-yl}sulfanyl)ethyl]acetamide,
N-{2-[(4-{N-[4-fluoro-3-(trifluoromethoxy)phenyl]-N'-hydroxycarbamimidoyl}-1,2,5-oxadiazol-3-yl)sulfanyl]ethyl}acetamide,
N-(3-bromo-4-fluorophenyl)-N'-hydroxy-4-[(6-hydroxyhexyl)sulfanyl]-1,2,5-oxadiazole-3-carboximidamide,
N-(3-bromo-4-fluorophenyl)-N'-hydroxy-4-[(3-hydroxy-4-methylpentyl)sulfanyl]-1,2,5-oxadiazole-3-carboximidamide,
N-(3-bromo-4-fluorophenyl)-4-[(2-{[2-(ethylamino)-3,4-dioxocyclobut-1-en-1-yl]amino}ethyl)sulfanyl]-N'-hydroxy-1,2,5-oxadiazole-3-carboximidamide,
N-(3-bromo-4-fluorophenyl)-4-[(2-carbamimidamidoethyl)sulfanyl]-N'-hydroxy-1,2,5-oxadiazole-3-carboximidamide,
S-{4-[N-(3-bromo-4-fluorophenyl)-N'-hydroxycarbamimidoyl]-1,2,5-oxadiazol-3-yl}homocysteine,
N-[2-({4-[N-(5-bromo-2,4-difluorophenyl)-N'-hydroxycarbamimidoyl]-1,2,5-oxadiazol-3-yl}sulfanyl)ethyl] acetamide,
N-[2-({4-[N-(3-bromophenyl)-N'-hydroxycarbamimidoyl]-1,2,5-oxadiazol-3-yl}sulfanyl)ethyl]acetamide,
N-(3-bromo-4-fluorophenyl)-N'-hydroxy-4-[2-{[(E)-1-(methyl amino)-2-nitroethenyl]amino}ethyl)sulfanyl]-1,2,5-oxadiazole-3-carboximidamide, 2-({4-[N-(3-bromo-4-fluorophenyl)-N'-hydroxycarbamimidoyl]-1,2,5-oxadiazol-3-yl}sulfanyl)-N-phenylacetamide,
N-[2-({4-[N-(4-fluorophenyl)-N'-hydroxycarbamimidoyl]-1,2,5-oxadiazol-3-yl}sulfanyl)ethyl]acetamide,
N-(3-bromo-4-fluorophenyl)-4-[(2,3-dihydroxypropyl)sulfanyl]-N'-hydroxy-1,2,5-oxadiazole-3-carboximidamide,
N-[2-({4-[N-(3-ethylphenyl)-N'-hydroxycarbamimidoyl]-1,2,5-oxadiazol-3-yl}sulfanyl)ethyl]acetamide,
N-(3-bromo-4-fluorophenyl)-N'-hydroxy-4-(pyrrolidin-3-ylsulfanyl)-1,2,5-oxadiazole-3-carboximidamide,
N-(3-bromo-4-fluorophenyl)-4-[(cyanomethyl)sulfanyl]-N'-hydroxy-1,2,5-oxadiazole-3-carboximidamide,
N-(3-bromo-4-fluorophenyl)-4-{[(1-cyanocyclopropyl)methyl]sulfanyl}-N'-hydroxy-1,2,5-oxadiazole-3-carboximidamide,
1-[({4-[N-(3-bromo-4-fluorophenyl)-N'-hydroxycarbamimidoyl]-1,2,5-oxadiazol-3-yl}sulfanyl)methyl]-N-methylcyclopropanecarboxamide,
3-({4-[N-(3-bromo-4-fluorophenyl)-N'-hydroxycarbamimidoyl]-1,2,5-oxadiazol-3-yl}sulfanyl)-N-methylpropanamide,
N-(3-bromo-4-fluorophenyl)-N'-hydroxy-4-{[2-(4-sulfamoylphenyl)ethyl]sulfanyl}-1,2,5-oxadiazole-3-carboximidamide,
N-(3-bromo-4-fluorophenyl)-N'-hydroxy-4-(piperidin-4-ylsulfanyl)-1,2,5-oxadiazazole-3-carboximidamide,
4-({2-[(2-amino-3,4-dioxocyclobut-1-en-1-yl)amino]ethyl}sulfanyl)-N-(3-bromo-4-fluorophenyl)-N'-hydroxy-1,2,5-oxadiazole-3-carboximidamide,
N-(3-bromo-4-fluorophenyl)-N'-hydroxy-4-[(2-hydroxy-2-phenylethyl)sulfanyl]-1,2,5-oxadiazole-3-carboximidamide,
N-(3-bromo-4-fluorophenyl)-4-{[2-({2-[(2,3-dihydroxypropyl)amino]-3,4-dioxocyclobut-1-en-1-yl}amino)ethyl]sulfanyl}-N'-hydroxy-1,2,5-oxadiazole-3-carboximidamide,
N-(3-bromo-4-fluorophenyl)-N'-hydroxy-4-[(1-sulfamoylpiperidin-4-yl)sulfanyl]-1,2,5-oxadiazole-3-carboximidamide,
2-({4-[N-(3-bromo-4-fluorophenyl)-N'-hydroxycarbamimidoyl]-1,2,5-oxadiazol-3-yl}sulfanyl)acetamide,
N-(3-bromo-4-fluorophenyl)-N'-hydroxy-4-{[(4-methylmorpholin-2-yl)methyl]sulfanyl}-1,2,5-oxadiazole-3-carboximidamide,
N-[2-({4-[N-(3-bromo-4-fluorophenyl)-N'-hydroxycarbamimidoyl]-1,2,5-oxadiazol-3-yl}sulfanyl)ethyl]-2,2,2-trifluoroacetamide,
N-(3-bromo-4-fluorophenyl)-4-{[(3-cyanobicyclo[1.1.1]pent-1-yl)methyl]sulfanyl}-N'-hydroxy-1,2,5-oxadiazole-3-carboximidamide,
3-({4-[N-(3-bromo-4-fluorophenyl)-N'-hydroxycarbamimidoyl]-1,2,5-oxadiazol-3-yl}sulfanyl)-N-methylazetidine-1-carboxamide,
N-(3-bromo-4-fluorophenyl)-4-[(1,1-dioxidotetrahydro-2H-thiopyran-4-yl)sulfanyl]-N'-hydroxy-1,2,5-oxadiazole-3-carboximidamide,
N-(3-bromo-4-fluorophenyl)-4-({[(2R)-5-oxopyrrolidin-2-yl]methyl}sulfanyl)-1,2,5-oxadiazole-3-carboximidamide,
N-(3-bromo-4-fluorophenyl)-4-({[(2S)-5-oxopyrrolidin-2-yl]methyl}sulfanyl)-1,2,5-oxadiazole-3-carboximidamide,
N-(3-bromo-4-fluorophenyl)-4-{[2-(N''-cyanocarbamimidamido)ethyl]sulfanyl}-N'-hydroxy-1,2,5-oxadiazole-3-carboximidamide,
N-(3-bromo-4-fluorophenyl)-N'-hydroxy-4-{[(6-oxo-1,6-dihydropyridin-2-yl)methyl]sulfanyl}-1,2,5-oxadiazole-3-carboximidamide,
4-[(1-acetylpiperidin-4-yl)sulfanyl]-N-(3-bromo-4-fluorophenyl)-N'-hydroxy-1,2,5-oxadiazole-3-carboximidamide,
N-(3-bromo-4-fluorophenyl)-N'-hydroxy-4-({[6-oxo-4-(trifluoromethyl)-1,6-dihydropyridin-2-yl]methyl}sulfanyl)-1,2,5-oxadiazole-3-carboximidamide,
N-(3-bromo-4-fluorophenyl)-4-{[2-({2-[(cyclopropylmethyl)amino]-3,4-dioxocyclobut-1-en-1-yl}amino)ethyl]sulfanyl}-N'-hydroxy-1,2,5-oxadiazole-3-carboximidamide,
N-(3-bromo-4-fluorophenyl)-N'-hydroxy-4-{[2-({2-[(2-hydroxyethyl)amino]-3,4-dioxocyclobut-1-en-1-yl}amino)ethyl]sulfanyl}-1,2,5-oxadiazole-3-carboximidamide,
N-(3-bromo-4-fluorophenyl)-N'-hydroxy-4-({2-[(2-morpholin-4-yl-3,4-dioxocyclobut-1-en-1-yl)amino]ethyl}sulfanyl)-1,2,5-oxadiazole-3-carboximidamide,
N-(3-bromo-4-fluorophenyl)-N'-hydroxy-4-({[6-oxo-5-(trifluoromethyl)-1,6-dihydropyridazin-3-yl]methyl}sulfanyl)-1,2,5-oxadiazole-3-carboximidamide,
N-(3-bromo-4-fluorophenyl)-4-({2-[(3,4-dioxo-2-piperidin-1-ylcyclobut-1-en-1-yl)amino]ethyl}sulfanyl)-N'-hydroxy-1,2,5-oxadiazole-3-carboximidamide,
N-(3-bromo-4-fluorophenyl)-N'-hydroxy-4-{[2-({2-[(1-methylethyl)amino]-3,4-dioxocyclobut-1-en-1-yl}amino)ethyl]sulfanyl}-1,2,5-oxadiazole-3-carboximidamide,
N-(3-bromo-4-fluorophenyl)-4-{[2-({3,4-dioxo-2-[(pyridin-4-ylmethyl)amino]cyclobut-1-en-1-yl}amino)ethyl]sulfanyl}-N'-hydroxy-1,2,5-oxadiazole-3-carboximidamide,
3-({4-[N-(3-bromo-4-fluorophenyl)-N'-hydroxycarbamimidoyl]-1,2,5-oxadiazol-3-yl}sulfanyl)propanamide,
1-methylethyl (2S,6S)-4-[2-({4-[N-(3-bromo-4-fluorophenyl)-N'-hydroxycarbamimidoyl]-1,2,5-oxadiazol-3-yl}sulfanyl)ethyl]-2,6,9-trimethyl-7-oxo-8-oxa-3,5-diaza-4-phosphadecan-1-oate 4-oxide (non-preferred name),
N-(3-bromo-4-fluorophenyl)-N'-hydroxy-4-{[(4-methyl-5-oxo-4,5-dihydro-1H-1,2,4-triazol-3-yl)methyl]sulfanyl}-1,2,5-oxadiazole-3-carboximidamide,
4-[(2-{[(E)-1-amino-2-nitroethenyl]amino}ethyl)sulfanyl]-N-(3-bromo-4-fluorophenyl)-N'-hydroxy-1,2,5-oxadiazole-3-carboximidamide,
4-[(2-{bis[(2-methoxyethyl)amino]phosphoryl}ethyl)sulfanyl]-N-(3-bromo-4-fluorophenyl)-N'-hydroxy-1,2,5-oxadiazole-3-carboximidamide,
diphenyl [2-({4-[N-(3-bromo-4-fluorophenyl)-N'-hydroxycarbamimidoyl]-1,2,5-oxadiazol-3-yl}sulfanyl)ethyl]phosphonate,
N-(3-bromo-4-fluorophenyl)-N'-hydroxy-4-{[(4-methyl-6-oxo-1,6-dihydropyridin-2-yl)methyl]sulfanyl}-1,2,5-oxadiazole-3-carboximidamide,
4-({2-[bis(methylamino)phosphoryl]ethyl}sulfanyl)-N-(3-bromo-4-fluorophenyl)-N'-hydroxy-1,2,5-oxadiazole-3-carboximidamide,
4-({4-[N-(3-bromo-4-fluorophenyl)-N'-hydroxycarbamimidoyl]-1,2,5-oxadiazol-3-yl}sulfanyl)-N-methylpiperidine-1-carboxamide,
ethyl N-[{[2-({4-[N-(3-bromo-4-fluorophenyl)-N'-hydroxycarbamimidoyl]-1,2,5-oxadiazol-3-yl}sulfanyl)ethyl]amino}(ethyl)phosphoryl]glycinate, 3-({4-[N-(3-bromo-4-fluorophenyl)-N'-hydroxycarbamimidoyl]-1,2,5-oxadiazol-3-yl}sulfanyl)-N-(2-methoxyethyl)propanamide, 3-({4-[N-(3-bromo-4-fluorophenyl)-N'-hydroxycarbamimidoyl]-1,2,5-oxadiazol-3-yl}sulfanyl)-N-(2-hydroxyethyl)propanamide, bis({[(1-methylethoxy)carbonyl]oxy}methyl) [3-({4-[N-(3-bromo-4-fluorophenyl)-N'-hydroxycarbamimidoyl]-1,2,5-oxadiazol-3-yl}sulfanyl)propyl]phosphonate, 2-({4-[N-(3-bromo-4-fluorophenyl)-N'-hydroxycarbamimidoyl]-1,2,5-oxadiazol-3-yl}sulfanyl)-N-ethylacetamide, 2-({4-[N-(3-bromo-4-fluorophenyl)-N'-hydroxycarbamimidoyl]-1,2,5-oxadiazol-3-yl}sulfanyl)-N,N-dimethylacetamide, 2-({4-[N-(3-bromo-4-fluorophenyl)-N'-hydroxycarbamimidoyl]-1,2,5-oxadiazol-3-yl}sulfanyl)-N-(2-hydroxyethyl)acetamide, 2-({4-[N-(3-bromo-4-fluorophenyl)-N'-hydroxycarbamimidoyl]-1,2,5-oxadiazol-3-yl}sulfanyl)-N-cyclopropylacetamide, 2-({4-[N-(3-bromo-4-fluorophenyl)-N'-hydroxycarbamimidoyl]-1,2,5-oxadiazol-3-yl}sulfanyl)-N-cyclobutylacetamide, N-(3-bromo-4-fluorophenyl)-N'-hydroxy-4-[(2-oxopropyl)sulfanyl]-1,2,5-oxadiazazole-3-carboximidamide, 4-({2-[bis(benzylamino)phosphoryl]ethyl}sulfanyl)-N-(3-bromo-4-fluorophenyl)-N'-hydroxy-1,2,5-oxadiazole-3-carboximidamide, 4-({[bis(methylamino)phosphoryl]methyl}sulfanyl)-N-(3-bromo-4-fluorophenyl)-N'-hydroxy-1,2,5-oxadiazole-3-carboximidamide, phenyl hydrogen [3-({4-[N-(3-bromo-4-fluorophenyl)-N'-hydroxycarbamimidoyl]-1,2,5-oxadiazol-3-yl}sulfanyl)propyl]phosphonate, ethyl N-{[3-({4-[N-(3-bromo-4-fluorophenyl)-N'-hydroxycarbamimidoyl]-1,2,5-oxadiazol-3-yl}sulfanyl)propyl](phenoxy)phosphoryl}glycinate, methyl 6-[({4-[N-(3-bromo-4-fluorophenyl)-N'-hydroxycarbamimidoyl]-1,2,5-oxadiazol-3-yl}sulfanyl)methyl]-3-oxo-2-oxa-5,7-diaza-6-phosphanonan-9-oate 6-oxide, N-(3-bromo-4-fluorophenyl)-N'-hydroxy-4-({[(4S)-3-methyl-2-oxoimidazolidin-4-yl]methyl}) sulfanyl)-1,2,5-oxadiazole-3-carboximidamide, N-(3-bromo-4-fluorophenyl)-N'-hydroxy-4-({[(4S)-1-methyl-2-oxoimidazolidin-4-yl]methyl}) sulfanyl)-1,2,5-oxadiazole-3-carboximidamide, N-(3-bromo-4-fluorophenyl)-N'-hydroxy-4-({[(4R)-1-methyl-2-oxoimidazolidin-4-yl]methyl}) sulfanyl)-1,2,5-oxadiazole-3-carboximidamide, N-(3-bromo-4-fluorophenyl)-N'-hydroxy-4-{[(2-oxo-1,3-oxazolidin-5-yl)methyl]sulfanyl}-1,2,5-oxadiazole-3-carboximidamide, 4-{[(2R)-2-amino-3-hydroxypropyl]sulfanyl}-N-(3-bromo-4-fluorophenyl)-N'-hydroxy-1,2,5-oxadiazole-3-carboximidamide, N-(3-bromo-4-fluorophenyl)-N'-hydroxy-4-[(2-morpholin-4-ylethyl)sulfanyl]-1,2,5-oxadiazole-3-carboximidamide, N-(3-bromo-4-fluorophenyl)-4-({2-[(butylcarbamoyl)amino]ethyl}sulfanyl)-N'-hydroxy-1,2,5-oxadiazole-3-carboximidamide, ethyl {[2-({4-[N-(3-bromo-4-fluorophenyl)-N'-hydroxycarbamimidoyl]-1,2,5-oxadiazol-3-yl}sulfanyl)ethyl]carbamoyl}carbamate, N-(3-bromo-4-fluorophenyl)-4-({2-[(cyclopentylcarbamoyl)amino]ethyl}sulfanyl)-N'-hydroxy-1,2,5-oxadiazole-3-carboximidamide, N-(3-bromo-4-fluorophenyl)-N'-hydroxy-4-[(2-{[(tetrahydro-2H-pyran-4-ylmethyl)carbamoyl]amino}ethyl)sulfanyl]-1,2,5-oxadiazole-3-carboximidamide, N-(3-bromo-4-fluorophenyl)-4-[(2-{[(furan-2-ylmethyl)carbamoyl]amino}ethyl)sulfanyl]-N'-hydroxy-1,2,5-oxadiazole-3-carboximidamide, N-(3-bromo-4-fluorophenyl)-N'-hydroxy-4-[(2-{[(2-methoxyethyl)carbamoyl]amino}ethyl)sulfanyl]-1,2,5-oxadiazole-3-carboximidamide, N-(3-chloro-4-fluorophenyl)-N'-hydroxy-4-{[(4-methyl-5-oxo-4,5-dihydro-1H-1,2,4-triazol-3-yl)methyl]sulfanyl}-1,2,5-oxadiazole-3-carboximidamide, N-(3-bromo-4-fluorophenyl)-N'-hydroxy-4-({2-[(2S)-2-(hydroxymethyl)pyrrolidin-1-yl]-2-oxoethyl}sulfanyl)-1,2,5-oxadiazole-3-carboximidamide, N-(3-bromo-4-fluorophenyl)-N'-hydroxy-4-({2-[(2R)-2-(hydroxymethyl)pyrrolidin-1-yl]-2-oxoethyl}sulfanyl)-1,2,5-oxadiazole-3-carboximidamide, N-(3-bromo-4-fluorophenyl)-N'-hydroxy-4-[(2-oxo-2-pyrrolidin-1-ylethyl)sulfanyl]-1,2,5-oxadiazole-3-carboximidamide, 2-({4-[N-(3-bromo-4-fluorophenyl)-N'-hydroxycarbamimidoyl]-1,2,5-oxadiazol-3-yl}sulfanyl)-N-(2-fluoroethyl)acetamide, 2-({4-[N-(3-bromo-4-fluorophenyl)-N'-hydroxycarbamimidoyl]-1,2,5-oxadiazol-3-yl}sulfanyl)-N-(2-hydroxypropyl)acetamide, 4-({2-[bis(dimethylamino)phosphoryl]ethyl}sulfanyl)-N-(3-bromo-4-fluorophenyl)-N'-hydroxy-1,2,5-oxadiazole-3-carboximidamide, N-(3-cyano-4-fluorophenyl)-4-{[(2S)-2,3-dihydroxypropyl]sulfanyl}-N'-hydroxy-1,2,5-oxadiazole-3-carboximidamide, N-(3-bromo-4-fluorophenyl)-N'-hydroxy-4-{[2-(5-oxo-4,5-dihydro-1,3,4-oxadiazol-2-yl)ethyl]sulfanyl}-1,2,5-oxadiazole-3-carboximidamide, N-{2-[(4-{N-[3-(difluoromethyl)-4-fluorophenyl]-N'-hydroxycarbamimidoyl})-1,2,5-oxadiazol-3-yl)sulfanyl]ethyl}acetamide, 2-({4-[N-(3-bromo-4-fluorophenyl)-N'-hydroxycarbamimidoyl]-1,2,5-oxadiazol-3-yl}sulfanyl)-N-[(1R,2R)-2-hydroxy-1-(hydroxymethyl)propyl]acetamide, 2-({4-[N-(3-bromo-4-fluorophenyl)-N'-hydroxycarbamimidoyl]-1,2,5-oxadiazol-3-yl}sulfanyl)-N-[(1s,3R,4S)-3,4-dihydroxycyclopentyl]acetamide, 2-({4-[N-(3-bromo-4-fluorophenyl)-N'-hydroxycarbamimidoyl]-1,2,5-oxadiazol-3-yl}sulfanyl)-N-[2-hydroxy-1-(hydroxymethyl)ethyl]acetamide, N-(3-cyano-4-fluorophenyl)-N'-hydroxy-4-({[(4S)-3-methyl-2-oxoimidazolidin-4-yl]methyl}sulfanyl)-1,2,5-oxadiazole-3-carboximidamide, N-(3-cyano-4-fluorophenyl)-4-{[(2R)-2,3-dihydroxypropyl]sulfanyl}-N'-hydroxy-1,2,5-oxadiazole-3-carboximidamide, N-(3-cyano-4-fluorophenyl)-N'-hydroxy-4-({[(2R)-5-oxopyrrolidin-2-yl]methyl}sulfanyl)-1,2,5-oxadiazole-3-carboximidamide, N-(3-cyano-4-fluorophenyl)-N'-hydroxy-4-({[(2S)-5-oxopyrrolidin-2-yl]methyl}sulfanyl)-1,2,5-oxadiazole-3-carboximidamide, N-(3-cyano-4-fluorophenyl)-N'-hydroxy-4-({[(4R)-3-methyl-2-oxoimidazolidin-4-yl]methyl}sulfanyl)-1,2,5-oxadiazole-3-carboximidamide, N-(3-bromo-4-fluorophenyl)-N'-hydroxy-4-{[2-(2-methyl-1H-imidazol-1-yl)ethyl]sulfanyl}-1,2,5-oxadiazole-3-carboximidamide, N-(3-bromo-4-fluorophenyl)-N'-hydroxy-4-{[2-(1,3-thiazol-4-yl)ethyl]sulfanyl})-1,2,5-oxadiazole-3-carboximidamide, N-(3-bromo-4-fluorophenyl)-N'-hydroxy-4-{[(1-methyl-1H-imidazol-2-yl)methyl]sulfanyl}-1,2,5-oxadiazole-3-carboximidamide, N-(3-bromo-4-fluorophenyl)-N'-hydroxy-4-{[2-(1H-1,2,4-triazol-1-yl)ethyl]sulfanyl}-1,2,5-oxadiazole-3-carboximidamide, N-(3-bromo-4-fluorophenyl)-N'-hydroxy-4-{[(5-methyl-1,2,4-oxadiazol-3-yl)methyl]sulfanyl}-1,2,5-oxadiazole-3-carboximidamide, N-(3-bromo-4-fluorophenyl)-N'-hydroxy-4-[(1,2,4-oxadiazol-3-ylmethyl)sulfanyl]-1,2,5-oxadiazole-3-carboximidamide, N-(3-bromo-4-fluorophenyl)-N'-hydroxy-4-[(1,3-thiazol-2-ylmethyl)sulfanyl]-1,2,5-oxadiazole-3-carboximidamide, N-(3-bromo-4-fluorophenyl)-N'-hydroxy-4-[(piperidin-3-ylmethyl)sulfanyl]-1,2,5-oxadiazole-3-carboximidamide, N-(3-bromo-4-fluorophenyl)-N'-hydroxy-4-[(1H-imidazol-4-ylmethyl)sulfanyl]-1,2,5-oxadiazole-3-carboximidamide, N-(3-bromo-4-fluorophenyl)-4-[(2-fluoroethyl)sulfanyl]-N'-hydroxy-1,2,5-oxadiazole-3-carboximidamide, N-(3-bromo-4-fluorophenyl)-4-(but-2-yn-1-ylsulfanyl)-N'-hydroxy-1,2,5-oxadiazole-3-carboximidamide, N-(3-bromo-4-fluorophenyl)-N'-hydroxy-4-[(tetrahydro-2H-pyran-4-ylmethyl)sulfanyl]-1,2,5-oxadiazole-3-carboximidamide, N-(3-bromo-4-fluorophenyl)-N'-hydroxy-4-[(2-piperazin-1-ylethyl)sulfanyl]-1,2,5-oxadiazazole-3-carboximidamide, N-(3-bromo-4-fluorophenyl)-N'-hydroxy-4-{[2-(4-methylpiperazin-1-yl)ethyl]sulfanyl})-1,2,5-oxadiazole-3-carboximidamide, 4-{[(2R)-2,3-dihydroxypropyl]sulfanyl}-N-[4-fluoro-3-(trifluoromethyl)phenyl]-N'-hydroxy-1,2,5-oxadiazole-3-carboximidamide, 4-{[(2S)-2,3-dihydroxypropyl]sulfanyl}-N-[4-fluoro-3-(trifluoromethyl)phenyl]-N'-hydroxy-1,2,5-oxadiazole-3-carboximidamide, N-[3-(difluoromethyl)-4-fluorophenyl]-4-{[(2S)-2,3-dihydroxypropyl]sulfanyl}-N'-hydroxy-1,2,5-oxadiazole-3-carboximidamide, N-[3-(difluoromethyl)-4-fluorophenyl]-4-{[(2R)-2,3-dihydroxypropyl]sulfanyl}-N'-hydroxy-1,2,5-oxadiazole-3-carboximidamide, N-(3-chloro-4-fluorophenyl)-4-{[(2R)-2,3-dihydroxypropyl]sulfanyl}-N'-hydroxy-1,2,5-oxadiazole-3-carboximidamide, N-(3-chloro-4-fluorophenyl)-4-{[(2S)-2,3-dihydroxypropyl]sulfanyl}-N'-hydroxy-1,2,5-oxadiazole-3-carboximidamide, N-(3-cyano-4-fluorophenyl)-N'-hydroxy-4-({2-[(methylsulfonyl)amino]ethyl}sulfanyl)-1,2,5-oxadiazole-3-carboximidamide, N-(3-bromo-4-fluorophenyl)-N'-hydroxy-4-{[2-(1H-imidazol-1-yl)ethyl]sulfanyl}-1,2,5-oxadiazole-3-carboximidamide, N-[(1R)-2-({4-[N-(3-bromo-4-fluorophenyl)-N'-hydroxycarbamimidoyl]-1,2,5-oxadiazol-3-yl}sulfanyl)-1-(hydroxymethyl)ethyl]acetamide, 2-({4-[N-(3-bromo-4-fluorophenyl)-N'-hydroxycarbamimidoyl]-1,2,5-oxadiazol-3-yl}sulfanyl)-N-[2-hydroxy-1-(hydroxymethyl)-1-methylethyl]acetamide, 2-({4-[N-(3-bromo-4-fluorophenyl)-N'-hydroxycarbamimidoyl]-1,2,5-oxadiazol-3-yl}sulfanyl)-N-[(2S)-2,3-dihydroxypropyl]acetamide, 2-({4-[N-(3-bromo-4-fluorophenyl)-N'-hydroxycarbamimidoyl]-1,2,5-oxadiazol-3-yl}sulfanyl)-N-[2-hydroxy-1-(hydroxymethyl)propyl]acetamide, 2-({4-[N-(3-bromo-4-fluorophenyl)-N'-hydroxycarbamimidoyl]-1,2,5-oxadiazol-3-yl}sulfanyl)-N-[(1r,3R,4S)-3,4-dihydroxycyclopentyl]acetamide, N-(3-cyano-4-fluorophenyl)-4-({2-[(cyclopropyl sulfonyl)amino]ethyl}sulfanyl)-N'-hydroxy-1,2,5-oxadiazole-3-carboximidamide, N-[(1R)-2-({4-[N-(3-cyano-4-fluorophenyl)-N'-hydroxycarbamimidoyl]-1,2,5-oxadiazol-3-yl}sulfanyl)-1-methylethyl]acetamide, N-[(1S)-2-({4-[N-(3-cyano-4-fluorophenyl)-N'-hydroxycarbamimidoyl]-1,2,5-oxadiazol-3-yl}sulfanyl)-1-methylethyl]acetamide, N-(3-cyano-4-fluorophenyl)-N'-hydroxy-4-{[2-(sulfamoylamino)ethyl]sulfanyl})-1,2,5-oxadiazole-3-carboximidamide, N-[2-({4-[N-(3-cyano-4-fluorophenyl)-N'-hydroxycarbamimidoyl]-1,2,5-oxadiazol-3-yl}sulfanyl)ethyl]-2-hydroxyacetamide, N-[3-(difluoromethyl)-4-fluorophenyl]-N'-hydroxy-4-({2-[(methyl sulfonyl)amino]ethyl}sulfanyl)-1,2,5-oxadiazole-3-carboximidamide, N-(3-chloro-4-fluorophenyl)-N'-hydroxy-4-({2-[(methyl sulfonyl)amino]ethyl}sulfanyl)-1,2,5-oxadiazole-3-carboximidamide, 2-({4-[N-(3-cyano-4-fluorophenyl)-N'-hydroxycarbamimidoyl]-1,2,5-oxadiazol-3-yl)}sulfanyl)-N-methylacetamide, 2-({4-[N-(3-cyano-4-fluorophenyl)-N'-hydroxycarbamimidoyl]-1,2,5-oxadiazol-3-yl)}sulfanyl)-N-oxetan-3-ylacetamide, (1R)—N-[2-({4-[N-(3-cyano-4-fluorophenyl)-N'-hydroxycarbamimidoyl]-1,2,5-oxadiazol-3-yl}sulfanyl)ethyl]-2,2-difluorocyclopropanecarboxamide, (1S)—N-[2-({4-[N-(3-cyano-4-fluorophenyl)-N'-hydroxycarbamimidoyl]-1,2,5-oxadiazol-3-yl}sulfanyl)ethyl]-2,2-difluorocyclopropanecarboxamide, N-(3-chloro-4-fluorophenyl)-4-[(2,3-dihydroxy-3-methylbutyl)sulfanyl]-N'-hydroxy-1,2,5-oxadiazole-3-carboximidamide, N-(3-bromo-4-fluorophenyl)-N'-hydroxy-4-[(4H-1,2,4-triazol-3-ylmethyl)sulfanyl]-1,2,5-oxadiazole-3-carboximidamide, N-(3-bromo-4-fluorophenyl)-N'-hydroxy-4-({(2R)-3-hydroxy-2-[(methyl sulfonyl)amino]propyl}sulfanyl)-1,2,5-oxadiazole-3-carboximidamide, N-(3-bromo-4-fluorophenyl)-N'-hydroxy-4-[(2-morpholin-4-yl-2-oxoethyl)sulfanyl]-1,2,5-oxadiazole-3-carboximidamide, N-(3-bromo-4-fluorophenyl)-N'-hydroxy-4-{[(2R)-3-hydroxy-2-(sulfamoylamino)propyl]sulfanyl}-1,2,5-oxadiazole-3-carboximidamide, N-(3-bromo-4-fluorophenyl)-4-((2-((3S,4R)-3,4-dihydroxypyrrolidin-1-yl)-2-oxoethyl)thio)-N'-hydroxy-1,2,5-oxadiazole-3-carboximidamide, N-(3-bromo-4-fluorophenyl)-4-((2-((3S,4S)-3,4-dihydroxypiperidin-1-yl)-2-oxoethyl)thio)-N'-hydroxy-1,2,5-oxadiazole-3-carboximidamide,
(R)-2-((4-(N-(3-bromo-4-fluorophenyl)-N'-hydroxycarbamimidoyl)-1,2,5-oxadiazol-3-yl)thio)-N-(1-hydroxypropan-2-yl)acetamide,
2-((4-(N-(3-bromo-4-fluorophenyl)-N'-hydroxycarbamimidoyl)-1,2,5-oxadiazol-3-yl)thio)-N-((3S,4S)-3-hydroxytetrahydro-2H-pyran-4-yl)acetamide,
2-((4-(N-(3-bromo-4-fluorophenyl)-N'-hydroxycarbamimidoyl)-1,2,5-oxadiazol-3-yl)thio)-N—(N-methyl sulfamoyl)acetamide,
(S)-2-((4-(N-(3-bromo-4-fluorophenyl)-N'-hydroxycarbamimidoyl)-1,2,5-oxadiazol-3-yl)thio)-N-(2-hydroxypropyl)acetamide,
(R)-2-((4-(N-(3-bromo-4-fluorophenyl)-N'-hydroxycarbamimidoyl)-1,2,5-oxadiazol-3-yl)thio)-N-(2-hydroxypropyl)acetamide,
2-((4-(N-(3-bromo-4-fluorophenyl)-N'-hydroxycarbamimidoyl)-1,2,5-oxadiazol-3-yl)thio)-N-(1-(hydroxymethyl)cyclopropyl)acetamide,
(S)-2-((4-(N-(3-bromo-4-fluorophenyl)-N'-hydroxycarbamimidoyl)-1,2,5-oxadiazol-3-yl)thio)-N-(2-hydroxypropyl)acetamide,
(R)-2-((4-(N-(3-bromo-4-fluorophenyl)-N'-hydroxycarbamimidoyl)-1,2,5-oxadiazol-3-yl)thio)-N-(2,3-dihydroxypropyl)-2-methylpropanamide,
(S)-2-((4-(N-(3-bromo-4-fluorophenyl)-N'-hydroxycarbamimidoyl)-1,2,5-oxadiazol-3-yl)thio)-N-(1-hydroxypropan-2-yl)acetamide,
2-((4-(N-(3-bromo-4-fluorophenyl)-N'-hydroxycarbamimidoyl)-1,2,5-oxadiazol-3-yl)thio)-N-(2-hydroxy-3-morpholinopropyl)acetamide,
2-((4-(N-(3-bromo-4-fluorophenyl)-N'-hydroxycarbamimidoyl)-1,2,5-oxadiazol-3-yl)thio)-N-(3,4-dihydroxy-2-methylbutan-2-yl)acetamide,
N-(3-bromo-4-fluorophenyl)-4-{[2-(dimethylamino)ethyl]sulfanyl}-N'-hydroxy-1,2,5-thiadiazole-3-carboximidamide,
N-(3-bromo-4-fluorophenyl)-4-{[2-({2-[(cyclopropylmethyl)amino]-3,4-dioxocyclobut-1-en-1-yl}amino)ethyl]sulfanyl}-N'-hydroxy-1,2,5-thiadiazole-3-carboximidamide, and
N-(3-bromo-4-fluorophenyl)-4-[(2-{[2-(cyclopropylamino)-3,4-dioxocyclobut-1-en-1-yl]amino}ethyl)sulfanyl]-N'-hydroxy-1,2,5-thiadiazole-3-carboximidamide;
N-(2-((4-(N-(3-bromo-4-fluorophenyl)-N'-hydroxycarbamimidoyl)-1,2,5-oxadiazol-3-yl)oxy)ethyl)acetamide,
2-((4-(N-(3-Bromo-4-fluorophenyl)-N'-hydroxycarbamimidoyl)-1,2,5-oxadiazol-3-yl)oxy)-N-(2-hydroxyethyl)acetamide,
N-(3-bromo-4-fluorophenyl)-N'-hydroxy-4-(2-(sulfamoylamino)ethoxy)-1,2,5-oxadiazole-3-carboximidamide,
4-(2-aminoethoxy)-N-(3-bromo-4-fluorophenyl)-N'-hydroxy-1,2,5-oxadiazole-3-carboximidamide,
N-(3-bromo-4-fluorophenyl)-N'-hydroxy-4-(2-(methyl sulfonamido)ethoxy)-1,2,5-oxadiazazole-3-carboximidamide or a pharmaceutically acceptable salt thereof.

15. A composition which comprises a pharmaceutically acceptable carrier and a compound of claim 1 or a pharmaceutically acceptable salt thereof.

16. A method for treating an IDO-associated disease or disorder in a mammalian subject wherein the method comprises administering to the subject an effective amount of a compound of claim 1 or a pharmaceutically acceptable salt thereof; wherein the IDO-associated disease or disorder is selected from colon cancer, pancreas cancer, breast cancer, prostate cancer, lung cancer, brian cancer, ovarian cancer, cervix cancer, renal cancer, head and neck cancer, lymphoma, leukemia, melanoma, Alzheimer's disease, Huntington's disease, asthma, rheumatoid arthritis, multiple sclerosis, allergic inflammation, inflammatory bowel disease, psoriasis, and systemic lupus erythematosus.

17. A method for treating an IDO-associated disease or disorder in a mammalian subject wherein the method comprises administering to the subject an effective amount of a compound of claim 1 or a pharmaceutically acceptable salt thereof in combination with another anti-cancer agent; wherein the IDO-associated disease or disorder is selected from colon cancer, pancreas cancer, breast cancer, prostate cancer, lung cancer, brian cancer, ovarian cancer, cervix cancer, renal cancer, head and neck cancer, lymphoma, leukemia, melanoma, Alzheimer's disease, Huntington's disease, asthma, rheumatoid arthritis, multiple sclerosis, allergic inflammation, inflammatory bowel disease, psoriasis, and systemic lupus erythematosus.

18. The method of claim 17, wherein the IDO-associated disease or disorder is selected from asthma, rheumatoid arthritis, multiple sclerosis, allergic inflammation, inflammatory bowel disease, psoriasis, and systemic lupus erythematosus.

19. The method of claim 17, wherein the IDO-associated disease or disorder is a cancer selected from colon cancer, pancreas cancer, breast cancer, prostate cancer, lung cancer, brain cancer, ovarian cancer, cervix cancer, testes cancer, renal cancer, head and neck cancer, lymphoma, leukemia, and melanoma.

* * * * *